United States Patent
Claremon et al.

(10) Patent No.: US 8,927,715 B2
(45) Date of Patent: Jan. 6, 2015

(54) INHIBITORS OF 11β-HYDROXYSTEROID DEHYDROGENASE TYPE 1

(75) Inventors: David A. Claremon, Maple Glen, PA (US); Suresh B. Singh, Kendall Park, NJ (US); Colin M. Tice, Ambler, PA (US); Yuanjie Ye, Ambler, PA (US); Salvacion Cacatian, Philadelphia, PA (US); Wei He, Audubon, PA (US); Robert Simpson, Wilmington, DE (US); Zhenrong Xu, Horsham, PA (US); Wei Zhao, Eagleville, PA (US)

(73) Assignee: Vitae Pharmaceuticals, Inc., Fort Washington, PA (US)

( * ) Notice: Subject to any disclaimer, the term of this patent is extended or adjusted under 35 U.S.C. 154(b) by 1140 days.

(21) Appl. No.: 12/310,457

(22) PCT Filed: Aug. 24, 2007

(86) PCT No.: PCT/US2007/018789
§ 371 (c)(1),
(2), (4) Date: Sep. 3, 2009

(87) PCT Pub. No.: WO2008/024497
PCT Pub. Date: Feb. 28, 2008

(65) Prior Publication Data
US 2011/0034455 A1    Feb. 10, 2011

Related U.S. Application Data

(60) Provisional application No. 60/840,203, filed on Aug. 25, 2006.

(51) Int. Cl.
| | | |
|---|---|---|
| *A61K 31/5377* | (2006.01) | |
| *C07D 471/10* | (2006.01) | |
| *A61K 31/438* | (2006.01) | |
| *C07D 221/20* | (2006.01) | |
| *C07D 401/10* | (2006.01) | |
| *A61K 31/496* | (2006.01) | |
| *C07D 413/10* | (2006.01) | |
| *A61P 3/00* | (2006.01) | |
| *A61P 9/12* | (2006.01) | |
| *A61P 9/00* | (2006.01) | |
| *A61P 25/22* | (2006.01) | |
| *A61P 25/28* | (2006.01) | |
| *A61P 25/24* | (2006.01) | |
| *A61P 15/08* | (2006.01) | |
| *C07D 211/26* | (2006.01) | |
| *C07D 413/06* | (2006.01) | |
| *C07D 211/22* | (2006.01) | |
| *C07D 491/107* | (2006.01) | |
| *C07D 211/16* | (2006.01) | |
| *C07D 211/34* | (2006.01) | |
| *C07D 401/08* | (2006.01) | |
| *C07D 401/06* | (2006.01) | |

(52) U.S. Cl.
CPC ............ *C07D 221/20* (2013.01); *C07D 471/10* (2013.01); *C07D 211/26* (2013.01); *C07D 413/06* (2013.01); *C07D 211/22* (2013.01); *C07D 491/107* (2013.01); *C07D 211/16* (2013.01); *C07D 211/34* (2013.01); *C07D 401/08* (2013.01); *C07D 401/06* (2013.01)
USPC ................ 546/17; 546/16; 546/18; 544/230; 544/126; 514/232.8; 514/278; 514/253.03

(58) Field of Classification Search
None
See application file for complete search history.

(56) References Cited

U.S. PATENT DOCUMENTS

| | | | | |
|---|---|---|---|---|
| 5,091,387 | A * | 2/1992 | Evans et al. .................... | 514/278 |
| 5,670,509 | A | 9/1997 | Evans et al. | |
| 6,943,199 | B2 | 9/2005 | De Lombaert et al. | |
| 2005/0261332 | A1 * | 11/2005 | Distefano et al. ............. | 514/300 |
| 2006/0270653 | A1 | 11/2006 | Drutu et al. | |

(Continued)

FOREIGN PATENT DOCUMENTS

| | | |
|---|---|---|
| EP | 0444945 A2 | 9/1991 |
| EP | 0450761 A1 | 10/1991 |

(Continued)

OTHER PUBLICATIONS

Evans et al. in Journal of Medicinal Chemistry 35(21) 3919-3927 (1992).*

(Continued)

*Primary Examiner* — Dennis Heyer
(74) *Attorney, Agent, or Firm* — McCarter & English LLP; Steven G. Davis; Michael J. DeGrazia

(57) ABSTRACT

This invention relates to novel compounds of the Formula (I*), pharmaceutically acceptable salts thereof, and pharmaceutical compositions thereof which are useful for the therapeutic treatment of diseases associated with the modulation or inhibition of 11β-HSD1 in mammals. The invention further relates to pharmaceutical compositions of the novel compounds and methods for their use in the reduction or control of the production of Cortisol in a cell or the inhibition of the conversion of cortisone to Cortisol in a cell.

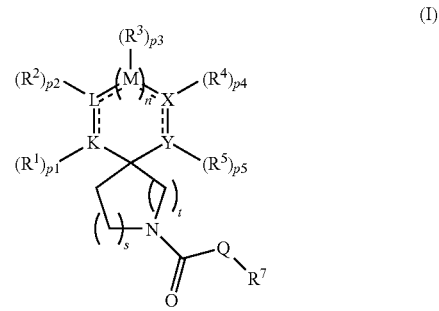

14 Claims, No Drawings

(56) References Cited

U.S. PATENT DOCUMENTS

| | | |
|---|---|---|
| 2007/0208001 A1 | 9/2007 | Zhuo et al. |
| 2008/0214807 A1 | 9/2008 | Schick et al. |

FOREIGN PATENT DOCUMENTS

| | | |
|---|---|---|
| WO | WO 95/14025 | 5/1995 |
| WO | WO 01/13917 A | 3/2001 |
| WO | WO 2004/056745 A | 7/2004 |
| WO | WO 2005/061512 A1 | 7/2005 |
| WO | WO 2005/063745 A2 | 7/2005 |
| WO | WO 2005/116002 A | 12/2005 |
| WO | WO 2006/002349 A | 1/2006 |
| WO | WO 2006/023852 A2 | 3/2006 |
| WO | WO 2006/040329 A | 4/2006 |
| WO | WO 2007/084314 A2 | 7/2007 |
| WO | WO 2007/103719 A | 9/2007 |

OTHER PUBLICATIONS

PCT International Search Report & Written Opinion—(PCT/US2007/018789) Date of Mailing Apr. 22, 2008.

Evans et al., "Orally Active, Nonpeptide Oxytocin Antagonists", Journal of Medicinal Chemistry, American Chemical Society, 1992, vol. 35, pp. 3919-3927.

Milad S. Bitar, "Glucocorticoid Dynamics and Impaired Wound Healing in Diabetes Mellitus", American Journal of Pathology, 1998, vol. 152, pp. 547-554.

Bitar et al., "Glucocorticoid-Dependent Impairment of Wound Healing in Experimental Diabetes: Amelioration by Adrenalectomy and RU 486", Journal of Surgical Research, 1999, vol. 82, pp. 234-243.

Bitar et al., "Heat-Shock Protein 72/73 and Impaired Wound Healing in Diabetic and Hypercortisolemic States", Surgery, 1999, vol. 125, pp. 594-601.

Bitar, "Insulin and Glucocorticoid-dependent Suppression of the IGF-I System in Diabetic Wounds", Surgery, 2000, vol. 127, pp. 687-695.

Malgorzata Wamil and Jonathan R. Seckl, "Inhibition of 11β-Hydroxysteroid Dehydrogenase Type 1 as a Promising Therapeutic Target", Drug Discovery Today, 2007, vol. 12, Nos. 13/14, pp. 504-520.

* cited by examiner

INHIBITORS OF 11β-HYDROXYSTEROID DEHYDROGENASE TYPE 1

RELATED APPLICATIONS

This application is the U.S. National Stage of International Application No. PCT/US2007/018789, filed Aug. 24, 2007, published in English, and claims the benefit of U.S. Provisional Application No. 60/840,203, filed Aug. 25, 2006, the entire teachings of which are incorporated herein by reference.

FIELD OF THE INVENTION

The present invention relates to inhibitors of 11β-hydroxy steroid dehydrogenase type 1 (11β-HSD1); pharmaceutical compositions thereof and methods of using the same.

BACKGROUND OF THE INVENTION

Glucocorticoids, such as cortisol (hydrocortisone), are steroid hormones that regulate fat metabolism, function and distribution, and play a role in carbohydrate, protein and fat metabolism. Glucocorticoids are also known to have physiological effects on development, neurobiology, inflammation, blood pressure, metabolism and programmed cell death. Cortisol and other corticosteroids bind both the glucocorticoid receptor (GR) and the mineralocorticoid receptor (MR), which are members of the nuclear hormone receptor superfamily and have been shown to mediate cortisol function in vivo. These receptors directly modulate transcription via DNA-binding zinc finger domains and transcriptional activation domains.

Until recently, the major determinants of glucocorticoid action were attributed to three primary factors: (1) circulating levels of glucocorticoid (driven primarily by the hypothalamic-pituitary-adrenal (HPA) axis); (2) protein binding of glucocorticoids in circulation; and (3) intracellular receptor density inside target tissues. Recently, a fourth determinant of glucocorticoid function has been identified: tissue-specific pre-receptor metabolism by glucocorticoid-activating and -inactivating enzymes. These 11β-hydroxysteroid dehydrogenase (11β-HSD) pre-receptor control enzymes modulate activation of GR and MR by regulation of glucocorticoid hormones. To date, two distinct isozymes of 11-beta-HSD have been cloned and characterized: 11β-HSD1 (also known as 11-beta-HSD type 1, 11betaHSD1, HSD11B1, and HSD11L) and 11β-HSD2. 11β-HSD1 is a bi-directional oxidoreductase that regenerates active cortisol from inactive 11-keto forms, whereas 11β-HSD2 is a unidirectional dehydrogenase that inactivates biologically active cortisol by converting it into cortisone.

The two isoforms are expressed in a distinct tissue-specific fashion, consistent with the differences in their physiological roles. 11β-HSD1 is widely distributed in rat and human tissues; expression of the enzyme and corresponding mRNA have been detected in human liver, adipose tissue, lung, testis, bone and ciliary epithelium. In adipose tissue, increased cortisol concentrations stimulate adipocyte differentiation and may play a role in promoting visceral obesity. In the eye, 11β-HSD1 may regulate intraocular pressure and may contribute to glaucoma; some data suggests that inhibition of 11β-HSD1 may cause a drop in intraocular pressure in patients with intraocular hypertension (Kotelevtsev, et al., (1997), Proc. Nat'l Acad. Sci. USA 94(26):14924-9). Although 11β-HSD1 catalyzes both 11-beta-dehydrogenation and the reverse 11-oxoreduction reaction, 11β-HSD1 acts predominantly as a NADPH-dependent oxoreductase in intact cells and tissues, catalyzing the formation of active cortisol from inert cortisone (Low, et al., (1994) J. Mol. Endocrin. 13: 167-174). In contrast, 11β-HSD2 expression is found mainly in mineralocorticoid target tissues such as kidney (cortex and medulla), placenta, sigmoid and rectal colon, salivary gland and colonic epithelial cell lines. 11β-HSD2 acts as an NAD-dependent dehydrogenase catalyzing the inactivation of cortisol to cortisone (Albiston, et al., (1994) Mol. Cell. Endocrin. 105: R11-R17), and has been shown to protect the MR from glucocorticoid excess (e.g., high levels of receptor-active cortisol) (Blum, et al., (2003) Prog. Nucl. Acid Res. Mol. Biol. 75:173-216).

Mutations in either the 11β-HSD1 or the 11β-HSD2 genes result in human pathology. For example, individuals with mutations in 11β-HSD2 are deficient in this cortisol-inactivation activity and, as a result, present with a syndrome of apparent mineralocorticoid excess (also referred to as "SAME") characterized by hypertension, hypokalemia, and sodium retention (Edwards, et al., (1988) Lancet 2: 986-989; Wilson, et al., (1998) Proc. Nat'l Acad. Sci. 95: 10200-10205). Similarly, mutations in 11β-HSD1 and in the gene encoding a co-localized NADPH-generating enzyme, hexose 6-phosphate dehydrogenase (H6PD), can result in cortisone reductase deficiency (CRD); these individuals present with ACTH-mediated androgen excess (hirsutism, menstrual irregularity, hyperandrogenism), a phenotype resembling polycystic ovary syndrome (PCOS) (Draper, et al., (2003) Nat. Genet. 34: 434-439).

Notably, disruption of homeostasis in the HPA axis by either deficient or excess secretion or action results in Cushing's syndrome or Addison's disease, respectively (Miller & Chrousos, *Endocrinology and Metabolism* (Felig & Frohman eds., McGraw-Hill: New York, $4^{th}$ Ed. (2001)) 387-524). Patients with Cushing's syndrome or receiving glucocorticoid therapy develop reversible visceral fat obesity. The phenotype of Cushing's syndrome patients closely resembles that of Reaven's metabolic syndrome (also known as Syndrome X or insulin resistance syndrome), the symptoms of which include visceral obesity, glucose intolerance, insulin resistance, hypertension, type 2 diabetes and hyperlipidemia (Reaven, (1993) Ann. Rev. Med. 44, 121-131). Although the role of glucocorticoids in human obesity is not fully characterized, there is mounting evidence that 11β-HSD1 activity plays an important role in obesity and metabolic syndrome (Bujalska, et al., (1997) Lancet 349: 1210-1213); (Livingstone, et al., (2000) Endocrinology 131, 560-563; Rask, et al., (2001) J. Clin. Endocrinol. Metab. 86, 1418-1421; Lindsay, et al., (2003) J. Clin. Endocrinol. Metab. 88: 2738-2744; Wake, et al., (2003) J. Clin. Endocrinol. Metab. 88, 3983-3988).

Data from studies in mouse transgenic models supports the hypothesis that adipocyte 11β-HSD1 activity plays a central role in visceral obesity and metabolic syndrome (Alberts, et al., (2002) Diabetologia. 45(11), 1526-32). Over-expression in adipose tissue of 11β-HSD1 under the control of the aP2 promoter in transgenic mice produced a phenotype remarkably similar to human metabolic syndrome (Masuzaki, et al., (2001) Science 294, 2166-2170; Masuzaki, et al., (2003) J. Clinical Invest. 112, 83-90). Moreover, the increased activity of 11β-HSD1 in these mice, is very similar to that observed in human obesity (Rask, et al., (2001) J. Clin. Endocrinol. Metab. 86, 1418-1421). In addition, data from studies with 11βHSD1-deficient mice produced by homologous recombination demonstrate that the loss of 11β-HSD1 leads to an increase in insulin sensitivity and glucose tolerance due to a tissue-specific deficiency in active glucocorticoid levels (Kotelevstev, et al., (1997) Proc. Nat'l Acad. Sci. 94: 14924-

14929; Morton, et al., (2001) J. Biol. Chem. 276, 41293-41300; Morton, et al., (2004) Diabetes 53, 931-938).

The published data supports the hypothesis that increased expression of 11β-HSD1 contributes to increased local conversion of cortisone to cortisol in adipose tissue and hence that 11β-HSD1 plays a role in the pathogenesis of central obesity and the appearance of the metabolic syndrome in humans (Engeli, et al., (2004) Obes. Res. 12: 9-17). Therefore, 11β-HSD1 is a promising pharmaceutical target for the treatment of the metabolic syndrome (Masuzaki, et al., (2003) Curr. Drug Targets Immune Endocr. Metabol. Disord. 3: 255-62). Furthermore, inhibition of 11β-HSD1 activity may prove beneficial in treating numerous glucocorticoid-related disorders. For example, 11β-HSD1 inhibitors could be effective in combating obesity and/or other aspects of the metabolic syndrome cluster, including glucose intolerance, insulin resistance, hyperglycemia, hypertension, and/or hyperlipidemia (Kotelevstev, et al., (1997) Proc. Nat'l Acad. Sci. 94, 14924-14929; Morton et al., (2001) J. Biol. Chem. 276, 41293-41300; Morton, et al., (2004) Diabetes 53, 931-938). In addition, inhibition of 11β-HSD1 activity may have beneficial effects on the pancreas, including the enhancement of glucose-stimulated insulin release (Billaudel & Sutter, (1979) Horm. Metab. Res. 11, 555-560; Ogawa, et al., (1992) J. Clin. Invest. 90, 497-504; Davani, et al., (2000) J. Biol. Chem. 275, 34841-34844). Inter-individual differences in general cognitive function has been linked to variability in the long-term exposure to glucocorticoids (Lupien, et al., (1998) Nat. Neurosci. 1: 69-73) and dysregulation of the HPA axis. Such chronic exposure to glucocorticoid excess in certain brain subregions has been theorized to contribute to the decline of cognitive function (McEwen & Sapolsky (1995) Curr. Opin. Neurobiol. 5, 205-216). Therefore, inhibition of 11β-HSD1 may reduce exposure to glucocorticoids in the brain and thereby protect against deleterious glucocorticoid effects on neuronal function, including cognitive impairment, dementia, and/or depression.

There is also evidence that glucocorticoids and 11β-HSD1 play a role in regulation of in intra-ocular pressure (IOP) (Stokes et al., (2000) Invest. Opthalmol. Vis. Sci. 41: 1629-1683; Rauz, et al., (2001) Invest. Opthalmol. Vis. Sci. 42: 2037-2042). If left untreated, elevated IOP can lead to partial visual field loss and eventually blindness. Thus, inhibition of 11β-HSD1 in the eye could reduce local glucocorticoid concentrations and IOP, and hence could be used to treat or prevent glaucoma and other visual disorders.

Transgenic aP2-11β-HSD1 mice exhibit high arterial blood pressure and have increased sensitivity to dietary salt. Additionally, plasma angiotensinogen levels are elevated in the transgenic mice, as are angiotensin II and aldosterone. Treatment of the mice with an angiotensin II antagonist alleviates the hypertension (Masuzaki, et al., (2003) J. Clinical Invest. 112, 83-90). This suggests that hypertension may be caused or exacerbated by 11β-HSD1 activity. Thus, 11β-HSD1 inhibitors may be useful for treatment of hypertension and hypertension-related cardiovascular disorders.

Glucocorticoids can have adverse effects on skeletal tissues, and prolonged exposure to even moderate glucocorticoid doses can result in osteoporosis (Cannalis, (1996) J. Clin. Endocrinol. Metab. 81, 3441-3447). In addition, 11β-HSD1 has been shown to be present in cultures of human primary osteoblasts as well as cells from adult bone (Cooper, et al., (2000) Bone 27: 375-381), and the 11β-HSD1 inhibitor carbenoxolone has been shown to attenuate the negative effects of glucocorticoids on bone nodule formation (Bellows, et al., (1998) Bone 23: 119-125). Thus, inhibition of 11β-HSD1 is predicted to decrease the local glucocorticoid concentration within osteoblasts and osteoclasts, thereby producing beneficial effects in various forms of bone disease, including osteoporosis.

As evidenced herein, there is a continuing need for new and improved drugs that inhibit 11β-HSD1. The novel compounds of the present invention are effective inhibitors of 11β-HSD1.

SUMMARY OF THE INVENTION

The present invention provides compounds of Formula I*:

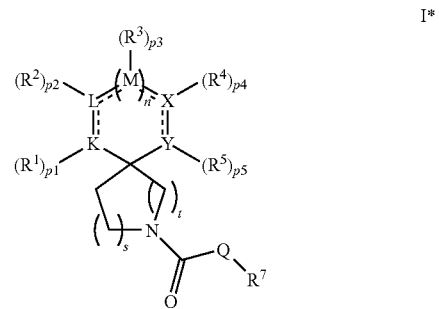

wherein:
K, L, M, X and Y are independently C, N or O, provided that the total number of nitrogen and oxygen atoms in the ring is 3 or leis and when K, L, M, X or Y is O, any adjacent member atom in the ring cannot be O;
the bonds between K, L, M, X and Y are single or double bonds provided that no consecutive double occur between member atoms of the ring;
n=0, 1, or 2;
s=1 or 2;
t=1 or 2;
$R^1$-$R^5$ are independently hydrogen, A-(5-tetrazolyl), A-(cycloalkyl), A-(heteroaryl), A-(heterocyclyl), A-(aryl), A-COOR$^6$, A-CON(R$^6$)$_2$, A-COR$^6$, A-SO$_2$R$^6$, A-CONHSO$_2$R$^6$, A-CONHSO$_2$OR$^6$, A-CONHSO$_2$N(R$^6$)$_2$, A-C≡N, alkyl, alkenyl, cycloalkyl, heteroaryl, heterocyclyl, aryl or arylalkyl, wherein the alkyl, alkenyl, cycloalkyl, heteroaryl, heterocyclyl, aryl, A-(cycloalkyl), A-(heteroaryl), A-(heterocyclyl), A-(aryl) or arylalkyl groups represented by $R^1$-$R^5$ are optionally and independently substituted with 1-3 groups independently selected from the group consisting of halogen, hydroxy, cyano, —N(R$^6$)$_2$, —NR$^6$C(O)N(R$^6$)$_2$, —NR$^6$C(O)R$^6$, (C$_1$-C$_6$)alkyl, halo(C$_1$-C$_6$)alkyl, (C$_1$-C$_6$)alkoxy, halo(C$_1$-C$_6$)alkoxy, CONH$_2$, —SO$_2$R$^6$, —NR$^6$SO$_2$R$^6$, —NR$^6$SO$_2$N(R$^6$)$_2$ and —NR$^6$SO$_2$OR$^6$;
when K, L, M, X, or Y is (—O—) or (—N=), then p1; p2, p3, p4 or p5, respectively, is 0; when K, L, M, X, or Y is (—N—), (—C=), or (—CH—), then p1, p2, p3, p4 or p5, respectively, is 1; when K, L, M, X or Y is (—C—), then p1, p2, p3, p4 or p5, respectively, is 2; and when K, L, M, X, or Y is (—C—), and $R^1$, $R^2$, $R^3$, $R^4$ or $R^5$ is connected through a double bond to K, L, M, X or Y, respectively, then p1, p2, p3, p4 or p5, respectively, is 1;
A is a single bond, (C$_1$-C$_6$)alkylene, (C$_1$-C$_6$)alkenylene, (C$_1$-C$_5$)alkylCH=, C(O)(C$_0$-C$_3$)alkyl(C$_3$-C$_6$)cycloalkyl(C$_0$-C$_3$)alkylene, C(O)(C$_1$-C$_6$)alkylene, C(O)(C$_2$-C$_6$)alkenylene, S(O)$_2$(C$_1$-C$_6$)alkylene, S(O)$_2$(C$_2$-C$_6$)alkenylene, or S(O)$_2$(C$_0$-C$_3$)alkyl(C$_3$-C$_6$)cycloalkyl(C$_0$-C$_3$)alkylene, each optionally substituted with up to 4 groups, R$^6$;
$R^1$, K, L and $R^2$ are taken together to form a fused benzene or pyridine ring, which is optionally substituted with 1-3 groups independently selected from the group consisting of halogen, hydroxy, cyano, —N(R$^6$)$_2$, —NR$^6$C(O)N(R$^6$)$_2$, —NR$^6$C(O)R$^6$, (C$_1$-C$_6$)alkyl, halo(C$_1$-C$_6$)alkyl, (C$_1$-C$_6$)alkoxy, halo(C$_1$-C$_6$)alkoxy, CON(R$^6$)$_2$, SO$_2$N(R$^6$)$_2$, —SO$_2$R$^6$, —NR$^6$SO$_2$R$^6$, —NR$^6$SO$_2$N(R$^6$)$_2$ and —NR$^6$SO$_2$OR$^6$; or R$^2$, L, M and R$^3$ are taken together to form a fused benzene or pyridine ring, which is optionally substituted with 1-3 groups independently selected from the group consisting of halogen, hydroxy, cyano, —N(R$^6$)$_2$, —NR$^6$C(O)N(R$^6$)$_2$, —NR$^6$C(O)R$^6$, (C$_1$-C$_6$)alkyl, halo(C$_1$-C$_6$)alkyl, (C$_1$-C$_6$)alkoxy, halo(C$_1$-C$_6$)alkoxy, CON(R$^6$)$_2$, SO$_2$N(R$^6$)$_2$, —SO$_2$R$^6$, —NR$^6$SO$_2$R$^6$, —NR$^6$SO$_2$N(R$^6$)$_2$ and —NR$^6$SO$_2$OR$^6$; or R$^2$, L, X and R$^4$ are taken together, when n=0, to form a fused benzene or pyridine ring, which is optionally substituted with 1-3 groups independently selected from the group consisting of halogen, hydroxy, cyano, —N(R$^6$)$_2$, —NR$^6$C(O)N(R$^6$)$_2$, —NR$^6$C(O)R$^6$, (C$_1$-C$_6$)alkyl, halo(C$_1$-C$_6$)alkyl, (C$_1$-C$_6$)alkoxy, halo(C$_1$-C$_6$)alkoxy, CON(R$^6$)$_2$, SO$_2$N(R$^6$)$_2$, —SO$_2$R$^6$, —NR$^6$SO$_2$R$^6$, —NR$^6$SO$_2$N(R$^6$)$_2$ and —NR$^6$SO$_2$OR$^6$, provided that n=0 and M and R$^3$ are absent; or R$^4$, X, Y and R$^5$ are taken together to form a fused benzene or pyridine ring, which is optionally substituted with 1-3 groups independently selected from the group consisting of halogen, hydroxy, cyano, —N(R$^6$)$_2$, —NR$^6$C(O)N(R$^6$)$_2$, —NR$^6$C(O)R$^6$, (C$_1$-C$_6$)alkyl, halo(C$_1$-C$_6$)alkyl, (C$_1$-C$_6$)alkoxy, halo(C$_1$-C$_6$)alkoxy, CON(R$^6$)$_2$, SO$_2$N(R$^6$)$_2$, —SO$_2$R$^6$, —NR$^6$SO$_2$R$^6$, —NR$^6$SO$_2$N(R$^6$)$_2$ and —NR$^6$SO$_2$OR$^6$; or the group consisting of R$^1$, K, L and R$^2$ and the group consisting of R$^4$, X, Y and R$^5$ are each taken together to form a fused benzene or pyridine ring, each of which is optionally substituted with 1-3 groups independently selected from the group consisting of halogen, hydroxy, cyano, —N(R$^6$)$_2$, —NR$^6$C(O)N(R$^6$)$_2$, —NR$^6$C(O)R$^6$, (C$_1$-C$_6$)alkyl, halo(C$_1$-C$_6$)alkyl, (C$_1$-C$_6$)alkoxy, halo(C$_1$-C$_6$)alkoxy, CON(R$^6$)$_2$, SO$_2$N(R$^6$)$_2$, —SO$_2$R$^6$, —NR$^6$SO$_2$R$^6$, —NR$^6$SO$_2$N(R$^6$)$_2$ and —NR$^6$SO$_2$OR$^6$;

R$^6$ is hydrogen, (C$_1$-C$_{10}$)alkyl, halo(C$_1$-C$_{10}$)alkyl, hydroxy (C$_1$-C$_{10}$)alkyl, (R$^6$)$_2$N(C$_1$-C$_{10}$)alkyl, aryl or arylalkyl, wherein the aryl and arylalkyl groups are optionally substituted with up to three groups independently selected from halogen, hydroxy, cyano, —N(R$^6$)$_2$, —NR$^6$C(O)N(R$^6$)$_2$, —NR$^6$C(O)R$^6$, (C$_1$-C$_6$)alkyl, halo(C$_1$-C$_6$)alkyl, (C$_1$-C$_6$)alkoxy, halo(C$_1$-C$_6$)alkoxy, CON(R$^6$)$_2$, SO$_2$N(R$^6$)$_2$, —SO$_2$R$^6$, —NR$^6$SO$_2$R$^6$, —NR$^6$SO$_2$N(R$^6$)$_2$ and —NR$^6$SO$_2$OR$^6$; or N(R$^6$)$_2$ is a heterocyclyl group containing at least one nitrogen atom, preferably selected from W$^1$-W$^7$:

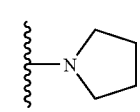
W$^1$

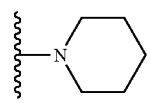
W$^2$

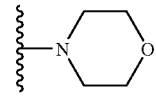
W$^3$

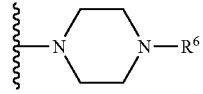
W$^4$

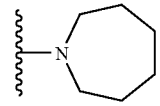
W$^5$

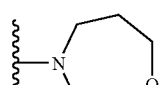
W$^6$

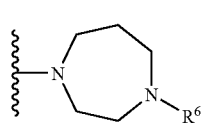
W$^7$

Q is O or NR$^6$; and

R$^7$ is a saturated C$_7$-C$_{17}$ bicycloalkyl or saturated C$_9$-C$_{12}$ tricycloalkyl in which 1-2 carbon atoms are optionally replaced with heteroatoms independently selected from N and O, and which is optionally substituted with 1-3 substituents independently selected from the group consisting of R$^6$, heteroaryl, oxo-substituted heteroaryl, amino-substituted heteroaryl, heterocyclyl, oxo-substituted heterocyclyl, halogen, hydroxy, hydroxy(C$_1$-C$_6$)alkyl, C(NOH)NH$_2$, CONHR$^6$, CH$_2$CONHR$^6$, CON(R$^6$)$_2$, CH$_2$CON(R$^6$)$_2$, SO$_2$NHR$^6$, SO$_2$N(R$^6$)$_2$, CO$_2$R$^6$, CH$_2$CO$_2$R$^6$, SO$_2$R$^6$, NHCOR$^6$, NR$^6$COR$^6$, NHCO$_2$R$^6$, NR$^6$CO$_2$R$^6$, NHSO$_2$R$^6$, and NR$^6$SO$_2$R$^6$; or an enantiomer, diastereomer, geometrical isomer or pharmaceutically acceptable salt thereof;

optionally, with the general provisos that:

(1) if R$^1$, K, L and R$^2$ form a fused benzene or pyridine ring, Q is NR$^6$, R$^6$ is H, Y is O, s=1, t=2, n=6, X is C, R$^4$ is H and R$^5$ is absent, then R$^7$ is not a 7- to 10-membered carbocyclic group or heterocyclic group;

(2) if R$^1$, K, L and R$^2$ form a fused benzene ring, Q is NR$^6$, R$^6$ is H, n=1, s=1, t=1 or 2, and M, X and Y are all carbon, then at least one of R$^3$, R$^4$ or R$^5$ must not be —(CH$_2$)$_n$—Z, wherein n=0 to 2, and Z is hydrogen, (C$_1$-C$_6$)alkyl, 2-pyridyl, 3-pyridyl, 4-pyridyl or substituted or unsubstituted phenyl wherein if the phenyl is substituted, there are 1 or 2 substituents independently selected from the group consisting of halogen, (C$_1$-C$_6$)alkyl, (C$_1$-C$_6$)alkoxy, carboxyl, cyano, loweralkylthio, carboxy-loweralkyl, nitro, —CF$_3$ or hydroxy. Preferably, if R$^1$, K, L and R$^2$ form a fused benzene ring, Q is NR$^6$, R$^6$ is H, n=1, s=1, t=1 or 2, and M, X and Y are all carbon, then at least one of R$^3$, R$^4$ or R$^5$ must not be —(CH$_2$)$_n$—Z, wherein n=0 to 2, and Z is hydrogen, C$_1$-C$_6$ alkyl, 2-pyridyl, 3-pyridyl, 4-pyridyl or substituted or unsubstituted phenyl; and (3) if R$^1$, K, L and R$^2$ form a fused benzene ring, Q is NR$^6$, R$^6$ is H, n=0, s=1, t=1 or 2, X is C or O and Y is C or O, then at least one of R$^4$ or R$^5$ must not be —CH$_2$)$_n$—Z, wherein n=0 to 2, and Z is hydrogen, (C$_1$-C$_6$)alkyl, 2-pyridyl, 3-pyridyl, 4-pyridyl or substituted or unsubstituted phenyl wherein if the phenyl is substituted, there are 1 or 2 substituents independently selected from the group consisting of halogen, ($C_1$-$C_6$)alkyl, ($C_1$-$C_6$)alkoxy, carboxyl, cyano, loweralkylthio, carboxy-loweralkyl, nitro, —$CF_3$ or hydroxy. Preferably, if $R^1$, K, L and $R^2$ form a fused benzene ring, Q is $NR^6$, $R^6$ is H, n=0, s=1, t=1 or 2, X is C or O and Y is C or O, then at least one of $R^4$ or $R^5$ must not be —$(CH_2)_n$—Z wherein n=0 to 2, and Z is hydrogen, ($C_1$-$C_6$)alkyl, 2-pyridyl, 3-pyridyl, 4-pyridyl or substituted or unsubstituted phenyl.

Additionally, embodiments of Formula I* can optionally have the following provisos:

4) if $R^1$, K, L and $R^2$ form a fused benzene ring; Q is O or $NR^6$; $R^6$ is H, phenyl, ($C_1$-$C_8$)alkyl, halo($C_1$-$C_8$)alkyl, or hydroxy($C_1$-$C_8$)alkyl; s=1 or 2; t=1 or 2; and 1) n is 0, X is C, and Y is N or O, 2) n is 1, X is N or O, Y is C, and M is C, or 3) n is 2, X is C, Y is C, and the M α to the fused benzene is C and the M β to the fused benzene is N or O; then $R^7$ must not be $C_7$-$C_{12}$ bicycloalkyl or $C_9$-$C_{12}$ tricycloalkyl;

5) if $R^1$, K, L and $R^2$ form a fused benzene ring; $R^4$ is H; $R^5$ is H; Q is NH; s=1, t=2; n=0; X is C; Y is C; there is an optional double bond between X and Y; then $R^7$ must not be substituted bicyclo[2.2.2]octane or substituted bicyclo[2.2.1]heptane;

6) if $R^1$, K, L and $R^2$ form a fused benzene or pyridine ring; X is N; Y is C; n=0, 1; M, when present, is C; s=1 or 2; t=1 or 2; Q is O or $NR^6$; $R^6$ is ($C_1$-$C_6$)alkyl; then $R^7$ must not be ($C_7$-$C_{12}$)bicycloalkyl or ($C_9$-$C_{12}$)tricycloalkyl, wherein the bicycloalkyl and tricycloalkyl are carbocycles; and 7) if $R^1$, K, L and $R^2$ form a fused benzene ring; t=1, 2; s=1, 2; Q=$NR^6$; $R^6$=H, ($C_1$-$C_{10}$)alkyl, halo($C_1$-$C_{10}$)alkyl, hydroxy($C_1$-$C_{10}$)alkyl, phenyl or arylalkyl; and 1) n=0, X is C, N, or O, and Y is C; or 2) n=1; M is C, N, or O; X=C, and Y=C; then $R^7$ must not be adamantyl, a bridged ($C_6$-$C_8$) bicycloalkyl or a ($C_9$-$C_{12}$)tricycloalkyl wherein one cycloalkyl of the tricycloalkyl moiety is fused to a bridged bicycloalkyl moiety.

It is understood that provisos 1-7 can be suitably applied to all embodiments of the invention described herein. It is further understood that, depending on the embodiment of the invention, one or more of provisos 1-7 (i.e., any combination of provisos) can optionally be included in the description of any embodiment. For example, provisos 4, 5, 6, or 7 can be individually applied to any embodiment; provisos 4 and 5, 4 and 6, or 4 and 7 can be applied in combination to any embodiment; provisos 5 and 6 or 5 and 7 can be applied in combination to any embodiment; provisos 6 and 7 can be applied in combination to any embodiment; provisos 4, 5 and 6 can be applied in combination to any embodiment; provisos 4, 5 and 7 can be applied in combination to any embodiment; provisos 4, 6 and 7 can be applied in combination to any embodiment; provisos 5, 6 and 7 can be applied in combination to any embodiment; or provisos 4, 5, 6 and 7 can be applied in combination to any embodiment.

Another embodiment of the invention is a compound of Formula I:

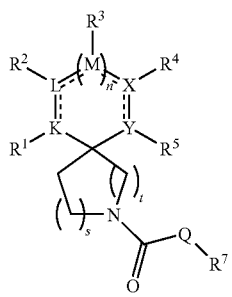

I wherein:

K, L, M, X and Y are independently C, N or O, provided that the total number of nitrogen and oxygen atoms in the ring is 3 or less and when K, L, M, X or Y is O, any adjacent member atom in the ring cannot be O;

the bonds between K, L, M, X and Y are single or double bonds provided that no consecutive double bonds occur between member atoms of the ring;

n=0, 1, or 2;

s=1 or 2;

t=1 or 2;

$R^1$-$R^5$ are independently hydrogen, A-(5-tetrazolyl), A-$COOR^6$, A-$CON(R^6)_2$, A-$COR^6$, A-$SO_2R^6$, A-$CONHSO_2R^6$, A-$CONHSO_2N(R^6)_2$, A-C≡N, alkyl, cycloalkyl, heteroaryl, aryl or arylalkyl, wherein the cycloalkyl, heteroaryl, aryl or arylalkyl groups represented by $R^1$-$R^5$ are optionally and independently substituted with 1-3 groups independently selected from the group consisting of halogen, cyano, ($C_1$-$C_6$)alkyl, halo($C_1$-$C_6$)alkyl, $CONH_2$ and $NR^6SO_2R^6$, except that any one or more of $R^1$-$R^5$ is absent where the atom to which such $R^1$-$R^5$ group would otherwise be connected is (i) O, or (ii) an N that is connected by a double bond to an adjacent atom;

A is a single bond, $C(R^6)_2$ or $C(R^6)_2C(R^6)_2$;

$R^1$, K, L and $R^2$ are taken together to form a fused benzene or pyridine ring, each of which is optionally substituted with 1-3 groups independently selected from the group consisting of halogen, cyano, ($C_1$-$C_6$)alkyl, halo($C_1$-$C_6$)alkyl, ($C_1$-$C_6$) alkoxy, halo($C_1$-$C_6$)alkoxy, $CONH_2$ and $NR^6SO_2R^6$; or $R^2$, L, M and $R^3$ are taken together to form a fused benzene or pyridine ring, each of which is optionally substituted with 1-3 groups independently selected from the group consisting of halogen, cyano, ($C_1$-$C_6$)alkyl, halo($C_1$-$C_6$)alkyl, ($C_1$-$C_6$) alkoxy, halo($C_1$-$C_6$)alkoxy, $CONH_2$ and $NR^6SO_2R^6$; or $R^2$, L, X and $R^4$ are taken together, when n=0, to form a fused benzene or pyridine ring, each Of which is optionally substituted with 1-3 groups independently selected from the group consisting of halogen, cyano, ($C_1$-$C_6$)alkyl, halo($C_1$-$C_6$)alkyl, ($C_1$-$C_6$)alkoxy, halo($C_1$-$C_6$)alkoxy, $CONH_2$ and $NR^6SO_2R^6$ provided that n=0 and M and $R^3$ are absent; or $R^4$, X, Y and $R^5$ are taken together to form a fused benzene or pyridine ring, each of which is optionally substituted with 1-3 groups independently selected from the group consisting of halogen, cyano, ($C_1$-$C_6$)alkyl, halo($C_1$-$C_6$)alkyl, ($C_1$-$C_6$) alkoxy, halo($C_1$-$C_6$)alkoxy, $CONH_2$ and $NR^6SO_2R^6$; or the group consisting of $R^1$, K, L and $R^2$ and the group consisting of $R^4$, X, Y and $R^5$ are each taken together to form a fused benzene or pyridine ring, each of which is optionally substituted with 1-3 groups independently selected from the group consisting of halogen, cyano, ($C_1$-$C_6$)alkyl, halo($C_1$-$C_6$)alkyl, ($C_1$-$C_6$)alkoxy, halo($C_1$-$C_6$)alkoxy, $CONH_2$ and $NR^6SO_2R^6$;

$R^6$ is hydrogen, ($C_1$-$C_{10}$)alkyl, aryl or arylalkyl;

Q is O or $NR^6$;

$R^7$ is a saturated $C_7$-$C_{12}$ bicycloalkyl or saturated $C_9$-$C_{12}$ tricycloalkyl in which 1-2 carbon atoms are optionally replaced with heteroatoms independently selected from N and O, and which is optionally substituted with 1-3 substituents independently selected from the group consisting of $R^6$, heteroaryl, oxo-substituted heteroaryl, amino-substituted heteroaryl, heterocyclyl, oxo-substituted heterocyclyl, halogen, hydroxy, hydroxymethyl, $C(NOH)NH_2$, $CONHR^6$, $CH_2CONHR^6$, $CON(R^6)_2$, $CH_2CON(R^6)_2$, $SO_2NHR^6$, $SO_2N(R^6)_2$, $CO_2R^6$, $CH_2CO_2R^6$, $SO_2R^6$, $NHCOR^6$, $NR^6COR^6$, $NHCO_2R^6$, $NR^6CO_2R^6$, $NHSO_2R^6$, and $NR^6SO_2R^6$; or an enantiomer, diastereomer, geometrical isomer or pharmaceutically acceptable salt thereof;

with the general provisos that:

(1) if $R^1$, K, L and $R^2$ form a fused benzene or pyridine ring, Q is $NR^6$, $R^6$ is H, Y is O, s=1, t=2, n=0, X is C, $R^4$ is H and $R^5$ is absent, then $R^7$ is not a 7- to 10-membered carbocyclic group or heterocyclic group;

(2) if $R^1$, K, L and $R^2$ form a fused benzene ring, Q is $NR^6$, $R^6$ is H, n=1, s=t=1 or 2, and M, X and Y are all carbon, then at least one of $R^3$, $R^4$ or $R^5$ must not be —$(CH_2)_n$—Z, wherein n=0 to 2, and Z is hydrogen, $(C_1-C_6)$alkyl, 2-pyridyl, 3-pyridyl, 4-pyridyl or substituted or unsubstituted phenyl wherein if the phenyl is substituted, there are 1 or 2 substituents independently selected from the group consisting of halogen, $(C_1-C_6)$alkyl, $(C_1-C_6)$alkoxy, carboxyl, cyano, loweralkylthio, carboxyloweralkyl, nitro, —$CF_3$ or hydroxy. Preferably, if $R^1$, K, L and $R^2$ form a fused benzene ring, Q is $NR^6$, $R^6$ is H, n=1, s=1, t=1 or 2, and M, X and Y are all carbon, then at least one of $R^3$, $R^4$ or $R^5$ must not be —$(CH_2)$—Z, wherein n=0 to 2, and Z is hydrogen, $C_1-C_6$ alkyl, 2-pyridyl, 3-pyridyl, 4-pyridyl or substituted or unsubstituted phenyl; and (3) if $R^1$, K, L and $R^2$ form a fused benzene ring, Q is $NR^6$, $R^6$ is H, n=0, s=1, t=1 or 2, X is C or O and Y is C or O, then at least one of $R^4$ or $R^5$ must not be —$(CH_2)_n$—Z, wherein n=0 to 2, and Z is hydrogen, $(C_1-C_6)$alkyl, 2-pyridyl, 3-pyridyl, 4-pyridyl or substituted or unsubstituted phenyl wherein if the phenyl is substituted, there are 1 or 2 substituents independently selected from the group consisting of halogen, $(C_1-C_6)$alkyl, $(C_1-C_6)$alkoxy, carboxyl, cyano, loweralkylthio, carboxyloweralkyl, nitro, —$CF_3$ or hydroxy. Preferably, if $R^1$, K, L and $R^2$ form a fused benzene ring, Q is $NR^6$, $R^6$ is H, n=0, s=1, t=1 or 2, X is C or O and Y is C or O, then at least one of $R^4$ or $R^5$ must not be —$(CH_2)_n$—Z wherein n=0 to 2, and Z is hydrogen, $(C_1-C_6)$alkyl, 2-pyridyl, 3-pyridyl, 4-pyridyl or substituted or unsubstituted phenyl.

Additionally, embodiments of Formula I can optionally have the following provisos:

4) if $R^1$, K, L and $R^2$ form a fused benzene ring; Q is O or $NR^6$; $R^6$ is H, phenyl, $(C_1-C_8)$alkyl, halo$(C_1-C_8)$alkyl, or hydroxy$(C_1-C_8)$alkyl; s=1 or 2; t=1 or 2; and 1) n is 0, X is C, And Y is N or O, 2) n is 1, X is N or O, Y is C, and M is C, or 3) n is 2, X is C, Y is C, and the M α to the fused benzene is C and the M β to the fused benzene is N or O; then $R^7$ must not be $C_7-C_{12}$ bicycloalkyl or $C_9-C_{12}$ tricycloalkyl;

5) if $R^1$, K, L and $R^2$ form a fused benzene ring; $R^4$ is H; $R^5$ is H; Q is NH; s=1, t=2; n=0; X is C; Y is C; there is an optional double bond between X and Y; then $R^7$ must not be substituted bicyclo[2.2.2]octane or substituted bicyclo[2.2.1]heptane;

6) if $R^1$, K, L and $R^2$ form a fused benzene or pyridine ring; X is N; Y is C; n=0, 1; M, when present, is C; s=1 or 2; t=1 or 2; Q is O or $NR^6$; $R^6$ is $(C_1-C_6)$alkyl; then $R^7$ must not be $(C_7-C_{12})$bicycloalkyl or $(C_9-C_{12})$tricycloalkyl, wherein the bicycloalkyl and tricycloalkyl are carbocycles; and 7) if $R^1$, K, L and $R^2$ form a fused benzene ring; t=1, 2; s=1, 2; Q=$NR^6$; $R^6$=H, $(C_1-C_{10})$alkyl, halo$(C_1-C_{10})$alkyl, hydroxy$(C_1-C_{10})$alkyl, phenyl or arylalkyl; and 1) n=0, X is C, N, or O, and Y is C; or 2) n=1; M is C, N, or O; X=C, and Y=C; then $R^7$ must not be adamantyl, a bridged $(C_6-C_8)$ bicycloalkyl or a $(C_9-C_{12})$tricycloalkyl wherein one cycloalkyl of the tricycloalkyl moiety is fused to a bridged bicycloalkyl moiety.

Preferred compounds of the invention are those of any embodiment of Formulae I* or I where none of K, L, M, X, and Y is a basic N, and the remainder of the variables are defined above.

Also preferred are compounds of any embodiment of Formulae I* or I where $R^1$, K, L and $R^2$ form a fused benzene ring, and the remainder of the variables are defined above.

Additionally compounds of the invention are those of any embodiment of Formulae I* or I wherein K, L, M, X, and Y are individually C or O; $R^1$-$R^5$ are independently H or alkyl; and/or the bonds between K, L, M, X, and Y are all single bonds, and the remainder of the variables are defined above.

Other compounds of the invention are those of any embodiment of Formula I* or I, wherein Q is O or NH, and the remainder of the variables are defined above.

Other preferred compounds of the invention are those of Formula I* or I wherein Q is $NR^6$ or O, $R^6$ is H and/or $R^7$ is 2-adamantyl, 1-hydroxy-4-adamantyl, 1-hydroxymethyl-4-adamantyl, 1-carbamoyl-4-adamantyl, 1-(methylsulfonyl)-4-adamantyl, 1-(aminosulfonyl)-4-adamantyl, 1-bicyclo[2.2.2]octyl, 1-carbamoyl-4-bicyclo[2.2.2]octyl, 9-bicyclo[3.3.1]nonyl or 3-carbamoyl-9-bicyclo[3.3.1]nonyl, and the remainder of the variables are defined above.

Other preferred compounds are those of Formula I* or I, wherein Q is O and/or $R^7$ is selected from the group consisting of 2-adamantyl, 1-hydroxy-4-adamantyl, 1-hydroxymethyl-4-adamantyl, and 1-carbamoyl-4-adamantyl, and the remainder of the variables are defined above.

Also preferred compounds are those of Formula I* or I, wherein n is 0, s is 1, and/or t is 2, and the remainder of the variables are defined above.

Specific Examples of Compounds of the Invention Are tert-Butyl 1'-(2-adamantyl)carbamoyl)spiro[indoline-3,4'-piperidine]-1-carboxylate;

N-(2-Adamantyl)spiro[indoline-3,4'-piperidine]-1'-carboxamide;

(±)-2-(1'-((2-Adamantyl)carbamoyl)-2,3-dihydrospiro[indene-1,4'-piperidine]-3-yl)acetic acid;

(±)-Methyl 2-(1'(2-adamantyl)carbamoyl)-2,3-dihydrospiro[indene-1,4'-piperidine]-3-yl)acetate;

(R)-Methyl 2-(1'-((2-adamantyl)carbamoyl)-2,3-dihydrospiro[indene-1,4'-piperidine]-3-yl)acetate;

(S)-Methyl 2-(1'-((2-adamantyl)carbamoyl)-2,3-dihydrospiro[indene-1,4'-piperidine]-3-yl)acetate;

2-(1'-(2-Adamantyl)carbamoyl)-2,3-dihydrospiro[indene-1,4'-piperidine]-3-yl)acetic acid, isomer B;

1-Acetyl-N-(2-adamantyl)spiro[indoline-3,4'-piperidine]-1'-carboxamide;

1'-((2-Adamantyl)carbamoyl)spiro[indene-1,4'-piperidine]-3-carboxylic acid;

(±)-1'-(2-Adamantyl)carbamoyl)-2,3-dihydrospiro[indene-1,4'-piperidine]-3-carboxylic acid;

(±)-1'-(2-Adamantyl)carbamoyl)-2,3-dihydrospiro[indene-1,4'-piperidine]-3-carboxylic acid;

Ethyl 1'-(2-adamantyl)carbamoyl)spiro[indene-1,4'-piperidine]-3-carboxylate;

(±)-Ethyl 1'-(cyclohexylcarbamoyl)-2,3-dihydrospiro[indene-1,4'-piperidine]-3-carboxylate;

N-(2-Adamantyl)-1-(methylsulfonyl)spiro[indoline-3,4'-piperidine]-1'-carboxamide;

2-adamantyl spiro[indoline-3,4'-piperidine]-1'-carboxylate;

2-adamantyl 5-fluorospiro[indoline-3,4'-piperidine]-1'-carboxylate;

2-adamantyl 5-methylspiro[indoline-3,4'piperidine]-1'-carboxylate;

2-adamantyl 1-acetylspiro[indoline-3,4'-piperidine]-1'-carboxylate;

(±)-2-adamantyl 3-(2-methoxy-2-oxoethyl)-2,3-dihydrospiro[indene-1,4'-piperidine]-1'-carboxylate;

(±)-2-(1'-((2-adamantyloxy)carbonyl)-2,3-dihydrospiro[indene-1,4'-piperidine]-3-yl)acetic acid; and (±)-2-adamantyl 3(2-(methylamino)-2-oxoethyl)-2,3-dihydrospiro[indene-1,4'-piperidine]-1'-carboxylate; or an enantiomer, diastereomer, geometrical isomer or pharmaceutically acceptable salt thereof.

Additional Examples of Compounds of the Invention Are 2-(1'-((2-Adamantyl)carbamoyl)-2,3-dihydrospiro[indene-1,4'-piperidine]-3-yl)acetic acid;
N-(2-adamantyl)-1,3-dihydrospiro[indene-2,3'-piperidine]-1'-carboxamide;
N-(2-adamantyl)-2,3-dihydrospiro[indene-1,4'-piperidine]-1'-carboxamide;
tert-butyl 1'-((2-adamantyl)carbamoyl)-1H-spiro[isoquinoline-4,4'-piperidine]-2(3H)-carboxylate;
N-(2-adamantyl)-2,3-dihydro-1H-spiro[isoquinoline-4,4'-piperidine]-1'-carboxamide;
2-acetyl-N-(2-adamantyl)-2,3-dihydro-1H-spiro[isoquinoline-4,4'-piperidine]-1'-carboxamide;
ethyl 3-(1'-((2-adamantyl)carbamoyl)-1H-spiro[isoquinoline-4,4'-piperidine]-2(3H)-yl)propanoate;
3-(1'-((2-adamantyl)carbamoyl)-1H-spiro[isoquinoline-4,4'-piperidine]-2(3H)-yl)propanoic acid;
N-(2-adamantyl)-2-(methylsulfonyl)-2,3-dihydro-1H-spiro[isoquinoline-4,4'-piperidine]-1'-carboxamide;
N1'-(2-adamantyl)-N2-methyl-1H-spiro[isoquinoline-4,4'-piperidine]-1',2(3H)-dicarboxamide;
ethyl 1'-((2-adamantyl)carbamoyl)-1H-spiro[isoquinoline-4,4'-piperidine]-2(3H)-carboxylate;
2-tert-butyl 1'-(2-adamantyl) 1H-spiro[isoquinoline-4,4'-piperidine]-1',2(3H)-dicarboxylate;
2-adamantyl 2,3-dihydro-1H-spiro[isoquinoline-4,4'-piperidine]-1'-carboxylate;
2-adamantyl 2-(methylsulfonyl)-2,3-dihydro-1H-spiro[isoquinoline-4,4'-piperidine]-1'-carboxylate;
2-adamantyl 2-(isopropylsulfonyl)-2,3-dihydro-1H-spiro[isoquinoline-4,4'-piperidine]-1'-carboxylate;
2-adamantyl 2-(5-cyanopyridin-2-yl)-2,3-dihydro-1H-spiro[isoquinoline-4,4'-piperidine]-1'-carboxylate;
(±)-ethyl 2-(7-bromo-1'-((2-adamantyl)carbamoyl)-2,3-dihydrospiro[indene-1,4'-piperidine]-3-yl)acetate;
(±)-2-((7-bromo-1'-((2-adamantyl)carbamoyl)-2,3-dihydrospiro[indene-1,4'-piperidine]-3-yl)acetic acid;
2-(7-bromo-1'((2-adamantyl)carbamoyl)-2,3-dihydrospiro[indene-1,4'-piperidine]-3-yl)acetic acid, isomer 1;
2-(7-bromo-1'-((2-adamantyl)carbamoyl)-2,3-dihydrospiro[indene-1,4'-piperidine]-3-yl)acetic acid, isomer 2;
(±)-N-(2-adamantyl)-3-(2-(methylsulfonamido)-2-oxoethyl)-2,3-dihydrospiro[indene-1,4'-piperidine]-1'-carboxamide;
(±)-3-(cyanomethyl)-N-cyclohexyl-2,3-dihydrospiro[indene-1,4'-piperidine]-1'-carboxamide;
(±)-3-((1H-tetrazol-5-yl)methyl)-N-(2-adamantyl)-2,3-dihydrospiro[indene-1,4'-piperidine]-1'-carboxamide;
(±)-ethyl 2-(1'-((2-adamantyl)carbamoyl)-7-methyl-2,3-dihydrospiro[indene-1,4'-piperidine]-3-yl)acetate;
(±)-2-(1'-((2-adamantyl)carbamoyl)-7-methyl-2,3-dihydrospiro[indene-1,4'-piperidine]-3-yl)acetic acid;
(±)-ethyl 2-(1'-((2-adamantyl)carbamoyl)-4-methyl-2,3-dihydrospiro[indene-1,4'-piperidine]-3-yl)acetate;
(±)-2-(1'-((2-adamantyl)carbamoyl)-4-methyl-2,3-dihydrospiro[indene-1,4'-piperidine]-3-yl)acetic acid;
(±)-ethyl 2-(1'-((2-adamantyl)carbamoyl)-7-chloro-2,3-dihydrospiro[indene-1,4'-piperidine]-3-yl)acetate;
(±)-2-(1'-((2-adamantyl)carbamoyl)-7-chloro-2,3-dihydrospiro[indene-1,4'-piperidine]-3-yl)acetic acid;
(±)-ethyl 2-(1'-((2-adamantyl)carbamoyl)-6-chloro-2,3-dihydrospiro[indene-1,4'-piperidine]-3-yl)acetate;
(±)-2-(1'-((2-adamantyl)carbamoyl)-6-chloro-2,3-dihydrospiro[indene-1,4'-piperidine]-3-yl)acetic acid;
(±)-ethyl 2-(1'-((2-adamantyl)carbamoyl)-5-chloro-2,3-dihydrospiro[indene-1,42-piperidine]-3-yl)acetate;
(±)-2-(1'-((2-adamantyl)carbamoyl)-5-chloro-2,3-dihydrospiro[indene-1,4'-piperidine]-3-yl)acetic acid;
(±)-2-(1'-((2-adamantyl)carbamoyl)-6-methyl-2,3-dihydrospiro[indene-1,4'-piperidine]-3-yl)acetic acid;
(±)-2-(1'-((2-adamantyl)carbamoyl)-5-methyl-2,3-dihydrospiro[indene-1,4'-piperidine]-3-yl)acetic acid;
(±)-2-(1'-((2-adamantyl)carbamoyl)-6-methoxy-2,3-dihydrospiro[indene-1,4'-piperidine]-3-yl)acetic acid;
(±)-2-(1'-((2-adamantyl)carbamoyl)-6-fluoro-2,3-dihydrospiro[indene-1,4'-piperidine]-3-yl)acetic acid;
(±)-ethyl 2-(7-bromo-1'-((1-adamantyl)carbamoyl)-2,3-dihydro spiro[indene-1,4'-piperidine]-3-yl)acetate;
(±)-2-(7-bromo-1'-((1-adamantyl)carbamoyl)-2,3-dihydrospiro[indene-1,4'-piperidine]-3-yl)acetic acid;
(±)-2-(7-bromo-1'-((2-adamantyloxy)carbonyl)-2,3-dihydrospiro[indene-1,4'-piperidine]-3-yl)acetic acid;
2-(7-bromo-1'((2-adamantyloxy)carbonyl)-2,3-dihydrospiro[indene-1,4'-piperidine]-3-yl)acetic acid, isomer 1;
2-(7-bromo-1'((2-adamantyloxy)carbonyl)-2,3-dihydrospiro[indene-1,4'-piperidine]-3-yl)acetic acid, isomer 2;
(±)-2-(6-methyl-1'42-adamantyloxy)carbonyl)-2,3-dihydrospiro[indene-1,4'-piperidine]-3-yl)acetic acid;
(±)-2-(5-methyl-1'((2-adamantyloxy)carbonyl)-2,3-dihydrospiro[indene-1,4'-piperidine]-3-yl)acetic acid;
2-(7-bromo-1'42-adamantyl)carbamoyl)-2,3-dihydrospiro[indene-1,4'-piperidine]-3-yl)propanoic acid;
(±)-ethyl 2-(7-bromo-1'-((2-adamantyl)carbamoyl)-2,3-dihydrospiro[indene-1,4'-piperidine]-3-yl)-2-methylpropanoate;
(±)-2-(7-bromo-1'42-adamantyl)carbamoyl)-2,3-dihydrospiro[indene-1,4'-piperidine]-3-yl)-2-methylpropanoic acid;
(±)-2-adamantyl 7-bromo-3-(2-(methylsulfonamido)-2-oxoethyl)-2,3-dihydrospiro[indene-1,4'-piperidine]-1'-carboxylate;
(±)-7-bromo-N-(2-adamantyl)-3-(2-(methylsulfonamido)-2-oxoethyl)-2,3-dihydrospiro[indene-1,4'-piperidine]-1'-carboxamide;
(±)-2-adamantyl 3-(2-(dimethylamino)-2-oxoethyl)-2,3-dihydrospiro[indene-1,4'-piperidine]-1'-carboxylate;
2-(1'-((1-carbamoyl-4-adamantyloxy)carbonyl)-2,3-dihydrospiro[indene-1,4'-piperidine]-3-yl)acetic acid;
2-(7-bromo-1'-(1-fluoro-4-adamantylcarbamoyl)-2,3-dihydrospiro[indene-1,4'-piperidine]-3-yl)acetic acid;
2-(7-bromo-1'-(1-fluoro-4-adamantylcarbamoyl)-2,3-dihydrospiro[indene-1,4'-piperidine]-3-yl)acetic acid, isomer 1;
2-(7-bromo-1'-(1-fluoro-4-adamantylcarbamoyl)-2,3-dihydrospiro[indene-1,4'-piperidine]-3-yl)acetic Acid, isomer 2;
2-(7-bromo-1'-(1-fluoro-4-adamantylcarbamoyl)-2,3'-dihydrospiro[indene-1,4'-piperidine]-3-yl)acetic acid, isomer 3;
2-(7-bromo-1'-(1-hydroxy-4-adamantylcarbamoyl)-2,3-dihydrospiro[indene-1,4'-piperidine]-3-yl)acetic acid;
2-(7-bromo-1'-(1-hydroxy-4-adamantylcarbamoyl)-2,3-dihydrospiro[indene-1,4'-piperidine]-3-yl)acetic acid, isomer 1;
2-(7-bromo-1'-(1-hydroxy-4-adamantylcarbamoyl)-2,3-dihydrospiro[indene-1,4'-piperidine]-3-yl)acetic acid, isomer 2;

2-(7-bromo-1'-(1-hydroxy-4-adamantylcarbamoyl)-2,3-dihydrospiro[indene-1,4'-piperidine]-3-yl)acetic acid, isomer 3;

(±)-2-(7-bromo-1'-(1,7-dihydroxy-4-adamantyl carbamoyl)-2,3-dihydrospiro[indene-1,4'-piperidine]-3-yl)acetic acid;

N-(2-adamantyl)-6-methoxy-3,4-dihydro-2H-spiro[isoquinoline-1,4'-piperidine]-1'-carboxamide;

N-(2-adamantyl)-3,4-dihydro-2H-spiro[naphthalene-1,4'-piperidine]-1'-carboxamide;

(2-adamantyl) 9-(2-methoxy-2-oxoethyl)-3-azaspiro[5.5]undecane-3-carboxylate;

2-(3-((2-adamantyl)oxycarbonyl)-3-azaspiro[5.5]undecan-9-yl)acetic acid;

methyl 2-(34(2-adamantyl)carbamoyl)-3-azaspiro[5,5]undecan-9-yl)acetate;

2-(3-((2-adamantyl)carbamoyl)-3-azaspiro[5.5]undecan-9-yl)acetic acid;

N-(2-adamantyl)-3H-spiro[isobenzofuran-1,4'-piperidine]-1'-carboxamide;

2-adamantyl 3H-spiro[isobenzofuran-1,4'-piperidine]-1'-carboxylate;

1-tert-butyl 1'-(trans-1-carbamoyl-4-adamantyl)spiro[indoline-3,4'-piperidine]-1,1'-dicarboxylate;

N-(2-adamantyl)-2-methylspiro[isoindoline-1,4'-piperidine]-1'-carboxamide;

N-(2-adamantyl)spiro[isoindoline-1,4'-piperidine]-1'-carboxamide;

7-Chloro-N-(2-adamantyl)-2-methylspiro[isoindoline-1,4'-piperidine]-1'-carboxamide;

2-(1'-((1-(benzylcarbamoyl)-4-adamantyloxy)carbonyl)-2,3-dihydrospiro[indene-1,4'-piperidine]-3-yl)acetic acid;

(±)-3-(2-amino-2-oxoethyl)-N-(2-adamantyl)-2,3-dihydrospiro[indene-1,4'-piperidine]-1'-carboxamide;

1-tert-butyl 1'-(2-adamantyl)spiro[indoline-3,4'-piperidine]-1,1'-dicarboxylate;

1-tert-butyl-1'-(2-adamantyl) 5-fluorospiro[indoline-3,4'-piperidine]-1,1'-dicarboxylate;

1-tert-butyl-1'-(2-adamantyl) 5-methylspiro[indoline-3,4'-piperidine]-1,1'-dicarboxylate;

(±)-3-(2-amino-2-oxoethyl)-7-bromo-N-(2-adamantyl)-2,3-dihydrospiro[indene-1,4'-piperidine]-1'-carboxamide;

N-(2-adamantyl)-1-oxo-1,3-dihydrospiro[indene-2,3'-piperidine]-1'-carboxamide;

N-(2-adamantyl)-1-hydroxy-1,3-dihydrospiro[indene-2,3'-piperidine]-1'-carboxamide;

N-(2-adamantyl)-2-methyl-3-thioxospiro[isoindoline-1,4'-piperidine]-1'-carboxamide;

N-(2-adamantyl)-3-thioxospiro[isoindoline-1,4'-piperidine]-1'-carboxamide;

7-chloro-N-(2-adamantyl)-2-methyl-3-thioxospiro[isoindoline-1,4'-piperidine]-1'-carboxamide;

7-chloro-N-(2-adamantyl)-2-(4-methoxybenzyl)-3-thioxospiro[isoindoline-1,4'-piperidine]-1'-carboxamide; and 7-chloro-N-(2-adamantyl)-2-methyl-3-thioxospiro[isoindoline-1,4'-piperidine]-1'-carboxamide; or an enantiomer, diastereomer, geometrical isomer or pharmaceutically acceptable salt thereof.

Additional compounds of the invention are those of Formula Ia:

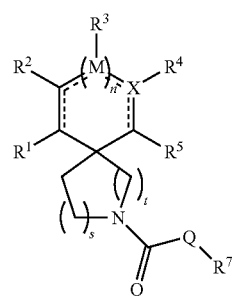

wherein:

M and X are C or N;

the bonds in the ring containing M and X are single or double bonds provided no consecutive double bonds occur between the member atoms of the ring;

n=0, or 1;

s=1;

t=1 or 2;

$R^1$-$R^5$ are independently hydrogen, $COOR^6$, $CH_2COOR^6$, $CON(R^6)_2$, $CH_2CON(R^6)_2$, $COR^E$, $SO_2R^6$, $CONHSO_2R^6$, $CH_2CONHSO_2R^6$, alkyl, cycloalkyl, heteroaryl, aryl or arylalkyl wherein the cycloalkyl, heteroaryl, aryl or arylalkyl groups represented by $R^1$-$R^5$ are optionally and independently substituted with 1-3 groups independently selected from the group consisting of halogen, cyano, $(C_1$-$C_6)$alkyl, halo$(C_1$-$C_6)$alkyl, $CONH_2$ and $NR^6SO_2R^6$, except that any one or more of $R^1$-$R^5$ is absent where the atom to which such $R^1$-$R^5$ group would otherwise be connected is (i) O, or (ii) an N that is connected by a double bond to an adjacent atom;

$R^6$ is hydrogen, $(C_1$-$C_{10})$alkyl, aryl or arylalkyl;

Q is O or $NR^6$; and $R^7$ is a saturated $C_7$-$C_{12}$ bicycloalkyl or saturated $C_9$-$C_{12}$ tricycloalkyl in which 1-2 carbon atoms are optionally replaced with heteroatoms independently selected from N and O, and which is optionally substituted with 1-3 substituents independently selected from the group consisting of $R^6$, heteroaryl, oxo-substituted heteroaryl, amino-substituted heteroaryl, heterocyclyl, oxo-substituted heterocyclyl, halogen, hydroxy, hydroxymethyl, $C(NOH)NH_2$, $CONHR^6$, $CH_2CONHR^6$, $CON(R^6)_2$, $CH_2CON(R^6)_2$, $SO_2NHR^6$, $SO_2N(R^6)_2$, $CO_2R^6$, $CH_2CO_2R^6$, $SO_2R^6$, $NHCOR^6$, $NR^6COR^6$, $NHCO_2R^6$, $NR^6CO_2R^6$, $NHSO_2R^6$, and $NR^6SO_2R^6$; or an enantiomer, diastereomer, geometrical isomer or pharmaceutically acceptable salt thereof.

Preferred compounds of the invention are those of Formula Ia where Q is $NR^6$ or O, $R^6$ is H and/or $R^7$ is 2-adamantyl, 1-hydroxy-4-adamantyl, 1-hydroxymethyl-4-adamantyl, 1-carbamoyl-4-adamantyl, 1-bicyclo[2.2.2]octyl, 1-carbamoyl-4-bicyclo[2.2.2]octyl, 9-bicyclo[3.3.1]nonyl or 3-carbamoyl-9-bicyclo[3.3.1]nonyl, and the remainder of the variables are defined above.

Preferred compounds of the invention are those of Formula Ia where none of K, L, M, X, and Y is a basic N, and the remainder of the variables are defined above.

Additional compounds of the invention are those according to Formula Ia':

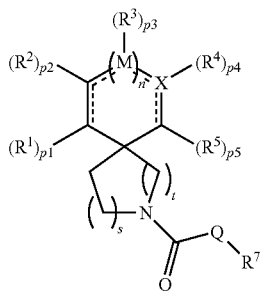

Ia' wherein:

M and X are C or N; the bonds in the ring containing M and X are single or double bonds provided no consecutive double bonds occur between the member atoms of the ring;

n=0, or 1;

s=1;

t=1 or 2;

$R^1$-$R^5$ are independently hydrogen, A-(5-tetrazolyl), A-(cycloalkyl), A-(heteroaryl), A-(heterocyclyl), A-(aryl), A-COOR$^6$, A-CON(R$^6$)$_2$, A-COR$^6$, A-SO$_2$R$^6$, A-CONHSO$_2$R$^6$, A-CONHSO$_2$OR$^6$, A-CONHSO$_2$N(R$^6$)$_2$, alkyl, alkenyl, cycloalkyl, heteroaryl, heterocyclyl, aryl or arylalkyl, wherein the alkyl, alkenyl, cycloalkyl, heteroaryl, heterocyclyl, aryl, A-(cycloalkyl), A-(heteroaryl), A-(heterocyclyl), A-(aryl) or arylalkyl groups represented by $R^1$-$R^5$ are optionally and independently substituted with 1-3 groups independently selected from the group consisting of halogen, hydroxy, cyano, —N(R$^6$)$_2$, —NR$^6$C(O)N(R$^6$)$_2$, —NR$^6$C(O) R$^6$, (C$_1$-C$_6$)alkyl, halo(C$_1$-C$_6$)alkyl, (C$_1$-C$_6$)alkoxy, halo(C$_1$-C$_6$)alkoxy, CONH$_2$, —SO$_2$R$^6$, —NR$^6$SO$_2$R$^6$, —NR$^6$SO$_2$N (R$^6$)$_2$ and —NR$^6$SO$_2$OR$^6$;

when K, L, M, X, or Y is (—O—) or (—N═), then p1, p2, p3, p4 or p5, respectively, is 0; when K, L, M, X, or Y is (—N—), (—C═), or (—CH—), then p1, p2, p3, p4 or p5, respectively, is 1; when K, L, M, X or Y is (—C—), then p1, p2, p3, p4 or p5, respectively, is 2; and when K, L, M, X, or Y is (—C—), and $R^1$, $R^2$, $R^3$, $R^4$ or $R^5$ is connected through a double bond to K, L, M, X or Y, respectively, then p1, p2, p3, p4 or p5, respectively, is 1;

A is a single bond, (C$_1$-C$_6$)alkylene, (C$_1$-C$_6$)alkenylene, (C$_1$-C$_5$)alkylCH═, C(O)(C$_0$-C$_3$)alkyl(C$_3$-C$_6$)cycloalkyl(C$_0$-C$_3$)alkylene, C(O)(C$_1$-C$_6$)alkylene, C(O)(C$_2$-C$_6$)alkenylene, S(O)$_2$(C$_1$-C$_6$)alkylene, S(O)$_2$(C$_2$-C$_6$)alkenylene, or S(O)$_2$ (C$_0$-C$_3$)alkyl(C$_3$-C$_6$)cycloalkyl(C$_0$-C$_3$)alkylene, each optionally substituted with up to 4 groups, R$^6$;

R$^6$ is hydrogen, (C$_1$-C$_{10}$)alkyl, halo(C$_1$-C$_{10}$)alkyl, hydroxy (C$_1$-C$_{10}$)alkyl, (R$^6$)$_2$N(C$_1$-C$_{10}$)alkyl, aryl or arylalkyl, wherein the aryl and arylalkyl groups are optionally substituted with up to three groups independently selected from halogen, hydroxy, cyano, —N(R$^6$)$_2$, —NR$^6$C(O)N(R$^6$)$_2$, —NR$^6$C(O)R$^6$, (C$_1$-C$_6$)alkyl, halo(C$_1$-C$_6$)alkyl, (C$_1$-C$_6$) alkoxy, halo(C$_1$-C$_6$)alkoxy, CON(R$^6$)$_2$, SO$_2$N(R$^6$)$_2$, —SO$_2$R$^6$, —NR$^6$SO$_2$R$^6$, —NR$^6$SO$_2$N(R$^6$)$_2$ and —NR$^6$SO$_2$OR$^6$; or N(R$^6$)$_2$ is a heterocyclyl group containing at least one nitrogen atom, preferably selected from W$^1$-W$^7$:

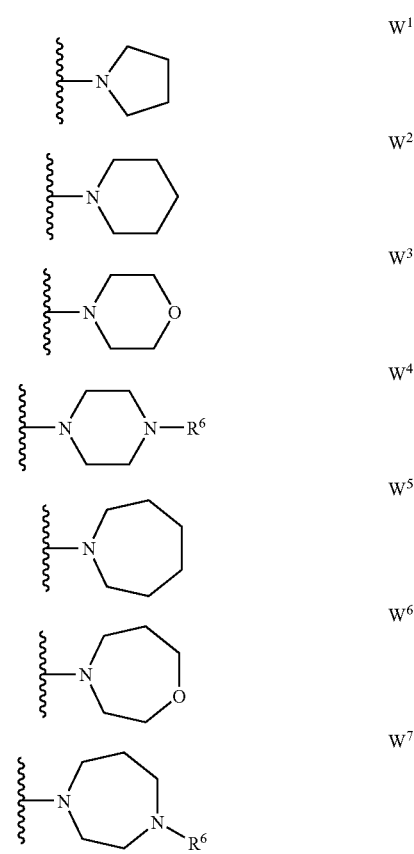

Q is O or NR$^6$; and $R^7$ is a saturated C$_7$-C$_{12}$ bicycloalkyl or saturated C$_9$-C$_{12}$ tricycloalkyl in which 1-2 carbon atoms are optionally replaced with heteroatoms independently selected from N and O, and which is optionally substituted with 1-3 substituents independently selected from the group consisting of R$^6$, heteroaryl, oxo-substituted heteroaryl, amino-substituted heteroaryl, heterocyclyl, oxo-substituted heterocyclyl, halogen, hydroxy, hydroxy(C$_1$-C$_6$)alkyl, C(NOH)NH$_2$, CONHR$^6$, CH$_2$CONHR$^6$, CON(R$^6$)$_2$, CH$_2$CON(R$^6$)$_2$, SO$_2$NHR$^6$, SO$_2$N(R$^6$)$_2$, CO$_2$R$^6$, CH$_2$CO$_2$R$^6$, SO$_2$R$^6$, NHCOR$^6$, NR$^6$COR$^6$, NHCO$_2$R$^6$, NR$^6$CO$_2$R$^6$, NHSO$_2$R$^6$, and NR$^6$SO$_2$R$^6$; or an enantiomer, diastereomer, geometrical isomer or pharmaceutically acceptable salt thereof.

Other particular compounds of the invention are according to Formula Ib:

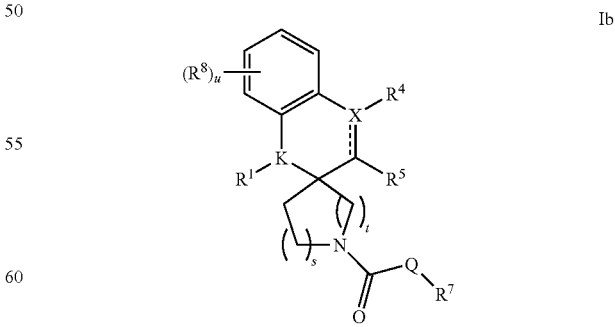

Ib wherein:

X and K are C, N or O;

s=1;

t=1 or 2;

u=0, 1, 2 or 3;

$R^8$ is independently selected from halogen, cyano, $(C_1-C_6)$alkyl, halo$(C_1-C_6)$alkyl, $(C_1-C_6)$alkoxy, halo$(C_1-C_6)$alkoxy, $CONH_2$ and $NR^6SO_2R^6$;

$R^1$, $R^4$ and $R^5$ is independently H, $COOR^6$, $CH_2COOR^6$, $CON(R^6)_2$; $CH_2CON(R^6)_2$, $COR^6$, $SO_2R^6$, $CONHSO_2R^6$, $CH_2CONHSO_2R^6$, alkyl, cycloalkyl, heteroaryl, aryl or arylalkyl wherein the cyclohexyl, heteroaryl, aryl or arylalkyl groups represented by $R^1$ and $R^4$-$R^5$ are optionally and independently substituted with 1-3 groups independently selected from the group consisting of halogen, cyano, $(C_1-C_6)$alkyl, halo$(C_1-C_6)$alkyl, $CONH_2$ and $NR^6SO_2R^6$, except that $R^4$ or $R^5$ is absent where the atom to which such $R^4$ or $R^5$ group would otherwise be connected is (i) O, or (ii) an N that is connected by a double bond to an adjacent atom;

$R^6$ is hydrogen, $(C_1-C_4)$alkyl, aryl or arylalkyl;

Q is O or $NR^6$; and $R^7$ is a saturated $C_7-C_{12}$ bicycloalkyl or saturated $C_9-C_{12}$ tricycloalkyl in which 1-2 carbon atoms are optionally replaced with heteroatoms independently selected from N and O, and which is optionally substituted with 1-3 substituents independently selected from the group consisting of $R^6$, heteroaryl, oxo-substituted heteroaryl, amino-substituted heteroaryl, heterocyclyl, oxo-substituted heterocyclyl, halogen, hydroxy, hydroxymethyl, $C(NOH)NH_2$, $CONHR^6$, $CH_2CONHR^6$, $CON(R^6)_2$, $CH_2CON(R^6)_2$, $SO_2NHR^6$, $SO_2N(R^6)_2$, $CO_2R^6$, $CH_2CO_2R^6$, $SO_2R^6$, $NHCOR^6$, $NR^6COR^6$, $NHCO_2R^6$, $NR^6CO_2R^6$, $NHSO_2R^6$, and $NR^6SO_2R^6$; or an enantiomer, diastereomer, geometrical isomer or pharmaceutically acceptable salt thereof.

Preferred compounds of the invention are those of Formula Do where Q is $NR^6$ or O, $R^6$ is H and/or $R^7$ is 2-adamantyl, 1-hydroxy-4, adamantyl, 1-hydroxymethyl-4-adamantyl, 1-carbamoyl-4-adamantyl, 1-bicyclo[2.2.2]octyl, 1-carbamoyl-4-bicyclo[2.2.2]octyl, 9-bicyclo[3.3.1]nonyl or 3-carbamoyl-9-bicyclo[3.3.1]nonyl.

More particular compounds of the invention are those of Formula Ib':

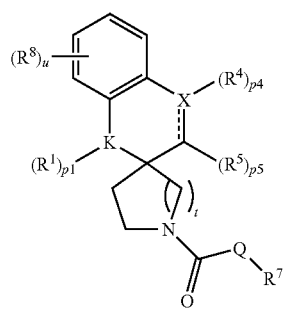

wherein X and K are C, N or O;
u=0, 1, 2 or 3;
n=0; or 1;
s=1;
t=1 or 2;

$R^1$, $R^4$ and $R^5$ are independently hydrogen, A-(5-tetrazolyl), A-(cycloalkyl), A-(heteroaryl), A-(heterocyclyl), A-(aryl), A-$COOR^6$, A-$CON(R^6)_2$, A-$COR^6$, A-$SO_2R^6$, A-$CONHSO_2R^6$, A-$CONHSO_2OR^6$, A-$CONHSO_2N(R^6)_2$, alkenyl, cycloalkyl, heteroaryl, heterocyclyl, aryl or arylalkyl, wherein the alkyl, alkenyl, cycloalkyl, heteroaryl, heterocyclyl, aryl, A-(cycloalkyl), A-(heteroaryl), A-(heterocyclyl), A-(aryl) or arylalkyl groups represented by $R^1$, $R^4$ and $R^5$ are optionally and independently substituted with 1-3 groups independently selected from the group consisting of halogen, hydroxy, cyano, $-N(R^6)_2$, $-NR^6C(O)N(R^6)_2$, $-NR^6C(O)R^6$, $(C_1-C_6)$alkyl, halo$(C_1-C_6)$alkyl, $(C_1-C_6)$alkoxy, halo$(C_1-C_6)$alkoxy, $CONH_2$, $-SO_2R^6$, $-NR^6SO_2R^6$, $-NR^6SO_2N(R^6)_2$ and $-NR^6SO_2OR^6$;

when K or X is (—O—) or (—N=), then p1 or p4, respectively, is 0; when K or X is (—N—), (—C=), or (—CH—), then p1 or p4, respectively, is 1; when K or X is (—C—), then p1 or p4, respectively, is 2; and when K or X is (—C—), and $R^1$ or $R^4$ is connected through a double bond to K or X, respectively, then p1 or p4, respectively, is 1;

A is a single bond, $(C_1-C_6)$alkylene, $(C_1-C_6)$alkenylene, $(C_1-C_5)$alkylCH=, $C(O)(C_0-C_3)$alkyl$(C_3-C_6)$cycloalkyl$(C_0-C_3)$alkylene, $C(O)(C_1-C_6)$alkylene, $C(O)(C_2-C_6)$alkenylene, $S(O)_2(C_1-C_6)$alkylene, $S(O)_2(C_2-C_6)$alkenylene, or $S(O)_2(C_0-C_3)$alkyl$(C_3-C_6)$cycloalkyl$(C_0-C_3)$alkylene, each optionally substituted with up to 4 groups, $R^6$;

$R^4$, X, Y and $R^5$ are taken together to form a fused benzene or pyridine ring, which is optionally substituted with 1-3 groups independently selected from the group consisting of halogen, hydroxy, cyano, $-N(R^6)_2$, $-NR^6C(O)N(R^6)_2$, $-NR^6C(O)R^6$, $(C)-C_6)$alkyl, halo$(C_1-C_6)$alkyl, $(C_1-C_6)$alkoxy, halo$(C_1-C_6)$alkoxy, $CON(R^6)_2$, $SO_2N(R^6)_2$, $-SO_2R^6$, $-NR^6SO_2R^6$, $-NR^6SO_2N(R^6)_2$ and $-NR^6SO_2OR^6$; or $R^6$ is hydrogen, $(C_1-C_{10})$alkyl, halo$(C_1-C_{10})$alkyl, hydroxy$(C_1-C_{10})$alkyl, $(R^6)_2N(C_1-C_{10})$alkyl, aryl or arylalkyl, wherein the aryl and arylalkyl groups are optionally substituted with up to three groups independently selected from halogen, hydroxy, cyano, $-N(R^6)_2$, $-NR^6C(O)N(R^6)_2$, $-NR^6C(O)R^6$, $(C_1-C_6)$alkyl, halo$(C_1-C_6)$alkyl, $(C_1-C_6)$alkoxy, halo$(C_1-C_6)$alkoxy, $CON(R^6)_2$, $SO_2N(R^6)_2$, $-SO_2R^6$, $-NR^6SO_2R^6$, $-NR^6SO_2N(R^6)_2$ and $-NR^6SO_2OR^6$; or $N(R^6)_2$ is a heterocyclyl group containing at least one nitrogen atom, preferably selected from $W^1$-$W^7$:

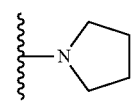

W¹

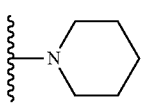

W²

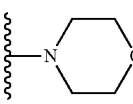

W³

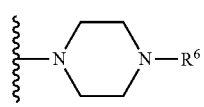

W⁴

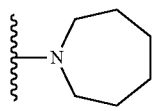

W⁵

-continued

W⁶

W⁷

Q is O or NR⁶; and

R⁷ is a saturated $C_7$-$C_{12}$ bicycloalkyl or saturated $C_9$-$C_{22}$ tricycloalkyl in which 1-2 carbon atoms are optionally replaced with heteroatoms independently selected from N and O, and which is optionally substituted with 1-3 substituents independently selected from the group consisting of R⁶, heteroaryl, oxo-substituted heteroaryl, amino-substituted heteroaryl, heterocyclyl, oxo-substituted heterocyclyl, halogen, hydroxy, hydroxy($C_1$-$C_6$)alkyl, C(NOH)NH₂, CONHR⁶, CH₂CONHR⁶, CON(R⁶)₂, CH₂CON(R⁶)₂, SO₂NHR⁶, SO₂N(R⁶)₂, CO₂R⁶, CH₂CO₂R⁶, SO₂R⁶, NHCOR⁶, NR⁶COR⁶, NHCO₂R⁶, NR⁶CO₂R⁶, NHSO₂R⁶, and NR⁶SO₂R⁶;

R⁸ is independently selected from halogen, hydroxy, cyano, —N(R⁶)₂, —NR⁶C(O)N(R⁶)₂, —NR⁶C(O)R⁶, ($C_1$-$C_6$)alkyl, halo($C_1$-$C_6$)alkyl, ($C_1$-$C_6$)alkoxy, halo($C_1$-$C_6$) alkoxy, CON(R⁶)₂, SO₂N(R⁶)₂, —SO₂R⁶, —NR⁶SO₂R⁶, —NR⁶SO₂N(R⁶)₂ and —NR⁶SO₂OR⁶; or an enantiomer, diastereomer, geometrical isomer or pharmaceutically acceptable salt thereof.

Also preferred are compounds of the invention of Formula Ic:

Ic wherein:

M, X and Y are independently C, N or O, provided that at least one of them is carbon and that when M, X, or Y is O, any adjacent member atom of the ring cannot be O;

the bonds between M and X and between X and Y are single or double bonds but are not both simultaneously double bonds;

n=0, 1 or 2;
s=1;
t=1 or 2;
u=0, 1, 2 or 3;

R⁸ is independently selected from halogen, cyano, ($C_1$-$C_6$) alkyl, halo($C_1$-$C_6$)alkyl, ($C_1$-$C_6$)alkoxy, halo($C_1$-$C_6$)alkoxy, CONH₂ and NR⁶SO₂R⁶;

R³, R⁴ and R⁵ are independently H, COOR⁶, CH₂COOR⁶, CON(R⁶)₂, CH₂CON(R⁶)₂, COR⁶, SO₂R⁶, CONHSO₂R⁶, CH₂CONHSO₂R⁶, alkyl, cycloalkyl, heteroaryl, aryl or arylalkyl, wherein the cyclohexyl, heteroaryl, aryl or arylalkyl groups represented by R³-R⁵ are optionally and independently substituted with 1-3 groups independently selected from the group consisting of halogen, cyano, ($C_1$-$C_6$)alkyl, halo($C_1$-$C_6$)alkyl, CONH₂ and NR⁶SO₂R⁶, except that R⁴ or R⁵ is absent where the atom to which such R⁴ or R⁵ group would otherwise be connected is (i) O, or (ii) an N that is connected by a double bond to an adjacent atom;

R⁶ is hydrogen, ($C_1$-$C_4$)alkyl, aryl or arylalkyl;

Q is O or NR⁶; and

R⁷ is a saturated $C_7$-$C_{12}$ bicycloalkyl or saturated $C_9$-$C_{12}$ tricycloalkyl in which 1-2 carbon atoms are optionally replaced with heteroatoms independently selected from N and O, and which is optionally substituted with 1-3 substituents independently selected from the group consisting of R⁶, heteroaryl, oxo-substituted heteroaryl, amino-substituted heteroaryl, heterocyclyl, oxo-substituted heterocyclyl, halogen, hydroxy, hydroxymethyl, C(NOH)NH₂, CONHR⁶, CH₂CONHR⁶, CON(R⁶)₂, CH₂CON(R⁶)₂, SO₂NHR⁶, SO₂N(R⁶)₂, CO₂R⁶, CH₂CO₂R⁶, SO₂R⁶, NHCOR⁶, NR⁶COR⁶, NHCO₂R⁶, NR⁶CO₂R⁶; NHSO₂R⁶, and NR⁶SO₂R⁶; or an enantiomer, diastereomer, geometrical isomer or pharmaceutically acceptable salt thereof.

Preferred compounds of the invention are those of Formula Ic wherein: n=0; X=C or N; Y=C; the bonds between M and X and between X and Y are single bonds; s=1 and t=2; R⁴ is H, COOR⁶ or CH₂COOR⁶; R⁵ is H; R⁶ is hydrogen or ($C_1$-$C_4$)alkyl; Q is O, NH or NR⁶; and/or R⁷ is 2-adamantyl, 1-hydroxy-4-adamantyl, 1-hydroxymethyl-4-adamantyl, 1-carbamoyl-4-adamantyl, 1-bicyclo[2.2.2]octyl, 1-carbamoyl-4-bicyclo[2.2.2]octyl, 9-bicyclo[3.3.1]nonyl or 3-carbamoyl-9-bicyclo[3.3.1]nonyl, and the remaining variables are as defined for Formula Ic.

Also preferred are compounds of Formula Ic where Q is NR⁶ or O, R⁶ is H and/or R⁷ is 2-adamantyl, 1-hydroxy-4-adamantyl, 1-hydroxymethyl-4-adamantyl or 1-carbamoyl-4-adamantyl, and the remaining variables are as defined for Formula Ic.

An additional embodiment of the invention is a compound of Formula Ic':

Ic' wherein M, X and Y are independently C, N or O, provided that at least one of them is carbon and that when M, X, or Y is O, any adjacent member atom of the ring cannot be O;

0, 1, or 2;
s=1 or 2;
t=1 or 2;
u=0, 1, 2 or 3;

R³-R⁵ are independently hydrogen, A-(5-tetrazolyl), A-(cycloalkyl), A-(heteroaryl), A-(heterocyclyl), A-(aryl), A-COOR⁶, A-CON(R⁶)₂, A-COR⁶, A-SO₂R⁶, A-CONHSO₂R⁶, A-CONHSO₂OR⁶, A-CONHSO₂N(R⁶)₂, A-C≡N, alkyl, alkenyl, cycloalkyl, heteroaryl, heterocyclyl; aryl or arylalkyl, wherein the alkyl, alkenyl, cycloalkyl, heteroaryl, heterocyclyl, aryl, A-(cycloalkyl), A-(heteroaryl), A-(heterocyclyl), A-(aryl) or arylalkyl groups represented by $R^3$-$R^5$ are optionally and independently substituted with 1-3 groups independently selected from the group consisting of halogen, hydroxy, cyano, —N($R^6$)$_2$, —$NR^6$C(O)N($R^6$)$_2$, —$NR^6$C(O)$R^6$, ($C_1$-$C_6$)alkyl, halo($C_1$-$C_6$)alkyl, ($C_1$-$C_6$)alkoxy, halo($C_1$-$C_6$)alkoxy, CONH$_2$, —SO$_2$$R^6$, —$NR^6$SO$_2$$R^6$, —$NR^6$SO$_2$N($R^6$)$_2$ and —$NR^6$SO$_2$O$R^6$;

when M, X, or Y is (—O—) or (—N═), then p3, p4 or p5, respectively, is 0; when M, X, or Y is (—N—), (—C═), or (—CH—), then p3, p4 or p5, respectively, is 1; when M, X or Y is (—C—), then p3, p4 or p5, respectively, is 2; and when M, X or Y is (—C—), and $R^3$, $R^4$ or $R^5$ is connected through a double bond to M, X or Y, respectively, then p3, p4 or p5, respectively, is 1;

A is a single bond, ($C_1$-$C_6$)alkylene, ($C_1$-$C_6$)alkenylene, ($C_1$-$C_5$)alkylCH═, C(O)($C_0$-$C_3$)alkyl($C_3$-$C_6$)Cycloalkyl ($C_0$-$C_3$)alkylene, C(O)($C_1$-$C_6$)alkylene, C(O)($C_2$-$C_6$)alkenylene, S(O)$_2$($C_1$-$C_6$)alkylene, S(O)$_2$($C_2$-$C_6$)alkenylene, or S(O)$_2$($C_0$-$C_3$)alkyl($C_3$-$C_6$)cycloalkyl($C_0$-$C_3$)alkylene, each optionally substituted with up to 4 groups, $R^6$;

$R^4$, X, Y and $R^5$ are taken together to form a fused benzene or pyridine ring, which is optionally substituted with 1-3 groups independently selected from the group consisting of halogen, hydroxy, cyano, —N($R^6$)$_2$, —$NR^6$C(O)N($R^6$)$_2$, —$NR^6$C(O)$R^6$, ($C_1$-$C_6$)alkyl, halo($C_1$-$C_6$)alkyl, ($C_1$-$C_6$)alkoxy, halo($C_1$-$C_6$)alkoxy, CON($R^6$)$_2$, SO$_2$N($R^6$)$_2$, —SO$_2$$R^6$, —$NR^6$SO$_2$$R^6$, —$NR^6$SO$_2$N($R^6$)$_2$ —$NR^6$SO$_2$O$R^6$;

$R^6$ is hydrogen, ($C_1$-$C_{10}$)alkyl, halo($C_1$-$C_{10}$)alkyl, hydroxy($C_1$-$C_{10}$)alkyl, ($R^6$)$_2$N($C_1$-$C_{10}$)alkyl, aryl or arylalkyl, wherein the aryl and arylalkyl groups are optionally substituted with up to three groups independently selected from halogen, hydroxy, cyano, —N($R^6$)$_2$, —$NR^6$C(O)N($R^6$)$_2$, —$NR^6$C(O)$R^6$, ($C_1$-$C_6$)alkyl, halo($C_1$-$C_6$)alkyl, ($C_1$-$C_6$)alkoxy, halo($C_1$-$C_6$)alkoxy, CON($R^6$)$_2$, SO$_2$N($R^6$)$_2$, —SO$_2$$R^6$, —$NR^6$SO$_2$$R^6$, —$NR^6$SO$_2$N($R^6$)$_2$ and —$NR^6$SO$_2$O$R^6$; or N($R^6$)$_2$ is a heterocyclyl group containing at least one nitrogen atom, preferably selected from $W^1$-$W^7$:

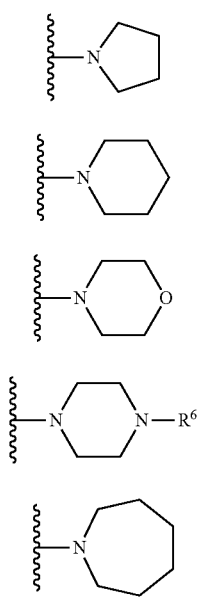

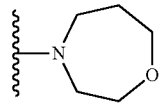

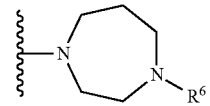

Q is O or $NR^6$;

$R^7$ is a saturated $C_7$-$C_{12}$ bicycloalkyl or saturated $C_9$-$C_{12}$ tricycloalkyl in which 1-2 carbon atoms are optionally replaced with heteroatoms independently selected from N and O, and which is optionally substituted with 1-3 substituents independently selected from the group consisting of $R^6$, heteroaryl, oxo-substituted heteroaryl, amino-substituted heteroaryl, heterocyclyl, oxo-substituted heterocyclyl, halogen, hydroxy, hydroxy($C_1$-$C_6$)alkyl, C(═NOH)NH$_2$, CONHR$^6$, CH$_2$CONHR$^6$, CON($R^6$)$_2$, CH$_2$CON($R^6$)$_2$, SO$_2$NHR$^6$, SO$_2$N($R^6$)$_2$, CO$_2$$R^6$, CH$_2$CO$_2$$R^6$, SO$_2$$R^6$, NHCOR$^6$, $NR^6$COR$^6$, NHCO$_2$$R^6$, $NR^6$CO$_2$$R^6$, NHSO$_2$$R^6$, and $NR^6$SO$_2$$R^6$; and $R^8$ is independently selected from halogen, hydroxy, cyano, —N($R^6$)$_2$, —$NR^6$C(O)N($R^6$)$_2$, —$NR^6$C(O)$R^6$, ($C_1$-$C_6$)$_{alkyl}$, halo($C_1$-$C_6$)alkyl, ($C_1$-$C_6$)alkoxy, halo($C_1$-$C_6$)alkoxy, CON($R^6$)$_2$, SO$_2$N($R^6$)$_2$, —SO$_2$$R^6$, —$NR^6$SO$_2$$R^6$, —$NR^6$SO$_2$N($R^6$)$_2$ and —$NR^6$SO$_2$O$R^6$; or an enantiomer, diastereomer, geometrical, isomer or pharmaceutically acceptable salt thereof.

Preferred compounds of the invention are those of Formula Ic' wherein: n=0; X═C or N; Y═C; the bonds between M and X and between X and Y are single bonds; s=1 and t=2; $R^4$ is H, COOR$^6$ or CH$_2$COOR$^6$; $R^5$ is H; $R^6$ is hydrogen or ($C_1$-$C_4$)alkyl; Q is O, NH or $NR^6$; and/or $R^7$ is 2-adamantyl, 1-hydroxy-4-adamantyl, 1-hydroxymethyl-4-adamantyl, 1-carbamoyl-4-adamantyl, 1-bicyclo[2.2.2]octyl, 1-carbamoyl-4-bicyclo[2.2.2]octyl, 9-bicyclo[3.3.1]nonyl or 3-carbamoyl-9-bicyclo[3.3.1]nonyl, and the remaining variables are as described for Formula Ic'.

Also preferred are compounds of Formula Ic' where Q is $NR^6$ or O, $R^6$ is H and/or $R^7$ is 2-adamantyl, 1-hydroxy-4-adamantyl, 1-hydroxymethyl-4-adamantyl or 1-carbamoyl-4-adamantyl, and the remaining variables are as described for Formula Ic'.

Also preferred are compounds of the invention of Formula Id:

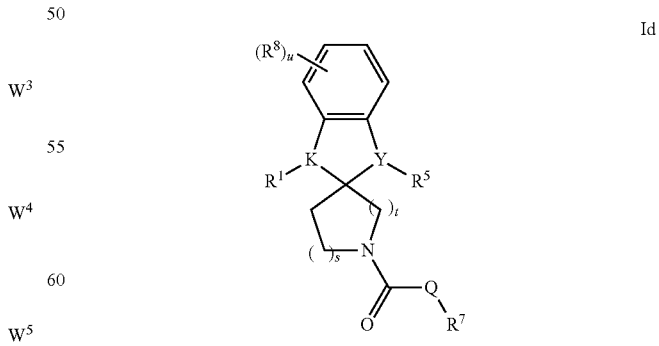

wherein:
K and Y are independently C, N or O;
s=1;
t=1 or 2;

$R^1$ and $R^5$ are independently H, $COOR^6$, $CH_2COOR^6$, $CON(R^6)_2$, $CH_2CON(R^6)_2$, $COR^6$, $SO_2R^6$, $CONHSO_2R^6$, $CH_2CONHSO_2R^6$, alkyl, cycloalkyl, heteroaryl, aryl or arylalkyl, wherein the cycloalkyl, heteroaryl, aryl or arylalkyl groups represented by $R^1$ and $R^5$ are optionally and independently substituted with 1-3 groups independently selected from the group consisting of halogen, cyano, $(C_1-C_6)$alkyl, halo$(C_1-C_6)$alkyl, $CONH_2$ and $NR^6SO_2R^6$, except that $R^1$ or $R^5$ is absent where the atom to which such $R^1$ or $R^5$ group would otherwise be connected is (i) O, or (ii) an N that is connected by a double bond to an adjacent atom;

$R^6$ is hydrogen, $(C_1-C_4)$alkyl, aryl or arylalkyl;

Q is O or $NR^6$;

u=0, 1, 2 or 3;

$R^8$ is independently selected from halogen, cyano, $(C_1-C_6)$ alkyl, halo$(C_1-C_6)$alkyl, $(C_1-C_6)$alkoxy, halo$(6-C_6)$alkoxy, $CONH_2$ and $NR^6SO_2R^6$; and $R^7$ is a saturated $C_7-C_{12}$ bicycloalkyl or saturated $C_9-C_{12}$ tricycloalkyl in which 1-2 carbon atoms are optionally replaced with heteroatoms independently selected from N and O, and which is optionally substituted with 1-3 substituents independently selected from the group consisting of $R^6$, heteroaryl, oxo-substituted heteroaryl, amino-substituted heteroaryl, heterocyclyl; oxo-substituted heterocyclyl, halogen, hydroxy, hydroxymethyl, $C(NOH)NH_2$, $CONHR^6$, $CH_2CONHR^6$, $CON(R^6)_2$, $CH_2CON(R^6)_2$, $SO_2NHR^6$, $SO_2N(R^6)_2$, $CO_2R^6$, $CH_2CO_2R^6$, $SO_2R^6$, $NHCOR^6$, $NR^6COR^6$, $NHCO_2R^6$, $NR^6CO_2R^6$; $NHSO_2R^6$, and $NR^6SO_2R^6$; or an enantiomer, diastereomer, geometrical isomer or pharmaceutically acceptable salt thereof.

Preferred compounds of the invention are those of Formula Id where Q is $NR^6$ or O; $R^6$ is H; and/or $R^7$ is 2-adamantyl, 1-hydroxy-4-adamantyl, 1-hydroxymethyl-4-adamantyl, 1-carbamoyl-4-adamantyl, 1-bicyclo[2.2.2]octyl, 1-carbamoyl-4-bicyclo[2.2.2]octyl, 9-bicyclo[3.3.1]nonyl or 3-carbamoyl-9-bicyclo[3.3.1]nonyl.

Further compounds of the invention are those according to Formula Id':

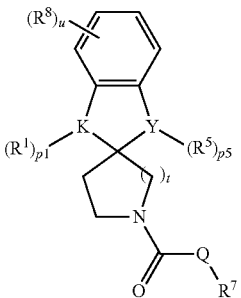

Id' wherein:

K and Y are independently C, N or O;

s=1;

t=1 or 2;

$R^1$ and $R^5$ are independently hydrogen, A-(5-tetrazolyl), A-(cycloalkyl), A-(heteroaryl), A-(heterocyclyl), A-(aryl), A-$COOR^6$, A-$CON(R^6)_2$, A-$COR^6$, A-$SO_2R^6$, A-$CONHSO_2R^6$, A-$CONHSO_2OR^6$, A-$CONHSO_2N(R^6)_2$, A-C≡N, alkyl, alkenyl, cycloalkyl, heteroaryl, heterocyclyl, aryl or arylalkyl, wherein the alkyl, alkenyl, cycloalkyl, heteroaryl, heterocyclyl, aryl, A-(cycloalkyl), A-(heteroaryl), A-(heterocyclyl), A-(aryl) or arylalkyl groups represented by $R^1$ and $R^5$ are optionally and independently substituted with 1-3 groups independently selected from the group consisting of halogen, hydroxy, cyano, —$N(R^6)_2$, —$NR^6C(O)N(R^6)_2$, —$NR^6C(O)R^6$, $(C_1-C_6)$alkyl, halo$(C_1-C_6)$alkyl, $(C_1-C_6)$ alkoxy, halo$(C_1-C_6)$alkoxy, $CONH_2$, —$SO_2R^6$, —$NR^6SO_2R^6$, —$NR^6SO_2N(R^6)_2$ and —$NR^6SO_2OR^6$;

when K or Y is (—O—) or (—N=), then p1 or p5, respectively, is 0; when K or Y is (—N—), (—C=), or (—CH—), then p1 or p5, respectively, is 1; when K or Y is (—C—), then p1 or p5, respectively, is 2; and when K or Y is (—C—), and $R^1$ or $R^5$ is connected through a double bond to K or Y, respectively, then p1 or p5, respectively, is 1;

A is a single bond, $(C_1-C_6)$alkylene, $(C_1-C_6)$alkenylene, $(C_1-C_5)$alkylCH=, $C(O)(C_0-C_3)$alkyl$(C_3-C_6)$cycloalkyl$(C_0-C_3)$alkylene, $C(O)(C_1-C_6)$alkylene, $C(O)(C_2-C_6)$alkenylene, $S(O)_2(C_1-C_6)$alkylene, $S(O)_2(C_2-C_6)$alkenylene, or $S(O)_2(C_0-C_3)$alkyl$(C_3-C_6)$cycloalkyl$(C_0-C_3)$alkylene, each optionally substituted with up to 4 groups, $R^6$;

$R^6$ is hydrogen, $(C_1-C_{10})$alkyl, halo$(C_1-C_{10})$alkyl, hydroxy$(C_1-C_{10})$alkyl, $(R^6)_2N(C_1-C_{10})$alkyl, aryl or arylalkyl, wherein the aryl and arylalkyl groups are optionally substituted with up to three groups independently selected from halogen, hydroxy, cyano, —$N(R^6)_2$, —$NR^6C(O)N(R^6)_2$, —$NR^6C(O)R^6$, $(C_1-C_6)$alkyl, halo$(C_1-C_6)$alkyl, $(C_1-C_6)$ alkoxy, halo$(C_1-C_6)$alkoxy, $CON(R^6)_2$, $SO_2N(R^6)_2$, —$SO_2R^6$, —$NR^6SO_2R^6$, —$NR^6SO_2N(R^6)_2$ and —$NR^6SO_2OR^6$; or $N(R^6)_2$ is a heterocyclyl group containing at least one nitrogen atom, preferably selected from $W^1$-$W^7$:

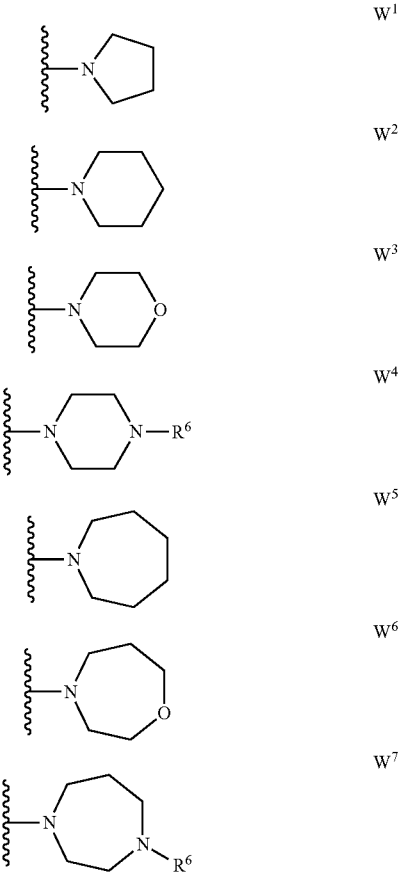

Q is O or $NR^6$; and $R^7$ is a saturated $C_7-C_{12}$ bicycloalkyl or saturated $C_9-C_{12}$ tricycloalkyl in which 2 carbon atoms are optionally replaced with heteroatoms independently selected from N and O, and which is optionally substituted with 1-3 substituents independently selected from the group consisting of $R^6$, heteroaryl, oxo-substituted heteroaryl, amino-substituted heteroaryl, heterocyclyl, oxo-substituted heterocyclyl, halogen, hydroxy, hydroxy($C_1$-$C_6$)alkyl, C(NOH)$NH_2$, CONH$R^6$, $CH_2$CONH$R^6$, CON($R^6$)$_2$, $CH_2$CON($R^6$)$_2$, $SO_2$NH$R^6$, $SO_2$N($R^6$)$_2$, $CO_2R^6$, $CH_2CO_2R^6$, $SO_2R^6$, NHCO$R^6$, N$R^6$CO$R^6$, NHCO$_2R^6$, N$R^6$CO$_2R^6$, NHSO$_2R^6$, and N$R^6$SO$_2R^6$;

u=0, 1, 2 or 3;

$R^8$ is independently selected from halogen, hydroxy, cyano, —N($R^6$)$_2$, —N$R^6$C(O)N($R^6$)$_2$, —N$R^6$C(O)$R^6$, ($C_1$-$C_6$)alkyl, halo($C_1$-$C_6$)alkyl, ($C_1$-$C_6$)alkoxy, halo($C_1$-$C_6$)alkoxy, CON($R^6$)$_2$, $SO_2$N($R^6$)$_2$, —$SO_2R^6$, —N$R^6SO_2R^6$, —N$R^6SO_2$N($R^6$)$_2$ and —N$R^6SO_2$O$R^6$; or an enantiomer, diastereomer, geometrical isomer or pharmaceutically acceptable salt thereof:

Another particular embodiment of the invention are compounds of the formula:

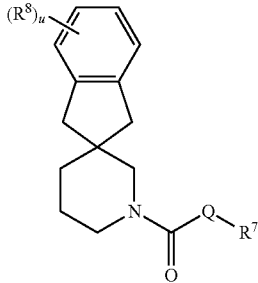

wherein Q is O or NH; and/or R7 is 2-adamantyl, 1-hydroxy-4-adamantyl, 1-(hydroxymethyl)-4-adamantyl, or 1-carbamoxyl-4-adamantyl; and the rest of the variables are as described for Formula Id'; or an enantiomer, diastereomer, geometrical isomer or pharmaceutically acceptable salt thereof.

Also preferred are compounds of the invention of Formula Ie:

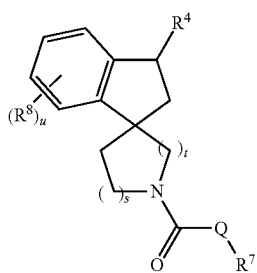

wherein $R^4$, $R^7$, Q, s and t are as defined for Formula I* above;

u=0, 1, 2 or 3;

$R^8$ is independently selected from halogen, hydroxy, cyano, —N($R^6$)$_2$, —N$R^6$C(O)N($R^6$)$_2$, —N$R^6$C(O)$R^6$, ($C_1$-$C_6$)alkyl, halo($C_1$-$C_6$)alkyl, ($C_1$-$C_6$)alkoxy, halo($C_1$-$C_6$)alkoxy, CON($R^6$)$_2$, $SO_2$N($R^6$)$_2$, —$SO_2R^6$, —N$R^6SO_2R^6$, —N$R^6SO_2$N($R^6$)$_2$ and —N$R^6SO_2$O$R^6$; or an enantiomer, diastereomer, geometrical isomer or pharmaceutically acceptable salt thereof.

Preferred compounds of the invention are those of Formula Ie where $R^4$ is hydrogen, A-(5-tetrazolyl), A-COO$R^6$, ACON($R^6$)$_2$, A-CONHSO$_2R^6$ or alkyl, where the alkyl represented by $R^4$ is optionally substituted with 1-3 groups independently selected from the group consisting of hydroxy, cyano, —N($R^6$)$_2$, —N$R^6$C(O)N($R^6$)$_2$, —N$R^6$C(O)$R^6$, ($C_1$-$C_6$)alkyl, halo($C_1$-$C_6$)alkyl, —CONH$_2$, —$SO_2R^6$, —N$R^6SO_2R^6$, —N$R^6SO_2$N($R^6$)$_2$ and —N$R^6SO_2$O$R^6$; A is a bond or ($C_1$-$C_3$)alkylene; s=1; t=2; Q is NH or O; $R^7$ is 2-adamantyl, 1-hydroxy-4-adamantyl, 1-hydroxymethyl-4-adamantyl, 1-carbamoyl-4-adamantyl, 1-(methylsulfonyl)-4-adamantyl, 1-(aminosulfonyl)-4-adamantyl, 1-bicyclo[2.2.2]octyl, 1-carbamoyl-4-bicyclo[2.2.2]octyl; 9-bicyclo[3.3.1]nonyl or 3-carbamoyl-9-bicyclo[3.3.1]nonyl; u=1; and/or $R^8$ is halogen or methyl; and the rest of the variables are as defined for Formula I* above.

Also preferred are compounds of the invention of Formula If:

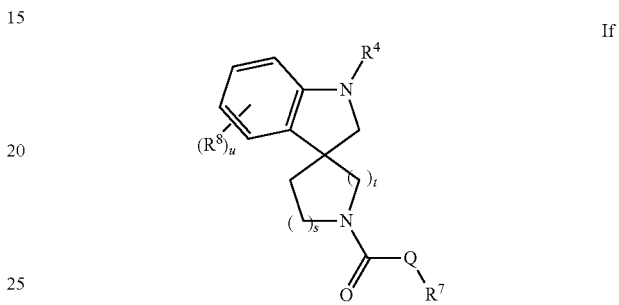

wherein $R^4$, $R^7$, Q, s and t are as defined for Formula I above;

u=0, 1, 2 or 3;

$R^8$ is independently selected from halogen, hydroxy, cyano, —N($R^6$)$_2$, —N$R^6$C(O)N($R^6$)$_2$, —N$R^6$C(O)$R^6$, ($C_1$-$C_6$)alkyl, halo($C_1$-$C_6$)alkyl, ($C_1$-$C_6$)alkoxy, halo($C_1$-$C_6$)alkoxy, CON($R^6$)$_2$, $SO_2$N($R^6$)$_2$, —$SO_2R^6$, —N$R^6SO_2R^6$, —N$R^6SO_2$N($R^6$)$_2$ and —N$R^6SO_2$O$R^6$; or an enantiomer, diastereomer, geometrical isomer or pharmaceutically acceptable salt thereof.

Preferred compounds of the invention are those of Formula If wherein $R^4$ is hydrogen, A-COO$R^6$, A-CO$R^6$ or A-$SO_2R^6$; A is a single bond, ($C_1$-$C_6$)alkylene, C(O)($C_1$-$C_6$)alkylene, or S(O)$_2$($C_1$-$C_6$)alkylene; s=1; t=2; Q is NH or O; $R^7$ is 2-adamantyl, 1-hydroxy-4-adamantyl, 1-hydroxymethyl-4-adamantyl, 1-carbamoyl-4-adamantyl, 1-(methylsulfonyl)-4-adamantyl, 1-(aminosulfonyl)-4-adamantyl, 1-bicyclo[2.2.2]octyl, 1-carbamoyl-4-bicyclo[2.2.2]octyl, 9-bicyclo[3.3.1]nonyl or 3-carbamoyl-9-bicyclo[3.3.1]nonyl; u=1; and/or $R^8$ is halogen or methyl; and the rest of the variables are as defined for Formula I* above.

Also preferred are compounds of the invention of Formula Ig:

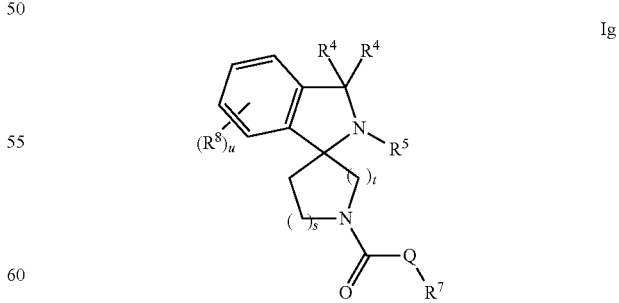

wherein $R^4$, $R^5$, $R^7$, Q, s and t are as defined for Formula I* above;

u=0, 1, 2 or 3;

$R^8$ is independently selected from halogen, hydroxy, cyano, —N($R^6$)$_2$, —N$R^6$C(O)N($R^6$)$_2$, —N$R^6$C(O)$R^6$, ($C_1$-

$C_6$)alkyl, halo($C_1$-$C_6$)alkyl, ($C_1$-$C_6$)alkoxy, halo($C_1$-$C_6$)alkoxy, CON($R^6$)$_2$, SO$_2$N($R^6$)$_2$, —SO$_2$R$^6$, —NR$^6$SO$_2$R$^6$, —NR$^6$SO$_2$N($R^6$)$_2$ and —NR$^6$SO$_2$OR$^6$; or an enantiomer, diastereomer, geometrical isomer or pharmaceutically acceptable salt thereof.

Preferred compounds of the invention are those of Formula Ig wherein $R^4$ and $R^5$ are independently selected from hydrogen and ($C_1$-$C_3$)alkyl; s=1; t=2; Q is NH or O; $R^7$ is 2-adamantyl, 1-hydroxy-4-adamantyl, 1-hydroxymethyl-4-adamantyl, 1-carbamoyl-4-adamantyl, 1-(methylsulfonyl)-4-adamantyl, 1-(aminosulfonyl)-4-adamantyl, 1-bicyclo[2.2.2]octyl; 1-carbamoyl-4-bicyclo[2.2.2]octyl, 9-bicyclo[3.3.1]nonyl or 3-carbamoyl-9-bicyclo[3.3.1]nonyl; u=1; and/or $R^8$ is halogen or methyl; and the rest of the variables are as defined for Formula I* above.

Also preferred are compounds of the invention of Formula Ih:

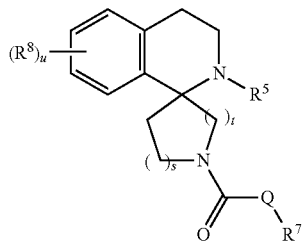

Ih wherein $R^5$, $R^7$, Q, s and t are as defined for Formula I* above;
u=0, 1, 2 or 3;
$R^8$ is independently selected from halogen, hydroxy, cyano, —N($R^6$)$_2$, —NR$^6$C(O)N($R^6$)$_2$, —NR$^6$C(O)R$^6$, ($C_1$-$C_6$)alkyl, halo($C_1$-$C_6$)alkyl, ($C_1$-$C_6$)alkoxy, halo($C_1$-$C_6$)alkoxy, CON($R^6$)$_2$, SO$_2$N($R^6$)$_2$, —SO$_2$R$^6$, —NR$^6$SO$_2$R$^6$, —NR$^6$SO$_2$N($R^6$)$_2$ and —NR$^6$SO$_2$OR$^6$; or an enantiomer, diastereomer, geometrical isomer or pharmaceutically acceptable salt thereof.

Preferred compounds of the invention are those of Formula Ih where $R^5$ is hydrogen or ($C_1$-$C_3$)alkyl; s=1; t=2; Q is NH or O; $R^7$ is 2-adamantyl, 1-hydroxy-4-adamantyl, 1-hydroxymethyl-4-adamantyl, 1-carbamoyl-4-adamantyl, 1-(methylsulfonyl)-4-adamantyl, 1-(aminosulfonyl)-4-adamantyl, 1-bicyclo[2.2.2]octyl, 1-carbamoyl-4-bicyclo[2.2.2]octyl, 9-bicyclo[3.3.1]nonyl or 3-carbamoyl-9-bicyclo[3.3.1]nonyl; u=1; and/or $R^8$ is halogen, methyl, or methoxy; and the rest of the variables are as defined for Formula I* above.

Also preferred are compounds of the invention of Formula Ii:

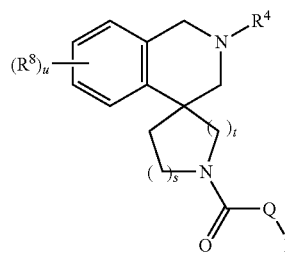

Ii wherein $R^4$, $R^7$, Q, s and t are as defined for Formula I* above;
u=0, 1, 2 or 3;
$R^8$ is independently selected from halogen, hydroxy, cyano, —N($R^6$)$_2$, —NR$^6$C(O)N($R^6$)$_2$, —NR$^6$C(O)R$^6$, ($C_1$-$C_6$)alkyl, halo($C_1$-$C_6$)alkyl, ($C_1$-$C_6$)alkoxy, halo($C_1$-$C_6$)alkoxy, CON($R^6$)$_2$, SO$_2$N($R^6$)$_2$, —SO$_2$R$^6$, —NR$^6$SO$_2$R$^6$, —NR$^6$SO$_2$N($R^6$)$_2$ and —NR$^6$SO$_2$OR$^6$; or an enantiomer, diastereomer, geometrical isomer or pharmaceutically acceptable salt thereof.

Preferred compounds of the invention are those of Formula Ii where $R^4$ is A-COOR$^6$, A-CON($R^6$)$_2$, A-COR$^6$, A-SO$_2$R$^6$, or alkyl; A is a single bond, ($C_1$-$C_6$)alkylene, ($C_1$-$C_6$)alkenylene, C(O)(C$_0$-$C_3$)alkylene(C$_3$-$C_6$)cycloalkyl(C$_0$-$C_3$)alkylene, C(O)($C_1$-$C_6$)alkylene or S(O)$_2$($C_1$-$C_6$)alkylene, optionally substituted with up to 2 ($C_1$-$C_3$)alkyl groups, and (ii) $R^6$ and N($R^6$)$_2$ are as defined for Formula I above; s=1; t=2; Q is NH or O; $R^7$ is 2-adamantyl, 1-hydroxy-4-adamantyl, 1-hydroxymethyl-4-adamantyl, 1-carbamoyl-4-adamantyl, 1-(methylsulfonyl)-4-adamantyl, 1-(aminosulfonyl)-4-adamantyl, 1-bicyclo[2.2.2]octyl; 1-carbamoyl-4-bicyclo[2.2.2]octyl, 9-bicyclo[3.3.1]nonyl or 3-carbamoyl-9-bicyclo[3.3.1]nonyl; u=1; and/or $R^8$ is halogen or methyl; and the rest of the variables are as defined for Formula I* above.

A further embodiment of the present invention is a compound according to formula Ij:

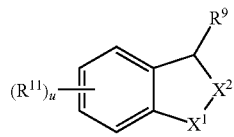

Ij wherein: $X^1$ is:

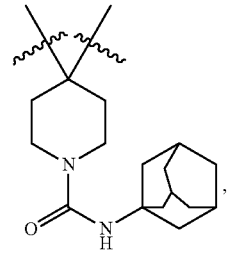 [SMILES: *C1(*)CCN(C(=O)NC23CC4CC(CC(C4)C2)C3)CC1]

and $X^2$ is NR$^{10}$; or $X^1$ is CH$_2$, and $X^2$ is:

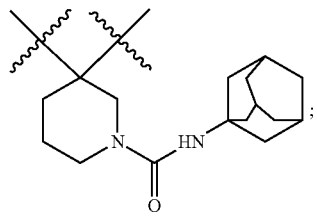 [SMILES: *C1(*)CCCN(C(=O)NC23CC4CC(CC(C4)C2)C3)C1]

u=0, 1, 2, 3 or 4; $R^9$ is oxo, hydroxy or thioxo; $R^{10}$ is H, ($C_1$-$C_6$)alkyl, or substituted or unsubstituted arylalkyl; and $R^{11}$ is independently selected from halogen, hydroxy, cyano, —N($R^6$)$_2$, —NR$^6$C(O)N($R^6$)$_2$, —NR$^6$C(O)R$^6$, ($C_1$-$C_6$)alkyl, halo($C_1$-$C_6$)alkyl, ($C_1$-$C_6$)alkoxy, halo($C_1$-$C_6$)alkoxy, CON($R^6$)$_2$, SO$_2$N($R^6$)$_2$, —SO$_2$R$^6$, —NR$^6$SO$_2$R$^6$, —NR$^6$SO$_2$N($R^6$)$_2$ and —NR$^6$SO$_2$OR$^6$; or a pharmaceutically acceptable salt thereof.

A particular embodiment of Formula Ij is a compound wherein $X^2$ is $NR^{10}$ and $X^1$ is:

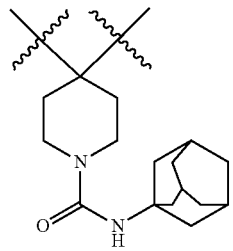 [SMILES: *C1(*)CCN(C(=O)NC23CC4CC(CC(C4)C2)C3)CC1]

A more particular embodiment of Formula Ij is a compound wherein $X^1$ and $X^2$ are defined as in the preceding paragraph, $R^9$ is thioxo and/or $R^{10}$ is H, methyl or 4-methoxybenzyl.

An additional embodiment of Formula Ij is a compound, wherein $X^1$ is $CH_2$, and $X^2$ is:

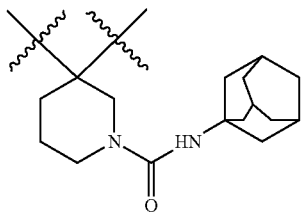 [SMILES: *C1(*)CCCN(C(=O)NC23CC4CC(CC(C4)C2)C3)C1]

A more particular embodiment of Formula Ij is a compound wherein $X^1$ and $X^2$ are defined in the preceding paragraph, $R^9$ is oxo or hydroxy, and/or u is 1 and $R^{11}$ is halogen. More particularly, in one embodiment, $R^{11}$ is chloro.

A more particular embodiment of Formula Ij is a compound wherein $X^1$ and $X^2$ are defined in the preceding paragraph, $R^9$ is oxo or hydroxy, and/or u is 0.

The present invention further provides a pharmaceutical composition comprising a disclosed 11β-HSD1 inhibitor, including a compound of the Formulae I*, I, Ia, Ia', Ib, Ib', Ic, Ic', Id, Id', Ie, If, Ig, Ih, Ii or Ij and a pharmaceutically acceptable carrier.

The present invention further provides a pharmaceutical composition comprising a disclosed 11β-HSD1 inhibitor, including a compound of the Formulae I, Ia, Ib, Ic, or Id and a pharmaceutically acceptable carrier.

The present invention further provides methods of modulating 11β-HSD1 comprising administering to a mammal in need thereof an effective amount of a disclosed 11β-HSD1 inhibitor, including a compound of Formulae I*, I, Ia, Ia', Ib, Ib', Ic, Ic', Id, Id', Ie, If, Ig, Ih, Ii or Ij.

The present invention further provides methods of modulating 11β-HSD1 by contacting 11β-HSD1 with a disclosed 11β-HSD1 inhibitor, including a compound of Formulae I, Ia, Ib, Ic, or Id.

The present invention further provides methods of inhibiting 11β-HSD1 comprising administering to a mammal in need thereof an effective amount of a disclosed 11β-HSD1 inhibitor, including a compound of Formulae I, Ia, Ib, Ic or Id.

The present invention further provides methods of inhibiting 11β-HSD1 comprising administering to a mammal in need thereof an effective amount of a disclosed 11β-HSD1 inhibitor, including a compound of Formulae I*, I, Ia, Ia', Ib, Ib', Ic, Ic', Id, Id', Ie, If, Ig, Ih, Ii or Ij.

The present invention further provides methods of inhibiting the conversion of cortisone to cortisol in a cell comprising administering to a mammal in need thereof an effective amount of a compound of Formulae I, Ia, Ib, Ic, or Id.

The present invention further provides methods of inhibiting the conversion of cortisone to cortisol in a cell comprising administering to a mammal in need thereof an effective amount of a disclosed 11β-HSD1 inhibitor, including a compound of Formulae I*, I, Ia, Ia', Ib, Ic, Ic', Id, Id', Ie, If, Ig, Ih, Ii or Ij.

The present invention further provides methods of inhibiting production of cortisol in a cell comprising administering to a mammal in need thereof an effective amount of a disclosed 11β-HSD1 inhibitor, including a compound of Formulae I, Ia, Ib, Ic, or Id.

The present invention further provides methods of inhibiting production of cortisol in a cell comprising administering to a mammal in need thereof an effective amount of a disclosed 11β-HSD1 inhibitor, including a compound of Formulae I*, I, Ia, Ia', Ib, Ib', Ic, Ic', Id, Id', Ie, If, Ig, Ih, Ii or Ij.

The present invention further provides methods of increasing insulin sensitivity comprising administering to a mammal in need thereof an effective amount of a disclosed 11β-HSD1 inhibitor, including a compound of Formulae I, Ia, Ib, Ic, or Id.

The present invention further provides methods of increasing insulin sensitivity comprising administering to a mammal in need thereof an effective amount of a disclosed 11β-HSD1 inhibitor, including a compound of Formulae I*, I, Ia, Ia', Ib, Ib', Ic, Ic', Id, Id', Ie, If, Ig, Ih, Ii or Ij.

The present invention further provides methods of treating diseases associated with activity or expression of 11β-HSD1 comprising administering to a mammal in need thereof an effective amount of a disclosed 11β-HSD1 inhibitor, including a compound of Formulae I, Ia, Ib, Ic, or Id.

The present invention further provides methods of treating diseases associated with activity or expression of 11β-HSD1 comprising administering to a mammal in need thereof an effective amount of a disclosed 11β-HSD1 inhibitor, including a compound of Formulae I*, I, Ia, Ia', Ib, Ib', Ic, Ic', Id, Id', Ie, If, Ig, Ih, Ii or Ij.

Also included in the present invention is the use of a disclosed 11β-HSD1 inhibitor, including a compound of Formulae I*, I, Ia, Ia', Ib, Ib', Ic, Ic', Id, Id', Ie, If, Ig, Ih, Ii or Ij or a pharmaceutically acceptable salt thereof for the manufacture of a medicament, wherein the values for the variables are as described above for the pharmaceutical composition of the invention. The medicament is for treating a disease or disorder related to the activity or expression of 11β-HSD1, inhibiting the conversion of cortisone to cortisol in a cell, inhibiting production of cortisol in a cell, increasing insulin sensitivity, modulating 11β-HSD1, and/or inhibiting 11β-HSD1.

Also included in the present invention is the use of a disclosed 11β-HSD1 inhibitor, including a compound of Formulae I*, I, Ia, Ia', Ib, Ib', Ic, Ic', Id, Id', Ie, If, Ig, Ih, Ii or Ij or a pharmaceutically acceptable salt thereof for therapy, such as treating a disease or disorder related to the activity or expression of 11β-HSD1, inhibiting the conversion of cortisone to cortisol in a cell, inhibiting production of cortisol in a cell, increasing insulin sensitivity, modulating 11β-HSD1, and/or inhibiting 11β-HSD1. Values for the variables of the Formulae are as described above.

Also included in the present invention is the use of a disclosed 11β-HSD1 inhibitor, including a compound of Formulae I*, I, Ia, Ia', Ib, Ib', Ic, Ic', Id, Id', Ie, If, Ig, Ih, Ii or Ij or a pharmaceutically acceptable salt thereof for treating a disease or disorder related to the activity or expression of 11β-HSD1, inhibiting the conversion of cortisone to cortisol in a cell, inhibiting production of cortisol in a cell, increasing insulin sensitivity, modulating 11β-HSD1, and/or inhibiting 11β-HSD1. Values for the variables of the Formulae are as described above.

DETAILED DESCRIPTION OF THE INVENTION

Definitions

When any variable (e.g., aryl, heterocyclyl, $R^1$, $R^2$, etc.) occurs more than once in a compound, its definition on each occurrence is independent of any other occurrence.

The term "alkyl" means a straight or branched hydrocarbon radical having 1-10 carbon atoms and includes, for example, methyl, ethyl, n-propyl, isopropyl, n-butyl, sec-butyl, isobutyl, tert-butyl, n-pentyl, n-hexyl, n-heptyl, n-octyl, n-nonyl, n-decyl and the like.

The term "loweralkyl" means a $C_1$-$C_7$ straight or branched alkyl group.

"Alkylene" means a saturated aliphatic straight-chain divalent hydrocarbon radical having the specified number of carbon atoms, e.g., —$(CH_2)_x$— wherein x is a positive integer such as 1-10, preferably 1-6. Thus, "($C_1$-$C_6$)alkylene" means a radical having from 1-6 carbon atoms in a linear or branched arrangement, with optional unsaturation or optional substitution.

The term "cycloalkyl" means a saturated hydrocarbon ring having 3-8 carbon atoms and includes, for example, cyclopropyl, cyclobutyl, cyclopentyl, cyclohexyl, cycloheptyl, cyclooctyl, and the like.

The term "bicycloalkyl" means two saturated hydrocarbon rings having a total of 7-12 carbon atoms which are joined by 1,1-fusion, 1,2-fusion or 1,n-fusion to give spirocyclic ring systems, fused ring systems and bridged ring systems respectively. Spirocyclic ring systems include, for example, spiro[2.4]heptane, spiro[2.5]octane, spiro[4.4]nonane, spiro[4.5]decane, spiro[5.5]undecane and the like. Fused ring systems include, for example, bicyclo[4.1.0]heptane, octahydro-1H-indene, decahydronaphthalene and the like. Bridged ring systems include for example, bicyclo[3.3.1]nonane, bicyclo[2.2.2]octane, bicyclo[2.2.1]heptane and the like.

The term "tricycloalkyl" means three saturated hydrocarbon ring having a total of 9-12 carbon atoms which are joined by any combination of 1,1-fusion, 1,2-fusion or 1,n-fusion and includes, for example, adamantyl, noradamantyl and the like.

The terms "alkoxy" and "alkylthio" are O-alkyl or S-alkyl, respectively, of 1-6 carbon atoms as defined above for "alkyl."

The term "aryl" means an aromatic radical which is a phenyl group, a phenylalkyl group, a phenyl group substituted with 1-4 substituents selected from alkyl as defined above, alkoxy as defined above, alkylthio as defined above, halogen, trifluoromethyl, dialkylamino as defined above for alkyl, nitro, cyano, and N,N-dialkyl-substituted amido as defined above for alkyl.

The term "heteroaryl" means a 5- and 6-membered heteroaromatic radical which may optionally be fused to a ring containing 1-4 heteroatoms selected from N, O, and S and includes, for example, a heteroaromatic radical which is 2- or 3-thienyl, 2- or 3-furanyl, 2- or 3-pyrrolyl, 2-, 3-, or 4-pyridinyl, 2-pyrazinyl, 2-, 4-, or 5-pyrimidinyl, 3- or 4-pyridazinyl, 1H-indol-6-yl, 1H-indol-5-yl, 1H-benzimidazol-6-yl, 1H-benzimidazol-5-yl, 2-, 4-, or 5-thiazolyl, 3-, 4-, or 5-pyrazolyl, 2-, 4-, or 5-imidazolyl and the like optionally substituted by a substituent selected from alkyl as defined above, halogen, dialkylamino as defined above for alkyl, nitro, cyano, and N,N-dialkyl substituted amido as defined above for alkyl.

The term "heterocyclyl" means a 4-, 5-, 6- and 7-membered saturated or partially unsaturated heterocyclic ring containing 1 to 4 heteroatoms independently selected from N, O, and S, and include pyrrolidine, piperidine, tetrahydrofuran, tetrahydropyran, tetrahydrothiophene, tetrahydrothiopyran, isoxazolidine, 1,3-dioxolane, 1,3-dithiolane, 1,3-dioxane, 1,4-dioxane, 1,3-dithiane, 1,4-dithiane, morpholine, thiomorpholine, thiomorpholine 1,1-dioxide, tetrahydro-2H-1,2-thiazine 1,1-dioxide, and isothiazolidine 1,1-dioxide.

The term "arylalkyl" means an aromatic radical attached to an alkyl radical wherein aryl and alkyl are as defined above, for example, benzyl, phenethyl, and the like.

The term "adamantyl" means an adamantane moiety bonded to another atom via the 1- or 2-position of adamantane.

The term "mammal" as used herein includes all mammals, including, but not limited to, humans.

A "carbocyclic group" comprises at least one ring formed entirely by carbon-carbon bonds. Such a group generally has from 1 to 3 fused or pendant rings, preferably one ring or two fused rings. Typically, each ring contains from 3 to 10 ring members, preferably from 5 to 8 ring members. Unless otherwise specified, such a ring may be aromatic or non-aromatic. Representative examples of carbocyclic groups are cycloalkyl groups (e.g., cyclopentane and cyclohexane), cycloalkenes and cycloalkynes, as well as aromatic groups such as phenyl, benzyl, naphthyl, phenoxyl, benzoxyl and phenylethanonyl. Carbon atoms present within a carbocyclic group may, of course, be further bonded to a variety of ring substituents, such as hydrogen, a halogen, cyano, nitro, $C_1$-$C_8$ alkyl, $C_2$-$C_8$ alkenyl, $C_2$-$C_8$ alkynyl, $C_1$-$C_8$ alkoxy, $C_1$-$C_8$ alkylthio, hydroxy, amino, mono or di($C_1$-$C_8$)alkylamino, ($C_3$-$C_7$)cycloalkyl($C_0$-$C_3$)alkyl, halo($C_1$-$C_8$)alkyl, halo($C_1$-$C_8$)alkoxy, $C_1$-$C_8$ alkanoyl, $C_1$-$C_8$ alkoxycarbonyl, —COOH, —$CONH_2$, mono- or di-($C_1$-$C_8$)alkylcarboxamido, —$SO_2NH_2$, and mono or di($C_1$-$C_8$)alkylsulfonamido.

A "heterocyclic group" comprises at least one ring in which at least one ring atom is a heteroatom (i.e., N, O or S), and the remainder of the ring atoms are carbon. Preferably, a heterocyclic group comprises 1-4 heteroatoms; within certain embodiments 1 or 2 heteroatoms is preferred. A heterocyclic group generally has from 1 to 3 fused or pendant rings, preferably one ring or two fused rings. Typically, each ring contains from 3 to 10 ring members, preferably from 5 to 8 ring members, and may be optionally substituted with from 1 to 5 substituents such as halogen, cyano, nitro, $C_1$-$C_8$ alkyl, $C_2$-$C_8$ alkenyl, $C_2$-$C_8$ alkynyl, $C_1$-$C_8$ alkoxy, $C_1$-$C_8$ alkylthio, hydroxy, amino, mono or di($C_1$-$C_8$)alkyl amino, halo($C_1$-$C_8$)alkyl, halo($C_1$-$C_8$)alkoxy, hydroxy($C_1$-$C_8$)alkyl, hydroxy($C_1$-$C_8$)alkoxy, $C_2$-$C_8$ alkanoyl, $C_1$-$C_8$ alkoxycarbonyl, —COOH, —$SO_2NH_2$, mono or dialkylsulfonamido, —C(O)$NH_2$ or mono or di($C_1$-$C_8$)alkylcarboxamido. Unless otherwise specified, a heterocyclic group may be aromatic or non-aromatic. As with a carbocyclic group, atoms within a heterocyclic ring may be further linked to a variety of ring substituents.

A heterocyclic ring may be attached to a pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. Preferably, if the total number of S and O atoms in the heterocycle exceeds 1, then these heteroatoms are not adjacent to one another. More preferably, the total number of S and O atoms in the heterocycle is not more than 1.

Examples of heterocyclic groups include, but are not limited to, acridinyl, azocinyl, benzimidazolyl, benzofuranyl, benzothio-furanyl, benzothiophenyl, benzoxazolyl, benzothiazolyl, benzotriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, dithiazinyl, dihydrofurotetrahydrofuran, furanyl, furazanyl, imidazolidinyl, imidazolinyl, imidazolyl, indazolyl, indolenyl, indolinyl, indolizinyl, indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, quinoxalinyl, quinuclidinyl, tetrahydrofuranyl, tetrahydroisoquinolinyl, tetrahydroquinolinyl, tetrazolyl, thiadiazinyl, thiadiazolyl, thianthrenyl, thiazolyl, thienyl, thienothiazolyl, thienooxazolyl, thienoimidazolyl, thiophenyl, triazinyl and xanthenyl. It will be apparent that any such heterocyclic groups may be substituted with one or more substituents as described above.

Preferred heterocyclic groups include, for example, pyridyl, pyrimidinyl (e.g., pyrimidin-2-yl), pyridinyl (pyridin-2-yl, pyridin-3-yl and pyridin-4-yl), morpholinyl (e.g., morpholin-4-yl), piperidinyl (e.g., piperidin-1-yl), pyrrolidinyl (e.g., pyrrolidin-1-yl), tetrazolyl, triazinyl, thienyl, coumarinyl, imidazolyl, oxazolyl, isoxazolyl, indolyl, pyrrolyl, pyrazolyl, quinolinyl, isoquinolinyl, thiazolyl, benzothiadiazolyl, triazolyl, pyrazinyl, furyl, thienyl, benzothienyl, benzofuranyl, tetrahydropyranyl, tetrahydrofuranyl, indanyl, and substituted derivatives of the foregoing such as methyl-tetrahydropyran-2-yl and 2-hydroxy-indan-1-yl.

The term "halogen" means fluorine, chlorine, iodine or bromine.

The term "basic nitrogen" refers to a nitrogen atom that is >50% protonated in aqueous solution at pH 7 and includes, for example, the nitrogen atoms dialkylamines and trialkylamines.

Compounds of Formulae I*, I, Ia, Ia', Ib, Ib', Ic, Ic', Id, Id', Ie, If, Ig, Ih, and Ii may exist in various stereoisomeric or tautomeric forms. The invention encompasses all such forms, including active compounds in the form of essentially pure enantiomers, racemic mixtures, and tautomers, including forms those not depicted structurally.

The compounds of the invention may be present in the form of pharmaceutically acceptable salts. For use in medicines, the salts of the compounds of the invention refer to non-toxic "pharmaceutically acceptable salts." Pharmaceutically acceptable salt forms include pharmaceutically acceptable acidic/anionic or basic/cationic salts.

Pharmaceutically acceptable acidic/anionic salts include, the acetate, benzenesulfonate, benzoate, bicarbonate, bitartrate, bromide; calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, mandelate, mesylate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate, and triethiodide salts.

The compounds of the invention include pharmaceutically acceptable anionic salt forms, wherein the anionic salts include the acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, mandelate, mesylate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate, and triethiodide salts.

When a disclosed compound or its pharmaceutically acceptable salt is named or depicted by structure, it is to be understood that solvates or hydrates of the compound or its pharmaceutically acceptable salts are also included. "Solvates" refer to crystalline forms wherein solvent molecules are incorporated into the crystal lattice during crystallization. Solvate may include water or nonaqueous solvents such as ethanol, isopropanol, DMSO, acetic acid, ethanolamine, and EtOAc. Solvates, wherein water is the solvent molecule incorporated-into the crystal lattice, are typically referred to as "hydrates". Hydrates include stoichiometric hydrates as well as compositions containing variable amounts of water.

When a disclosed compound or its pharmaceutically acceptable salt is named or depicted by structure, it is to be understood that the compound, including solvates thereof, may exist in crystalline forms, non-crystalline forms or a mixture thereof. The compound or its pharmaceutically acceptable salts or solvates may also exhibit polymorphism (i.e. the capacity to occur in different crystalline forms). These different crystalline forms are typically known as "polymorphs." It is to be understood that when named or depicted by structure, the disclosed compound and its pharmaceutically acceptable salts, solvates or hydrates also include all polymorphs thereof. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. One of ordinary skill in the art will appreciate that different polymorphs may be produced, for example, by changing or adjusting the conditions used in solidifying the compound. For example, changes in temperature, pressure, or solvent may result in different polymorphs. In addition, one polymorph may spontaneously convert to another polymorph under certain conditions.

The invention also includes various isomers and mixtures thereof. "Isomer" refers to compounds that have the same composition and molecular weight but differ in physical and/or chemical properties. The structural difference may be in constitution (geometric isomers) or in the ability to rotate the plane of polarized light (stereoisomers).

Certain of the disclosed aspartic protease inhibitors may exist in various stereoisomeric forms. Stereoisomers are compounds that differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable.

Diastereomers are stereoisomers that are not related as mirror images, most commonly because they contain two or more asymmetrically substituted carbon atoms. The symbol "*" in a structural formula represents the presence of a chiral carbon center. "R" and "S" represent the configuration of substituents around one or more chiral carbon atoms. Thus, "R*" and "S*" denote the relative configurations of substituents around one or more chiral carbon atoms. When a chiral center is not defined as R or S, a mixture of both configurations is present.

"Racemate" or "racemic mixture" means a compound of equimolar quantities of two enantiomers, wherein such mixtures exhibit no optical activity; i.e., they do not rotate the plane of polarized light.

"Geometric isomer" means isomers that differ in the orientation of substituent atoms in relationship to a carbon-carbon double bond, to a cycloalkyl ring, or to a bridged bicyclic system. Atoms (other than H) on each side of a carbon-carbon double bond may be in an E (substituents are on opposite sides of the carbon-carbon double bond) or Z (substituents are oriented on the same side) configuration.

The compounds of the invention may be prepared as individual isomers by either isomer-specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods.

When a disclosed compound is named or depicted by structure without indicating the stereochemistry, and the compound has at least one chiral center, it is to be understood that the name or structure encompasses one enantiomer of inhibitor free from the corresponding optical isomer, a racemic mixture of the inhibitor and mixtures enriched in one enantiomer relative to its corresponding optical isomer. A pharmaceutical composition of the invention may, alternatively or in addition to a compound of Formulae I*, I, Ia, Ia', Ib, Ib', Ic, Ic', Id, Id', Ie, If, Ig, Ih, Ii or Ij, comprise a pharmaceutically acceptable salt of a compound of Formulae I*, I, la, Ia', Ib, Ib', Ic, Ic', Id, Id', Ie, If, Ig, Ih, Ii or Ij, or a prodrug or pharmaceutically active metabolite of such a compound or salt and one or more pharmaceutically acceptable carriers therefor.

"Prodrug" means a pharmaceutically acceptable form of an effective derivative of a compound (or a salt thereof) of the invention, wherein the prodrug may be: 1) a relatively active precursor which converts in vivo to a compound of the invention; 2) a relatively inactive precursor which converts in vivo to a compound of the invention; or 3) a relatively less active component of the compound that contributes to therapeutic activity after becoming available in vivo (i.e., as a metabolite). See "Design of Prodrugs", ed. H. Bundgaard, Elsevier, 1985.

"Metabolite" means a pharmaceutically acceptable form of a metabolic derivative of a compound (or a salt thereof) of the invention, wherein the derivative is an active compound that contributes to therapeutic activity after becoming available in vivo.

"Effective amount" means that amount of active compound agent that elicits the desired biological response in a subject. Such response includes alleviation of the symptoms of the disease or disorder being treated. The effective amount of a compound of the invention in such a therapeutic method is from about 10 mg/kg/day to about 0.01 mg/kg/day, preferably from about 0.5 mg/kg/day to 5 mg/kg/day.

"Inhibiting 11β-HSD1" means to decrease the activity of the 11β-HSD1 enzyme.

"Modulating 11β-HSD1" means to impact the activity of the 11β-HSD1 enzyme by altering its natural activity. Modulation can be analogous to inhibition when a disease or disorder relating to the activity 11β-HSD1 would be effectively treated by suppressing the activity of the enzyme.

"Pharmaceutically acceptable carrier" means compounds and compositions that are of sufficient purity and quality for use in the formulation of a composition of the invention and that, when appropriately administered to an animal or human, do not produce an adverse reaction.

"Treatment" or "treating", as used herein, refers to partially or totally inhibiting, delaying, or reducing the severity of the disease or disorder related to 11β-HSD1. The terms "treatment" and "treating" also encompass the prophylactic administration of a compound of the invention to a subject susceptible to a disease or disorder related to the activity or expression of 11β-HSD1 in an effort to reduce the likelihood of a subject developing the disease or disorder, or slowing or preventing progression of the disease. Prophylactic treatment includes suppression (partially or completely) of the disease or disorder, and further includes reducing the severity of the disease or disorder, if onset occurs. Prophylactic treatment is particularly advantageous for administration to mammals at risk for developing a disease or disorder related to 11β-HSD1.

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Additionally, the compounds of the present invention can be administered intranasally or transdermally.

It will be obvious to those skilled in the art that the following dosage forms may comprise as the active ingredient, either compounds or a corresponding pharmaceutically acceptable salt of a compound of the present invention.

For preparing pharmaceutical compositions from the compounds of the present invention, pharmaceutically acceptable carriers can either be solid or liquid. Solid form preparations include powders, tablets, pills, capsules, cachets, suppositories, and dispersable granules. A solid carrier can be one or more substances which may also act as diluents, flavoring agents, solubilizers, lubricants, suspending agents, binders, preservatives, tablet disintegrating agents, or an encapsulating material. In powders, the carrier is a finely divided solid which is in a mixture with the finely divided active ingredient.

In tablets, the active ingredient is mixed with the carrier having the necessary binding properties in suitable proportions and compacted in the shape and size desired.

The powders and tablets preferably contain from about one to about seventy percent of the active ingredient. Suitable carriers are magnesium carbonate, magnesium stearate, talc, sugar, lactose, pectin, dextrin, starch, gelatin, tragacanth, methylcellulose, sodium carboxymethylcelluose, a low melting wax, cocoa butter, and the like. Tablets, powders, cachets, lozenges, fast-melt strips, capsules and pills can be used as solid dosage forms containing the active ingredient suitable for oral administration.

For preparing suppositories, a low melting wax, such as a mixture of fatty acid glycerides or cocoa butter, is first melted and the active ingredient is dispersed homogeneously therein, as by stirring. The molten homogeneous mixture is then poured into convenient sized molds, allowed to cool, and thereby to solidify.

Liquid form preparations include solutions, suspensions, retention enemas, and emulsions, for example, water or water propylene glycol solutions. For parenteral injection, liquid preparations can be formulated in solution in aqueous polyethylene glycol solution.

Aqueous solutions suitable for oral administration can be prepared by dissolving the active ingredient in water and adding suitable colorants, flavors, stabilizing, and thickening agents as desired. Aqueous suspensions for oral administration can be prepared by dispersing the finely divided active ingredient in water with viscous material, such as natural or synthetic gums, resins, methylcellulose, sodium carboxymethyl cellulose, and other well-known suspending agents.

The pharmaceutical composition is preferably in unit dosage form. In such form, the composition is subdivided into unit doses containing appropriate quantities of the active ingredient. The unit dosage form can be a packaged preparation, the package containing discrete quantities of, for example, tablets, powders, and capsules in vials or ampules. Also, the unit dosage form can be a tablet, cachet, capsule, or lozenge itself, or it can be the appropriate amount of any of these in packaged form.

The quantity of active ingredient in a unit dose preparation may be varied or adjusted from about 0.1 mg to about 1000.0 mg, preferably from about 0.1 mg to about 100 mg. The dosages, however, may be varied depending upon the requirements of the patient, the severity of the condition being treated, and the compound being employed. Determination of the proper dosage for a particular situation is within the skill in the art. Also, the pharmaceutical composition may contain, if desired, other compatible therapeutic agents.

In therapeutic treatment or as a method-of-use as an inhibitor of 11β-HSD1 or an inhibitor in the production of cortisol in the cell, the active ingredient is preferably administered orally in a solid dosage form as disclosed above in an amount of about 0.1 mg to about 100 mg per daily dose where the dose is administered once or more than once daily.

The compounds of the invention are useful for ameliorating or treating disorders or diseases in which decreasing the level of cortisol is effective in treating a disease state. Thus, the compounds of the invention can be used in the treatment or prevention of diabetes mellitus, obesity, metabolic syndrome, insulin resistance, cardiovascular disease, dyslipidemia, atherosclerosis, lipodystrophy, osteoporosis, glaucoma, Cushing's syndrome, depression, anxiety and Alzheimer's disease, cognitive decline (including age-related cognitive decline), polycystic ovarian syndrome and infertility. In addition, compounds modulate the function of B and T cells of the immune system.

A pharmaceutical composition of the invention may, alternatively or in addition to a compound of Formulae I*, I, Ia, Ia', Ib, Ib', Ic, Ic', Id, Id', Ie, If, Ig, Ih, Ii or Ij, comprise a pharmaceutically acceptable salt of a compound of Formulae I*, I, Ia, Ia', Ib, Ib', Ic, Ic', Id, Id', Ie, If, Ig, Ih, Ii or Ij, or a prodrug or pharmaceutically active metabolite of such a compound or salt and one or more pharmaceutically acceptable carriers therefor.

The pharmaceutical compositions of the invention are 11β-HSD1 inhibitors. Said compositions contain compounds having a mean inhibition constant ($IC_{50}$) against 11β-HSD1 of between about 1,000 nM to about 0.001 nM; preferably between about 50 nM to about 0.001 nM; and more preferably between about 5 nM to about 0.01 nM. The invention includes a therapeutic method for treating or ameliorating an 11β-HSD1 mediated disorder in a subject in need thereof comprising administering to a subject in need thereof an effective amount of a compound of Formulae I*, I, Ia, Ia', Ib, Ib', Ic, Ic', Id, Id', Ie, If, Ig, Ih, Ii or Ij, or the enantiomers, diastereomers, or salts thereof or composition thereof.

The compounds of the invention are useful for ameliorating or treating disorders or diseases in which decreasing the level of cortisol is effective in treating a disease state. Thus, the compounds of the invention can be used in the treatment or prevention of diabetes mellitus, obesity, symptoms of metabolic syndrome, glucose intolerance, hyperglycemic, hypertension, hyperlipidemia, insulin resistance, cardiovascular disease, dyslipidemia, atherosclerosis, lipodystrophy, osteoporosis, glaucoma, Cushing's syndrome, Addison's Disease, visceral fat obesity associated with glucocorticoid therapy, depression, anxiety, Alzheimer's disease, dementia, cognitive decline (including age-related cognitive decline), polycystic ovarian syndrome and infertility. In addition, the compounds modulate the function of B and T cells of the immune system and can therefore be used to treat diseases such as tuberculosis, leprosy and psoriasis. They can also be used to promote wound healing, particularly in diabetic patients.

Additional diseases or disorders that are related to 11β-HSD1 activity include those selected from the group consisting of lipid disorders, hypertriglyceridemia, hypercholesterolemia, low HDL levels, high LDL levels, vascular restenosis, pancreatitis, abdominal obesity, neurodegenerative disease, retinopathy, nephropathy, neuropathy, diabetes, coronary heart disease, stroke, peripheral vascular disease, Cushing's syndrome, hyperinsulinemia, viral diseases, and Syndrome X.

An embodiment of the invention includes administering an 11β-HSD1 inhibiting compound of Formula I or pharmaceutical composition thereof in a combination therapy with one or more additional agents for the treatment of diabetes, dyslipidemia, cardiovascular disease, hypertension, obesity, cancer or glaucoma. Agents for the treatment of diabetes include insulins, such as Humulin® (Eli Lilly), Lantuse® (Sanofi Aventis), Novolin (Novo Nordisk), and Exubera® (Pfizer); PPAR gamma agonists, such as Avandia® (rosiglitazone maleate, GSK) and Actos® (pioglitazone hydrochloride, Takeda/Eli Lilly); sulfonylureas, such as Amaryl® (glimepiride, Sanofi Aventis), Diabeta® (glyburide, Sanofi Aventis), Micronase®/Glynase® (glyburide, Pfizer), and Glucotrol®/Glucotrol XL® (glipizide, Pfizer); meglitinides, such as Prandin®/NovoNorm® (repaglinide, Novo Nordisk), Starlix® (nateglinide, Novartis), and Glufast® (mitiglinide, Takeda); biguanides, such as Glucophase®/Glucophase XR® (metformin HCl, Bristol Myers Squibb) and Glumetza (metformin HCl, Depomed); thiazolidinediones; amylin analogs; GLP-1 analogs; DPP-IV inhibitors, such as Januvia® (sitagliptin, Merck); PTB-1B inhibitors; protein kinase inhibitors (including AMP-activated protein kinase inhibitors); glucagon antagonists; glycogen synthase kinase-3 beta inhibitors; glucose-6-phosphatase inhibitors; glycogen phosphorylase inhibitors; sodium glucose co-transporter inhibitors, and α-glucosidase inhibitors, such as Precose®/Glucobay®/Prandase®/Glucor® (acarbose, Bayer) and Glyset® (miglitol, Pfizer). Agents for the treatment of dyslipidemia and cardiovascular disease include statins, fibrates and ezetimibe. Agents for the treatment of hypertension include α-blockers, β-blockers, calcium channel blockers, diuretics, angiotensin converting enzyme (ACE) inhibitors, dual ACE and neutral endopeptidase (NEP) inhibitors, angiotensin-receptor blockers (ARBs), aldosterone synthase inhibitor, aldosterone-receptor antagonists, or endothelin receptor antagonist. Agents for the treatment of obesity include orlistat, phentermine, sibutramine and rimonabant.

An embodiment of the invention includes administering an 11β-HSD1 inhibiting compound of Formula I or composition thereof in a combination therapy with one or more other 11β-HSD1 inhibitors (whether such inhibitors are also compounds of Formula I or are compounds of a different class/genus), or with combination products, such as Avandamet® (metformin HCl and rosiglitazone maleate, GSK); Avandaryl® (glimepiride and rosiglitazone maleate, GSK); Metaglip® (glipizide and metformin HCl, Bristol Myers Squibb); Janumet® (sitagliptin and metformin, Merck) and Glucovance® (glyburide and metformin HCl, Bristol Myers Squibb).

The following abbreviations have the indicated meanings:

| Abbreviation | Meaning |
| --- | --- |
| BINAP | 2,2'-bis(diphenylphosphino)-1,1'-binaphthyl |
| Boc | tert-butoxy carbonyl or t-butoxy carbonyl |
| (Boc)₂O | di-tert-butyl dicarbonate |
| Cbz | Benzyloxycarbonyl |
| CbzCl | Benzyl chloroformate |
| CDI | carbonyldiimidazole |
| d | day |
| DAST | diethylaminosulfur trifluoride |
| DBU | 1,8-diazabicyclo[5.4.0]undec-7-ene |
| DCC | N,N'-dicyclohexylcarbodiimide |
| DCU | N,N'-dicyclohexylurea |
| DIAD | diisopropyl azodicarboxylate |
| DIBAL, DIBAH | diisobutylaluminum hydride |
| DIEA | N,N-diisopropylethylamine |
| DMAP | 4-(dimethylamino)pyridine |
| DMF | N,N-dimethylformamide |
| DMPU | 1,3-dimethyl-3,4,5,6-tetrahydro-2(1H)-pyrimidinone |
| 2,4-DNP | 2,4-dinitrophenylhydrazine |
| EDC•HCl | 1-[3-(dimethylamino)propyl]-3-ethylcarbodiimide hydrochloride |
| equiv | equivalents |
| EtOAc | ethyl acetate |
| Fmoc | 1-[[(9H-fluoren-9-ylmethoxy)carbonyl]oxy]- |
| Fmoc-OSu | 1-[[(9H-fluoren-9-ylmethoxy)carbonyl]oxy]-2,5-pyrrolidinedione |
| HCl | hydrochloric acid |
| HOBt | 1-hydroxybenzotriazole |
| HATU | 2-(7-Aza-1H-benzotriazole-1-yl)-1,1,3,3-tetramethyluronium hexafluorophosphate |
| HBTU | 2-(1H-Benzotriazole-1-yl)-1,1,3,3-tetramethyluronium hexafluorophosphate |
| HPLC | high pressure-liquid chromatography |
| KHMDS | potassium hexamethyldisilazane |
| LAH or LiAlH₄ | lithium aluminum hydride |
| LC-MS | liquid chromatography-mass spectroscopy |
| LHMDS | lithium hexamethyldisilazane |
| MeCN | acetonitrile |
| MeOH | methanol |
| min | minute |
| MS | mass spectrum |
| MsCl | methanesulfonyl chloride |
| NaH | sodium hydride |
| NaHCO₃ | sodium bicarbonate |
| NaN₃ | sodium azide |
| NaOH | sodium hydroxide |
| Na₂SO₄ | sodium sulfate |
| NMM | N-methylmorpholine |
| NMP | N-methylpyrrolidinone |
| Pd₂(dba)₃ | tris(dibenzylideneacetone)dipalladium(0) |
| Pd(OAc)₂ | Palladium(II)Acetate |
| Pd(OH)₂ | PalladiumHydroxide |
| PE | petroleum ether |
| PtO₂ | Platinum Oxide |
| quant | quantitative yield |
| rt | room temperature |
| satd | saturated |
| SOCl₂ | thionyl chloride |
| SFC | supercritical fluid chromatography |
| SPA | scintillation proximity assay |
| SPE | solid phase extraction |
| TBS | t-butyldimethylsilyl |
| TBSCl | t-butyldimethylsilyl chloride |
| TEA | triethylamine or Et₃N |
| TEMPO | 2,2,6,6-tetramethyl-1-piperidinyloxy free radical |
| Teoc | 1-[2-(trimethylsilyl)ethoxycarbonyloxy]- |
| Teoc-OSu | 1-[2-(trimethylsilyl)ethoxycarbonyloxy]pyrrolidin-2,5-dione |
| TFA | trifluoroacetic acid |
| THF | tetrahydrofuran |
| TLC | thin layer chromatography |
| TMS | trimethylsilyl |
| TMSCl | chlorotrimethylsilane or trimethylsilyl chloride |
| $t_R$ | retention time |
| TsOH | p-toluenesulfonic acid |

General Description of Synthesis

Compounds of Formulae I*, I, Ia, Ib, Ic, Id, Ie, If, Ig, Ih, Ii and Ij can be prepared by several processes. In the discussion below n, s, t, u, A, K, L, M, X, Y, Q and $R^1$-$R^{8a}$ have the meanings indicated above unless otherwise noted. In cases where the synthetic intermediates and final products of Formulae I*, I, Ia, Ib, Ic, Id, Ie, If, Ig, Ih, Ii or Ij described below contain potentially reactive functional groups, for example amino, hydroxyl, thiol and carboxylic acid groups, that may interfere with the desired reaction, it may be advantageous to employ protected forms of the intermediate. Methods for the selection, introduction and subsequent removal of protecting groups are well known to those skilled in the art. (See, e.g., T. W. Greene & P. G. M. Wuts, "Protective Groups in Organic Synthesis" John Wiley & Sons, Inc., New York 1999). Such protecting group manipulations are assumed in the discussion below and not described explicitly. Generally reagents in the reaction schemes are used in equimolar amounts; however, in certain cases it may be desirable to use an excess of one reagent to drive a reaction to Completion. This is especially the case when the excess reagent can be readily removed by evaporation or extraction. Bases employed to neutralize HCl in reaction mixtures are generally used in slight to substantial excess (1.05-5 equivalents).

In the first process of the invention a compound of Formula I or I* wherein Q=O is prepared by reaction of an amine of formula II with a chloroformate of formula III in the presence of an organic or inorganic base, for example N,N-diisopropylethylamine or $K_2CO_3$, in an inert solvent such as $CH_2Cl_2$, MeCN or THF at −20° C. to 80° C., preferably 0° C. to 25° C. for between 0.5 h and 24 h.

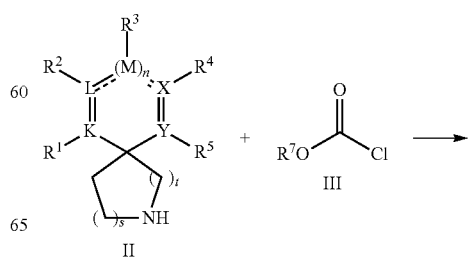

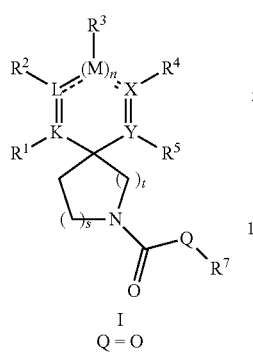

Many spirocyclic amines of Formula II can be prepared by previously described routes or can be purchased. Tert-butyl spiro[indoline-3,4'-piperidine]-1-carboxylate (Formula II wherein K, L, Y=C; X=N; R¹, K, L and R² form a fused benzene ring; n=0; s=1; t=2; =CO₂t-Bu; R⁵=H; R³ absent; single bonds from L to X and X to Y):

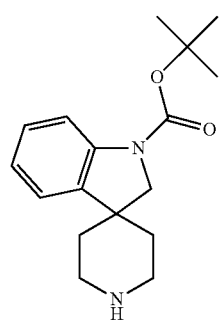 [SMILES: CC(C)(C)OC(=O)N1CC2(CCNCC2)c2ccccc21]

can be prepared from benzyl spiro[indoline-3,4'-piperidine]-1'-carboxylate as disclosed in Example 21 of U.S. Pat. No. 7,045,527, which is hereby incorporated by reference.

The following substituted tert-butyl spiro[indoline-3,4'-piperidine]-1-carboxylate were purchased from WuXi Pharmatech (Shanghai, China):

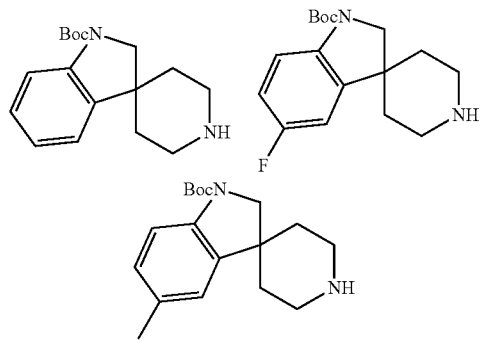

(±)-2-(2,3-Dihydrospiro[indene-1,4'-piperidine]-3-yl) acetic acid (Formula II wherein K, L, X, Y=C; R¹, K, L and R² form a fused benzene ring; n=0; s=1; t=2; R⁴=CH₂CO₂H; R⁵=H; R³ absent; single bonds from L to X and X to Y):

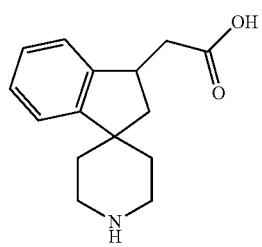 [SMILES: O=C(O)CC1CC2(CCNCC2)c2ccccc21]

can be prepared by deprotection of 2-(1'-(tert-butoxycarbonyl)-2,3-dihydrospiro[indene-1,4'-piperidine]-3-yl)acetic acid as disclosed in Example 98 (Steps A and B) of U.S. Pat. No. 5,578,593, which is hereby incorporated by reference.

The parent compound and the following substituted (±)-2-(2,3-dihydrospiro[indene-1,4'-piperidine]-3-yl)acetic acid were purchased from WuXi Pharmatech (Shanghai, China) as their N-Boc or ethyl ester derivatives:

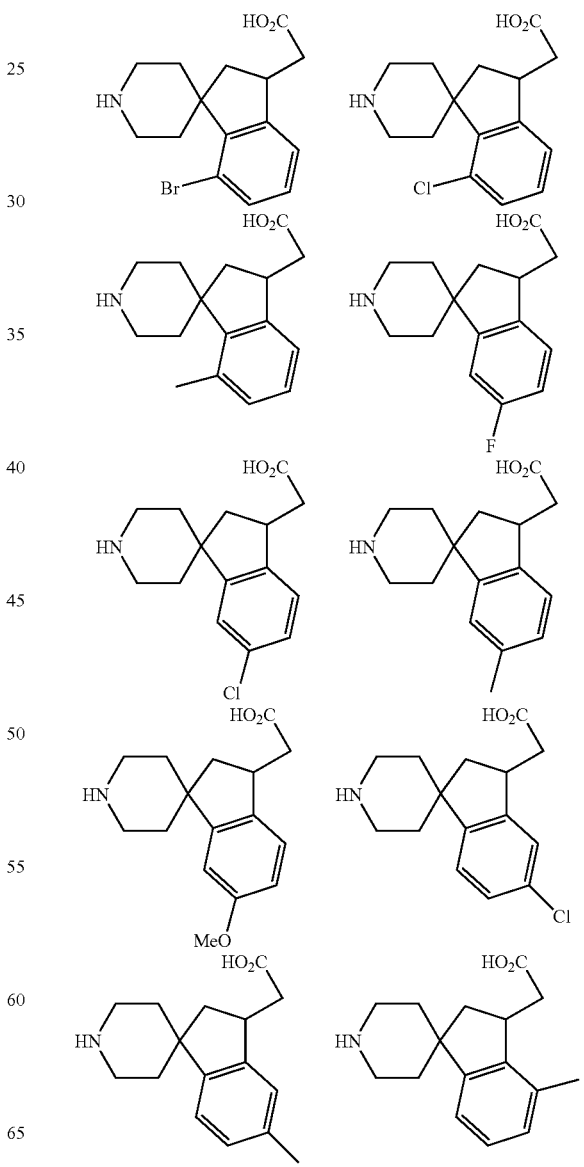

Ethyl 2-(7-bromospiro[indene-1,4'-piperidine]-3(2H)-ylidene)acetate was purchased from WuXi Pharmatech (Shanghai, China):

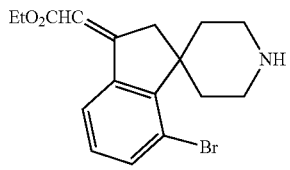

2-(3-azaspiro[5.5]undecan-9-yl)acetic acid was purchased from WuXi Pharmatech (Shanghai, China):

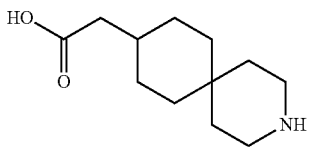 [SMILES: O=C(O)CC1CCC2(CCNCC2)CC1]

Tert-butyl 3,9-diazaspiro[5.5]undecane-3-carboxylate (Formula II wherein K, L, X, Y=C; M=N; $R^1$, $R^2$, $R^4$ and $R^5$=H; n=1; s=1; t=2; $R^3$=t-BuOCO; single bonds from K to L, L to M, M to X and X to Y):

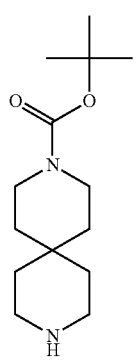

can be prepared from 1-benzylpiperidin-4-one as disclosed in Example 1 of U.S. Pat. No. 5,451,578, which is hereby incorporated by reference. This compound was purchased from WuXi Pharmatech (Shanghai, China).

Tert-butyl 2,8-diazaspiro[4.5]decane-2-carboxylate (Formula II wherein K, X, Y=C; L=N; n=0; s=1; t=2; $R^1$, $R^4$ and $R^5$=H; $R^2$=t-BuOCO; single bonds from K to L, L to X and X to Y):

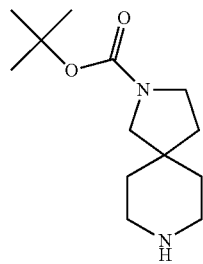 [SMILES: CC(C)(C)OC(=O)N1CCC2(CCNCC2)C1]

can be prepared from 8-benzyl-2-oxa-8-azaspiro[4.5]decane-1,3-dione as disclosed in Example 19 (Steps A-G) of US Published Patent Application 2003/055244, which is hereby incorporated by reference. This compound was purchased from WuXi Pharmatech (Shanghai, China).

Tert-Butyl 2,7-diazaspiro[4.5]decane-2-Carboxylate (Formula II wherein K, X, Y=C; L=N; n=0; s=2; t=1; $R^1$, $R^4$ and $R^5$=H; $R^3$=t-BuOCO; single bonds from K to L, L to X and X to Y):

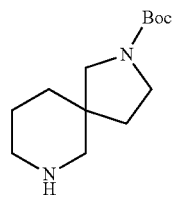 [SMILES: CC(C)(C)OC(=O)N1CCC2(CCCNC2)C1]

was purchased from WuXi Pharmatech (Shanghai, China) (catalog number SA-008).

2,3-Dihydrospiro[indene-1,4'-piperidine] (Formula II wherein K, L, X, Y=C; $R^1$, K, L and $R^2$ form a fused benzene ring; n=0; s=1; t=2; $R^4$ and $R^5$=H; $R^3$ absent; single bonds from L to X and from X to Y):

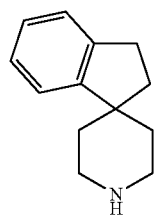 [SMILES: c1ccc2c(c1)CCC21CCNCC1]

can be prepared from indene using the procedures disclosed by Chambers, M. S., et al., *J. Med. Chem.* 1992, 35, 2033-2039, Scheme II. This compound was purchased from WuXi Pharmatech (Shanghai, China).

Spiro[fluorene-9,4'-piperidine] (Formula II wherein K, L, X, Y=C; $R^1$, K, L and $R^2$ form a fused benzene ring; $R^4$, X, Y and $R^5$ form a fused benzene ring; n=0; s=1; t=2; $R^3$ is absent; single bonds from L to X):

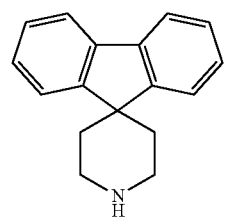 [SMILES: c1ccc2c(c1)-c1ccccc1C21CCNCC1]

can be prepared from fluorene as disclosed in Example 17 (Steps A-B) of U.S. Pat. No. 5,578,593, which is hereby incorporated by reference.

Ethyl spiro[indene-1,4'-piperidine]-3-carboxylate (Formula II wherein K, L, X, Y=C; $R^1$, K, L and $R^2$ form a fused benzene ring; n=0; s=1; t=2; $R^4$=CH$_2$CO$_2$Et; $R^5$=H; $R^3$ absent; single bond from L to X and double bond from X to Y):

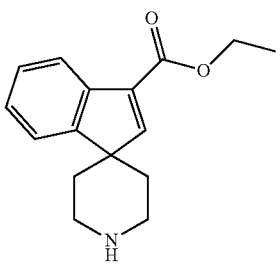 [SMILES: CCOC(=O)C1=CC2(CCNCC2)c2ccccc21]

can be prepared by deprotection of 1'-tert-butyl 3-ethyl spiro [indene-1,4'-piperidine]-1',3'-dicarboxylate which can be prepared from tert-butyl 3-oxo-2,3-dihydrospiro[indene-1,4'-piperidine]-1'-carboxylate as disclosed in Example 1 (Steps A-C) of U.S. Pat. No. 5,965,565, which is hereby incorporated by reference. This compound was purchased from WuXi Pharmatech (Shanghai, China).

(±)-2,3-Dihydrospiro[indene-1,4'-piperidine]-3-carboxylic acid (Formula II wherein K, L, X, Y=C; $R^1$, K, L and $R^2$ form a fused benzene ring; n=0; s=1; t=2; $R^4$=$CO_2H$; $R^5$=H; $R^3$ absent; single bonds from L to X and from X to Y):

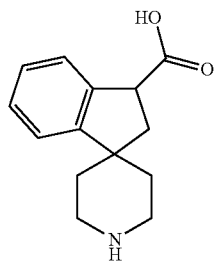 [SMILES: O=C(O)C1CC2(CCNCC2)c2ccccc21]

can be prepared by deprotection of 1'-(tert-butoxycarbonyl)-2,3-dihydrospiro[indene-1,4'-piperidine]-3-carboxylic acid which can be prepared from tert-butyl 3-oxo-2,3-dihydrospiro[indene-1,4'-piperidine]-1'-carboxylate as disclosed in Example 1 (Steps A-D) of U.S. Pat. No. 5,965,565, which is hereby incorporated by reference. This compound was purchased from WuXi Pharmatech (Shanghai, China).

1,3-Dihydrospiro[indene-2,3'-piperidine] (Formula II wherein K, L, X, Y=C; $R^2$, L, X and $R^4$ form a fused benzene ring; n=0; s=2; t=1; $R^1$ and $R^5$=H; $R^3$ is absent; single bonds from K to L and from X to Y):

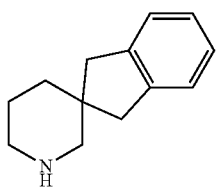 [SMILES: c1ccc2c(c1)CC1(CCCNC1)C2]

can be prepared from ethyl nipecotate using the procedures disclosed by Yang, L., et al., *Bioorg. Med. Chem. Lett.* 1998, 8, 107-112, Scheme 3.

(±)-2,3-Dihydrospiro[indene-1,3'-pyrrolidine] (Formula II wherein K, L, X, Y=C; $R^1$, K, L and $R^4$ form a fused benzene ring; n=0; s=1; t=1; $R^4$ and $R^5$=H; $R^3$ is absent; single bonds from L to X and from X to Y):

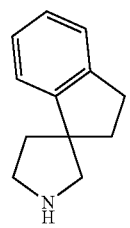 [SMILES: c1ccc2c(c1)CCC21CCNC1]

can be prepared as described in Sarges R., et al., *J. Med. Chem.* 1988, 31, 230-243 (Compound 95, Table XVI).

1,4-dioxa-8-azaspiro[4.6]undecane (Formula II wherein K and Y=O; L and Y=C; n=0; s=2; t=2; $R^2$ and $R^4$=H; M, $R^1$, $R^3$ and $R^5$ are absent; single bonds from K to L, from L to X and from X to Y):

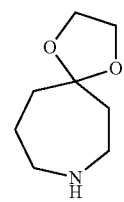

can be prepared from ethyl hexahydro-4-oxazepine-1-carboxylate as disclosed in Example A3 (Steps (a) and (b)) of US Published Patent Application 2003/0139393, which is hereby incorporated by reference.

3H-spiro[isobenzofuran-1,4'-piperidine] (Formula II wherein $R^1$, K, L and $R^2$ form a fused benzene ring; X is C; Y is O; n=0; s=1; t=2; $R^4$ is H; M, $R^3$ and $R^5$ are absent; single bonds from L to X and from X to Y):

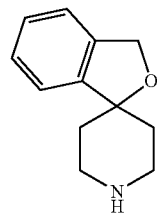 [SMILES: c1ccc2c(c1)COC21CCNCC1]

can be prepared as described in Cheng, C. Y., et al., *Tetrahedron* 1996, 52, 10935. 3H-spiro[isobenzofuran-1,4'-piperidine] was purchased from J & W PharmLab LLC (Morrisville, Pa., USA).

2H-spiro[benzofuran-3,4'-piperidine] (Formula II wherein $R^1$, K, L and $R^2$ form a fused benzene ring; X is O; Y is C; n=0; s=1; t=2; $R^5$ is H; M, $R^3$ and $R^4$ are absent; single bonds from L to X and from X to Y):

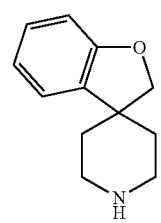 [SMILES: c1ccc2c(c1)OCC21CCNCC1]

can be prepared as described in Parham, W. E., et al., *J. Org. Chem.* 1976, 41, 2628.

5-chloro-1-(methylsulfonyl)spiro[indoline-3,3'-pyrrolidine] (Formula II wherein $R^1$, K, L and $R^2$ form a fused chlorine substituted benzene ring; X is N; Y is C; n=0; s=1; t=1; $R^4$ is $SO_2Me$; $R^5$ is H; M and $R^3$ and absent; single bonds from L to X and from X to Y):

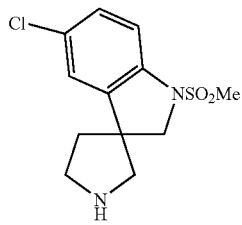

can be prepared as disclosed in Example 3 (Steps A-C) of WO 2005/061512 A1, which is hereby incorporated by reference.

3,4-Dihydro-2H-spiro[naphthalene-1,3'-pyrrolidine] (Formula E wherein $R^1$, K, L and $R^2$ form a fused benzene ring; K, L, M, X and Y art C; n=1; s 1; t=1; $R^3$, $R^4$ and $R^5$ are H; single bonds from L to M, from M to X and from X to Y):

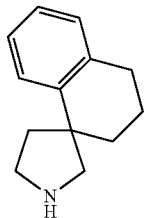 [SMILES: c1ccc2c(c1)CCCC21CCNC1]

can be prepared as described in Crooks, P. A., et al., *J. Med. Chem.* 1980, 23, 679.

3,4-dihydro-2H-spiro[naphthalene-1,4'-piperidine] was purchased from WuXi Pharmatech (Shanhai, China):

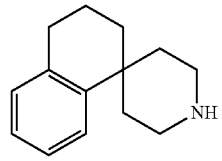 [SMILES: c1ccc2c(c1)CCCC21CCNCC1]

Tert-butyl 1H-Spiro[isoquinoline-4,4'-piperidine]-2(3H)-carboxylate was purchased from WuXi Pharmatech (Shanhai, China):

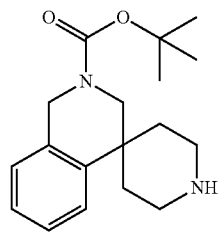 [SMILES: CC(C)(C)OC(=O)N1Cc2ccccc2C2(CCNCC2)C1]

6-Methoxy-3,4-dihydro-2H-spiro[isoquinoline-1,4'-piperidine]:

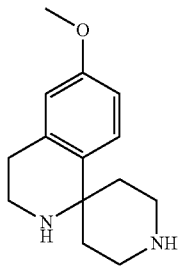 [SMILES: COc1ccc2c(c1)CCNC21CCNCC1]

was prepared as disclosed in Procedure A in U.S. Pat. No. 7,109,207 (Column 25, Line 5), which is hereby incorporated by reference.

Spiro[chroman-2,4'-piperidine] (Formula II wherein $R^2$, L, M and $R^3$ form a fused benzene ring; K=0; M, L, X and Y are C; n=1; s=1; t=2; $R^4$ and $R^5$ are H; single bonds from L to M, from M to X and from X to Y):

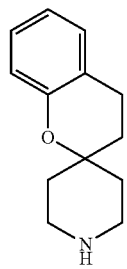 [SMILES: c1ccc2c(c1)CCC1(CCNCC1)O2]

can be prepared as disclosed in Example 12 (Step A) of U.S. Pat. No. 5,536,716, which is hereby incorporated by reference.

Spiro[chroman-2,4'-piperidine]-4-carboxylic acid (Formula II wherein $R^2$, L, M and $R^3$ form a fused benzene ring; K=0; L, M, X and Y are C; n=1; s=1; t=2; $R^4$ is $CO_2H$; $R^5$ is H; single bonds from L to M, from M to X and from X to Y):

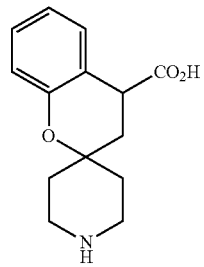 [SMILES: O=C(O)C1CC2(CCNCC2)Oc2ccccc21]

was prepared by deprotection of 1'-(tert-butoxycarbonyl) spiro[chroman-2,4'-piperidine]-4-carboxylic acid, which was purchased from WuXi Pharmatech (Shanghai, China) (catalog number BBA-0011).

2-(spiro[chroman-2,4'-piperidine]-4-yl)acetic acid (Formula II wherein $R^2$, L, M and $R^3$ form a fused benzene ring; K=0; L, M, X and Y are C; n=1; s=1; t=2; $R^4$ is $CH_2CO_2H$; $R^5$ is H; single bonds from L to M, from M to X and from X to Y):

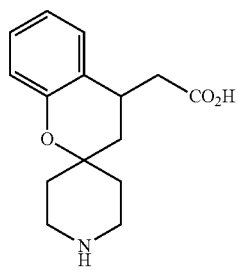 [SMILES: O=C(O)CC1CC2(CCNCC2)Oc2ccccc21]

was prepared by deprotection of 2-(1'-(tert-butoxycarbonyl) spiro[chroman-2,4'-piperidine]-4-yl)acetic acid, which was purchased from WuXi Pharmatech (Shanghai, China) (catalog number BBA-0012).

In the first process of the invention, chloroformates of formula III are prepared by reaction of alcohols of formula IV with phosgene or triphosgene in an inert solvent such as toluene, $CH_2Cl_2$ or THF in the presence of a base such as pyridine at $-20°$ C. to $80°$ C., preferably $0°$ C. to $25°$ C. for between 0.5 h and 24 h.

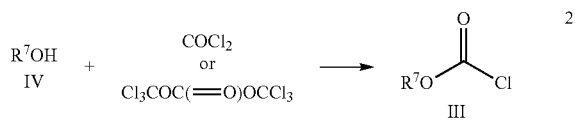

In the second process of the invention, a compound of Formula I or I* wherein Q=NH is prepared by reaction of an amine of formula II with an isocyanate of formula V in the presence of an organic or inorganic base, for example N,N-diisopropylethylamine or $K_2CO_3$, in an inert solvent such as $CH_2Cl_2$, MeCN or THF at $-20°$ C. to $80°$ C., preferably $0°$ C. to $25°$ C. for between 0.5 h and 24 h.

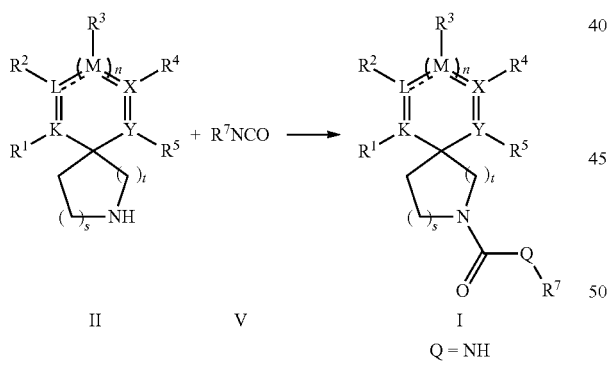

Isocyanates of formula V are prepared by reaction of amines of formula VI with phosgene or triphosgene in, for example, a mixture of $CH_2Cl_2$ and satd aq $NaHCO_3$ at $-10°$ C. to $80°$ C., preferably $0°$ C. to $25°$ C. for between 0.5 h and 24 h.

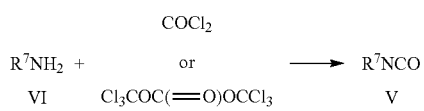

In the third process of the invention, a compound of Formula I or I* wherein Q=$NR^6$ is prepared by reaction of an amine of formula II with a compound of Formula VII wherein LG is a leaving group such as halide, aryloxide or azole, for example chloride, p-nitrophenoxide or imidazolide, in an inert solvent such as $CH_2Cl_2$, MeCN or THF at $0°$ C. to $120°$ C., preferably $25°$ C. to $75°$ C. for between 0.5 h and 24 h.

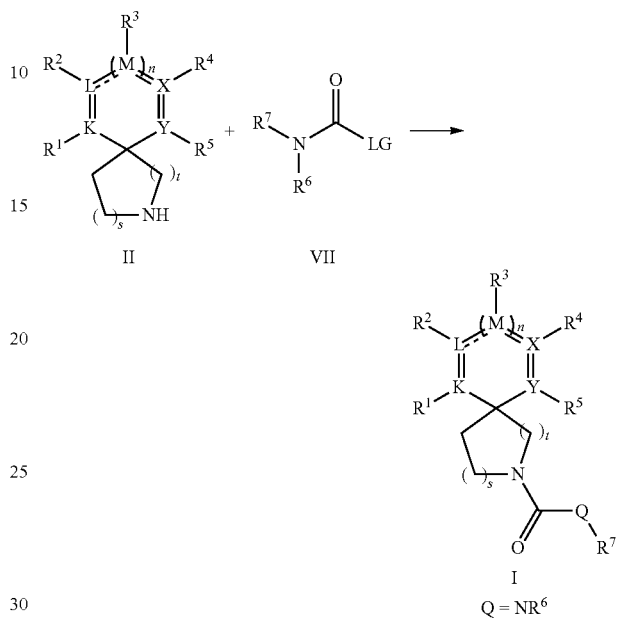

Intermediates of formula VII wherein LG=aryloxide are prepared by reaction of amines of formula VIII with an aryl chloroformate IX in, for example, MeCN or $CH_2Cl_2$ in the presence of DIEA or powdered $NaHCO_3$ at $-10°$ C. to $50°$ C., preferably $0°$ C. to $25°$ C. for between 0.5 h and 24 h.

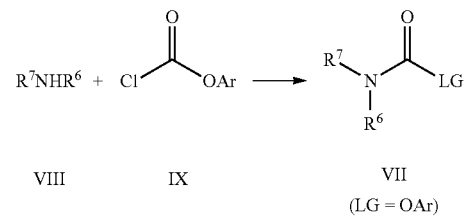

Intermediates of formula VII wherein LG=Cl and $R^6$ is not H are prepared by treatment of amines of formula VIII with phosgene or triphosgene at $-70°$ C. to $25°$ C. in an inert solvent such as $CH_2Cl_2$, THF or MeCN for between 30 min and 24 h.

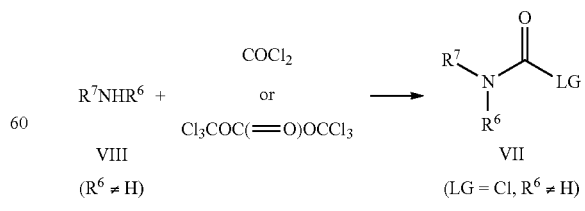

Intermediates of formula VII wherein LG=1-imidazolyl and are prepared by treatment of amines of formula VIII with carbonyl diimidazole in an inert solvent such as $CH_2Cl_2$, THF, toluene or MeCN at −40° C. to 60° C., preferably at −10° C. to 30° C., for 15 min to 12 h.

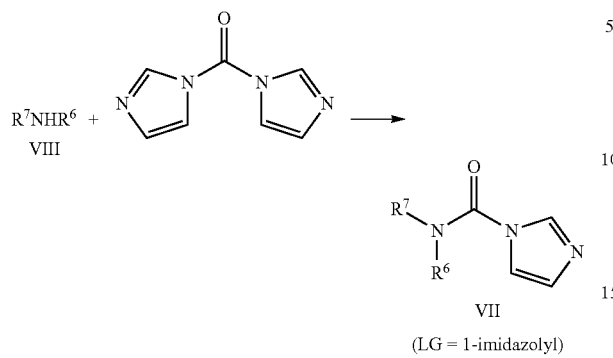

(LG = 1-imidazolyl)

In the fourth process of the invention, a compound of Formula I or I* wherein Q=NR$^6$ is prepared by reaction of an intermediate of formula IX, wherein LG is a leaving group such as such as halide, aryloxide or azole, for example chloride, p-nitrophenoxide or imidazolide, with an amine of formula VIII in an inert solvent such as CH$_2$Cl$_2$, MeCN or THF at 0° C. to 120° C., preferably 25° C. to 75° C. for between 0.5 h and 24 h.

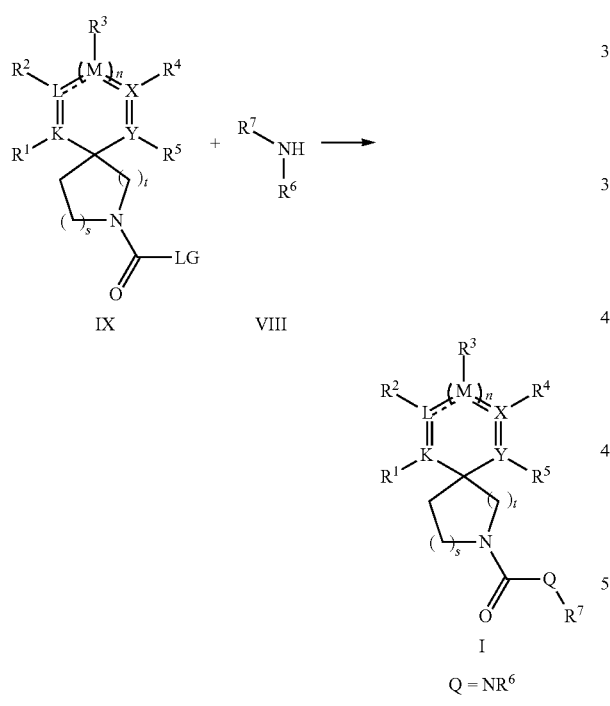

Q = NR$^6$

Intermediates of Formula IX are prepared from intermediates of Formula II using procedures and conditions analogous to those described above for the preparation of intermediates of Formula VII from amines of Formula VIII.

In the fifth process of the invention, a compound of Formula I or I* wherein Q=O is prepared by reaction of an intermediate of formula IX, wherein LG is a leaving group such as halide, aryloxide or azole, for example chloride, p-nitrophenoxide or imidazolide, with an alcohol of formula IV an inert solvent such as CH$_2$Cl$_2$, MeCN or THF at 25° C. to 150° C., preferably 25° C. to 100° C. for between 0.5 h and 24 h.

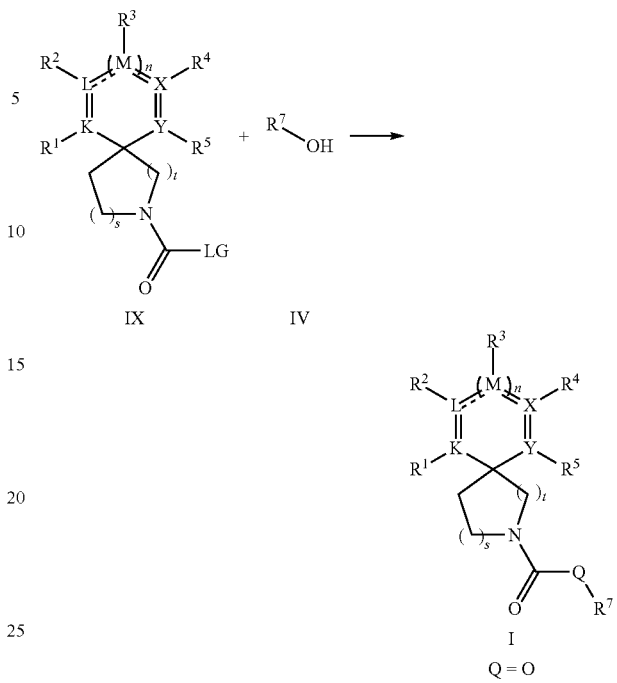

Q = O

In the sixth process of the invention, a compound of Formula I or I* is prepared by derivatizing compound of Formula I or I* that has a reactive site such as an amine or carboxylic acid. Examples of the sixth process include the following:

a) reaction of a compound of Formula I or I* wherein X=N and R$^4$=H with an acid chloride of Formula X in an inert solvent such as CH$_2$Cl$_2$, toluene or THF in the presence of a soluble organic base such as pyridine or triethylamine or in the presence of an aqueous base (Schotten-Baumann conditions) at −40° C. to 50° C., preferably from −20° C. to 5° C. for between 0.5 h and 30 h, to give a compound of Formula I or I* wherein X=N and R$^4$=COR$^6$:

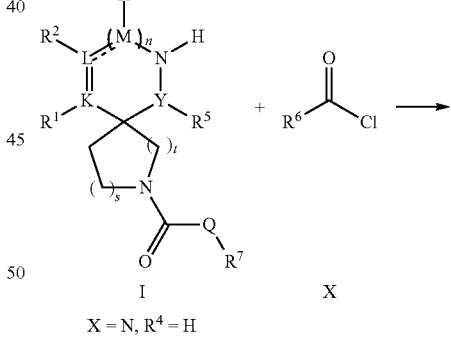

X = N, R$^4$ = H

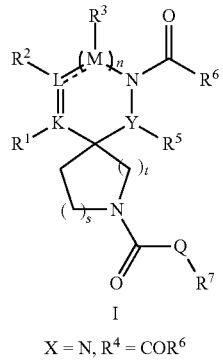

X = N, R$^4$ = COR$^6$ b) reaction of a compound of Formula I or I* wherein X=N and $R^4$=H with a sulfonyl chloride of Formula XI in an inert solvent such as $CH_2Cl_2$ or THF in the presence of an amine base such as pyridine or DMAP at 0° C. to 125° C., preferably 20° C. to 100° C., to give a compound of formula I or I* wherein X=N and $R^4$=$SO_2R^6$:

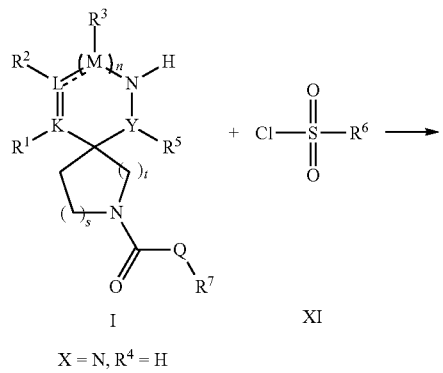

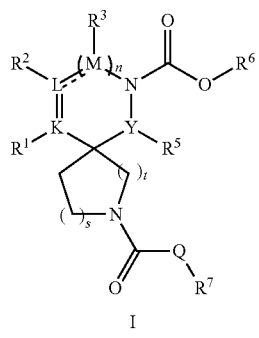

c) reaction of a compound of Formula I or I* wherein X=N and $R^4$=H with a chloroformate of Formula XII in the presence of an organic or inorganic base, for example N,N-diisopropylethylamine or $K_2CO_3$, in an inert solvent such as $CH_2Cl_2$, MeCN or THF at −20° C. to 80° C., preferably 0° C. to 25° C. for between 0.5 h and 24 h to give a compound of formula I or I* wherein X=N and $R^4$=$CO_2R^6$:

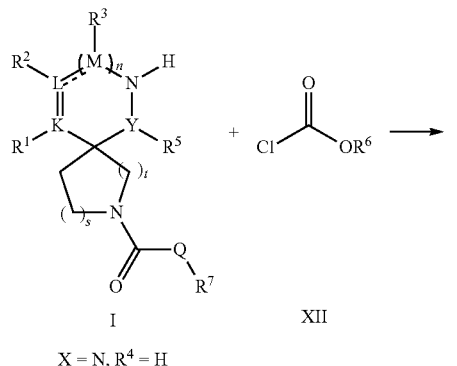

-continued d) reaction of a compound of Formula I or I* wherein X=C and $R^4$=$ACO_2H$ with an alcohol of Formula XIII in the presence of an acid such as anhydrous HCl gas at 0° C. to 25° C. for between 0.5 h and 24 h, to give a compounds of formula I or I* wherein X=C and $R^4$=$ACO_2R^6$:

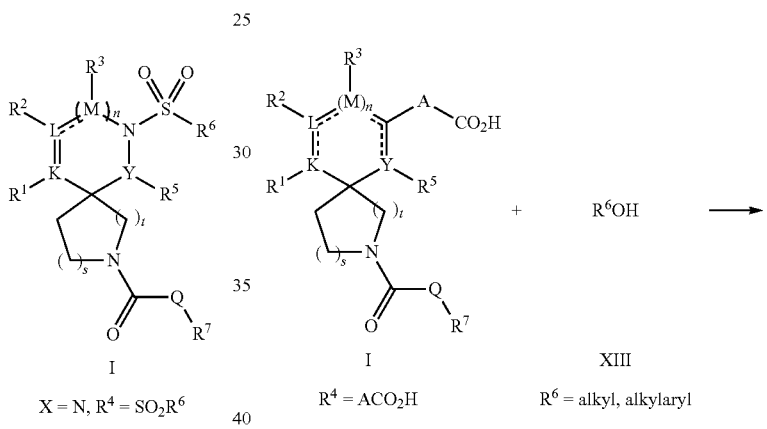

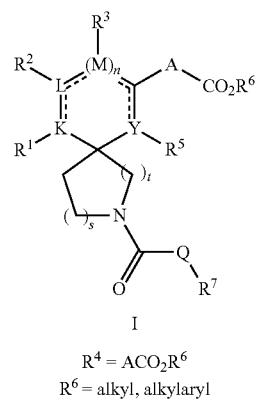

e) reaction of a compound of Formula I or I* wherein X=CH and $R^4$=$ACO_2H$ with an amine of Formula XIV in the presence of a peptide bond forming reagent such as EDC/HOBt, PyBOP or HATU in $CH_2Cl_2$ or DMF at 0° C. to 40° C. for between 0.5 h and 24 h to give a compound of formula I or I* wherein X=CH and $R^4$=$ACON(R^6)_2$:

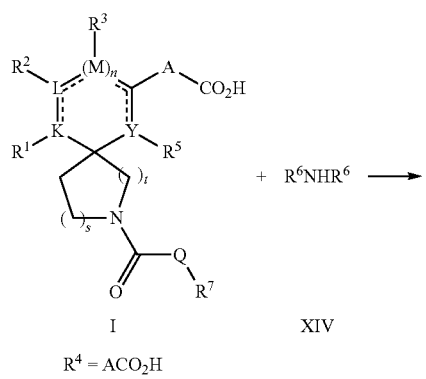

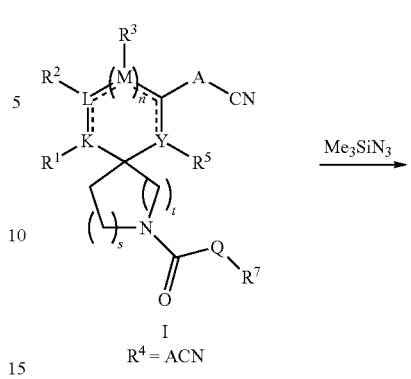

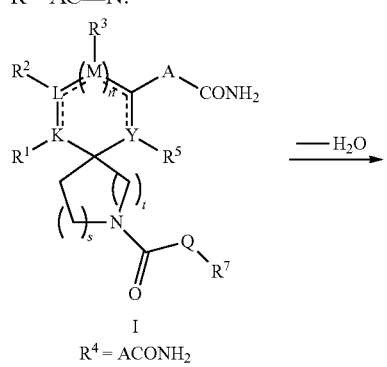

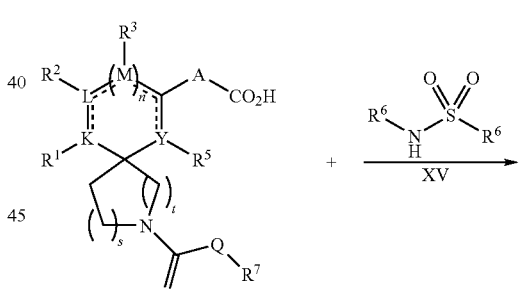

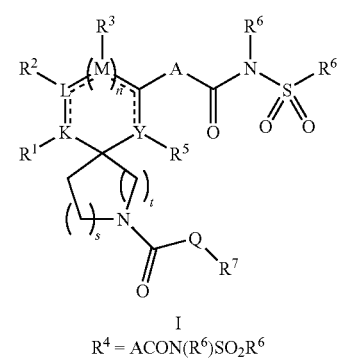

f) reaction of a compound of formula I or I* wherein X=C and $R^4$=ACONH$_2$ with a dehydrating agent such as trifluoroacetic anhydride or POCl$_3$ in the presence of pyridine or 2,6-lutidine in CH$_2$Cl$_2$ or THF at $-70°$ C. to $25°$ C. for 0.5 h give a compound of formula I or I* wherein X=C and $R^4$=AC≡N:

g) reaction of a compound of Formula I or I* wherein X=C and $R^4$=AC≡N with azidotrimethylsilane in toluene or xylenes in the presence of (Bu$_3$Sn)$_2$O at $80°$ C. to $175°$ C. for between 0.5 h and 24 h to give a compound of formula I or I* wherein X=C and $R^4$=A-(5-tetrazolyl):

h) reaction of a compound of Formula I or I* wherein X=C and $R^4$=ACO$_2$H with a sulfonamide of formula XV in the presence of carbonyl diimidazole in an inert solvent such as CH$_2$Cl$_2$ or THF at $0°$ C. to $50°$ C. to give a compound of Formula I or I* wherein X=C and $R^4$=AC(O)NR$^6$SO$_2$R$^6$:

i) reaction of a compound of Formula I or I* wherein $R^7$ is a bi- or tricycloalkyl group bearing a $CO_2Me$ substituent with an alkali metal hydroxide in a mixture of water and a lower alkanol or THF at 0° C. to 50° C. between 3 h and 24 h to give a compound of Formula I or I* wherein $R^7$ is a bi- or tricycloalkyl group bearing a $CO_2H$ substituent:

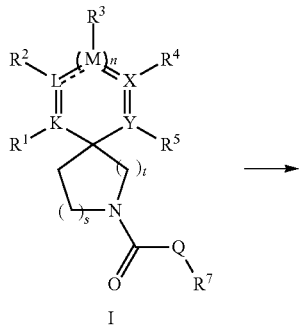

I
$R^7$ = a bi- or tricycloalkyl group substituted with $CO_2Me$

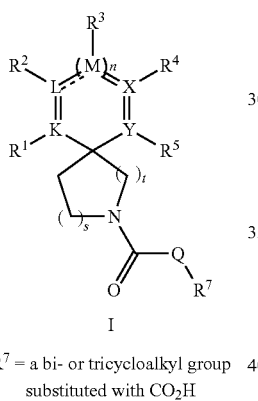

I
$R^7$ = a bi- or tricycloalkyl group substituted with $CO_2H$ j) reaction of a compound of Formula I or I* wherein $R^7$ is a bi- or tricycloalkyl group bearing a $CO_2Me$ substituent with a nucleophilic species such as iodide or a thiol anion to give a compound of Formula I or I* wherein $R^7$ is a bi- or tricycloalkyl group bearing a $CO_2H$ substituent:

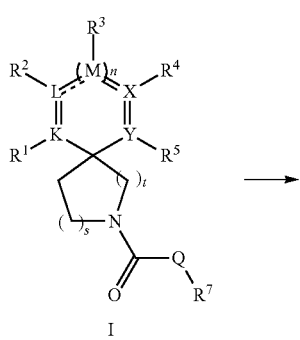

I
$R^7$ = a bi- or tricycloalkyl group substituted with $CO_2Me$

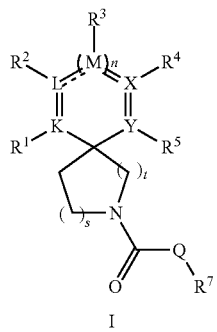

I
$R^7$ = a bi- or tricycloalkyl group substituted with $CO_2H$ k) a two step reaction of a compound of Formula I or I* wherein $R^7$ is a bi- or tricycloalkyl group bearing a $CO_2H$ substituent with thionyl chloride or ox $CH_2Cl_2$ at −20° C. to 80° C. for between 0.5 h and 24 h to convert the $CO_2H$ substituent to an acid chloride substituent followed by treatment with at least one equivalent of ammonia in an inert solvent such as $CH_2Cl_2$ or THF, optionally in the presence of a base such as triethylamime or pyridine, at −20° C. to 40° C. to give a compound of Formula I or I* wherein $R^7$ is a bi- or tricycloalkyl group bearing a $CONH_2$ substituent:

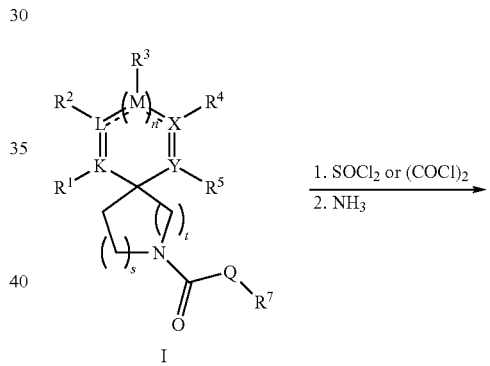

I
$R^7$ = a bi- or tricycloalkyl group substituted with $CO_2H$

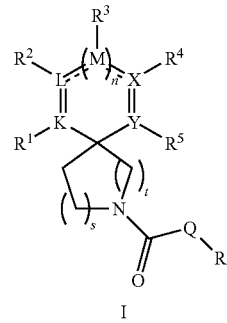

I
$R^7$ = a bi- or tricycloalkyl group substituted with $CONH_2$ l) reaction of a compound of Formula I or I* wherein $R^7$ is a bi- or tricycloalkyl group bearing a $CO_2Me$ substituent with an alkali borohydride in THF at −20° C. to 50° C. for between 1 h and 24 h to give a compound of Formula I or I* wherein $R^7$ is a bi- or tricycloalkyl group bearing a $CH_2OH$ substituent:

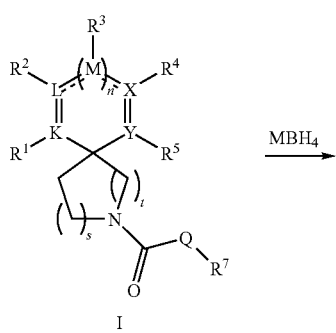

R⁷ = a bi- or tricycloalkyl group substituted with CO₂Me

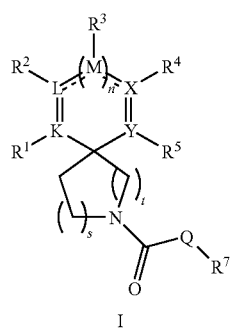

R⁷ = a bi- or tricycloalkyl group substituted with CH₂OH

Purification Methods

Unless otherwise specified, prep HPLC refers to preparative reverse phase HPLC on a C-18 column eluted with a water/acetonitrile gradient containing 0.01% TFA run on a Gilson 215 system.

Analytical Methods

LC-MS Method 1
Column: Chromolith SpeedRod, RP-18e, 50×4.6 mm; Mobil phase: A: 0.01% TFA/water, B: 0.01% TFA/CH₃CN; Flow rate: 1 mL/min; Gradient:

| Time (min) | A % | B % |
|---|---|---|
| 0.0 | 90 | 10 |
| 2.0 | 10 | 90 |
| 2.4 | 10 | 90 |
| 2.5 | 90 | 10 |
| 3.0 | 90 | 10 |

LC-MS Method 2
Column: YMC ODS-AQ, S-5 mm, 12 nm, 50×2.0 mm ID; Column temperature 40° C.; Mobil phase: A: H₂O+0.1% TFA, B: MeCN+0.05% TFA; Flow rate: 0.8 mL/min; Gradient:

| Time (min) | A % | B % |
|---|---|---|
| 0.00 | 100 | 0 |
| 0.4 | 100 | 0 |
| 2.00 | 40 | 60 |
| 2.50 | 40 | 60 |
| 2.51 | 100 | 0 |
| 4.00 | 100 | 0 |

LC-MS (16 min) Method 3
Column: Chromolith SpeedRod, RP-18e, 50×4.6 mm; Mobil phase: A: 0.01% TFA/water, 0.01% TFA/CH₃CN; Flow rate: 1 mL/min; Gradient:

| Time (min) | A % | B % |
|---|---|---|
| 0.0 | 90 | 10 |
| 14.0 | 10 | 90 |
| 15.0 | 10 | 90 |
| 15.1 | 90 | 10 |
| 16.0 | 90 | 10 |

Method 4 (10-80)

| Column | YMC-PACK ODS-AQ, 50 × 2.0 mm 5 μm | |
|---|---|---|
| Mobile Phase | A: water (4 L) + TFA (1.5 mL)) | |
| | B: acetonitrile (4 L) + TFA (0.75 mL)) | |
| | TIME (min) A % B % | |
| | 0 90 10 | |
| | 2.2 20 80 | |
| | 2.5 20 80 | |
| Flow Rate | 1 mL/min | |
| Wavelength | UV 220 nm | |
| Oven Temp | 50° C. | |
| MS ionization | ESI | |

Method 5 (30-90)

| Column | YMC-PACK ODS-AQ, 50 × 2.0 mm 5 μm | |
|---|---|---|
| Mobile Phase | A: water (4 L) + TFA (1.5 mL)) | |
| | B: acetonitrile (4 L) + TFA (0.75 mL)) | |
| | TIME (min) A % B % | |
| | 0 70 30 | |
| | 2.2 10 90 | |
| | 2.5 10 90 | |
| Flow Rate | 1 mL/min | |
| Wavelength | UV220 | |
| Oven Temp | 50° C. | |
| MS ionization | ESI | |

Method 6 (50-100)

| Column | Sepax HP 50 × 2.0 mm 5 μm | |
|---|---|---|
| Mobile Phase | A: water (4 L) + TFA (1.5 mL)) | |
| | B: acetonitrile (4 L) + TFA (0.75 mL)) | |
| | TIME (min) A % B % | |
| | 0 50 50 | |
| | 2.2 0 100 | |
| | 2.48 0 100 | |
| Flow Rate | 1 ml/min | |
| Wavelength | UV220 | |
| Oven Temp | 50° C. | |
| MS ionization | ESI | |

Synthetic Preparations

Preparation 1

2-Adamantyl Isocyanate

A vigorously stirred mixture of 2-aminoadamantane hydrochloride (5.01 g, 26.7 mmol), CH$_2$Cl$_2$ (50 mL) and satd aq NaHCO$_3$ (50 mL) was cooled in an ice bath. After 15 min, solid triphosgene (2.64 g, 8.9 mmol) was added. The mixture was stirred in the ice bath for 30 min and the layers were separated. The aqueous layer was extracted with CH$_2$Cl$_2$ (100 mL). The combined organic layers were washed with brine (50 mL), dried over MgSO$_4$ and concentrated under reduced pressure to afford the title compound (3.55 g, 75%) as a white solid.

Preparation 2

2-Adamantyl Chloroformate

The title compound was prepared from 2-adamantanol as disclosed in Example 74 (Step (a)) of U.S. Pat. No. 5,270,302, which is hereby incorporated by reference.

Preparation 3

1-Methoxycarbonyl-4-adamantyl chloroformate

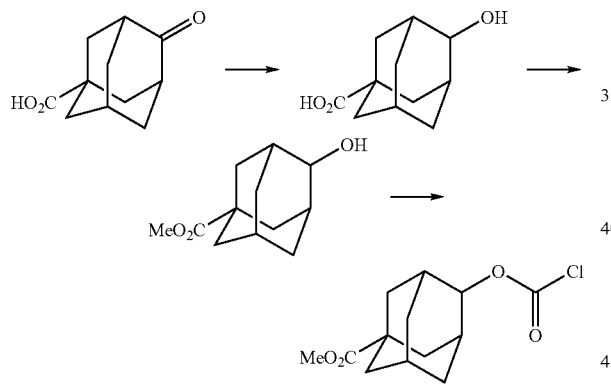

Step 1

A stirred solution of 4-oxoadamantane-1-carboxylic acid (4.42 g, 22.8 mmol) in MeOH (100 mL) was cooled in an ice bath and NaBH$_4$ tablets (4×1 g, 106 mmol) were added at 15 min intervals. The ice bath was allowed to melt and the mixture was stirred overnight at rt and concentrated under reduced pressure. The residue was diluted with 5% aq HCl (100 mL) and extracted with ether (2×125 mL). The combined ether extracts were dried over MgSO$_4$ and concentrated to give 4-hydroxyadamantane-1-carboxylic acid (4.47 g, quant) as an off-white solid which was used directly.

Step 2

To a stirred solution of 4-hydroxyadamantane-1-carboxylic acid (4.47 g, 22.8 mmol) in MeOH (75 mL) was added 4 M HCl in dioxane (25 mL, 100 mmol). The mixture was stirred at rt for 2 d and concentrated. The residue was purified by chromatography on a 40-g silica cartridge eluted with a 0-80% EtOAc in hexanes gradient to afford methyl 4-hydroxyadamantane-1-carboxylate (4.04 g, 84%) as a clear, colorless oil.

Step 3

A stirred solution of methyl 4-hydroxyadamantane-1-carboxylate (1.01 g, 4.8 mmol) and pyridine (0.38 mL, 4.8 mmol) in CH$_2$Cl$_2$ (25 mL) was cooled in an ice bath and a solution of triphosgene (0.48 g, 1.6 mmol) in CH$_2$Cl$_2$ (10 mL) was added dropwise over 15 min. The mixture ice bath was allowed to melt and the mixture was stirred for 3 h. The mixture was evaporated to dryness and the residue was triturated with EtOAc (100 mL). The filtrate was concentrated to afford 1-methoxycarbonyl-4-adamantyl chloroformate (1.19 g, 91%) as an oil which solidified on standing.

Preparation 4

Spiro[indene-2,3'-piperidin]-1(3H)-one

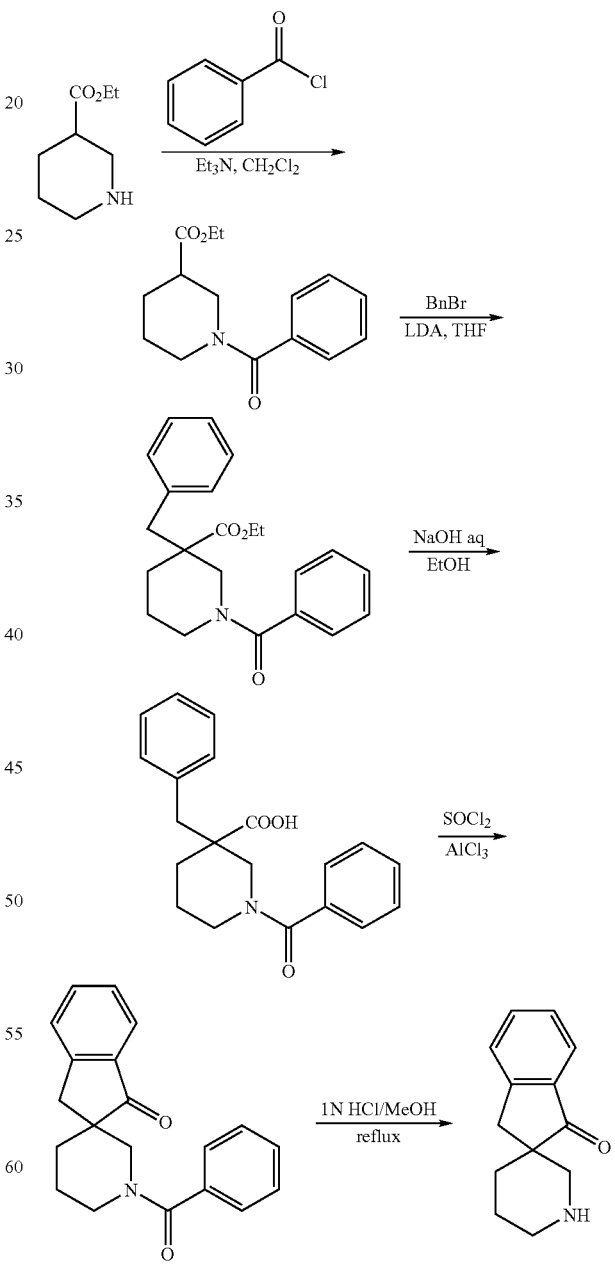

Step 1

To a solution of ethyl piperidine-3-carboxylate (67.74 g, 266 mmol) in dry CH$_2$Cl$_2$ (300 mL) was added TEA (40.34 g, 399 mmol) at 0° C. Benzoyl chloride (41.13 g, 293 mmol) was added slowly to control any rise in reaction temperature. After addition was complete, the mixture was stirred at rt overnight. The mixture was washed with 1N aq HCl and brine. The organic layer was dried with anhydrous $Na_2SO_4$ and concentrated to leave a residue, which was purified by silica gel column chromatography (petroleum/ethyl acetate 5:1 to 3:1) to afford ethyl 1-benzoylpiperidine-3-carboxylate (62.63 g, 90%). $^1$H NMR ($CD_3OD$, 400 $MH_z$): δ=1.41 (t, 3H), 1.52 (m, 2H), 1.85 (m, 2H), 2.36 (s, 1H), 3.29 (m, 2H), 3.81 (m, 4H), 7.22 (m, 3H), 7.42 (m, 2H).

Step 2

To a solution of ethyl 1-benzoylpiperidine-3-carboxylate (9.22 g, 35 mmol) in dry THF (55 mL) at −78° C. was added dropwise LDA (39 mmol, 1.1 eq) in 45 mL of dry THF. After addition, the reaction was stirred for 1 h. Then benzyl bromide (6.54 g, 39 mmol, 1.1 eq) was added dropwise under the an atmosphere of N2. The reaction was stirred for another 3 h. The solution was added dropwise 5% HCl at 0° C. and concentrated. The aqueous residue was extracted with $CH_2Cl_2$. The combined organic extracts were dried over anhydrous $Na_2SO_4$ and evaporated to afford ethyl 1-benzoyl-3-benzylpiperidine-3-carboxylate (11.16 g, 91%). $^1$H NMR ($CD_3OD$, 400 $MH_z$): δ=1.30 (t, 3H), 1.50~1.55 (m, H), 2.75 (m, 2H), 3.65 (m, 4H), 4.09 (m, 2H), 7.08 (m, 2H), 7.22 (m, 3H), 7.48 (m, 5H).

Step 3.

Ethyl 1-benzoyl-3-benzylpiperidine-3-carboxylate (6.308 g; 18 mmol) was hydrolyzed with 1 N aq NaOH (220 mL) in ethanol (110 mL) for 20 h at rt. The ethanol was removed by rotary evaporation and the aqueous layer was extracted once with $CH_2Cl_2$. The pH of the aqueous layer was adjusted to pH=3-4 with 1 N aq HCl and extracted with $CH_2Cl_2$ (3×). The organic phase was dried over anhydrous $Na_2SO_4$, filtered and evaporated to give 1-benzoyl-3-benzylpiperidine-3-carboxylic acid (3.24 g, 55.7%). $^1$H NMR ($CD_3OD$, 400 $MH_z$): δ=1.12 (m, 3H), 1.50~1.72 (m, 4H), 2.18 (m, 1H), 2.75 (d, 1H), 3.05 (m, 1H), 3.16 (m, 1H), 4.08 (m, 2H), 7.08 (m, 2H), 7.22 (m, 3H), 7.48 (m, 5H).

Step 4

A mixture of 1-benzoyl-3-benzyl-piperidine-3-carboxylic acid (6.71 g, 20.7 mmol) and thionyl chloride (2.70 g, 22.77 mmol) in dry $CH_2Cl_2$ (25 mL) was heated to reflux for 30 min. The resulting solution was concentrated in vacuum to give alight brown oil. A solution of this oil in dry $CH_2Cl_2$ (25 mL) was added dropwise to a mixture of $AlCl_3$ (3.59 g, 26.91 mmol) in $CH_2Cl_2$ (10 mL) at 0° C. The mixture was stirred for 15 min at 0° C. and then heated to reflux for 45 min. The mixture was cooled and poured onto crushed ice and 12 N aq HCl. The organic layer was separated, washed with 3 N aq HCl, saturated $Na_2CO_3$, water and brine. Finally the organic layer was concentrated to give a residue, which was purified by silica gel column chromatography (petroleum/ethyl acetate 5:1 to 1:1) to afford 1'-benzoylspiro[indene-2,3'-piperidin]-1(3H)-one (3.24 g, 51%). $^1$H NMR ($CD_3OD$, 400 MHz): δ=1.61 (m, 4H), 2.68 (m, 2H), 3.46 (m, 4H), 7.34 (m, 8H), 7.64 (m, 2H).

Step 5

1'-benzoylspiro[indene-2,3'-piperidin]-1(3H)-one (2.476 g, 8.11 mmol) was dissolved in methanol (40 mL). 1 N aq HCl (80 mL) was added dropwise and the mixture was refluxed overnight. The methanol was removed in vacuo. The pH of the solution was adjusted to 8 using saturated $Na_2CO_3$, and the solution was extracted with $CH_2Cl_2$. The combined organic extracts were dried over anhydrous $Na_2SO_4$ and then concentrated to afford a residue, which was purified by silica gel column chromatography to afford spiro[indene-2,3'-piperidin]-1(3H)-one (460 mg, 28%). $^1$H NMR ($CD_3OD$, 400 $MH_z$): δ=1.63 (m, 2H), 1.82 (m, 1H), 1.87-2.00 (m, 1H), 2.70 (d, 1H), 2.82 (m, 1H), 3.00 (m, 3H), 3.20 (d, 1H), 7.32 (m, 1H), 7.45 (m, 1H), 7.57 (m, 1H), 7.79 (m, 1H).

Preparation 5

Ethyl 2-(7-bromo-2,3-dihydrospiro[indene-1,4'-piperidine]-3-yl)propanoate

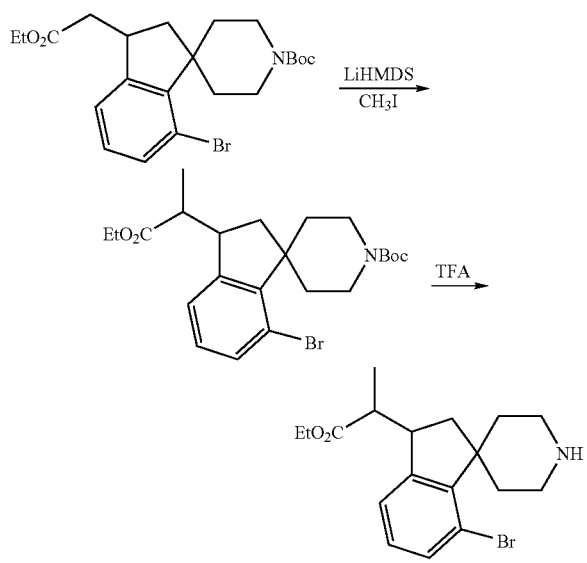

Step 1

To a solution of tert-butyl 7-bromo-3-(2-ethoxy-2-oxoethyl)-2,3, dihydrospiro[indene-1,4'-piperidine]-1'-carboxylate (500 mg, 1.11 mmol) was added LiHMDS (2.4 mL, 1 M, 2.4 mmol) at −10° C. under nitrogen. The mixture was stirred for 1 h and $CH_3I$ (472 mg, 3.3 mmol) was added. After addition, the mixture was stirred overnight. The solution was quenched with satd aq $NH_4Cl$, the organic phase was separated, dried and concentrated to give crude product which was purified by preparative TLC to give tert-butyl 7-bromo-3-(1-ethoxy-1-oxopropan-2-yl)-2,3-dihydrospiro[indene-1,4'-piperidine]-1'-carboxylate (60 mg, 11%). $^1$H NMR: (400 MHz, $CDCl_3$): δ=0.96 (d, 3H), 1.23 (t, 3H), 1.28 (m, 1H), 1.41 (s, 9H), 1.62 (m, 1H), 2.32 (m, 2H), 2.73 (m, 3H), 3.08 (m, 1H), 3.61 (m, 1H), 4.07 (d, 2H), 4.12 (q, 2H), 6.94 (m, 2H), 7.28 (m, 1H).

Step 2

Tert-butyl 7-bromo-3-(1-ethoxy-1-oxopropan-2-yl)-2,3-dihydrospiro[indene-1,4'-piperidine]-1'-carboxylate (300 mg, 0.645 mol) was dissolved in 20% TFA at 0° C. The reaction mixture was stirred for 1' h at rt. The solvent was removed under reduced pressure to give ethyl 2-(7-bromo-2,3-dihydrospiro[indene-1,4'-piperidine]-3-yl)propanoate (235 mg, 100%). $^1$H NMR: (400 MHz, $CDCl_3$): δ=0.98 (d, 3H), 1.23 (t, 3H), 1.61-1.73 (m, 4H), 2.42 (m, 2H), 2.73 (m, 1H), 3.01 (m, 1H), 3.23 (m, 3H), 3.48 (m, 3H), 3.68 (d, 1H), 4.21 (q, 2H), 7.03 (m, 2H), 7.38 (d, 1H).

Preparation 6

Ethyl 2-(7-bromo-2,3-dihydrospiro[indene-1,4'-piperidine]-3-yl)-2-methylpropanoate

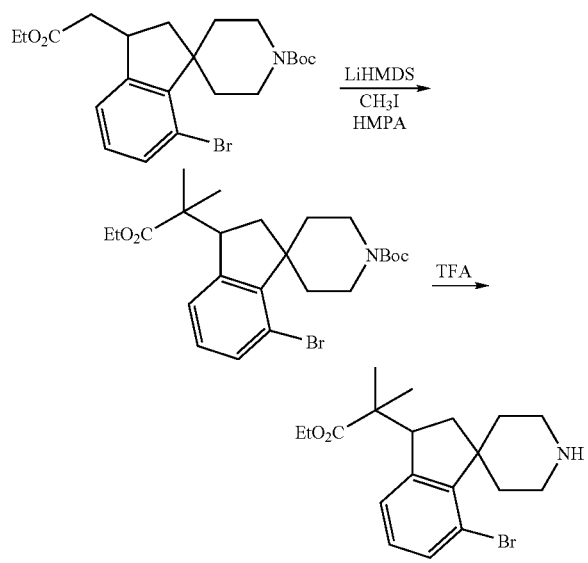

Step 1

To a solution of tert-butyl 7-bromo-3-(2-ethoxy-2-oxoethyl)-2,3-dihydrospiro[indene-1,4'-piperidine]-1'-carboxylate (500 mg, 1.11 mmol) was added LiHMDS (2.4 mL, 1 M, 2.4 mmol) followed by HMPA at −10° C. under $N_2$. The mixture was stirred for 1 h and $CH_3I$ (142 mg, 8.8 mmol) was added to the solution. After addition, the mixture was stirred overnight. The solution was quenched by saturated $NH_4Cl$, the organic phase was separated, dried and concentrated to give the crude product which was purified by preparative TLC to give (±)-tert-butyl 7-bromo-3-(1-ethoxy-2-methyl-1-oxopropan-2-yl)-2,3-dihydrospiro[indene-1,4'-piperidine]-1'-carboxylate (350 mg, 67%). $^1H$ NMR: (400 MHz, $CDCl_3$): δ=1.12 (s, 3H), 1.26 (s, 3H), 1.30 (m, 3H), 1.32 (m, 2H), 1.48 (s, 9H), 2.29 (m, 1H), 2.42 (m, 1H), 2.93 (m, 3H), 3.16 (m, 1H), 3.78 (m, 1H), 4.16 (m, 2H), 4.25 (m, 2H), 6.94 (d, 1H) 7:02 (t, 1H) 7.37 (d, 1H).

Step 2

(±)-Tert-butyl 7-bromo-3-(1-ethoxy-2-methyl-1-oxopropan-2-yl)-2,3-dihydrospiro[indene-1,4'-piperidine]-1'-carboxylate (152 mg, 0.317 mol) was dissolved in 20% TFA at 0° C. The mixture was stirred for 1 h at rt. The solvent was removed under reduced pressure to give (±)-ethyl 2-(7-bromo-2,3-dihydrospiro[indene-1,4'-piperidine]-3-yl)-2-methylpropanoate which was used without purification (120 mg, 100%).

Preparation 7

4-aminoadamantan-1-ol

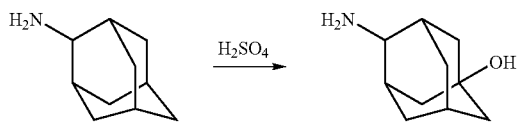

To 2-aminoadamantane (10 g, 54 mmol) was added $H_2SO_4$ (150 mL) and $HNO_3$ (15 ml) at 0° C. and the mixture was stirred overnight. The mixture was poured onto ice and adjusted to pH=10-11 using 40% aq NaOH under ice bath. The mixture was extracted with $CH_2Cl_2$. The organic layer was dried, filtered and concentrated to give 4-aminoadamantan-1-ol (3.0 g, 14%).

Preparation 8

1-fluoro-4-aminoadamantane

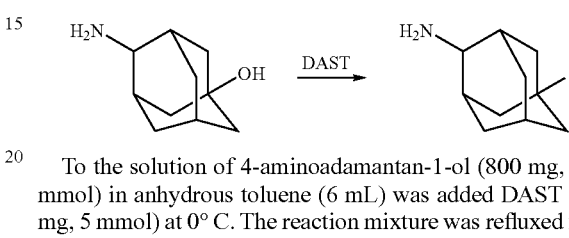

To the solution of 4-aminoadamantan-1-ol (800 mg, 4.79 mmol) in anhydrous toluene (6 mL) was added DAST (780 mg, 5 mmol) at 0° C. The reaction mixture was refluxed for 8 h. The mixture was cooled to rt and quenched with aq $NaHCO_3$. The mixture was concentrated and extracted with $CH_2Cl_2$ (2×). The combined organic extracts were dried, filtered and concentrated to give 1-fluoro-4-aminoadamantane (700 mg), which was used without purification.

Preparation 9

1,7-dihydroxy-4-aminoadamantane

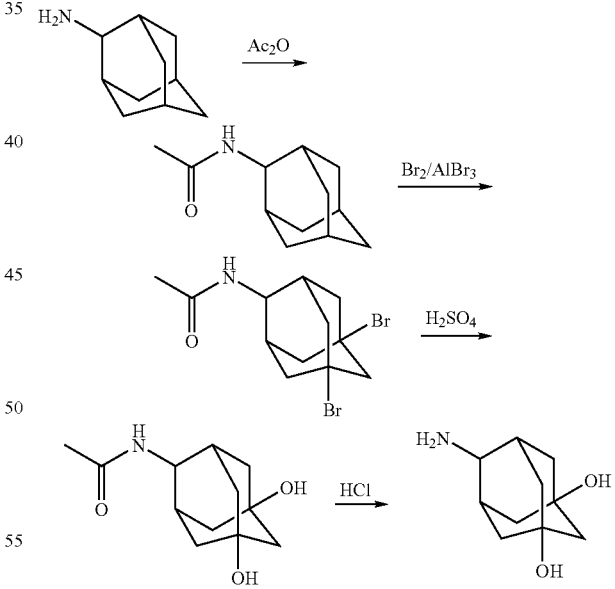

Step 1

A solution of 2-aminoadamantane (20 g, 108 mmol) in dry pyridine (120 mL) was treated with acetic anhydride (12 mL, 128 mmol) and stirred overnight at rt. The mixture was dilute with EtOAc and washed with water, 1 N aq phosphoric acid and brine. The organic layer was dried, filtered and concentrated to give N-(2-adamantyl)acetamide (12.5 g, 60%). $^1H$ NMR (400 MHz, $CDCl_3$): δ=1.57 (m, 2H), 1.67 (m, 3H), 1.72 (m, 1H), 1.77 (m, 6H), 1.85 (m, 2H), 1.94 (s, 3H), 3.97 (t, 1H), 5.78 (br, 1H).

Step 2

To bromine (20 mL, 40 mmol) and aluminum bromide (3.2 g, 20 mmol) was added N-(2-adamantyl)acetamide (4 g, 20 mmol) in portions. The reaction mixture was heated to 90° C. and stirred overnight. The mixture was cooled to rt and poured into ice/water. Satd aq sodium bisulfite was added slowly followed by dilution with $CH_2Cl_2$. The organic layer was separated, washed with brine, dried, filtered and concentrated. The crude product was purified by column chromatography to afford N-(5,7-dibromo-2-adamantyl)acetamide (1.98 g, 28%).

Step 3

To N-(5,7-dibromo-2-adamantyl)acetamide (2 g, 5.73 mmol) and $Ag_2SO_4$ (3.90 g, 12.6 mmol) was slowly added concentrated $H_2SO_4$ (14 mL). After addition was complete, the reaction mixture was heated to 80° C. for 3 h. The mixture was cooled to rt and poured into ice/water. The mixture was filtered, and the filtrate was neutralized with solid KOH. The mixture was filtered, and the solids were washed with methanol. The filtrate was concentrated, and the residue was triturated with methanol. The mixture was filtered, and filtrate was concentrated. The crude product was purified by preparative TLC (DCM/MeOH=5:1) to give N-(5,7-dihydroxy-2-adamantyl)acetamide (192 mg, 15%). $^1$H-NMR (400 MHz, DMSO): δ=1.21 (m, 2H), 1.42 (m, 6H), 1.74 (m, 2H), 1.77 (m, 3H), 1.96 (m, 2H), 4.48 (d, 1H), 7.65 (m, 1H).

Step 4

To N-(5,7-dihydroxy-2-adamantyl)acetamide (110 mg, 0.489 mmol) was added 4N aq HCl (3 mL) slowly. The reaction mixture was heated to 80° C. overnight. The mixture was cooled to rt and concentrated. The residue was treated with satd aq $NaHCO_3$. The water was removed under reduced pressure, and the solid was triturated with methanol. The mixture was filtered, and the solids were washed with methanol. The filtrate was concentrated give to 6-aminoadamantane-1,3-diol (50 mg, 56%). $^1$H-NMR (400 MHz, $D_2O$): δ=1.45 (m, 2H), 1.63 (m, 6H), 1.73 (m, 4H), 2.12 (m, 2H), 3.27 (m, 1H).

Preparation 10

7-chloro-2-(4-methoxybenzyl)spiro[isoindoline-1,4'-piperidine]-3-thione

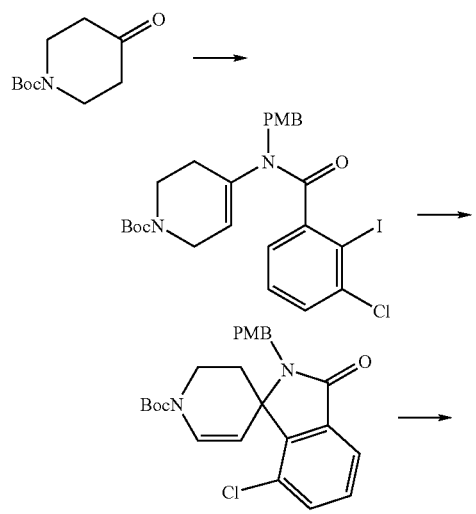

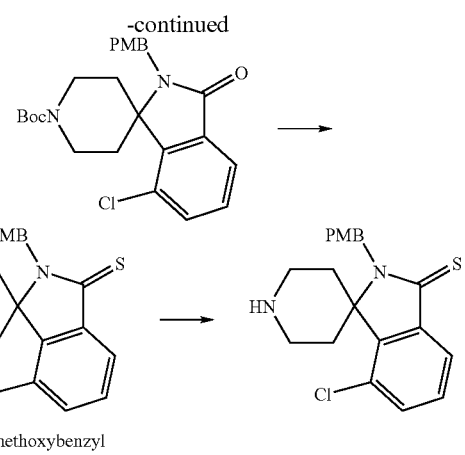

PMB = 4-methoxybenzyl

Step 1

A 100-mL flask was charged with 3-chloro-2-iodobenzoic (2.43 g, 8.64 mmol, 0.90 equiv) and thionyl chloride (15 mL). The solution was vigorously stirred, then 1 drop of DMF added and the mixture heated to reflux for 4 h. During this time the acid dissolved to give a pale yellow solution. The cooled mixture was evaporated and toluene (50 mL) added, then removed in vacuo. The evaporation/dissolution with toluene/evaporation procedure was repeated twice and the pale yellow 3-chloro-2-iodobenzoyl chloride was placed on the vacuum line.

In a separate flask a toluene (30 mL) solution tert-butyl 4-oxopiperidine-1-carboxylate (2.45 g, 12.32 mmol, 1.25 equiv), 4-methoxybenzylamine (1.352 g, 9.6 mmol, 1.0 equiv) and $MgSO_4$ (~20 g) were heated to reflux overnight. The mixture was filtered through a bed of Celite, the cake was washed with toluene (~30 mL) and the filtrate was evaporated. The amber residue was dissolved in $CH_2Cl_2$ (100 mL) and TEA (1.94 g, 2.7 mL, 19.2 mmol, 2.0 equiv) and DMAP (117 mg, 0.96 mmol, 0.1 equiv) were added. The 3-chloro-2-iodobenzoyl chloride prepared above was dissolved in $CH_2Cl_2$ (10 mL) and the resultant solution added to the enamine solution over a ~10 min period, then stirred overnight. The reaction was quenched by addition of 1.0 M aq HCl (100 mL) and the mixture was transferred to a separatory funnel. The organic layer was washed with brine, dried over $Na_2SO_4$, filtered, and evaporated. The residue was purified by flash chromatography on silica gel (120 g) eluting with 19-71% EtOAc in hexanes tert-butyl 4-(3-chloro-2-iodo-N-(4-methoxybenzyl)benzamido)-5,6-dihydropyridine-1(2H)-carboxylate (~3.19 g, ~5.47 mmol, ~63% yield), contaminated with ~5% 3-chloro-2-iodo-N-(4-methoxylbenzyl)benzamide, was isolated as a pale yellow foam.

Step 2

Tert-butyl 4-(3-chloro-2-iodo-N-(4-methoxybenzyl)benzamido)-5,6-dihydropyridine-1(2H)-carboxylate (~3.19 g, ~5.47 mmol) was dissolved in DMF (30 mL) in a three neck flask fitted with a condenser and the mixture was purged with $N_2$ gas for ~1 h. Against a counterflow of $N_2$ the flask was quickly opened and $Pd(OAc)_2$ (61 mg, 0.274 mmol, 5 mol %), rac-BINAP (340 mg, 0.548 mmol, 10 mol %), DIEA (1.56 g, 2.1 mL, 11.0 mmol, 2.0 equiv) and $Et_4NCl$ (980 mg, 5.47 mmol, 1.0 equiv) were added. The mixture was heated to reflux for 17 h. After this time, the iodide had been consumed and the mixture was cooled to rt and evaporated. The residue was taken up in $EtOAc/H_2O$ and the layers were separated. The organic layer was washed with brine, dried over $Na_2SO_4$, and evaporated. The crude product was purified by flash chromatography on silica gel, eluting with 20-80% EtOAc in hexanes tert-butyl 7-chloro-2-(4-methoxybenzyl)-3-oxo-2',3'-dihydro-1'H-spiro[isoindoline-1,4'-pyridine]-1'-carboxylate was isolated as a pale yellow foam (1.72 g, 69%).

Step 3

Tert-butyl 7-chloro-2-(4-methoxybenzyl)-3-oxo-2',3'-dihydro-1'H-spiro[isoindoline-1,4'-pyridine]-1'-carboxylate (1.69 g, 3.71 mmol, 1.0 equiv) and PtO₂ (100 mg, 0.440 mmol, 12 mol %) were added to a solution of 1:1 4.0 M HCl:MeCN (200 mL). The mixture was transferred to a Parr hydrogenation vessel and hydrogenated at 55 psi for 3 d. After this time the vessel was vented and the pale yellow solution filtered through a bed of Celite. The mixture was evaporated and the residue was dissolved in 1:1 MeCN:10% aq K₂CO₃ (200 mL); Boc₂O (1.21 g, 5.56 mmol, 1.5 equiv) was added and the mixture was stirred for 17 h. After this time the solution was evaporated and the residue was diluted with EtOAc. The organic layer was washed with 1.0 M aq HCl and brine, dried over Na₂SO₄, and evaporated. The reduced product was purified by flash chromatography on silica gel, eluting with 20-80% EtOAc in hexanes. Tert-butyl 7-chloro-2-(4-methoxybenzyl)-3-oxospiro[isoindoline-1,4'-piperidine]-1'-carboxylate was isolated as a pale yellow foam (0.702 g, 1.54 mmol, 42%).

Step 4

Tert-butyl 7-chloro-2-(4-methoxybenzyl)-3-oxospiro[isoindoline-1,4'-piperidine]-1'-carboxylate (50 mg, 0.110 mmol, 1.0 equiv) and Lawesson's reagent (220 mg, 0.55 mmol, 5.0 equiv) were added to toluene (10 mL) and the mixture heated to 80° C. for 17 h. The mixture was cooled to rt and filtered through a plug of Celite. The filtrate was evaporated and the residue purified by flash chromatography on silica (4 g, eluting with 19-71% EtOAc in hexanes tert-butyl 7-chloro-2-(4-methoxybenzyl)-3-thioxospiro[isoindoline-1,4'-piperidine]-1'-carboxylate (52 mg, 0.11 mmol, >99% yield) was isolated as a pale yellow solid.

Step 5

Tert-butyl 7-chloro-2-(4-methoxybenzyl)-3-thioxospiro[isoindoline-1,4'-piperidine]-1'-carboxylate (52 mg, 0.11 mmol) was dissolved in neat TFA (~2 mL): After 0.5 h LC-MS showed removal of the boc group. The mixture was evaporated to afford crude 7-chloro-2-(4-methoxybenzyl) spiro[isoindoline-1,4'-piperidine]-3-thione as its TFA salt which was used without purification.

7-chloro-2-methylspiro[isoindoline-1,4'-piperidine]-3-thione was prepared following procedures analogous to those described in Preparation 10 using methylamine in Step 1 in place of 4-methoxybenzylamine.

2-methylspiro[isoindoline-1,4'-piperidine]-3-thione was prepared following procedures analogous to those described in Preparation 10 using 2-iodobenzoyl chloride in place of 3-chloro-2-iodobenzoyl chloride and methylamine in place of 4-methoxybenzylamine in Step 1.

Preparation 11

Spiro[isoindoline-1,4'-piperidine]-3-thione

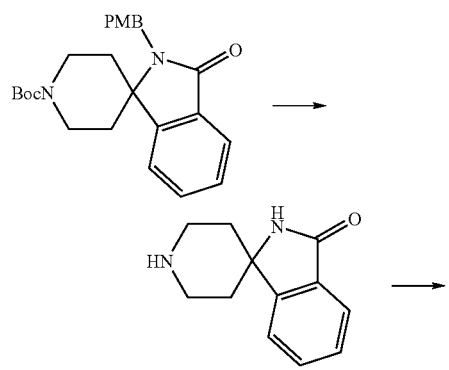

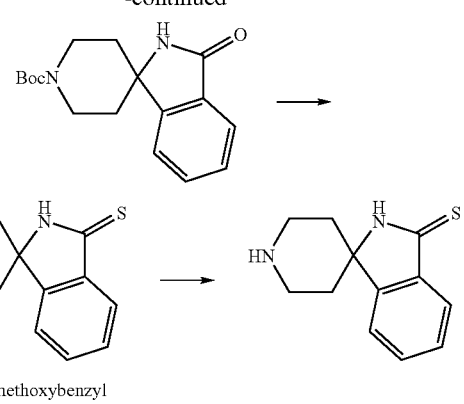

PMB = 4-methoxybenzyl

Step 1

Tert-butyl 2-(4-methoxybenzyl)-3-oxospiro[isoindoline-1,4'-piperidine]-1'-carboxylate (50 mg, 0.12 mmol, 1.0 equiv) and TFA (7 mL) were heated to 75° C. for 19 h. After this time LC-MS showed removal of the Boc- and p-methoxybenzyl groups. The mixture was concentrated to leave crude spiro[isoindoline-1,4'-piperidin]-3-one which was used directly.

Step 2

Crude spiro[isoindoline-1,4'-piperidin]-3-one was dissolved in 1:1 MeCN:10% aq K₂CO₃ (20 mL) and Boc₂O (50 mg, 0.23 mmol, 2.0 equiv) added. The mixture stirred for 3 h. The solution was evaporated and the mixture was diluted with EtOAc. The organic layer was washed with 1.0 M aq HCl and brine, dried over Na₂SO₄, and evaporated. The residue was purified by flash chromatography on silica, eluting with 20-80% EtOAc in hexanes to afford tert-butyl 3-oxospiro[isoindoline-1,4'-piperidine]-1'-carboxylate.

Steps 3 and 4

Tert-butyl 3-oxospiro[isoindoline-1,4'-piperidine]-1'-carboxylate and Lawesson's reagent (~150 mg, ~0.37 mmol, 3 equiv) were dissolved in toluene and heated to reflux overnight. The mixture was evaporated, taken up in CH₂Cl₂, (~10 mL) and filtered through a plug of Celite. The filtrate was treated with TFA (~2 mL). The mixture was stirred for 3 h at rt and evaporated to afford crude spiro[isoindoline-1,4'-piperidine]-3-thione as its TFA salt.

Preparation 12

Tert-butyl 7-chloro-3-hydroxy-3H-spiro[isobenzofuran-1,4'-piperidine]-1'-carboxylate

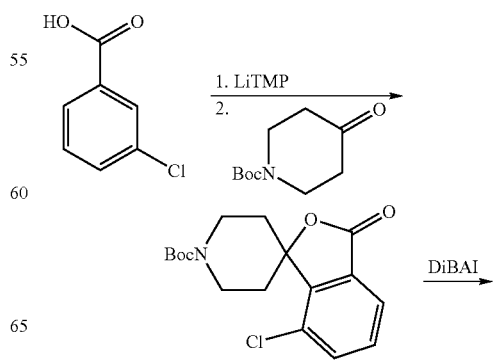

-continued

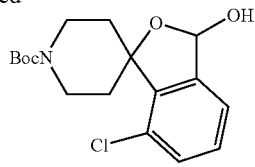

Step 1

2.5 M n-BuLi in hexanes (9.2 mL, 23 mmol) was added To a stirred solution of 2,2,6,6-tetramethylpiperidine (3.2 g, 23 mmol) in anhydrous THF (30 mL) at −20° C. under $N_2$. The mixture was stirred for 1 h. at −20° C. and then cooled to −78° C. 3-Chlorobenzoic acid (1.8 g, 11.5 mmol) in anhydrous THF (20 mL) was slowly added dropwise and the mixture was stirred for 1 h at −78° C. The mixture was treated with tert-butyl 4-oxopiperidine-1-carboxylate (2.29 g, 11.5 mmol) and the resulting solution was warmed to rt and stirred overnight. The mixture was quenched with water and extracted with EtOAc (3×30 mL). The organic layers were combined, washed with brine, dried over $Na_2SO_4$, filtered and concentrated to give the crude product, which was Purified by chromatography to give tert-butyl 7-chloro-3-oxo-3H-spiro[isobenzofuran-1,4'-piperidine]-1'-carboxylate (500 mg, 13%). $^1$H NMR (CD$_3$OD): δ=1.45 (s, 9H), 2.60 (m, 2H), 3.20 (b, 2H), 4.20 (b, 2H), 7.48 (m, 1H), 7.55 (m, 1H), 7.75 (m, 1H).

Step 2.

DIBAL (1 M, 2.4 mL, 2.4 mmol) was added to a solution of tert-butyl-7-chloro-3-oxo-3H-Spiro[isobenzofuran-1,4'-piperidine]-1'-carboxylate (200 ing, 0.6 mmol) in $CH_2Cl_2$ (5 mL) at −78° C. The mixture was stirred at −70° C. for 30 min. After the starting material was consumed, the reaction was quenched with methanol, followed by satd aq potassium sodium tartarate tetrahydrate, and stirred for 1 h. The mixture was filtered and the filtrate was extracted with $CH_2Cl_2$ (3×15 mL). The combined organic layers were dried over $Na_2SO_4$, filtered and concentrated in vacuo to give the crude product, which was purified by preparative TLC to provide tert-butyl 7-chloro-3-hydroxy-3,1-spiro[isobenzofuran-1,4'-piperidine]-1'-carboxylate (160 mg, 78%). $^1$H NMR (CDCl$_3$): δ=1.44 (s, 9H), 1.51 (m, 2H), 1.64 (m, H), 2.30-2.64 (m, 2H), 3.18 (m, 2H), 4.00-4.18 (m, 2H), 6.35-6.56 (m, 1H), 7.06 (m, 1H), 7.27 (m, 2H).

The following examples are intended to illustrate various embodiments of the invention and are not intended in any way to restrict the scope thereof.

EXAMPLES

Example 1

Tert-butyl 1'-((2-adamantyl)carbamoyl)spiro[indoline-3,4'-piperidine]-1-carboxylate

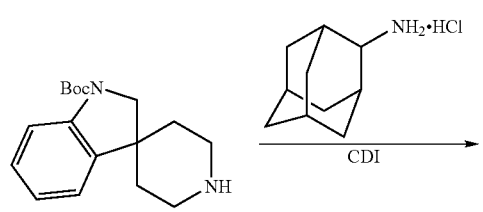

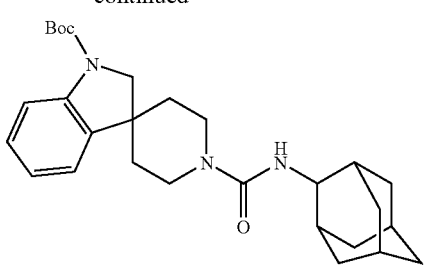

A stirred solution of 2-adamantanamine hydrochloride (81.1 mg, 0.432 mmol) and DIEA (557 mg, 4.32 mmol) in anhydrous $CH_2Cl_2$ (5 mL) was cooled to 0° C. and CDI (84 mg, 0.52 mmol) was added. The mixture was stirred for 1 h at 0° C. and tert-butyl spiro[indoline-3,4'-piperidine]-1-carboxylate (140 mg, 0.43 mmol) in anhydrous $CH_2Cl_2$ (5 mL) was added. The reaction mixture was allowed to warm to rt and stirred overnight. The reaction mixture was concentrated and the residue was purified by preparative TLC to provide tert-butyl 1'-((2-adamantyl)carbamoyl)spiro[indoline-3,4'-piperidine]-1-carboxylate as a white solid (50 mg, 25%). $^1$H NMR (CD$_3$OD, 400 MH$_z$): δ=1.58~2.01 (m, 28H), 2.92 (t, 2H), 3.91 (d, 2H), 4.09 (d, 2H), 5.85 (d, 1H), 6.95~7.85 (m, 4H); MS: 466 (M$^+$+1); LC-MS (4 min) $t_R$=2.70 min, m/z=466.

Example 2

N-(2-Adamantyl)spiro[indoline-3,4'-piperidine]-1'-carboxamide

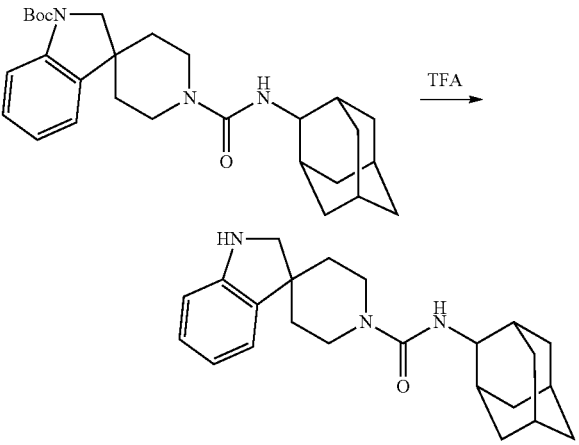

A 10-mL round-bottomed flask was charged with tert-butyl 1'-((2-adamantyl)carbamoyl)spiro[indoline-3,4'-piperidine]-1-carboxylate (50 mg, 0.107 mmol) and 20% trifluoroacetic acid in $CH_2Cl_2$ (2 mL). The mixture was stirred for 1 h at 0° C. The solution was concentrated under vacuum and the crude product was purified by preparative HPLC to provide N-(2-adamantyl)spiro[indoline-3,4'-piperidine]-1'-carboxamide (10 mg, 25%). $^1$H NMR (CD$_3$OD, 400 MH$_z$): δ=1.60~2.00 (m, 18H), 3.00 (t, 2H), 3.86 (d, 3H), 4.08 (d, 2H), 7.40~7.50 (m, 4H); LC-MS (4 min) $t_R$=1.93 min, m/z=366 (M$^+$+1).

Example 3

(±)-2-(1'-((2-Adamantyl)carbamoyl)-2,3-dihydrospiro[indene-1,4'-piperidine]-3-yl)acetic acid

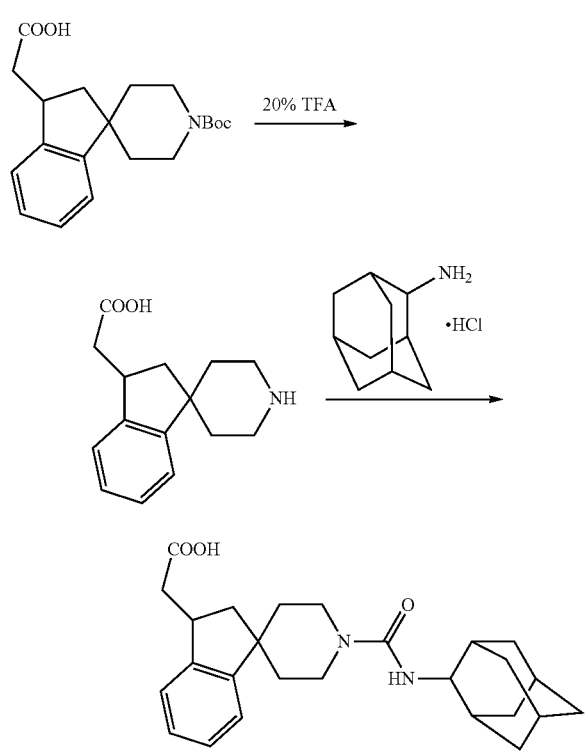

Step 1

2-(1'-(Tert-butoxycarbonyl)-2,3-dihydrospiro[indene-1,4'-piperidine]-3-yl)acetic acid (200 mg, 0.58 mmol) was added to a solution of 20% trifluoroacetic acid in anhydrous CH$_2$Cl$_2$ (3 mL) at 0° C. The reaction solution was stirred at rt for 2 h until the starting material had been consumed. The solution was concentrated to give crude 2-(2,3-dihydrospiro[indene-1,4'-piperidine]-3-yl)acetic acid (160 mg) which was used in the next step without further purification.

Step 2

To a solution of 2-aminoadamantane hydrochloride (120 mg, 0.64 mmol) and CDI (141 mg, 0.87 mmol) in anhydrous CH$_2$Cl$_2$ (4 mL) at 0° C. was added DIEA (374 mg, 2.90 mmol). The mixture was stirred at 0° C. for 1 h. A solution of compound 2-(2,3-dihydrospiro[indene-1,4'-piperidine]-3-yl)acetic acid (142 mg, 0.58 mmol) was added dropwise slowly. The mixture was stirred at rt overnight and concentrated to give the crude product. A portion of the crude product was purified by preparative HPLC to give 2-1'-((2-adamantyl)carbamoyl)-2,3-dihydrospiro[indene-1,4'-piperidine]-3-yl)acetic acid (60 mg, 36%). $^1$H NMR: (400 MHz, CDCl$_3$): δ=1.56-1.73 (m, 6H), 1.74-1.90 (m, 10H), 1.95 (m, 2H), 2.10 (m, 1H), 2.45 (m, 1H), 2.60 (m, 1H), 3.01 (m, 3H), 3.65 (m, 1H), 3.87-3.99 (m, 3H), 7.15-7.26 (m, 4H); LC-MS (4 min) t$_R$=2.70 min, m/z=423 (M$^+$+1).

Example 4

(±)-Methyl 2-(1'-((2-adamantyl)carbamoyl)-2,3-dihydrospiro[indene-1,4'-piperidine]-3-yl)acetate

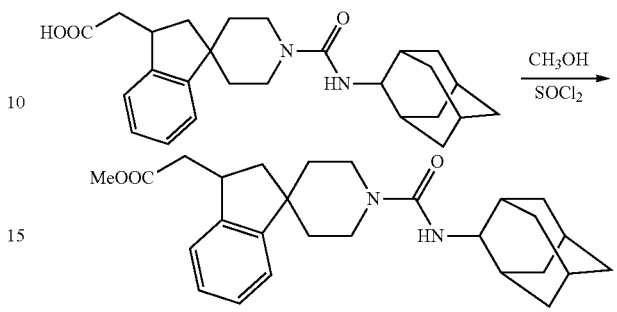

To a solution of 2-1'-((2-adamantyl)carbamoyl)-2,3-dihydrospiro[indene-1,4'-piperidine]-3-yl)acetic acid (150 mg, 0.355 mmol) in methanol (2 mL) at 0° C. was added thionyl chloride (54 mg, 0.46 mmol). The mixture was stirred at rt overnight and concentrated. The residue was purified by preparative TLC to give methyl 2-(1'-((2-adamantyl)carbamoyl)-2,3-dihydrospiro[indene-1,4'-piperidine]-3-yl)acetate (62.8 mg, 41%). $^1$H NMR (400 MHz, CDCl$_3$): δ=1.52-1.73 (m, 6H), 1.73-1:81 (m, 3H), 1.82-1.90 (m, 7H), 1.95 (m, 2H), 2.10 (m, 1H), 2.45 (m, 1H), 2.60 (m, 1H), 3.01 (m, 3H), 3.65 (m, 1H), 3.74 (s, 1H), 3.86 (d, 1H), 3.99 (m, 2H), 4.87 (s, 1H), 7.13-7.26 (m, 4H); LC-MS (4 min) t$_R$=2.38 min, m/z=437 (M$^+$+1).

Example 5

Separation of the Enantiomers of Methyl 2-(1'-((2-adamantyl)carbamoyl)-2,3-dihydrospiro[indene-1,4'-piperidine]-3-yl)acetate Methyl 2-(1'-((2-adamantyl)carbamoyl)-2,3-dihydrospiro[indene-1,4'-piperidine]-3-yl)acetate was submitted to preparative HPLC on a 10 mm×250 mm Chiral Technologies Chiralcel OD-H column eluted with 4 mL min$^{-1}$ of 10% isopropanol in hexanes containing 0.025% diethylamine for 30 min. The isomer that eluted first (t$_R$=23 min) was designated Example 5A. $^1$H NMR (CDCl$_3$) δ=2.05 (m, 1H), 2.43 (m, 1H), 2.60 (m, 1H), 2.92 (m, 1H), 3.05 (m, 2H), 3.65 (m, 1H), 3.74 (s, 3H), 3.90 (d, 1H), 4.00 (m, 1H), 4.82 (d, 1H).

The isomer that eluted second (t$_R$=26.5 min) was designated Example 5B. $^1$H NMR (CDCl$_3$) δ=2.05 (m, 1H), 2.43 (m, 1H), 2.60 (m, 1H), 2.92 (m, 1H), 3.05 (m, 2H), 3.65 (m, 1H), 3.74 (s, 3H), 3.90 (d, 1H), 4.00 (m, 1H), 4.82 (d, 1H).

Example 6

2-(1'-((2-Adamantyl)carbamoyl)-2,3-dihydrospiro[indene-1,4'-piperidine]-3-yl)acetic acid

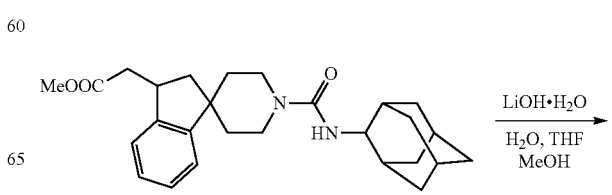

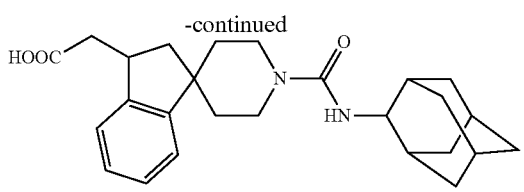

To a stirred solution of methyl 2-(1'-((2-adamantyl)carbamoyl)-2,3-dihydrospiro[indene-1,4'-piperidine]-3-yl)acetate isomer A (2.0 mg, 5 µmol) in water (0.25 mL), THF (0.25 mL) and methanol (0.5 mL) was added LiOH.H$_2$O (10 mg, 0.23 mmol). The mixture was stirred overnight at rt. The mixture was diluted with 5% aq HCl (10 mL) and extracted with EtOAc (2×40 mL). The combined organic extracts were dried over Na$_2$SO$_4$ and concentrated to leave crude 2-(1'-((2-adamantyl)carbamoyl)-2,3-dihydrospiro[indene-1,4'-piperidine]-3-yl)acetic acid isomer A (3 mg, quant) as an oil. $^1$H NMR (CDCl$_3$) δ=2.49 (m, 1H), 2.63 (m, 1H), 3.00 (m, 1H), 3.1 (1H), 3.65 (1H), 3.92 (1H), 4.02 (2H); LC-MS (3 min) $t_R$=1.90 min, m/z=423.

The same procedure was applied to methyl 2-(1'-((2-adamantyl)carbamoyl)-2,3-dihydrospiro[indene-1,4'-piperidine]-3-yl)acetate isomer B (2.7 mg, 6 µmol) to afford crude 2-(1'-((2-adamantyl)carbamoyl)-2,3-dihydrospiro[indene-1,4'-piperidine]-3-yl)acetic acid isomer B (2.85 mg, quant) as an oil. $^1$H NMR (CDCl$_3$) δ=2.49 (m, 1H), 2.63 (m, 1H), 3.00 (m, 1H), 3.1 (1H), 3.65 (1H), 3.92 (1H), 4.02 (2H); LC-MS (3 min) $t_R$=1.90 min, m/z=423.

Example 7

1-Acetyl-N-(2-adamantyl)spiro[indoline-3,4'-piperidine]-1'-carboxamide

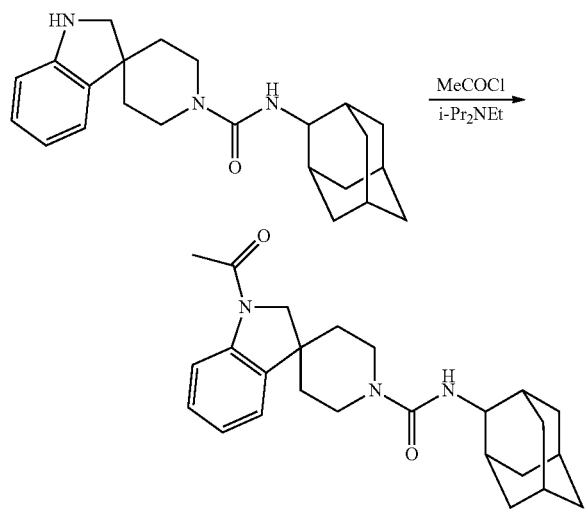

To a solution N-(2-adamantyl)spiro[indoline-3,4'-piperidine]-1'-carboxamide (50 mg, 0.108 mmol) and DIEA (27.86 g, 0.22 mmol) in dry CH$_2$Cl$_2$ (2-mL) at 0° C. under nitrogen was added dropwise a solution of acetyl chloride (9.28 mg, 0.12 mmol) in CH$_2$Cl$_2$ (0.5 mL). The mixture was stirred overnight at rt and evaporated to give a residue, which was purified by preparative HPLC to provide a white solid 1-acetyl-N-(2-adamantyl)spiro[indoline-3,4'-piperidine]-1'-carboxamide (5.2 mg, 12%). $^1$H NMR (400 MHz, CD$_3$OD): δ=1.61 (s, 1H), 1.653 (d, 2H), 1.72 (s, 1H), 1.88 (m, 10H), 2.015 (d, 5H), 2.286 (s, 3H), 3.027 (t, 2H), 3.867 (s, 1H), 4.088 (d, 4H), 7.044 (t, 1H), 7.191 (t, 2H), 8.082 (d, 1H); LC-MS (4 min) $t_R$=1.59 min, m/z=408(M$^+$+1).

Example 8 tert-Butyl 94(2-adamantyl)carbamoyl)-3,9-diazaspiro[5.5]undecane-3-carboxylate

A procedure analogous to that described Example 1 was followed using tert-butyl 3,9-diazaspiro[5.5]undecane-3-carboxylate. $^1$H NMR (CD$_3$OD) δ=1.45 (s, 9H), 1.49 (m, 8H), 1.72-2.00 (m, 12H), 3.40 (m, 8H), 3.82 (s, 1H), 5.69 (m, 1H); LC-MS (4 min) $t_R$=2.40 min m/z=432.

Example 9 tert-Butyl 8-((2-adamantyl)carbamoyl)-2,8-diazaspiro[4.5]decane-2-carboxylate

A procedure analogous to that described Example 1 was followed using tert-butyl 2,8-diazaspiro[4.5]decane-2-carboxylate. $^1$H NMR (CD$_3$OD) δ=1.46 (s, 9H), 1.58 (m, 6H), 1.73-2.06 (m, 14H), 3.20 (s, 2H), 3.25-3.54 (m, 6H), 3.82 (s, 1H); LC-MS (4 min) $t_R$=2.92 min, m/z 418.

Example 10

(±)-tert-Butyl 7((2-adamantyl)carbamoyl)-2,7-diazaspiro[4.5]decane-2-carboxylate A procedure analogous to that described Example 1 was followed using tert-butyl 2,7-diazaspiro[4.5]decane-2-carboxylate. $^1$H NMR (CDCl$_3$) δ=1.44 (s, 9H), 1.50-1.90 (m, 21H), 3.01-3.42 (m, 8H), 3.92 (m, 1H), 4.79 (m, 1H); LC-MS (4 min) $t_R$=2.25, m/z=418.

Example 11

1'-((2-Adamantyl)carbamoyl)spiro[indene-1,4'-piperidine]-3-carboxylic acid

A procedure analogous to that described Example 3 was followed using 1'-(tert-butoxycarbonyl)spiro[indene-1,4'-piperidine]-3-carboxylic acid in Step 1. $^1$H NMR (CD$_3$OD) δ=1.29 (d, 2H), 1.63 (d, 2H), 1.85 (m, 8H), 2.00 (m, 4H), 2.13 (m, 2H), 3.25 (m, 2H), 3.89 (s, 1H), 4.16 (m, 2H), 7.26 (m, 2H), 7.38 (m, 1H), 7.85 (s, 1H), 7.92 (m, 1H), LC-MS (4 min) $t_R$=2.48 min, m/z=407.

Example 12

(±)-1'-((2-Adamantyl)carbamoyl)-2,3-dihydrospiro[indene-1,4'-piperidine]-3-carboxylic acid A procedure analogous to that described Example 3 was followed using 1'-(tert-butoxycarbonyl)-2,3-dihydrospiro[indene-1,4'-piperidine]-3-carboxylic acid in Step 1. $^1$H NMR (CD$_3$OD) δ=1.54 (m, 1H), 1.65 (m, 3H), 1.82 (m, 9H), 1.98 (m, 5H), 2.46 (m, 2H), 3.06 (m, 2H), 3.86 (s, 1H), 4.06 (m, 3H), 7.21 (m, 3H), 7.39 (m, 1H); LC-MS (4 min) $t_R$=2.44 min, m/z=409.

Example 13

(±)-1'-((2-Adamantyl)carbamoyl)spiro[chroman-2,4'-piperidine]-4-carboxylic acid

A procedure analogous to that described Example 3 was followed using 1'-(tert-butoxycarbonyl)spiro[chroman-2,4'-piperidine]-4-carboxylic acid in Step 1. $^1$H NMR (CD$_3$OD) δ=1.65 (m, 3H), 1.84 (m, 10H), 1.96 (m, 4H), 2.16 (m, 1H), 3.15 (m, 1H), 3.36 (m, 1H), 3.86 (m, 4H), 6.86 (m, 2H), 7.15 (m, 1H), 7.23 (m, 1H) LC-MS (4 min) $t_R$=2.44 min, m/z=425.

Example 14

(±)-2-(1'-(Cyclohexylcarbamoyl)spiro[chroman-2,4'-piperidine]-4-yl)acetic acid

A procedure analogous to that described Example 3 was followed using 2-0 '-(tert-butoxycarbonyl)spiro[chroman-2,4'-piperidine]-4-yl)acetic acid in Step 1. $^1$H NMR (CD$_3$OD) δ=1.61 (m, 3H), 1.74-1.90 (m, 11H), 1.96 (m, 4H), 2.05 (m, 1H), 2.48 (m, 1H), 3.00 (m, 1H), 3.13 (m, 1H), 3.39 (m, 2H), 3.74 (m, 1H), 3.84 (m, 2H), 6.84 (m, 2H), 7.08 (m, 1H0, 7.23 (m, 1H); LC-MS (4 min) $t_R$=2.52 min, m/z=439.

Example 15

Ethyl 1'-((2-adamantyl)carbamoyl)spiro[indene-1,4'-piperidine]-3-carboxylate

A procedure analogous to that described Example 4 was followed using 1'-((2-adamantyl)carbamoyl)spiro[indene-1,4'-piperidine]-3-carboxylic acid and ethanol. $^1$H NMR (CD$_3$OD) δ=1.40 (m, 5H), 1.63 (m, 2H), 1.84 (m, 8H), 1.98 (m, 5H), 2.11 (m, 2H), 3.25 (m, 2H), 3.89 (m, 1H), 4.15 (m, 2H), 4.36 (m, 2H0, 7.26 (m, 2H), 7.39 (m, 1H), 7.84 (s, 1H), 7.91 (m, 1H); LC-MS (4 min) $t_R$=2.19 min, m/z=435.

Example 16

(±)-Ethyl 1'-(cyclohexylcarbamoyl)-2,3-dihydrospiro[indene-1,4'-piperidine]-3-carboxylate A procedure analogous to that described Example 4 was followed using 1'-((2-adamantyl)carbamoyl)-2,3-dihydrospiro[indene-1,4'-piperidine]3-carboxylic acid and ethanol. $^1$H NMR (CD$_3$OD) δ=1.29 (t, 3H), 1.54 (m, 1H), 1.64 (m, 2H), 1.86 (m, 9H), 1.96 (m, 5H), 2.43 (m, 2H), 3.04 (m, 2H), 3.86 (s, 1H), 4.06 (m, 2H), 4.15 (m, 1H), 4.20 (m, 1H), 7.20 (m, 3H), 7.34 (m, 1H); LC-MS (4 min) $t_R$=2.12 min, m/z=437.

Example 17

(±)-Ethyl 1'-(cyclohexylcarbamoyl)spiro[chroman-2,4'-piperidine]-4-carboxylate

A procedure analogous to that described Example 4 was followed using 1'4(2-adamantyl)carbamoyl)spiro[chroman-2,4'-piperidine]-4-carboxylic acid and ethanol. $^1$H NMR (CD$_3$OD) δ=1.29 (t, 3H), 1.60 (m, 3H), 1.70 (m, 1H), 1.83 (m, 9H), 1.96 (m, 4H), 2.11 (m, 2H), 3.14 (m, 1H), 3.48 (m, 1H), 3.80 (m, 3H), 3.94 (m, 1H), 4.21 (m, 2H), 6.84 (m, 2H), 7.16 (m, 2H); LC-MS (4 min) $t_R$=2.10 min, m/z=453.

Example 18

(±)-Ethyl 2-1'-((2-adamantyl)carbamoyl)spiro[chroman-2,4'-piperidine]-4-yl)acetate A procedure analogous to that described Example 4 was followed using 2-0'4(2-adamantyl)carbamoyl)spiro[chroman-2,4'-piperidine]-4-yl)acetic acid and ethanol. $^1$H NMR (CD$_3$OD) δ=1.24 (t, 3H), 1.50 (m, 1H), 1.60 (m, 1H), 1.83 (m, 10H), 1.97 (m, 3H), 2.01 (m, 2H), 2.45 (m, 1H), 3.00 (m, 1H), 3.12 (m, 1H), 3.47 (m, 2H), 3.73 (m, 1H), 3.84 (m, 2H), 4.15 (m, 2H), 6.84 (m, 2H), 7.08 (m, 1H), 7.20 (m, 1H); LC-MS (4 min) $t_R$=2.19 min, m/z=467.

Example 19

N-(2-Adamantyl)-1-(methylsulfonyl)spiro[indoline-3,4'-piperidine]-1'-carboxamide A procedure analogous to that described in Example 7 was followed using methanesulfonyl chloride. $^1$H NMR (CD$_3$OD) δ=1.63 (m, 2H), 1.75 (m, 2H), 1.83 (m, 9H), 1.98 (m, 5H), 2.98 (s, 3H), 3.04 (m, 1H), 3.86 (s, 1H), 3.93 (s, 2H), 4.16 (d, 2H), 7.04 (m, 1H), 7.22 (m, 2H), 7.37 (m, 1H); LC-MS (4 min) $t_R$=1.67 min, =444.

Example 20

2-Adamantyl spiro[indoline-3,4'-piperidine]-1'-carboxylate

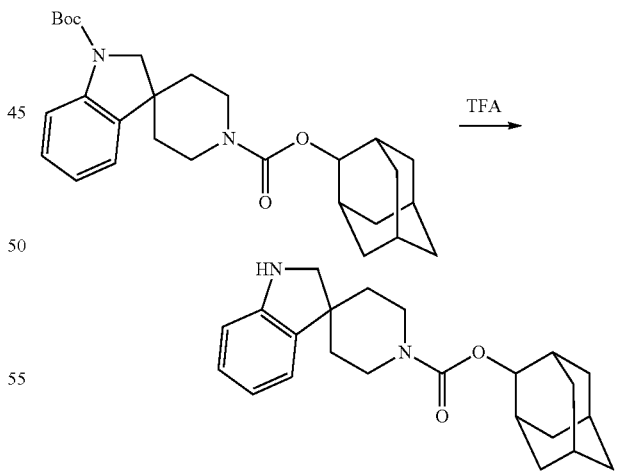

The title compound was prepared from 1-tert-butyl 1'-(2-adamantyl) spiro[indoline-3,4'-piperidine]-1,1'-dicarboxylate following a procedure analogous to Example 2. LC-MS Method 4 $t_R$=2.319 min, m/z=367.2; $^1$H NMR (CD$_3$OD) δ=1.31 (m, 1H), 1.66 (m, 2H), 1.72-1.88 (m, 8H), 1.96 (m, 4H), 2.05 (m, 5H), 2.15 (m, 1H), 3.03-3.26 (m, 2H), 3.36 (s, 1H), 3.81 (s, 2H), 4.25 (s, 2H), 7.41 (m, 4H).

Example 21

2-Adamantyl 5-fluorospiro[indoline-3,4'-piperidine]-1'-carboxylate

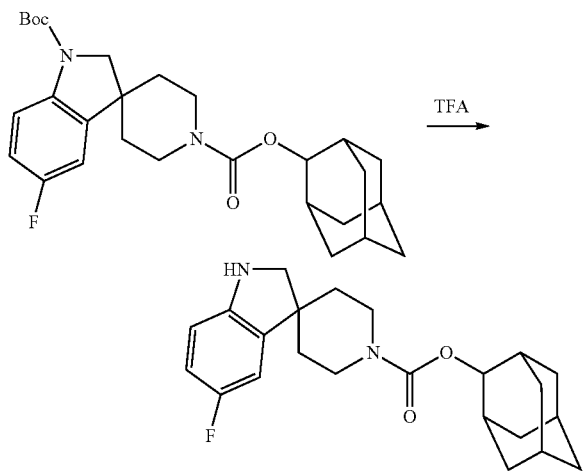

The title compound was prepared from 1-tert-butyl 1'-(2-adamantyl) 5-fluorospiro[indoline-3,4'-piperidine]-1,1'-dicarboxylate following a procedure analogous to Example 2. LC-MS Method 4 $t_R$=2.111 min, m/z=385.2; $^1$H NMR (CD$_3$OD) δ=1.60-1.71 (m, 2H), 1.75-1.85 (m, 8H), 1.90-2.11 (m, 8H), 2.91-328 (m, 2H), 3.91 (m, 2H), 4.25 (s, 2H), 4.85 (m, 1H), 7.19-7.25 (m, 1H), 7.31-7.38 (m, 1H), 7.48-7.51 (m, 1H).

Example 22

2-Adamantyl 5-methylspiro[indoline-3,4'-piperidine]-1'-carboxylate

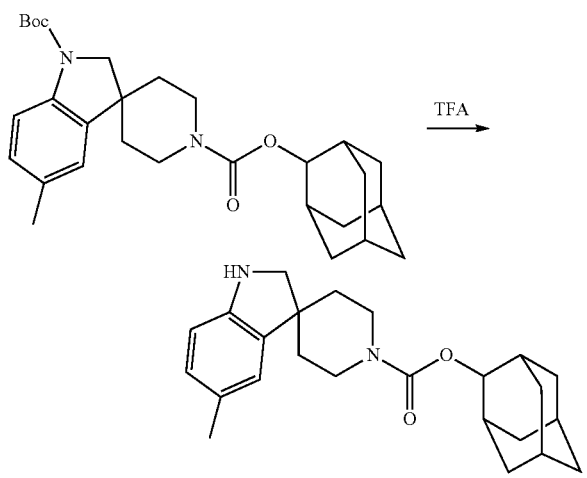

The title compound was prepared from 1-tert-butyl 1'-(2-adamantyl) 5-methylspiro[indoline-3,4'-piperidine]-1,1'-dicarboxylate following a procedure analogous to Example 2. LC-MS Method 4 $t_R$=1.958 min, m/z=381.2; $^1$H NMR (CD$_3$OD) δ=1.66 (m, 4H), 1.75 (m, 1H), 1.79 (m, 8H), 1.90 (d, 2H), 2.11 (m, 4H), 2.21 (m, 1H), 2.32 (m, 3H), 2.95-3.22 (m, 2H), 3.44 (m, 2H), 4.05-4.20 (m, 2H), 6.61 (d, 1H), 6.85 (d, 2H).

Example 23

2-Adamantyl 1-acetylspiro[indoline-3,4'-piperidine]-1'-carboxylate

A procedure analogous to that described Example 7 was followed using 2-adamantyl spiro[indoline-3,4'-piperidine]-1'-carboxylate. LC-MS Method 5 $t_R$=2.874 min, m/z=431.1; $^1$H NMR (CD$_3$OD) δ=1.68 (m, 5H), 1.74-1.95 (m, 1H), 2.06 (m, 5H), 2.32 (s, 3H), 3.13 (br, 2H), 4.11 (s, 2H), 4.23 (s, 2H), 7.08 (m, 1H), 7.22 (m, 2H), 8.11 (m, 1H).

Example 24

(±)-2-Adamantyl 3-(2-methoxy-2-oxoethyl)-2,3-dihydrospiro[indene-1,4'-piperidine]-1'-carboxylate

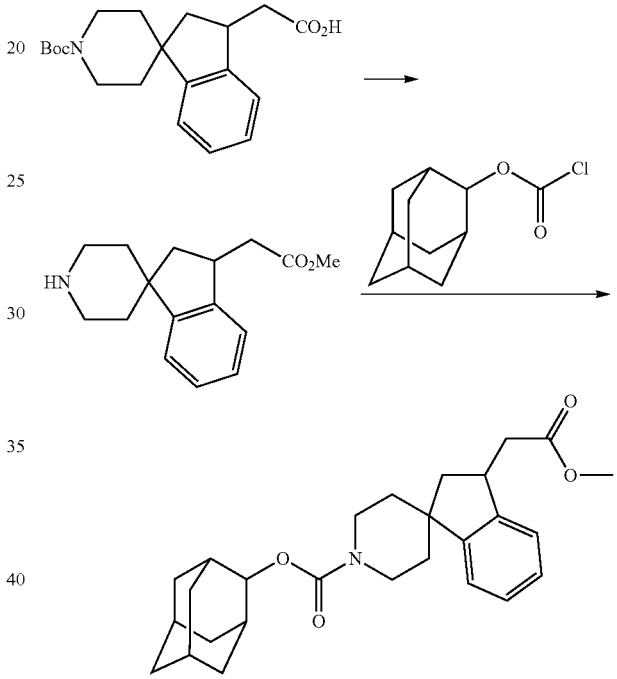

Step 1

To a solution of (±)-2-(1'-(tert-butoxycarbonyl)-2,3-dihydrospiro[indene-1,4'-piperidine]-3-yl)acetic acid (200 mg, 0.579 mmol) in methanol (2 mL) was added dropwise SOCl$_2$ (137.43 mg, 1.158 mmol) at 0° C. The above mixture was allowed to stir at rt overnight. LC-MS showed that the starting material was consumed completely. The mixture was evaporated to give (±)-methyl 2-(2,3-dihydrospiro[indene-1,4'-piperidine]-3-yl)acetate (140.8 mg, 94%). $^1$H NMR (400 MHz, CD$_3$OD): δ=1.65 (m, 1H), 1.70-1.90 (m, 3H), 2.32 (m, 1H), 2.50 (m, 1H), 2.67 (m, 1H), 2.96 (m, 1H), 3.12-3.30 (m, 2H), 3.34-3.50 (m, 2H), 2.66 (m, 1H), 3.72 (s, 3H), 7.24 (m, 4H).

Step 2

To a solution of the 2-adamantyl chloroformate (144.04 mg, 0.671 mmol) and TEA (135.5 mg, 1.342 mmol) in anhydrous CH$_2$Cl$_2$ (2 mL) was added (±)-methyl dihydrospiro[indene-1,4'-piperidine]-3-yl)acetate-(174 mg, 0.671 mmol) at 0° C. in several portions. The above mixture was allowed to stir at rt overnight. LC-MS showed that the starting material was consumed completely. The mixture was evaporated to give a residue, which was purified by preparative HPLC to afford (±)-2-adamantyl 3-(2-methoxy-2-oxoethyl)-2,3-dihydrospiro[indene-1,4'-piperidine]-1'-carboxylate (101 mg, 34%). ¹H NMR (400 MHz, CD₃OD): δ=1.48-1.69 (m, 614), 1.70-2.01 (m, 8H), 2.06-2.1.2 (m, 5H), 2.39-251 (m, 1H), 2.62-2.73 (m, 1H), 2.85-3.21 (m, 3H), 3.55-3.65 (m, 1H), 3.75 (m, 3H), 4.05-4.20 (m, 2H), 4.81 (m, 1H), 7.18 (m, 4H).

Example 25

2-(1'-((2-Adamantyloxy)carbonyl)-2,3-dihydrospiro[indene-1,4'-piperidine]-3-yl)acetic acid

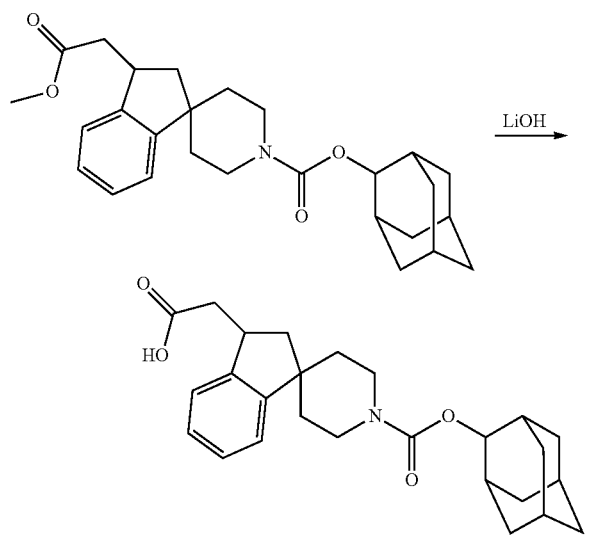

2-adamantyl-3-(2-methoxy-2-oxoethyl)-2,3-dihydrospiro[indene-1,4'-piperidine]-1'-carboxylate (26 mg, 0.06 mmol) was dissolved in MeOH (1 mL) in an ice-water bath. A solution of LiOH.H₂O (4.99 mg, 0.119 mmol) in water (0.2 mL) was added dropwise and the mixture was stirred for 8 h at rt. LC-MS showed that the starting material was consumed completely. The mixture was evaporated to give a residue, which was purified by preparative HPLC to afford 2-(1'-((2-adamantyloxy)carbonyl)-2,3-dihydrospiro[indene-1,4'-piperidine]-3-yl)acetic acid (12.2 mg, 48%). ¹H NMR (400 MHz, CD₃OD): δ=0.91 (m, 2H), 1.32 (m, 3H), 1.53-1.71 (m, 6H), 1.75-1.93 (m, 8H), 1.93-2.18 (m, 4H), 2.24 (m, 1H), 2.63 (m, 1H), 2.77 (m, 1H), 2.96-3.24 (br, 2H), 3.62 (m, 1H), 4.10-4.28 (br, 2H), 4.72 (s, 1H), 7.15 (m, 3H), 7.24 (m, 1H).

Example 26

(±)-2-Adamantyl 3-(2-(methylamino)-2-oxoethyl)-2,3-dihydrospiro[indene-1,4'-piperidine]-1'-carboxylate

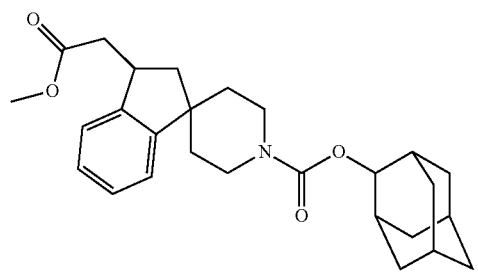

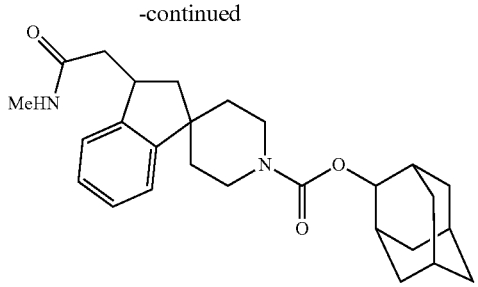

(±)-2-Adamantyl 3-(2-methoxy-2-oxoethyl)-2,3-dihydrospiro[indene-1,4'-piperidine]-1'-carboxylate (33 mg, 0.075 mmol) was added to a solution of methylamine in alcohol (2 mL) at 0° C. The above mixture was heated under reflux overnight. LC-MS showed that the starting material was consumed completely. The mixture was evaporated to give a residue, which was purified by preparative HPLC to obtain (±)-2-adamantyl 3-(2-(methylamino)-2-oxoethyl)-2,3-dihydrospiro[indene-1,4'-piperidine]-1'-carboxylate (12 mg, 37%). ¹H-NMR (400 MHz, CD₃OD): δ=-1.52-1.67 (m, 6H), 1.84 (m, 6H), 1.93 (m, 2H), 2.07 (M, 5H), 2.28 (m, 1H), 2.56 (m, 1H), 2.77 (m, 4H), 3.12 (br, 2H), 3.62 (m, 1H), 4.19 (br, 2H), 7.18 (m, 4H).

Example 27

N-(2-Adamantyl)-1,3-dihydrospiro[indene-2,3'-piperidine]-1'-carboxamide

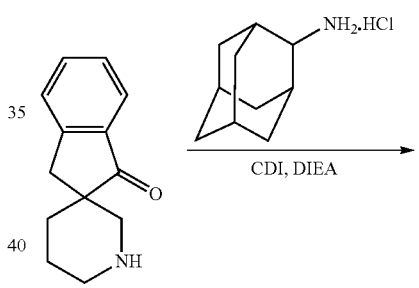

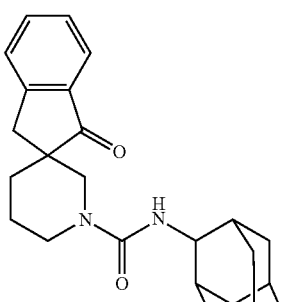

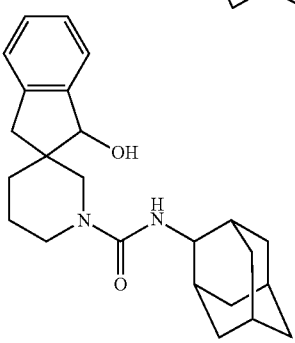

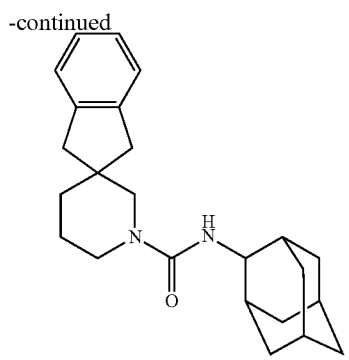

Step 1

To a solution of 2-aminoadamantane hydrochloride (126 mg, 0.68 mmol) and DIEA (872 mg, 6 mmol) in anhydrous $CH_2Cl_2$ (3 mL) was added CDT (120 mg, 0.74 mmol) at 0° C. and stirred for 1 h at 0° C. Then spiro[indene-2,3'-piperidin]-1(3H)-one (136 mg, 0.68 mmol) in anhydrous $CH_2Cl_2$ (2 mL) was added dropwise to the above mixture at 0° C. The reaction mixture was stirred overnight under nitrogen at rt. The reaction mixture was evaporated to give a residue, which was purified by preparative TLC and then by preparative HPLC to afford N-(2-adamantyl)-1-oxo-1,3-dihydrospiro[indene-2,3'-piperidine]-1'-carboxamide (32 mg, 12%). $^1$HNMR ($CD_3OD$, 400 MHZ): δ=1.51~1.75 (m, 3H), 1.76~1.81 (m, 4H), 1.82-2.01 (m, 11H), 3.00 (m, 3H), 3.22 (m, 3H), 3.72 (m, 2H), 4.03 (m, 1H), 7.41 (m, 1H), 7.53 (m, 1H), 7.71 (m, 2H).

Step 2

To a solution of N-(2-adamantyl)-1-oxo-1,3-dihydrospiro[indene-2,3'-piperidine]-1'-carboxamide (3.0 mg, 0.079 mmol) in MeOH (3 mL) was added $NaBH_4$ (12 mg, 0.317 mmol) at 0° C. under nitrogen. The reaction mixture was stirred for 4 h under $N_2$ at rt. The reaction mixture was evaporated to give a residue, which was purified by preparative HPLC to afford N-(2-adamantyl)-1-hydroxy-1,3-dihydrospiro[indene-2,3'-piperidine]-1'-carboxamide (12 mg, 40%). $^1$HNMR ($CD_3OD$, 400 MHZ): δ=1.51-1.75 (m, 5H), 1.78~1.81 (m, 4H), 1.82~2.00 (m, 11H), 2.50 (m, 1H), 3.00 (d, 1H), 3.20 (m, 1H), 3.55 (m, 1H), 3.65 (m, 1H), 3.81 (s, 1H), 4.75 (s, 1H), 7.22 (m, 3H), 7.388 (m, 1H).

Step 3

To a solution of N-(2-adamantyl)-1-hydroxy-1,3-dihydrospiro[indene-2,3'-piperidine]-1'-carboxamide (20 mg, 0.052 mmol) in ethanol (3 mL) was added $Pd(OH)_2$ (10 mg), then the reaction mixture was stirred for 4 h at rt under a hydrogen atmosphere. The reaction mixture was filtered and the filtrate was evaporated to give a residue, which was purified by preparative HPLC to afford N-(2-adamantyl)-1,3-dihydrospiro[indene-2,3'-piperidine]-1'-carboxamide (5 mg, 29%): LC-MS Method 5 $t_R$=3.057 min, m/z=365.2; $^1$H NMR ($CD_3OD$, 400 MHz): δ=1.55 (m, 2H), 1.66 (m, 2H), 1.78 (m, 7H), 1.84 (m, 7H), 2.69-2.83 (m, 4H), 3.21 (s, 2H), 3.45 (m, 2H), 3.77 (s, 1H), 7.09 (m, 2H), 7.14 (m, 2H).

Example 28

N-(2-Adamantyl)-2,3-dihydrospiro[indene-1,4'-piperidine]-1'-carboxamide

The title compound was prepared following a procedure analogous to that described in Example 1 using 2,3-dihydrospiro[indene-1,4'-piperidine]. LC-MS Method 5 $t_R$=1.946 min, m/z=365; NMR ($CD_3OD$) δ=1.54 (d, 2H), 1.63 (d, 2H), 1.72-2.02 (m, 14H), 2.14 (m, 2H), 2.94 (m, 2H), 3.09 (m, 2H), 3.87 (m, 1H), 4.03 (d, 2H), 4.61 (s, 1H), 5.79 (m, 1H), 7.12-7.20 (m, 4H).

Example 29

Tert-butyl 1'-((2-adamantyl)carbamoyl)-1H-spiro[isoquinoline-4,4'-piperidine]-2(3H)-carboxylate The title compound was prepared following a procedure analogous to that described in Example 1 using tert-butyl 1H-spiro[isoquinoline-4,4'-piperidine]-2(3H)-carboxylate. LC-MS Method $t_R$=3.036 min, m/z=480.3; NMR ($CDCl_3$) δ=1.49 (s, 9H), 1.64 (m, 7H), 1.76 (m, 5H), 1.86 (m, 7H), 1.95-2.03 (m, 4H), 3.06-3.21 (m, 2H), 3.71 (m, 2H), 3.91 (m, 2H), 3.99 (s, 1H), 4.62 (s, 2H), 4.82 (m, 1H), 7.08 (m, 1H), 7.19 (m, 2H), 7.35 (m, 1H).

Example 30

N-(2-Adamantyl)-2,3-dihydro-1H-spiro[isoquinoline-4,4'-piperidine]-1'-carboxamide The title compound was prepared from tert-butyl 1'4(2-adamantyl)carbamoyl)-1H-spiro[isoquinoline-4,4'-piperidine]-2(3H)-carboxylate following a procedure analogous to that described in Example 2. LC-MS Method 4 $t_R$=1.741 min, m/z=380.3; $^1$H NMR ($CDCl_3$) δ=1.66-1.79 (m, 7H), 1.79-2.01 (m, 11H), 2.17 (m, 2H), 3.14 (m, 2H), 3.58 (m, 2H), 3.93 (m, 3H), 4.41 (s, 2H), 5.86-6.19 (br, 5H), 7.12 (d, 1H), 7.32 (m, 1H), 7.44 (m, 2H).

Example 31

2-Acetyl-N-(2-adamantyl)-2,3-dihydro-1H-spiro[isoquinoline-4,4'-piperidine]-1'-carboxamide The title compound was prepared from N-(2-adamantyl)-2,3-dihydro-1H-spiro[isoquinoline-4,4'-piperidine]-1'-carboxamide following a procedure analogous to that described in Example 7. LC-MS Method 4 $t_R$=2.931 min, m/z=422.2; $^1$H NMR ($CD_3OD$) δ=1.33 (m, 1H), 1.54-1.68 (m, 4H), 1.86 (m, 10H), 1.95-2.08 (m, 7H), 2.24 (d, 3H), 3.19 (m, 2H), 3.81-3.98 (m, 5H), 7.17-7.24 (m, 3H), 7.39 (m, 1H).

Example 32

Ethyl 3-(1'-((2-adamantyl)carbamoyl)-1H-spiro[isoquinoline-4,4'-piperidine]-2(3H)-yl)propanoate

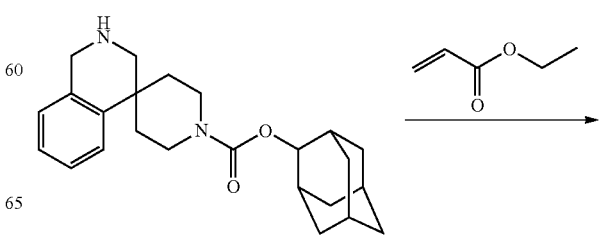

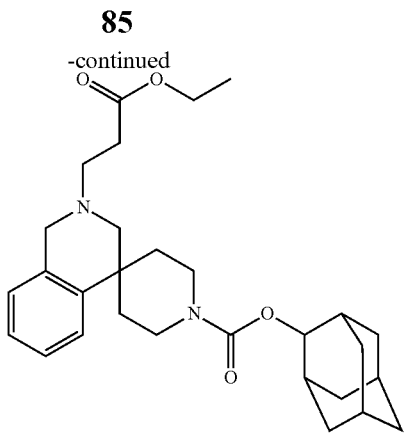

To a solution of 2-adamantyl 2,3-dihydro-1H-spiro[isoquinoline-4,4'-piperidine]-1'-carboxylate (40 mg, 0.11 mmol) and TEA (37 mg, 0.32 mmol) in CH$_2$Cl$_2$ (2 mL) was dropwise a solution of acrylic acid ethyl ester (13 mg, 0.13 mmol) in CH$_2$Cl$_2$ slowly at 0° C. under nitrogen atmosphere. The mixture was stirred at rt overnight. The mixture was concentrated to give the crude product, which was purified by preparative TLC followed by preparative HPLC to afford ethyl 3-(1'-((2-adamantyl)carbamoyl)-1H-spiro[isoquinoline-4,4'-piperidine]-2(3H)-yl)propanoate (4 mg, yield: 7%). LC-MS Method 4 $t_R$=5.21 min, m/z=481.3; $^1$H NMR (CD$_3$OD, 400 MH$_z$): δ=1.25 (m, 4H), 1.58 (m. 5H), 1.72 (m, 3H), 1.84 (m, 7H), 1.88-2.17 (m, 5H), 2.53-2.92 (m, 6H), 2.94-3.22 (m, 2H), 3.68 (s, 1H), 4.09-4.17 (m, 4H), 4.88 (s, 1H), 7.02 (d, 1H), 7.10-7.26 (m, 2H), 7.32 (d, 1H).

Example 33

3-(1'-((2-Adamantyl)carbamoyl)-1H-spiro[isoquinoline-4,4'-piperidine]-2(3H)-yl)propanoic acid The title compound was prepared using a method analogous to that of Example 6. LC-MS Method 4 $t_R$=4.78 min, m/z=453.3; $^1$H NMR (CD$_3$OD) δ=1.72 (m, 2H), 1.86-1.97 (m, 8H), 2.01 (m, 2H), 2.04-2.17 (m, 6H), 2.95 (m, 2H), 3.18 (m, 1H), 3.53-3.61 (m, 3H), 3.73 (s, 2H), 4.22 (m, 2H), 4.45 (s, 2H), 7.24 (m, 1H), 7.34 (m, 1H), 7.46 (m, 1H), 7.56 (m, 1H).

Example 34

N-(2-Adamantyl)-2-(methylsulfonyl)-2,3-dihydro-1H-spiro[isoquinoline-4,4'-piperidine]-1'-carboxamide

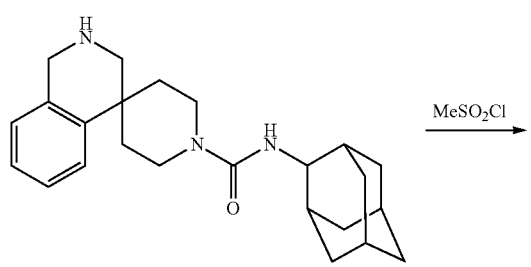

A vial, equipped with a flea stir bar, was charged with methanesulfonyl chloride (4.5 μL, 58 μmol), DIEA (15 μL, 90 μmol) and CH$_2$Cl$_2$ (1 mL). A solution of N-(2-adamantyl)-2,3-dihydro-1H-spiro[isoquinoline-4,4'-piperidine]-1'-carboxamide (25 mg, 53 μmol) in CH$_2$Cl$_2$ (1 mL) was added and the mixture was stirred overnight. A 10-mL Chem-Elut cartridge was wetted with 5% aq HCl (6 mL) and allowed to stand for 5 min. The reaction mixture was applied to the cartridge and eluted with ether (20 mL). The eluate was evaporated to dryness and the residue was purified by preparative HPLC to afford N-(2-adamantyl)-2-(methylsulfonyl)-2,3-dihydro-1H-spiro[isoquinoline-4,4'-piperidine]-1'-carboxamide (8 mg, 33%). LC-MS Method 1 $t_R$=1.89 min, =458; $^1$H NMR (CDCl$_3$) δ=1.60-2.15 (18H), 2.92 (s, 3H), 3.13 (m, 2H), 3.51 (s, 2H), 3.90 (d, 2H), 3.99 (s, 1H), 4.45 (s, 2H), 4.88 (1H), 7.05-7.40 (4H).

Example 35

N1'-(2-Adamantyl)-N2-methyl-1H-spiro[isoquinoline-4,4'-piperidine]-1',2(3H)-dicarboxamide

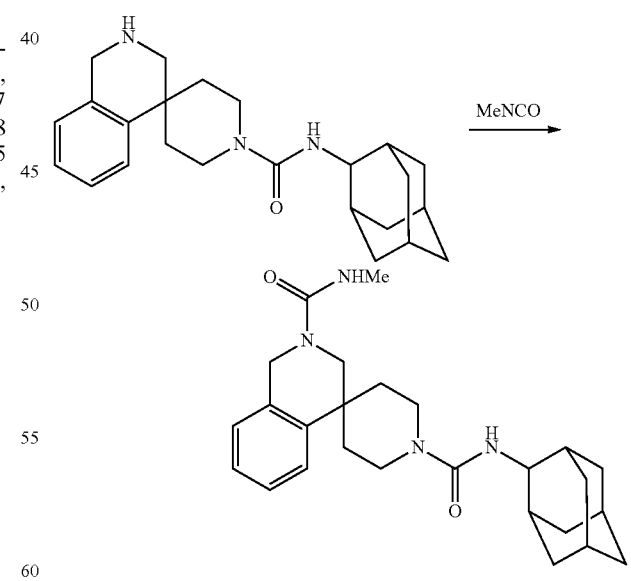

A vial was charged with N-(2-adamantyl)-2,3-dihydro-1H-spiro[isoquinoline-4,4'-piperidine]-1'-carboxamide (15 mg, 40 μmol), i-Pr2NEt (11 μL, 60 μmol) and CH$_2$Cl$_2$ (1 mL). Methyl isocyanate (3 μL, 43 μmol) was added and the mixture was stirred overnight at rt. A 10-mL Chem-Elut cartridge was wetted with 5% aq HCl (6 mL) and allowed to stand for 5 min.

The reaction mixture was applied to the cartridge and eluted with ether (20 mL). The eluate was evaporated to dryness and the residue was purified by preparative HPLC to afford N1'-(2-adamantyl)-N2-methyl-1H-spiro[isoquinoline-4,4'-piperidine]-1',2(3H)-dicarboxamide (7.7 mg, 44%). LC-MS Method 1 $t_R$=1.77 min, m/z=437; $^1$H NMR (CDCl$_3$) δ=1.60-2.10 (18H), 2.80 (1H), 2.88 (s, 3H), 3.25 (m, 2H), 3.77 (s, 2H), 3.88 (d, 2H), 3.98 (s, 1H), 4.52 (s, 2H), 4.87 (1H), 7.05-7.40 (4H).

Example 36

Ethyl 1'-((2-adamantyl)carbamoyl)-1H-spiro[isoquinoline-4,4'-piperidine]-2(3H)-carboxylate The title compound was prepared following a procedure analogous to that described in Example 35 using ethyl chloroformate instead of methyl isocyanate. LC-MS Method 1 $t_R$=2.1 min, m/z=452; $^1$H NMR (CDCl$_3$) δ=1.30 (t, 3H), 1.60-2.10 (18H), 3.20 (m, 2H), 3.77 (2H), 3.90 (d, 2H), 3.99 (s, 1H), 4.20 (m, 2H), 4.66 (s, 2H), 4.85 (s, 1H), 7.05-7.40 (4H).

Example 37

2-Tert-butyl 1'-(2-adamantyl) 1H-spiro[isoquinoline-4,4'-piperidine]-1',2(3H)-dicarboxylate

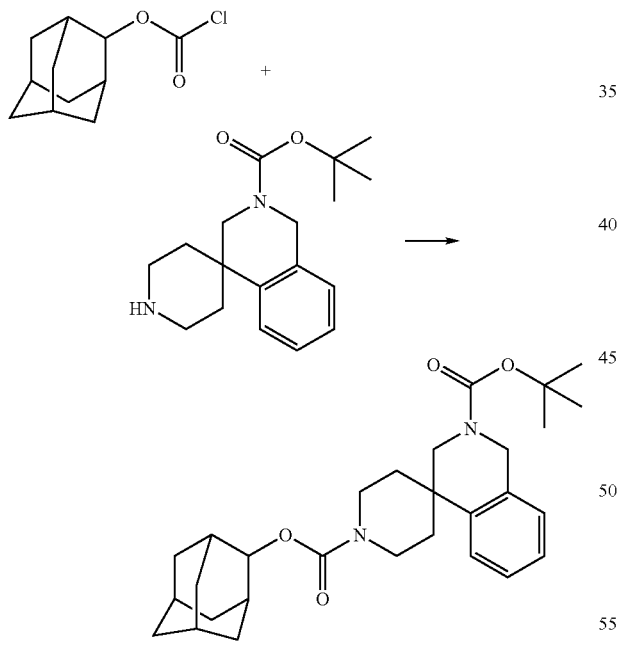

Tert-butyl 1H-spiro[isoquinoline-4,4'-piperidine]-2(3H)-carboxylate (199 mg, 0.659 mmol) and i-Pr$_2$NEt (139 μL, 1.25 equiv.) were dissolved in CH$_2$Cl$_2$ (10 mL) and stirred for 1.5 h at rt. LC-MS showed the reaction was complete. The mixture was diluted with ether (50 mL), washed with 3% aq HCl (2×15 mL), satd aq NaHCO$_3$ (15 mL) and brine (10 mL), and dried over Na$_2$SO$_4$. Filtration and concentration afforded 2-tert-butyl 1'-(2-adamantyl) 1H-spiro[isoquinoline-4,4'-piperidine]-1',2(3H)-dicarboxylate (246 mg, 80.5%) as a white foam-like solid. LC-MS Method 1 $t_R$=2.59 min, m/z=503; $^1$H NMR (CDCl$_3$) δ=7.34 (t, 1H), 7.20 (m, 2H), 7.09 (d, 1H), 4.88 (t, 2H), 4.62 (s, 2H), 4.16 (d, 2H), 3.72 (s, 1H), 3.25-3.03 (m, 2H), 1.50 (s, 9H).

Example 38

2-Adamantyl 2,3-dihydro-1H-spiro[isoquinoline-4,4'-piperidine]-1'-carboxylate

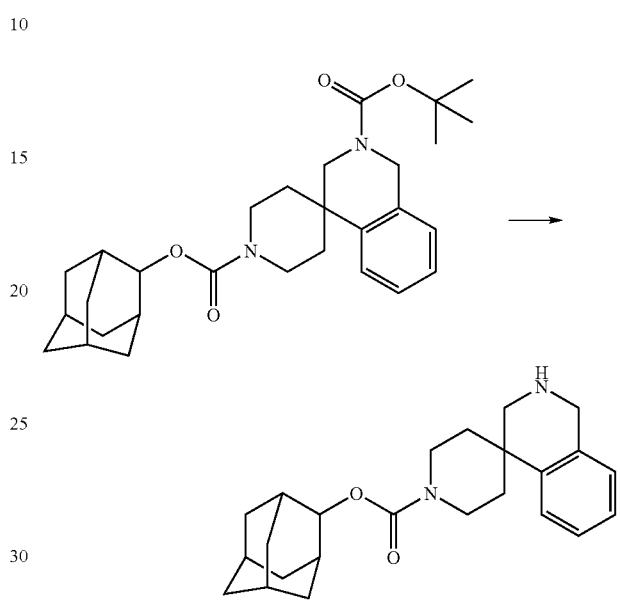

2-Tert-butyl 1'-(2-adamantyl) 1H-spiro[isoquinoline-4,4'-piperidine]-1',2(3H)-dicarboxylate (35 mg, 0.073 mmol) was dissolved in 1:2 TFA/CH$_2$Cl$_2$ (6 mL) and stirred for 30 min at rt. The mixture was concentrated to afford crude 2-adamantyl 2,3-dihydro-1H-spiro[isoquinoline-4,4'-piperidine]-1'-carboxylate (29 mg, quant). LC-MS Method 1 $t_R$=1.48 min, m/z=381; $^1$H NMR (CD$_3$OD) δ=7.52 (d, 1H), 7.38 (t, 1H), 7.28 (t, 1H), 7.21 (d, 1H), 4.85 (s, 1H), 4.38 (s, 2H), 4.19 (m, 2H), 3.68 (s, 2H), 3.28-3.01 (m, 2H).

Example 39

2-Adamantyl 2-(methylsulfonyl)-2,3-dihydro-1H-spiro[isoquinoline-4,4'-piperidine]-1'-carboxylate The title compound was prepared from 2-adamantyl 2,3-dihydro-1H-spiro[isoquinoline-4,4'-piperidine]-1'-carboxylate following a procedure analogous to that described in Example 34. LC-MS Method 1 $t_R$=2.16 min, m/z=459; $^1$H NMR (CDCl$_3$) δ=7.37 (d, 1H), 7.28 (t, 1H), 7.21 (t, 1H), 7.08 (d, 1H), 4.88 (s, 1H), 4.45 (br s, 2H), 4.18 (d, 2H), 3.12 (br s, 2H), 2.92 (s, 3H).

Example 40

2-Adamantyl 2-(isopropylsulfonyl)-2,3-dihydro-1H-spiro[isoquinoline-4,4'-piperidine]-1'-carboxylate The title compound was prepared from 2-adamantyl 2,3-dihydro-1H-spiro[isoquinoline-4,4'-piperidine]-1'-carboxylate following a procedure analogous to that described in Example 34 using isopropylsulfonyl chloride in place of methanesulfonyl chloride. LC-MS Method 1 $t_R$=2.31 min, m/z=487; $^1$H NMR (CDCl$_3$) δ=7.36 (d, 1H), 7.26 (t, 1H), 7.20

(t, 1H), 7.05 (d, 1H), 4.88 (s, 1H), 4.56 (br s, 2H), 4.18 (d, 2H), 4.35 (m, 1H), 2.99 (m, 4H), 1.42 (d, 6H).

Example 41

2-Adamantyl 2-(5-cyanopyridin-2-yl)-2,3-dihydro-1H-spiro[isoquinoline-4,4'-piperidine]-1'-carboxylate

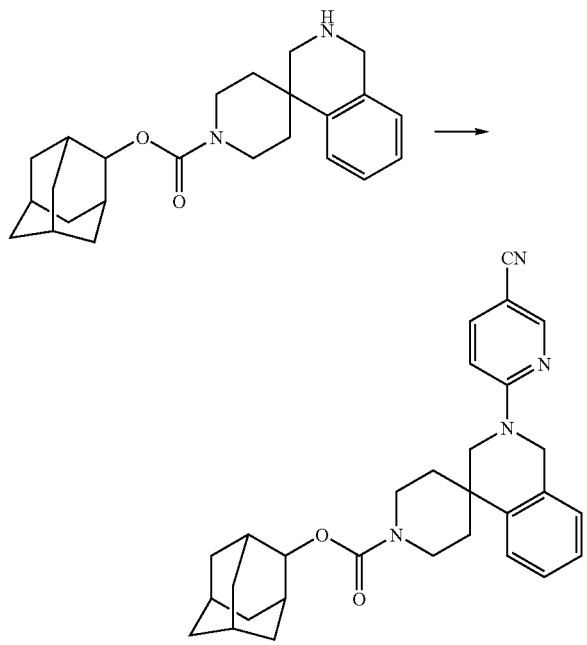

Crude 2-adamantyl 2,3-dihydro-1H-spiro[isoquinoline-4,4'-piperidine]-1'-carboxylate (21 mg, 0.054 mmol), 6-chloro-3-pyridine carbonitrile (11 mg, 1.5 equiv.) and DIEA (20 µL, 2 equiv.) were dissolved in dry DMF (1.5 mL). The mixture was heated in microwave oven for 20 min at 150° C. The mixture was diluted with ether (10 mL), washed with 3% aq HCl (2×4 mL), concentrated and purified by preparative HPLC to afford 2-adamantyl 2-(5-cyanopyridin-2-yl)-2,3-dihydro-1H-spiro[isoquinoline-4,4'-piperidine]-1'-carboxylate (9.5 mg, 37%). LC-MS Method 1 $t_R$=2.48 min, m/z=483; $^1$H NMR. (CDCl$_3$) δ=8.67 (br s, 1H), 8.50 (d, 1H), 7.76 (m, 1H), 7.41 (dd, 1H), 7.30 (m, 1H), 7.21 (d, 1H), 6.78 (m, 1H), 4.89 (s, 1H), 4.73 (s, 2H), 4.13 (d, 4H), 3.31 (t, 2H).

Example 42

(±)-Ethyl 2-(7-bromo-1'-((2-adamantyl)carbamoyl)-2,3-dihydrospiro[indene-1,4'-piperidine]-3-yl)acetate

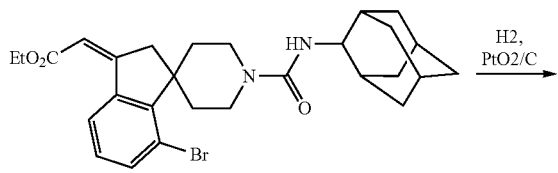

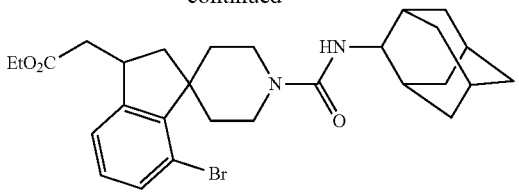

To a solution of ethyl 2-(7-bromo-1'-(2-adamantylcarbamoyl)spiro[indene-1,4'-piperidine]-3(2H)-ylidene)acetate (4 g, 8 mmol) in EtOH (50 mL) was added PtO$_2$ (400 mg) at rt under N$_2$. Then the reaction mixture was stirred at rt for 6 h under H$_2$. The reaction mixture was filtered and the filtrate was concentrated to leave crude (±)-ethyl 2-(7-bromo-1'-((2-adamantyl)carbamoyl)-2,3-dihydrospiro[indene-1,4'-piperidine]-3-yl)acetate.

Preparative HPLC followed by chiral HPLC afforded the two enantiomers.

Isomer 1 (1.0 g, 25%): $^1$H NMR (CD$_3$OD): δ=1.23 (t, 3H), 1.38 (m, 2H), 1.62 (d, 2H), 1.72 (m, 1H), 1.78 (m, 8H), 1.95 (m, 4H), 2.42 (m, 2H), 2.86 (m, 1H), 3.06 (m; 3H), 3.59 (m, 1H), 3.86 (m, 1H), 4.14 (m, 2H), 4.18 (m, 2H), 7.06 (m, 1H), 7.19 (m, 1H), 7.36 (m, 1H).

Isomer 2 (1.0 g, 25%): $^1$H NMR (CD$_3$OD): δ=1.23 (t, 3H), 1.38 (m, 2H), 1.62 (d, 2H), 1.72 (m, 1H), 1.78 (m, 8H), 1.95 (m, 4H), 2.42 (m, 2H), 2.86 (m, 1H), 3.06 (m, 3H), 3.59 (m, 1H), 3.86 (m, 1H), 4.14 (m, 2H), 4.18 (m, 2H), 7.06 (m, 1H), 7.19 (m, 1H), 7.37 (m, 1H).

The title compound was also prepared from (±)-ethyl 2-(7-bromo-2,3-dihydrospiro[indene-1,4'-piperidine]-3-yl)acetate following a procedure analogous to that described in Example 66 Step 1. LC-MS Method 5 $t_R$=1.761 min, m/z=531.1; $^1$H NMR (CDCl$_3$) δ=1.21-1.31 (m, 3H), 1.40-1.50 (m. 2H), 1.64-1.80 (m, 7H), 1.80-1.90 (m, 6H), 1.94 (m, 2H), 2.35-2.53 (m, 3H), 2.53-2.80 (m, 8H), 2.80-2.92 (m, 2H), 2.98-3.19 (m, 3H), 3.45-3.64 (m, 2H), 3.89-4.01 (m, 3H), 4.20 (m, 2H), 7.05-7.15 (m, 2H), 7.40 (m, 1H).

Example 43

(±)-2-(7-Bromo-1'-((2-adamantyl)carbamoyl)-2,3-dihydrospiro[indene-1,4'-piperidine]-3-yl)acetic acid

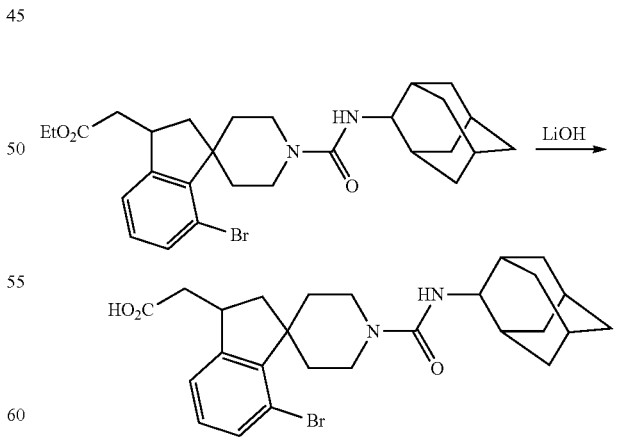

To a solution of ethyl 2-(7-bromo-1'-((2-adamantyl)carbamoyl)-2,3-dihydrospiro[indene-1,4'-piperidine]-3-yl)acetate isomer 1 (1.49 g, 3 mmol) in ethanol (15 mL) was added 2 M aq LiOH.H$_2$O (15 mL, 30 mmol) at 0° C. and the mixture was stirred overnight at rt. The reaction mixture was washed with 1N aq HCl until pH=5-6. The combined organic layers were dried over Na$_2$SO$_4$, filtered and concentrated to afford 2-(7-bromo-1'-((2-adamantyl)carbamoyl)-2,3-dihydrospiro[indene-1,4'-piperidine]-3-yl)acetic acid isomer 1 (1.27 g, 90%). LC-MS Method 5 $t_R$=1.435 min, m/z=503.2; $^1$H NMR (CDCl$_3$): δ=1.48-1.57 (m, 2H), 1.68 (m, 3H), 1.69-1.88 (m, 9H), 1.93 (m, 2H), 2.49-2.52 (m, 2H), 2.63-2.72 (m, 1H), 2.89-3.17 (m, 4H), 3.52-3.67 (m, 1H), 3.89-4.04 (m, 3H), 4.91 (m, 1H), 7.03-7.18 (m, 2H), 7.39 (m, 1H).

To a solution of ethyl 2-(7-bromo-1'-((2-adamantyl)carbamoyl)-2,3-dihydrospiro[indene-1,4'-piperidine]-3-yl)acetate, isomer 2 (1.57 g, 3 mmol) in ethanol (15 mL) was added 2 M aq LiOH.H$_2$O (15 mL, 30 mmol) at 0° C. and the mixture was stirred overnight at rt. The reaction mixture was washed with 1 aq N HCl until pH=5-6. The combined organic layers were dried over Na$_2$SO$_4$, filtered and concentrated to obtain 2-(7-bromo-1'-((2-adamantyl)carbamoyl)-2,3-dihydrospiro[indene-1,4'-piperidine]-3-yl)acetic acid isomer 2 (1.33 g, 90%). LC-MS Method 5 $t_R$=1.44 min, m/z=503.1; $^1$H NMR (CD$_3$OD): δ=1.19-1.48 (m, 2H), 1.48-1.62 (m, 4H), 1.65-1.95 (m, 12H), 2.20-2.66 (m, 3H), 2.70-3.12 (m, 4H), 3.50 (m, 1H), 3.70-4.08 (m, 3H), 4.89 (m, 1H), 6.90-7.15 (m, 2H), 7.40 (m, 1H).

Application of a similar procedure to (±)-ethyl 2-(7-bromo-1'-((2-adamantyl)carbamoyl)-2,3-dihydrospiro[indene-1,4'-piperidine]-3-yl)acetate afforded (±)-2-(7-bromo-1'-((2-adamantyl)carbamoyl)-2,3-dihydrospiro[indene-1,4'-piperidine]-3-yl)acetic acid. LC-MS Method 5 $t_R$=1.419 min, m/z=503; $^1$H NMR (CD$_3$OD) δ=1.37-1.46 (m, 2H), 1.60-1.68 (m, 2H), 1.71-1.80 (m, 1H), 1.82-1.91 (m, 8H), 1.91-2.06 (m, 5H), 2.40-2.50 (m, 2H), 2.70-2.81 (m, 1H), 2.93 (m, 1H), 3.00-3.15 (m, 3H), 3.56-3.67 (m, 1H), 3.88 (s, 1H), 4.05-4.12 (d, 2H), 7.11 (m, 1H), 7.22 (d, 1H), 7.39 (d, 1H).

Example 44

(±)-N-(2-Adamantyl)-3-(2-(methylsulfonamido)-2-oxoethyl)-2,3-dihydrospiro[indene-1,4'-piperidine]-1'-carboxamide

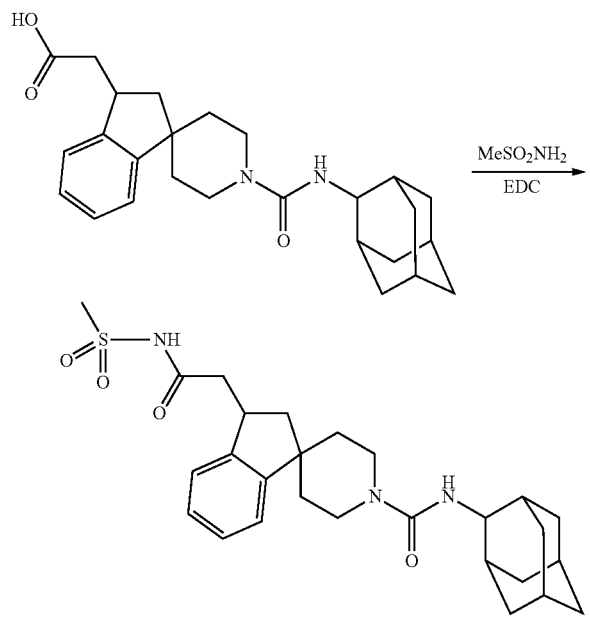

To a stirred mixture of (±)-2-(1'-((2-adamantyl)carbamoyl)-2,3-dihydrospiro[indene-1,4'-piperidine]-3-yl)acetic acid (33 mg, 78 μmol), DMAP (14.3 mg, 117 μmol) and EDC.HCl (21 mg, 117 μmol) in CH$_2$Cl$_2$ (3 mL) was added methanesulfonamide (7.4 mg, 78 μmol). The mixture was stirred overnight at rt. A 10-mL Chem-Elut cartridge was wetted with 5% aq HCl (6 mL) and allowed to stand for 5 min. The reaction mixture was applied to the cartridge and eluted with ether (40 mL). The eluate was evaporated to leave a white solid (34 mg). Preparative HPLC afforded (±)-N-(2-adamantyl)-3-(2-(methylsulfonamido)-2-oxoethyl)-2,3-dihydrospiro[indene-1,4'-piperidine]-1'-carboxamide (25.4 mg, 65%). LC-MS Method 1 $t_R$=1.85 min, m/z=500; $^1$H NMR (CDCl$_3$) δ=1.45-2.10 (21H), 2.55 (m, 2H), 3.07 (m, 1H), 3.33 (s, 3H), 3.77 (m, 2H), 3.95 (s, 1H), 4.02 (d, 1H), 4.90 (1H), 7.10-7.30 (4H), 9.70 (1H).

Example 45

(±)-3-(Cyanomethyl)-N-cyclohexyl-2,3-dihydrospiro[indene-1,4'-piperidine]-1'-carboxamide

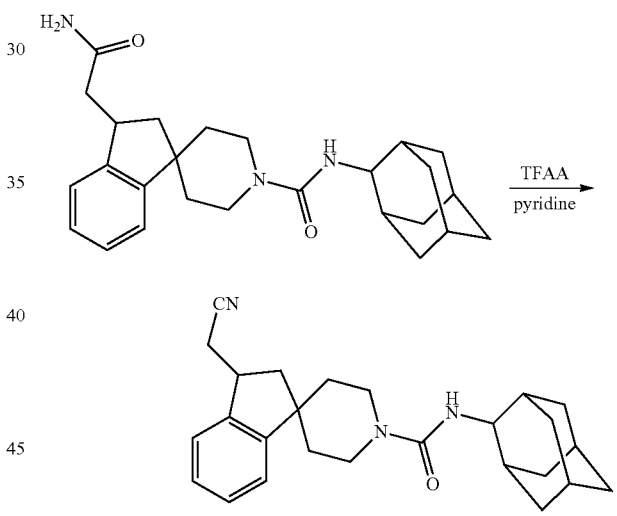

A solution of trifluoroacetic anhydride (39 mg, 0.18 mmol) in dioxane (2 mL) was added dropwise to a stirred, ice-cooled solution of (±)-3-(2-amino-2-oxoethyl)-N-(2-adamantyl)-2,3-dihydrospiro[indene-1,4'-piperidine]-1'-carboxamide (60 mg, 0.14 mmol) and pyridine (63 mg, 0.28 mmol). The reaction mixture was stirred at rt overnight. The mixture was diluted with water and extracted with EtOAc. The organic layer was washed with water and brine, dried over Na$_2$SO$_4$, and concentrated. The crude product was purified by preparative TLC to afford (±)-3-(cyanomethyl)-N-cyclohexyl-2,3-dihydrospiro[indene-1,4'-piperidine]-1'-carboxamide (10 mg, 18%). LC-MS Method 5 $t_R$=1.508 min, m/z=404.2; $^1$H NMR (CDCl$_3$) δ=1.60-1.73 (m, 5H), 1.77-1.82 (m, 5H), 1.85-1.94 (m, 2H), 2.07-2.14 (m, 1H), 2.51-2.62 (m, 3H), 2.71-2.83 (m, 114), 2.98-3.10 (m, 2H), 3.46-3.55 (m, 1H), 3.82-3.94 (m, 3H), 7.10-7.15 (m, 1H), 7.20-7.28 (m, 3H).

Example 46

(±)-3-((1H-Tetrazol-5-yl)methyl)-N-(2-adamantyl)-2,3-dihydrospiro[indene-1,4'-piperidine]-1'-carboxamide

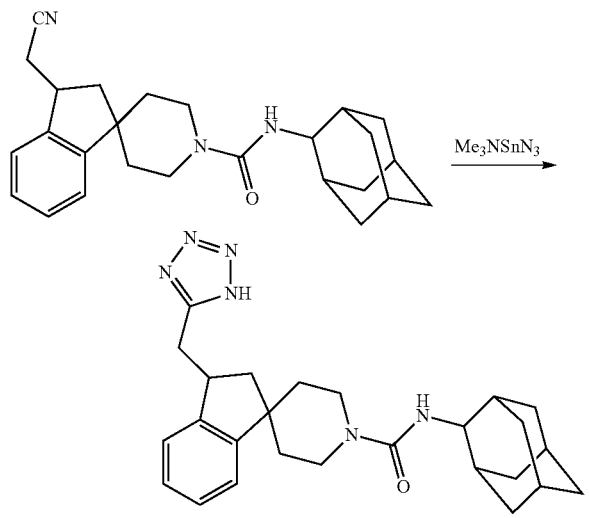

To a solution of (±)-3-(cyanomethyl)-N-cyclohexyl-2,3-dihydrospiro[indene-1,4'-piperidine]-1'-carboxamide (30 mg, 0.075 mmol) in toluene (2 mL), Me$_3$SnN$_3$ (80 mg, 0.375 mmol) was added. The reaction mixture was stirred at 80° C. overnight. The mixture was concentrated. The crude product was purified by preparative HPLC to afford (±)-3-((1H-tetrazol-5-yl)methyl)-N-(2-adamantyl)-2,3-dihydrospiro[indene-1,4'-piperidine]-1'-carboxamide (15 mg, 45%). LC-MS Method 5 $t_R$=1.28 min, m/z=447.3; $^1$H NMR (CD$_3$OD): δ=1.62-1.69 (m, 2H), 1.71-1.86 (m, 4H), 1.89-2.24 (m, 13H), 2.56-2.68 (m, 1H), 3.09-3.29 (m, 3H), 3.49 (s, 1H), 3.66-3.74 (m, 1H), 3.1-3.90 (m, 1H), 3.99 (s, 1H), 4.09-4.21 (m, 2H), 7.27 (d, 1H), 7.30-7.49 (m, 3H).

Example 47

(±)-Ethyl 2-(1'-((2-adamantyl)carbamoyl)-7-methyl-2,3-dihydrospiro[indene-1,4'-piperidine]-3-yl)acetate The title compound was prepared from (±)-ethyl 2-(7-methyl-2,3-dihydrospiro[indene-1,4'-piperidine]-3-yl)acetate following a procedure analogous to that described in Example 53. LC-MS Method 6 $t_R$=1.301 min, m/z=465.2; $^1$H NMR (CDCl$_3$) δ=1.22-1.34 (m, 3H), 1.48-1.70 (m, 9H), 1.70-1.79 (m, 4H), 1.82 (m, 8H), 1.93 (m, 2H), 2.00-2.13 (m, 1H), 2.37 (m, 1H), 2.47 (s, 3H), 2.53-2.70 (m, 2H), 2.89-3.01 (m, 2H), 3.09 (m, 1H), 3.48-3.59 (m, 1H), 3.87-4.01 (m, 3H), 4.16-4.22 (m, 2H), 4.98 (br, 1H), 6.94-7.02 (m, 2H), 7.13 (m, 1H).

Example 48

(±)-2-(1'-((2-Adamantyl)carbamoyl)-7-methyl-2,3-dihydrospiro[indene-1,4'-piperidine]-3-yl)acetic acid The title compound was prepared from (±)-ethyl 2-(1'-((2-adamantyl)carbamoyl)-7-methyl-2,3-dihydrospiro[indene-1,4'-piperidine]-3-yl)acetate following a procedure analogous to that described in Example 43. LC-MS Method 5 $t_R$=1.37 min, m/z=437.3; $^1$H NMR (CDCl$_3$) δ=1.45-1.58 (m, 3H), 1.59-1.67 (m, 2H), 1.67-1.75 (m, 4H), 1.76-1.84 (m, 6H), 1.85-1.93 (m, 2H), 1.98-2.10 (m, 1H), 2.37 (s, 3H), 2.40-2.47 (m, 1H), 2.50-2:69 (m, 2H), 2.90-3.13 (m, 3H), 3.47-3.52 (m, 1H), 3.80-3.93 (m, 3H), 5.08-5.42 (m, 5H), 6.92-6.98 (m, 2H), 7.06-7.12 (m, 1H).

Example 49

(±)-Ethyl 2(1'-((2-adamantyl)carbamoyl)-4-methyl-2,3-dihydrospiro[indene-1,4'-piperidine]-3-yl)acetate The title compound was prepared from (±)-ethyl 2-(4-methyl-2,3-dihydrospiro[indene-1,4'-piperidine]-3-yl)acetate following a procedure analogous to that described in Example 53. LC-MS Method 5 tR=1.741 min, m/z=465.2; $^1$H NMR (CDCl$_3$) δ=1.19-1.31 (m, 5H), 1.42-1.52 (m, 1H), 1.59-1.69 (m, 3H), 1.69-1.89 (m, 8H), 1.93 (m, 4H), 1.99-2.08 (m, 1H), 2.17-2.29 (m, 2H), 2.32 (s, 3H), 2.84-2.94 (m, 1H), 2.94-3.11 (m, 2H), 3.71 (m, 2H), 3.84-3.99 (m, 3H), 4.13-4.22 (m, 2H), 7.05-7.16 (m, 2H), 7.18 (m, 1H).

Example 50

(±)-2-(1'-((2-Adamantyl)carbamoyl)-4-methyl-2,3-dihydrospiro[indene-1,4'-piperidine]-3-yl)acetic acid The title compound was prepared from (±)-ethyl 2-(1'-((2-adamantyl)carbamoyl)-4-methyl-2,3-dihydrospiro[indene-1,4'-piperidine]-3-yl)acetate following a procedure analogous to that described in Example 43. LC-MS Method 5 tR=1.413 min, m/z=437.2; $^1$H NMR (CDCl$_3$) δ=1.24 (m, 2H), 1.44-1.54 (d, 1H), 1.59-1.69 (m, 4H), 1.71-1.99 (m, 9H), 2.01-2.15 (m, 3H), 2.21-2.29 (m, 1H), 2.34 (m, 4H), 2.92-3.01 (m, 1H), 3.01-3.14 (m, 1H), 3.65-3.79 (m, 1H), 3.83-4.01 (m, 3H), 4.06-4.14 (m, 1H), 6.95-7.07 (m, 2H), 7.17 (m, 1H).

Example 51

(±)-Ethyl 2-(1'-((2-adamantyl)carbamoyl)-7-chloro-2,3-dihydrospiro[indene-1,4'-piperidine]-3-yl)acetate The title compound was prepared from (±)ethyl 2-(7-chlorO-2,3-dihydrospiro[indene-1,4'-piperidine]-3-yl)acetate following a procedure analogous to that described in Example 53. LC-MS Method 5 tR=1.701 min, m/z=485.2; $^1$H NMR (CD$_3$OD) δ=1.39 (m, 3H), 1.42 (m. 2H), 1.60-1.73 (m, 3H), 1.77-2.01 (m, 12H), 2.32 (m, 1H), 2.50 (m, 1H), 2.69 (m, 1H), 2.72-3.08 (m, 4H), 3.58 (m, 1H), 3.86 (s, 1H), 4.05 (m, 2H), 4.15 (m, 2H), 7.15 (s, 3H).

Example 52

(±)-2-(1'-((2-Adamantyl) carbamoyl)-7-chloro-2,3-dihydrospiro[indene-1,4'-piperidine]-3-yl)acetic acid The title compound was prepared from (E)-ethyl 2-(1'-((2-adamantyl)carbamoyl)-7-chloro-2,3-dihydrospiro[indene-1,4'-piperidine]-3-yl)acetate following a procedure analogous to that described in Example 43. LC-MS Method 5 $t_R$=1.406 min, =457.2; $^1$HNMR (CD$_3$OD) δ=1.29 (s, 2H), 1.41-1.52 (m. 2H), 1.56-1.73 (m, 3H), 1.73-1.91 (m, 8H), 1.92-2.05 (m, 4H), 2.31-2.50 (m, 2H), 2.69-2.80 (m, 1H), 2.87-3.00 (m, 3H), 3.02-3.15 (m, 1H), 3.59 (m, 1H), 3.84 (s, 1H), 4.01-4.10 (m, 2H), 7.10-7.19 (m, 3H).

Example 53

(±)-Ethyl 2-(1'-((2-adamantyl)carbamoyl)-6-chloro-2,3-dihydrospiro[indene-1,4'-piperidine]-3-yl)acetate

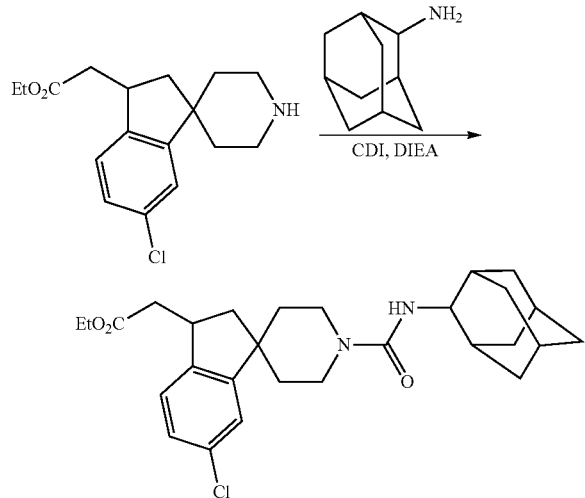

A solution of 2-aminoadamantane (123 mg, 0.66 mmol), CDI (107 mg, 0.66 mmol), DIEA (232 mg, 0.18 mmol) was stirred at 0° C. for 1 h. Then (±)-ethyl 2-(6-chloro-2,3-dihydrospiro[indene-1,4'-piperidine]-3-yl)acetate (180 mg, 0.60 mmol) was added to the solution and the mixture was stirred at rt overnight. The solvent was removed and the residue was purified by preparative TLC to give (±)-ethyl 2-(1'-((2-adamantyl)carbamoyl)-6-chloro-2,3-dihydrospiro[indene-1,4'-piperidine]-3-yl)acetate (250 mg, 86%). LC-MS Method 6 $t_R$=1.492 min, m/z=485.2; $^1$H NMR (CDCl$_3$): δ=1.29 (t, 3H), 1.56-1.66 (m, 4H), 1.66-1.80 (m, 6H), 1.85 (m, 5H), 1.93 (m, 2H), 2.04-2.16 (m, 1H), 2.37-2.49 (m, 1H), 2.56-2.65 (m, 1H), 2.88-2.92 (m, 1H), 3.00-3.20 (m, 2H), 3.55-3.66 (m, 1H), 3.81-3.90 (m, 1H), 3.90-4.00 (m, 2H), 4.20 (q, 2H), 5.26-5.50 (m, 3H), 7.07-7.14 (m, 2H), 7.19 (m, 1H).

Example 54

(±)-2-(1'-((2-Adamantyl)carbamoyl)-6-chloro-2,3-dihydro spiro[indene-1,4'-piperidin]-3-yl)acetic acid

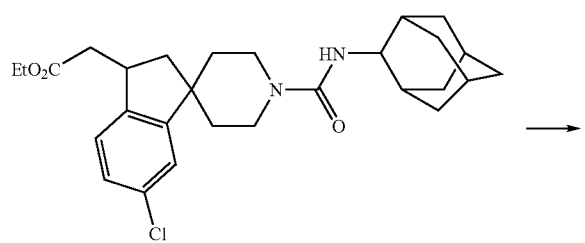

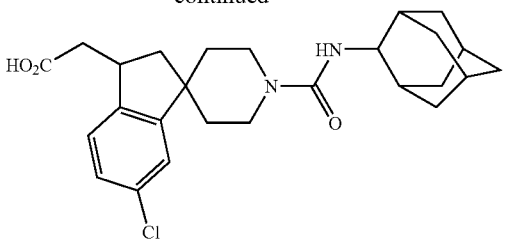

To a solution of (±)-ethyl 2-(1'-((2-adamantyl)carbamoyl)-6-chloro-2,3-dihydrospiro[indene-1,4'-piperidine]-3-yl)acetate (150 mg, 0.3 mmol) in MeOH (3 mL), LiOH (15 mg, 0.6 mmol) was added and the mixture was stirred for 2 h. The solution was concentrated to give the residue, which was purified by preparative HPLC to obtain (±)-2-(1'-((2-adamantyl)carbamoyl)-6-chloro-2,3-dihydrospiro[indene-1,4'-piperidine]-3-yl)acetic acid (10 mg, 7%). LC-MS Method 5 $t_R$=1.485 min, m/z=457.2; $^1$H NMR (CD$_3$OD): δ=1.59-1.76 (m, 6H), 1.86-1.99 (m, 8H), 1.99-2.19 (m, 6H), 2.48-2.57 (m, 1H), 2.78 (m, 1H), 2.95 (m, 1H), 3.00-3.09 (m, 1H), 3.11-3.23 (m, 1H), 3.69 (m, 1H), 3.94 (s, 1H), 4.06-4.19 (m, 2H), 7.26 (m, 3H).

Example 55

(±)-Ethyl 2-(1'-((2-adamantyl)carbamoyl)-5-chloro-2,3-dihydrospiro[indene-1,4'-piperidine]-3-yl)acetate The title compound was prepared from (±)ethyl 2-(5-chloro-2,3-dihydrospiro[indene-1,4'-piperidine]-3-yl)acetate following a procedure analogous to that described in Example 53. LC-MS Method 5 $t_R$=2.323 min, m/z=485.2; $^1$H NMR (CDCl$_3$) δ=1.29 (t, 3H), 1.54-1.69 (m, 6H), 1.73 (m, 4H), 1.79-1.89 (m, 6H), 1.92 (m, 2H), 2.04-2.16 (m, 1H), 2.36-2.47 (m, 1H), 2.56-2.63 (m, 1H), 2.82-2.90 (m, 1H), 2.99-3.19 (m, 2H), 3.34-3.58 (m, 4H), 3.60 (m, 2H), 3.81-3.89 (m, 1H), 3.94 (m, 2H), 4.16-4.24 (m, 2H), 7.08 (d, 1H), 7.13 (s, 1H), 7.22 (d, 1H).

Example 56

(±)-2-(1'-((2-Adamantyl)carbamoyl)-5-chloro-2,3-dihydrospiro[indene-1,4'-piperidine]-3-yl)acetic acid The title compound was prepared from (±)-ethyl 2-(1'-((2-adamantyl)carbamoyl)-5-chloro-2,3-dihydrospiro[indene-1,4'-piperidine]-3-yl)acetate following a procedure analogous to that described in Example 54. LC-MS Method 5 $t_R$=1.442 min, m/z=457.2; $^1$H NMR (CDCl$_3$) δ=1.21-1.32 (m, 4H), 1.43 (m, 1H), 1.49-1.70 (m, 6H), 1.72-1.91 (m, 10H), 1.88-2.11 (m, 3H), 2.42-2.51 (m, 1H), 2.64 (m, 1H), 2.8.5-3.11 (m, 4H), 3.56-3.67 (m, 1H), 3.82-4.00 (m, 3H), 4.80-4.91 (m, 1H), 6.99-7.10 (m, 1H), 7.11-7.20 (m, 2H).

Example 57

(±)-2-(1'-((2-Adamantyl)carbamoyl)-6-methyl-2,3-dihydrospiro[indene-1,4'-piperidine]-3-yl)acetic acid

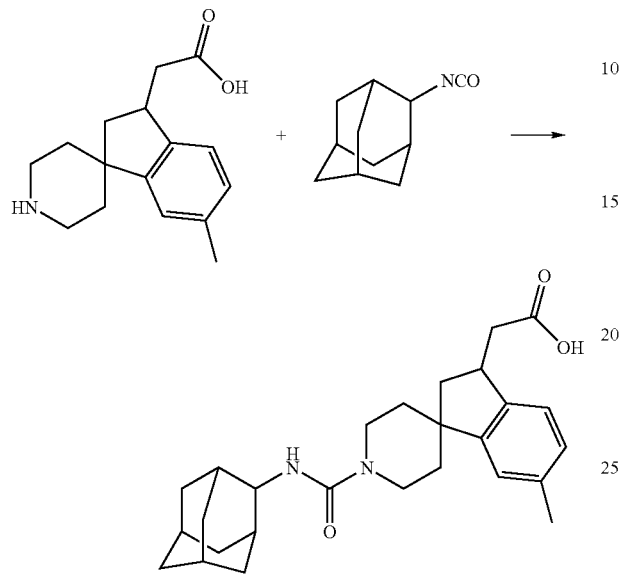

(±)-2-(6-Methyl-2,3-dihydrospiro[indene-1,4'-piperidine]-3-yl)acetic acid (0.071 mmol), 2-adamantyl isocyanate (14 mg, 1 equiv) and i-Pr$_2$NEt (37 μL, 3 equiv.) were dissolved in CH$_2$Cl$_2$ (3 mL) and put on a shaker for 1 h at rt. The mixture was diluted with EtOAc (10 mL), washed with 3% aq HCl (2×4 mL), concentrated and purified by preparative HPLC to afford (±)-2-(1'-((2-adamantyl)carbamoyl)-6-methyl-2,3-dihydrospiro[indene-1,4'-piperidine]-3-yl)acetic acid (20.4 mg, 66% yield). LC-MS Method 1 $t_R$=1.93 min, m/z=437; 1H NMR (CDCl3) 7.05 (q, 2H), 6.96 (s, 1H), 4.94 (br s, 1H), 3.98 (s, 2H), 3.89 (d, 1H), 3.59 (m, 1H), 3.10-2.93 (m, 3H), 2.63 (dd, 1H), 2.43 (dd, 1H), 2.33 (s, 3H), 2.09 (td, 1H).

Example 58

(±)-2-(1'-((2-Adamantyl)carbamoyl)-5-methyl-2,3-dihydrospiro[indene-1,4'-piperidine]-3-yl)acetic acid The title compound was prepared from (±)-2-(5-methyl-2,3-dihydrospiro[indene-1,4'-piperidine]-3-yl)acetic acid following a procedure analogous to that described in Example 57. LC-MS Method 1 $t_R$=1.94 min, m/z=437; $^1$H NMR (CDCl$_3$) δ=7.05 (s, 2H), 7.00 (s, 1H), 4.90 (br s, 1H), 3.99 (s, 2H), 3.89 (d, 2H), 3.61 (m, 1H), 3.10-2.93 (m, 3H), 2.63 (dd, 1H), 2.44 (dd, 1H), 2.33 (s, 3H), 2.08 (td, 1H).

Example 59

(±)-2-(1'-((2-Adamantyl)carbamoyl)-6-methoxy-2,3-dihydrospiro[indene-1,4'-piperidine]-3-yl)acetic acid The title compound was prepared from (±)-2-(6-methoxy-2,3-dihydrospiro[indene-1,4'-piperidine]-3-yl)acetic acid following a procedure analogous to that described in Example 57. LC-MS Method 1 $t_R$=1.83 min, m/z=453; $^1$H NMR (CDCl$_3$) δ=7.05 (d, 1H), 6.78 (dd, 1H), 6.73 (d, 1H), 4.97 (br s, 1H), 3.97 (s, 2H), 3.88 (d, 1H), 3.78 (s, 3H), 3.61 (m, 1H), 3.11-2.92 (m, 3H), 2.62 (dd, 1H), 2.46 (dd, 1H), 2.05 (td, 1H).

Example 60

(±)-2-(1'-((2-Adamantyl)carbamoyl)-6-fluoro-2,3-dihydrospiro[indene-1,4'-piperidine]-3-yl)acetic acid The title compound was prepared from (±)-2-(6-fluoro-2,3-dihydrospiro[indene-1,4'-piperidine]-3-yl)acetic acid following a procedure analogous to that described in Example 57. LC-MS Method 1 $t_R$=1.87 min, m/z=441; $^1$H NMR (CDCl$_3$) δ=7.13 (dd, 6.90 (td, 1H), 6.83 (dd, 1H), 3.97 (m, 2H), 3.90 (d, 1H), 3.60 (m, 1H), 3.14-2.90 (m, 3H), 2.65 (dd, 1H), 2.47 (dd, 1H), 2.04 (td, 1H).

Example 61

(±)-Ethyl 2-(7-bromo-1'-((1-adamantyl)carbamoyl)-2,3-dihydrospiro[indene-1,4'-piperidine]-3-yl)acetate The title compound was prepared from (±)-ethyl 2-(7-bromo-2,3-dihydrospiro[indene-1,4'-piperidine]-3-yl)acetate and 1-adamantyl isocyanate following a procedure analogous to that described in Example 57. LC-MS Method 1 tR=2.32 min, m/z=531; $^1$H NMR (CDCl$_3$) δ=7.38 (d, 1H), 7.12-7.04 (m, 2H), 4.19 (q, 2H), 3.87 (m, 2H), 3.57 (m, 1H), 3.13-2.83 (m, 4H), 2.63 (dd, 1H), 2.44 (m, 2H), 1.42 (d, 2H), 1.29 (t, 3H).

Example 62

(±)-2-(7-Bromo-1'-((1-adamantyl)carbamoyl)-2,3-dihydrospiro[indene-1,4'-piperidine]-3-yl)acetic acid The title compound was prepared from (±)-ethyl 2-(7-bromo-1'-((1-adamantyl)carbamoyl)-2,3-dihydrospiro[indene-1,4'-piperidine]-3-yl)acetate following a procedure analogous to that described in Example 54. LC-MS Method 1 $t_R$=1.99 min, m/z=503; $^1$H NMR (CDCl$_3$) δ=7.40 (d, 1H), 7.16-7.06 (m, 2H), 3.87 (m, 2H), 3.59 (m, 1H), 3.17-2.93 (m, 4H), 2.68 (dd, 1H), 2.48 (m, 2H), 1.44 (d, 2H).

Example 63

(±)-2-(7-Bromo-1'-((2-adamantyloxy)carbonyl)-2,3-dihydrospiro[indene-1,4'-piperidine]-3-yl)acetic acid

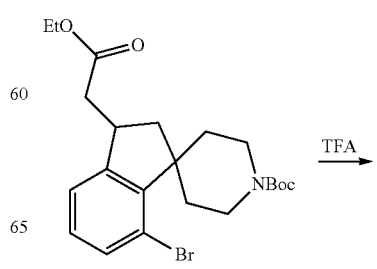

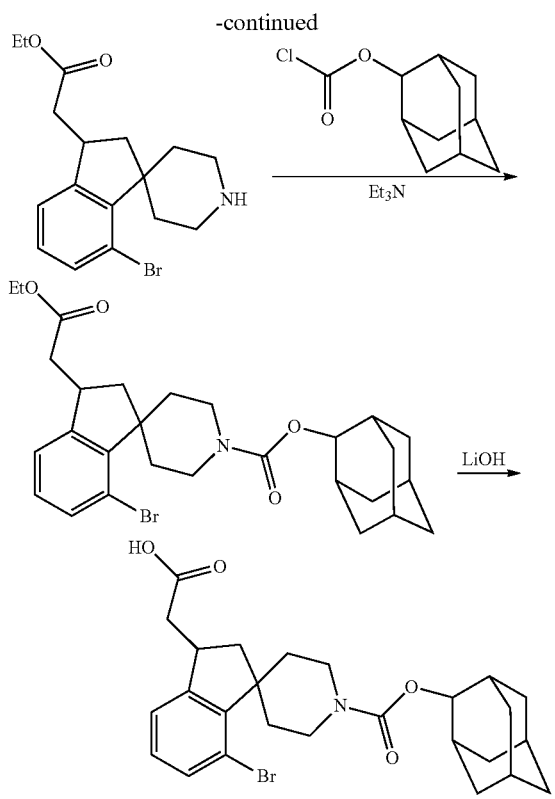

Step 1
A 100-mL of flask was charged with (±)-tert-butyl 7-bromo-3-(2-ethoxy-2-oxoethyl)-2,3-dihydrospiro[indene-1,4'-piperidine]-1'-carboxylate (500 mg, 1.1 mmol) dissolved in 20% TFA in CH$_2$Cl$_2$ solution (15 mL) at 0° C. The mixture was stirred for 0.5 h at 0° C. Then the mixture was concentrated to give crude (±)-ethyl 2-(7-bromo-2,3-dihydrospiro[indene-1,4'-piperidine]-3-yl)acetate which was used in the next step without further purification.

Step 2
A 100-mL flask was charged with (±)-ethyl 2-(7-bromo-2,3-dihydrospiro[indene-1,4'-piperidine]-3-yl)acetate (457 mg, 1.3 mmol) dissolved in dry CH$_2$Cl$_2$ (10 mL). TEA (394 mg, 3.9 mmol) was added at 0° C. and stirred for 1 h. 2-adamantyl chloroformate (301 mg, 1.4 mmol) was added and the mixture was stirred overnight. The mixture was concentrated to give a residue was purified by column chromatography to give (±)-(2-adamantyl) 7-bromo-3-(2-ethoxy-2-oxoethyl)-2,3-dihydrospiro[indene-1,4'-piperidine]-1'-carboxylate (270 mg, 39%). The enantiomers were separated by chiral HPLC to give isomer 1 (100 mg, 14%) and isomer 2 (100 mg, 14%).

Step 3
A 25-mL of flask was charged with (2-adamantyl) 7-bromo-3-(2-ethoxy-2-oxoethyl)-2,3-dihydrospiro[indene-1,4'-piperidine]-1'-carboxylate isomer 1 (100 mg, 0.19 mmol) dissolved in MeOH (3 mL). LiOH (10 mg, 0.38 mmol) dissolved in H$_2$O (3 mL) was added and the mixture was stirred for 2 h at it. The mixture was concentrated to remove MeOH. The aqueous layer was acidified with 1 N aq HCl (5 mL) and extracted with EtOAc (3×5 mL). The organic layers were combined, washed with brine, dried over Na$_2$SO$_4$, filtered and concentrated to give 2-(7-bromo-1'-((2-adamantyloxy)carbonyl)-2,3-dihydrospiro[indene-1,4'-piperidine]-3-yl)acetic acid isomer 1 (45 mg, 47%). LC-MS Method 5 tR=1.604 min, m/z=504.1; $^1$H NMR (CD$_3$OD): δ=1.26 (m, 1H), 1.37 (d, 2H), 1.61-2.09 (m, 15H), 2.41 (m, 2H), 2.72 (m, 1H), 1.39 (m, 1H), 3.01-3.22 (m, 3H), 3.55 (m, 1H); 4.11-4.29 (b, 2H), 7.06 (m, 1H), 7.20 (d, 1H), 7.36 (d, 1H).

(2-Adamantyl) 7-bromo-3-(2-ethoxy-2-oxoethyl)-2,3-dihydrospiro[indene-1,4'-piperidine]-1'-carboxylate isomer 2 was converted to 2-(7-bromo-1'-((2-adamantyloxy)carbonyl)-2,3-dihydrospiro[indene-1,4'-piperidine]-3-yl)acetic acid isomer 2 using a similar procedure. LC-MS Method 5 $t_R$=1.604 min, m/z=502.1; $^1$H NMR (CD$_3$OD) δ=1.37 (d, 2H), 1.62 (d, 3H), 1.70-1.95 (m, 8H), 2.05 (m, 4H), 2.40 (m, 2H), 2.70 (m, 114), 2.87 (m, 1H), 2.92-3.20 (b, 2H), 3.55 (m, 1H), 4.10-4.30 (b, 2H), 7.05 (m, 1H), 7.20 (d, 1H), 7.35 (d, 1H).

(±)-(2-Adamantyl) 7-bromo-3-(2-ethoxy-2-oxoethyl)-2,3-dihydrospiro[indene-1,4'-piperidine]-1'-carboxylate was converted to (±)-2-(7-bromo-1'-((2-adamantyloxy)carbonyl)-2,3-dihydrospiro[indene-1,4'-piperidine]-3-yl)acetic acid using a similar procedure. LC-MS Method 6 $t_R$=1.698 min, m/z=504.1; $^1$H NMR (CDCl$_3$) δ=0.81-1.02 (m, 4H), 1.20-1.46 (m, 4H), 1.46-1.92 (m, 1514), 1.92-2.11 (m, 4H), 2.31-2.85 (m, 5H), 2.92-3.19 (m, 3H), 3.56-3.70 (m, 2H), 4.15-4.36 (m, 2H), 4.60-4.81 (m, 3H), 4.89 (s, 1H), 7.04-7.15 (m, 2H), 7.40 (m, 1H).

Example 64

(±)-2-(6-Methyl-1'-((2-adamantyloxy)carbonyl)-2,3-dihydrospiro[indene-1,4'-piperidine]-3-yl)acetic acid The title compound was prepared from 2-(6-methyl-2,3-dihydrospiro[indene-1,4'-piperidine]-3-yl)acetic acid and 2-adamantyl chloroformate following a procedure analogous to that described in Example 57. LC-MS Method 1 $t_R$=2.24 min, m/z=438; $^1$H NMR (CDCl$_3$) δ=7.06 (q, 2H), 6.97 (s, 1H), 4.88 (s, 1H), 4.20 (t, 2H), 3.60 (m, 1H), 3.13-2.94 (m, 3H), 2.64 (dd, 1H), 2.48 (dd, 1H), 2.35 (s, 3H).

Example 65

(±)-2-(5-Methyl-1'-((2-adamantyloxy)carbonyl)-2,3-dihydrospiro[indene-1,4'-piperidine]-3-yl)acetic acid The title compound was prepared from 2-(5-methyl-2,3-dihydrospiro[indene-1,4'-piperidine]-3-yl)acetic acid and 2-adamantyl chloroformate following a procedure analogous to that described in Example 57. LC-MS Method 1 $t_R$=2.24 min, m/z=0.438; $^1$H NMR (CDCl$_3$) δ=7.06 (m, 2H), 7.00 (s, 1H), 4.88 (s, 1H), 4.19 (t, 2H), 3.61 (m, 1H), 3.03 (m, 3H), 2.64 (dd, 1H), 2.48 (dd, 1H), 2.34 (s, 3H).

Example 66

2-(7-Bromo-1'-((2-adamantyl)carbamoyl)-2,3-dihydrospiro[indene-1,4'-piperidine]-3-yl)propanoic acid

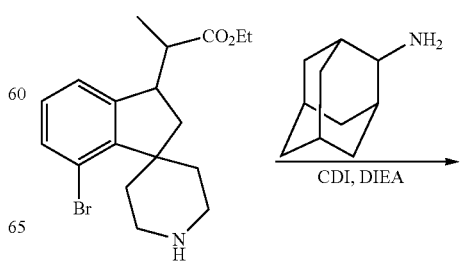

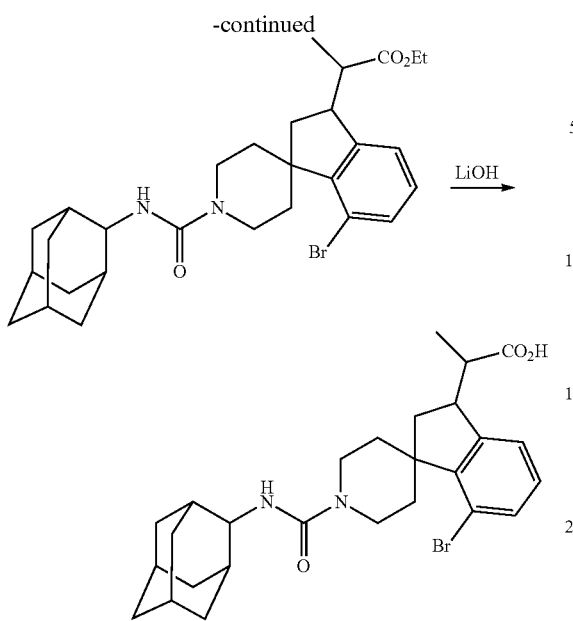

Step 1

To a solution of (±)-ethyl 2-(7-bromo-2,3-dihydrospiro[indene-1,4'-piperidine]-3-yl)propanoate (160 mg, 0.906 mmol) in dry CH₂Cl₂ was added CDI (176 mg, 1.08 mmol) and DIEA (1.16 g, 9.06 mmol) at 0° C. under N₂. The mixture was stirred for 1 h, and 2-adamantanamine hydrochloride (331 mg, 0.906) in CH₂Cl₂ was added. The reaction mixture was stirred at rt overnight. The solvent was removed under reduced pressure to leave a residue which was purified by preparative TLC to give (±)-ethyl 2-(7-bromo-1'-(2-adamantylcarbamoyl)-2,3-dihydrospiro[indene-1,4'-piperidine]-3-yl)propanoate (200 mg, 41%). ¹H NMR: (400 MHz, CDCl₃): δ=1.11 (s, 3H), 1.22 (s, 3H), 1.26 (m, 3H), 1.45 (m, 2H), 1.52 (m, 3H), 1.73 (m, 4H), 1.85 (m, 7H), 1.95 (s, 2H), 2.44 (m, 2H), 3.02-3.26 (m, 4H), 3.79 (m, 2H), 3.98 (m, 3H), 4.25 (m, 2H), 6.93 (m, 1H), 7.01 (m, 1H), 7.35 (m, 1H).

Step 2

To a solution (±)-ethyl 2-(7-bromo-1'-(2-adamantylcarbamoyl)-2,3-dihydrospiro[indene-1,4'-piperidine]-3-yl)propanoate (63 mg, 0.122 mmol) in anhydrous MeOH (1 mL) was added LiOH.H₂O (10 mg, 0.244 mmol) in H₂O (0.1 mL). The reaction mixture was stirred at rt overnight. The mixture was concentrated to give crude product, which was purified by preparative TLC to afford 2-(7-bromo-1'-((2-adamantyl)carbamoyl)-2,3-dihydrospiro[indene-1,4'-piperidine]-3-yl)propanoic acid. ¹H NMR: (400 MHz, CDCl₃): δ=1.04 (s, 3H), 1.21 (s, 3H), 1.34-1.43 (m, 2H), 1.60-1.71 (m, 3H), 1.76-2.08 (m, 13H), 2.29-2.40 (m, 1H), 2.51-2.61 (m, 1H), 2.99-3.27 (m, 3H), 3.89 (m, 2H), 4.02-4.14 (m, 2H), 7.01 (m, 1H), 7.21-7.33 (m, 2H).

Example 67

(±)-Ethyl 2-(7-bromo-1'-((2-adamantyl)carbamoyl)-2,3-dihydrospiro[indene-1,4'-piperidine]-3-yl)-2-methylpropanoate The title compound was prepared from (±)-ethyl 2-(7-bromo-2,3-dihydrospiro[indene-1,4'-piperidine]-3-yl)-2-methylpropanoate following a procedure analogous to that described in Example 66 Step 1. LC-MS Method 5 $t_R$=1.982 min, m/z=559.1; ¹H NMR (CDCl₃) δ=1.12 (s, 3H), 1.23 (s, 3H), 1.27 (m, 3H), 1.45 (m, 2H), 1.57-1.75 (m, 3H), 1.79 (m, 4H), 1.89 (m, 7H), 1.95 (s, 2H), 2.45 (m, 2H), 3.02-3.26 (m, 4H), 3.80 (m, 2H), 3.92 (m, 3H), 4.21 (m, 2H), 6.93 (m, 1H), 7.01 (m, 1H), 7.35 (m, 1H).

Example 68

(±)-2-(7-Bromo-1'-((2-adamantyl)carbamoyl)-2,3-dihydro spiro[indene-1,4'-piperidine]-3-yl-2-methyl-propanoic acid

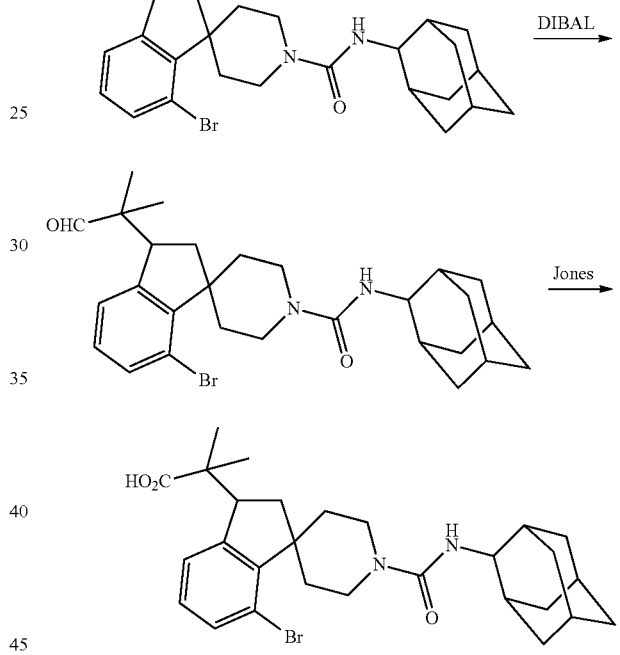

Step 1

To a solution of (±)-ethyl 2-(7-bromo-1'-((2-adamantyl)carbamoyl)-2,3-dihydrospiro[indene-1,4'-piperidine]-3-yl)-2-methylpropanoate (100 mg, 0.18 mmol) in anhydrous toluene was added DIBAL-H (0.4 mL, 1 M) at −78° C. The mixture was stirred for 30 min and quenched with MeOH. The organic layer was separated, dried and concentrated to give crude (±)-7-bromo-N-(2-adamantyl)-3-(2-methyl-1-oxopropan-2-yl)-2,3-dihydrospiro[indene-1,4'-piperidine]-1'-carboxamide which was used for the next step without purification.

Step 2

To a solution of crude (±)-7-bromo-N-(2-adamantyl)-3-(2-methyl-1-oxopropan-2-yl)-2,3-dihydrospiro[indene-1,4'-piperidine]-1'-carboxamide (40 mg, 0.0778 mmol) in dry acetone was added H₂Cr₂O₇ (234 mg, 0.8 mmol), and the solution was stirred for 1 h. 0.5 Treatment of the mixture with NaBH₄ and concentration afforded the crude product which was purified by preparative HPLC to give (±)-2-(7-bromo-1'-

((2-adamantyl)carbamoyl)-2,3-dihydrospiro[indene-1,4'-piperidine]-3-yl)-2-methylpropanoic acid (1.55 mg, 5%). LC-MS Method 5 $t_R$=1.504 min, m/z=531; $^1$H NMR: (400 MHz, CDCl$_3$): δ=1.04 (s, 3H), 1.21 (s, 3H), 1.34-1.43 (m, 2H), 1.60-1.71 (m, 3H), 1.76-2.08 (m, 13H), 2.29-2.40 (m, 1H), 2.51-2.61 (m, 1H), 2.99-3.27 (m, 3H), 3.89 (m, 2H), 4.02-4.14 (m; 2H), 7.01 (m, 1H), 7.21-7.33 (m, 2H).

Example 69

(±)-2-Adamantyl 7-bromo-3-(2-(methylsulfonamido)-2-oxoethyl)-2,3-dihydrospiro[indene-1,4'-piperidine]-1'-carboxylate The title compound was prepared from 2-(7-bromo-1'-(2-adamantyloxycarbonyl)-2,3-dihydrospiro[indene-1,4'-piperidine]-3-yl)acetic acid following a procedure analogous to that described in Example 44. LC-MS Method 5 $t_R$=1.648 min, m/z=581.1; $^1$H NMR (CD$_3$OD) δ=1.42 (m, 2H), 1.65 (m, 2H), 1.70-1.88 (m, 8H), 1.88-2.12 (m, 7H), 2.39-2.50 (m, 2H), 2.74 (m, 2H), 2.94 (m, 2H), 2.97-3.15 (m, 4H), 3.64 (m, 2H), 4.10-4.29 (m, 2H), 7.10 (m, 1H), 7.22 (m, 1H), 7.39 (m, 1H).

Example 70

(±)-7-Bromo-N-(2-adamantyl)-3-(2-(methylsulfonamido)-2-oxoethyl)-2,3-dihydrospiro[indene-1,4'-piperidine]-1'-carboxamide The title compound was prepared from (±)-2-(7-bromo-1'-((2-adamantyl)carbamoyl)-2,3-dihydrospiro[indene-1,4'-piperidine]-3-yl)acetic acid following a procedure analogous to that described in Example 44. LC-MS Method 5 $t_R$=1.406 min, m/z=579.9; $^1$H NMR (CDCl$_3$) δ=1.24 (m, 1H), 1.31-1.44 (m, 4H), 1.60-1.79 (m, 7H), 1.84 (m, 7H), 1.91 (m, 2H), 2.51-2.65 (m, 3H), 2.85-2.99 (m, 2H), 3.00-3.18 (m, 2H), 3.31 (s, 3H), 3.60-3.74 (m, 2H), 3.80 (d, 1H), 3.92-4.08 (m, 2H), 4.91 (d, 1H), 7.06 (m, 1H), 7.13 (d, 1H), 7.38 (d, 1H).

Example 71

(±)-2-Adamantyl 3-(2-(dimethylamino)-2-oxoethyl)-2,3-dihydrospiro[indene-1,4'-piperidine]-1'-carboxylate The title compound was prepared from (±)-2-adamantyl 3-(2-methoxy-2-oxoethyl)-2,3-dihydrospiro[indene-1,4'-piperidine]-1'-carboxylate and dimethylamine following a procedure analogous to that described in Example 26. LC-MS Method 5 $t_R$=2.959 min, m/z=473.2; $^1$H NMR (CD$_3$OD) δ=1.56 (m, 6H), 1.83 (m, 6H), 1.93 (d, 2H), 2.04 (m, 5H), 2.51 (m, 1H), 2.64 (m, 1H), 2.99 (s, 4H), 3.08 (s, 4H), 3.65 (m, 1H), 4.09-4.22 (br, 2H), 7.18 (m, 4H).

Example 72

2-(1'-((1-(3,5-Dimethoxybenzylcarbamoyl)-4-adamantyloxy)carbonyl)-2,3-dihydrospiro[indene-1,4'-piperidine]-3-yl)acetic acid

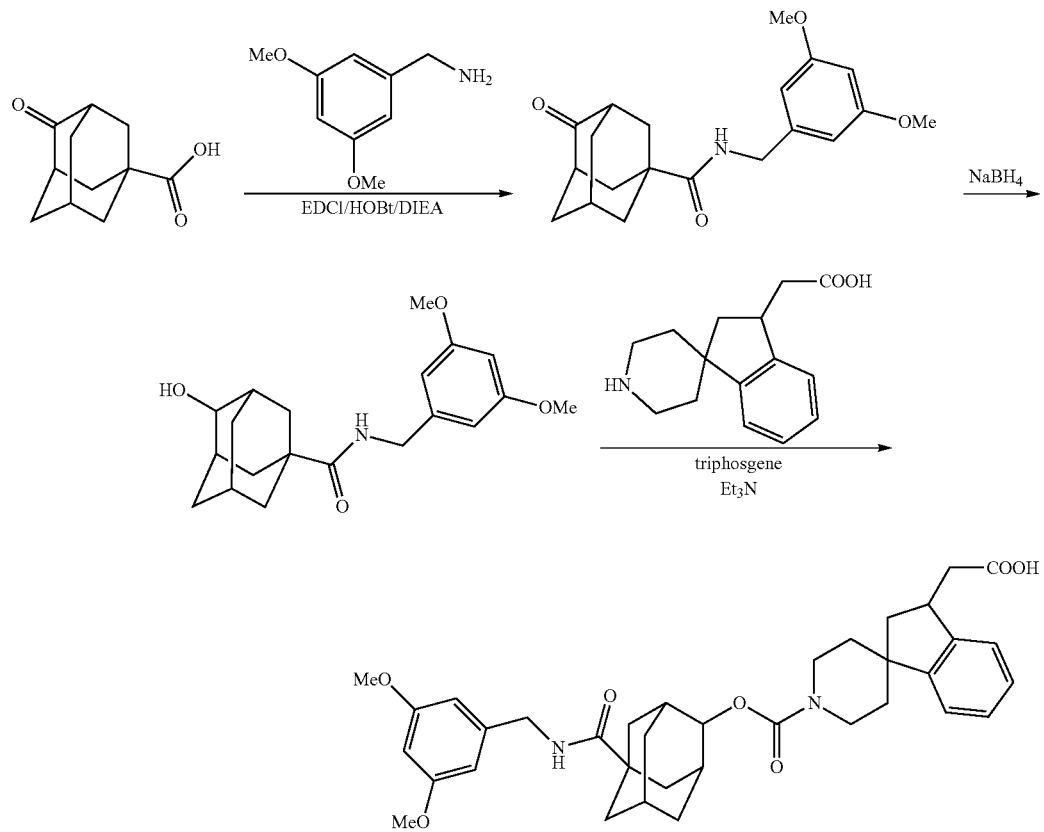

Step 1

4-oxoadamantane-1-carboxylic acid (200 mg, 1.03 mol), (3,5-dimethoxyphenyl)methanamine (172 mg, 1.03 mmol), EDCI (410 mg, 2.06 mmol), and HOBt (280 mg, 2.06 mmol) were dissolved in dry $CH_2Cl_2$. DIEA (1.3 g, 10 mmol) was added under nitrogen at 0° C. and the mixture was stirred overnight at rt. The mixture was washed with water and brine. The organic layer was dried and concentrated to give crude product which was purified by preparative TLC to give N-(3, 5-dimethoxybenzyl)-4-oxoadamantane-1-carboxamide (231 mg, 65%). $^1$H NMR: (400 MHz, $CDCl_3$): δ=1.62 (s, 4H) 1.95-2.25 (m, 13H), 2.59 (s, 2H), 3.78 (s, 3H), 3.83 (s, 3H), 4.35 (d, 2H), 6.05 (s, 1H), 6.44 (m, 2H), 7.15 (d, 1H).

Step 2

To a solution of N-(3,5-dimethoxybenzyl)-4-oxoadamantane-1-carboxamide (230 mg, 0.670 mol) in anhydrous $CH_3OH$ was added $NaBH_4$ (100 mg, 2.7 mmol) at 0° C. The reaction mixture was stirred for 1 h at rt. The solvent was removed under reduced pressure, diluted with $CH_2Cl_2$ and washed with water. The organic layer was separated, dried, and concentrated to give N-(3,5-dimethoxybenzyl)-4-hydroxyadamantane-1-carboxamide (230 mg, 100%). $^1$H NMR: (400 MHz, $CDCl_3$): δ=1.40 (d, 1H), 1.46-1.62 (m, 6H), 1.70-1.82 (m, 5H), 1.84-1.95 (m, 3H) 2.01-2.14 (m, 2H), 3.75 (s, 3H), 3.80 (s, 3H), 3.82 (s, 1H), 4.29 (d, 2H), 5.98 (s, 1H), 6.40 (m, 0.2H), 7.08 (d, 1H).

Step 3

To a solution of N-(3,5-dimethoxybenzyl)-4-hydroxyadamantane-1-carboxamide (210 mg, 0.608 mmol) and TEA (307 mg, 3.04 mmol) in dry $CH_2Cl_2$ was added triphosgene (72 mg, 0.234 mmol) at 0° C. under $N_2$. The mixture was stirred for 1 h, and (±)-2-(2,3-dihydrospiro[indene-1,4'-piperidine]-3-yl)acetic acid (130 mg, 0.608 mmol) in $CH_2Cl_2$ was added. The reaction mixture was stirred overnight at rt. The solvent was removed under reduced pressure. The residue was diluted with $CH_2Cl_2$ and then washed with water. The organic layer was dried, filtered and concentrated to afford crude product, which was purified by preparative TLC to give 2-(1'-((1-(3,5-dimethoxybenzylcarbamoyl)4-adamantyloxy) carbonyl)-2,3-dihydrospiro[indene-1,4'-piperidine]-3-yl) acetic acid (50 mg, 14%). LC-MS Method 5 $t_R$=1.341 min, m/z=617.1; $^1$H NMR: (400 MHz, $CDCl_3$): δ=1.22-1.51 (m, 5H), 1.63 (s, 3H), 1.75-1.96 (m, 12H), 2.08 (m, 3H), 2.22-2.38 (m, 3H), 2.60-3.12 (m, 12H) □3.41 (s, 2H), 3.58-3.82 (m, 6H), 4.00 (m, 2H), 4.33 (d, 0.214), 4.74 (d, 1H), 6.11 (d, 1H), 6.30-6.50 (m, 2H), 6.96-7.15 (m, 4H).

Example 73

2-(1'-((1-Carbamoyl-4adamantyloxy)carbonyl)-2,3-dihydrospiro[indene-1,4'-piperidine]-3-yl)acetic acid

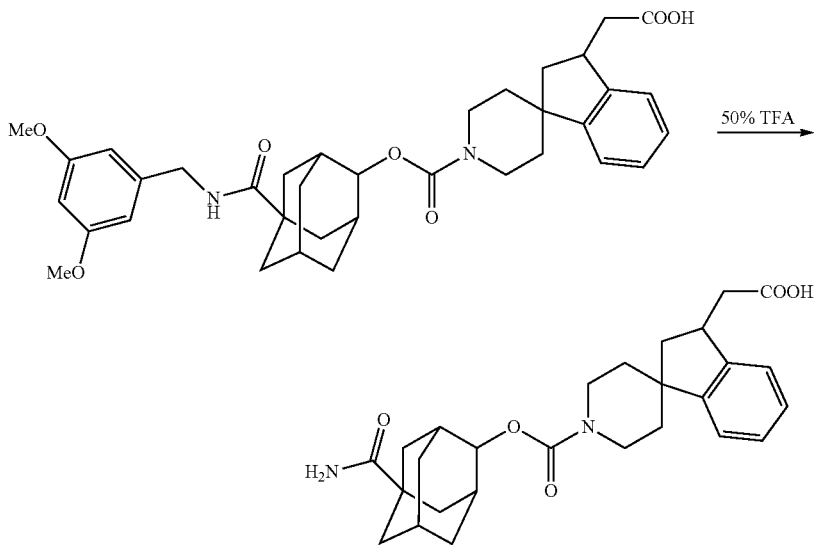

To a solution of 2-(1'-((1-(3,5-dimethoxybenzylcarbamoyl)-4-adamantyloxy)carbonyl)-2,3-dihydrospiro[indene-1, 4'-piperidine]-3-yl)acetic acid (40 mg, 0.096 mmol) was added 50% TFA (2.5 mL) at 0° C. The reaction mixture was stirred for 4 h at rt. The TFA was neutralized, and the solution was dried and concentrated to give crude product which was purified by preparative HPLC to give 2-(1'-((1-carbamoyl-4-adamantyloxy)carbonyl)-2,3-dihydrospiro[indene-1,4'-piperidine]-3-yl)acetic acid (2 mg, 7%). LC-MS Method 4 $t_R$=2.078 min, m/z=467.2; $^1$H NMR: (400 MHz, $CDCl_3$): δ=0.88 (m, 3H), 1.29 (m, 3H), 1.52-1.68 (m, 8H), 1.60-1.69 (m, 4H), 1.78-1.94 (m, 13H), 1.95-2.10 (m, 9H), 2.19-2.30 (m, 3H), 2.46 (m, 1H), 2.68 (m, 1H), 2.90-3.15 (m, 3H), 3.65 (m, 1H), 4.12-4.27 (m, 2H), 4.83-4.91 (m, 1H), 5.65-5.79 (m, 1H), 7.15-7.24 (m, 4H).

Example 74

2-(7-Bromo-1'-(1-fluoro-4-adamantylcarbamoyl)-2, 3-dihydrospiro[indene-1,4'-piperidine]-3-yl)acetic acid, isomers 1 and 2

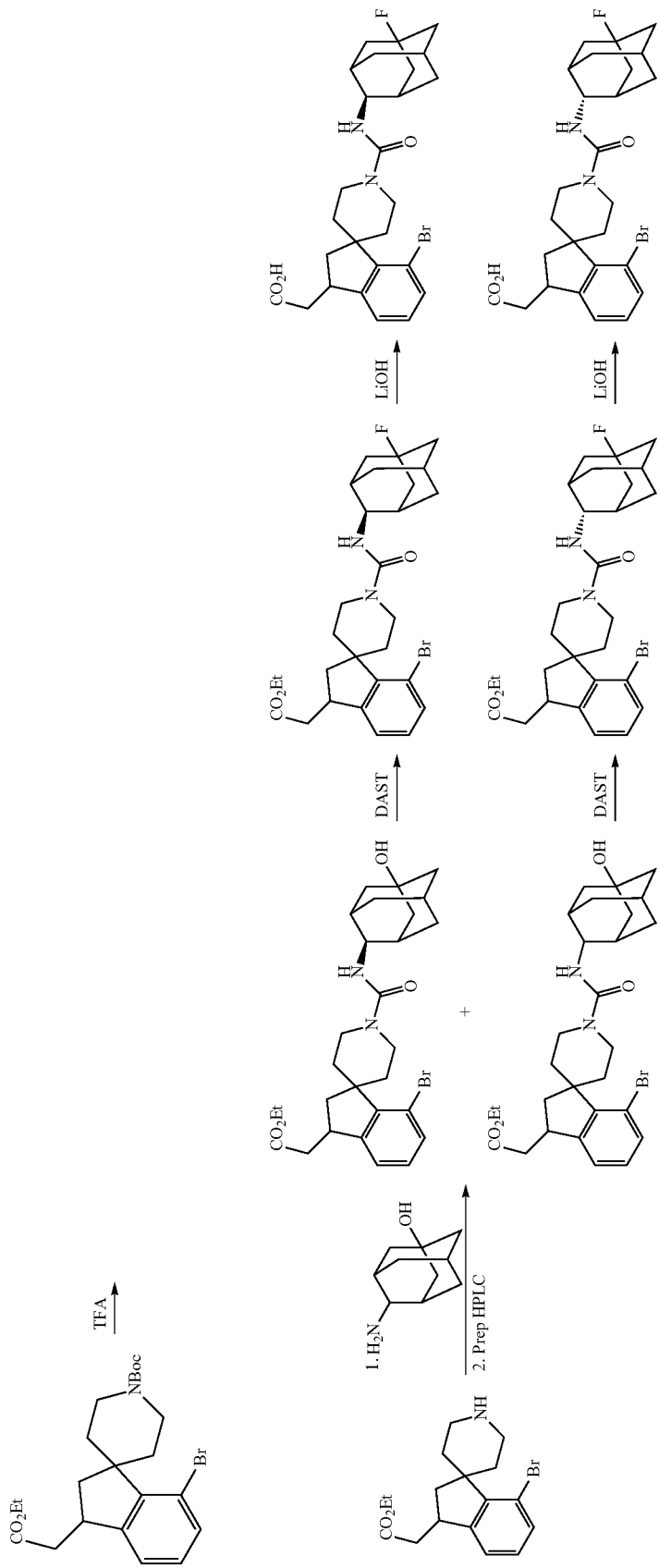

Step 1

To (±)-tert-butyl 7-bromo-3-(2-ethoxy-2-oxoethyl)-2,3-dihydrospiro[indene-1,4'-piperi-dine]-1'-carboxylate isomer 1 (500 mg, 1.10 mmol) was added 20% TFA in CH$_2$Cl$_2$ (25 mL) at 0° C. The mixture was stirred for 1 h and concentrated to give (±)-ethyl 2-(7-bromo-2,3-dihydrospiro[indene-1,4'-piperidine]-3-yl)acetate isomer 1 (498 mg, crude).

Step 2

A solution of 4-aminoadamantan-1-ol (628 mg, 3.76 mmol) in dry CH$_2$Cl$_2$ (2 mL) was added CDI (736 mg, 4.52 mmol) and DIEA (3.24 g, 25.12 mmol) at 0° C. under N$_2$ and the mixture was stirred for 1 h. Ethyl 2-(7-bromo-2,3-dihydrospiro[indene-1,4'-piperidine]-3-yl)acetate (1.10 g, 3.14 mmol) was added and the mixture was stirred overnight. The mixture was washed with 5% aq HCl, and the organic layer was concentrated to give the crude product. Purification by preparative TLC followed by preparative HPLC gave two isomers of ethyl 2-(7-bromo-1'-((1-hydroxy-4-adamantyl)carbamoyl)-2,3-dihydrospiro[indene-1,4'-piperidine]-3-yl)acetate.

Step 3

To a solution of ethyl 2-(7-bromo-1'-((1-hydroxy-4-adamantyl)carbamoyl)-2,3-dihydrospiro[indene-1,4'-piperi-dine]-3-yl)acetate isomer 1 (150 mg, 0.275 mmol) in dry CH$_2$Cl$_2$ (5 mL) was added DAST (0.1 mL) at −78° C. The mixture was stirred for 4 h and quenched with NaHCO$_3$. The mixture was extracted with CH$_2$Cl$_2$. The organic layer was dried, filtered and concentrated to give the crude product, which was purified by preparative TLC to give ethyl 2-(7-bromo-1'-((1-fluoro-4-adamantyl)carbamoyl)-2,3-dihydrospiro[indene-1,4'-piperidine]-3-yl)acetate isomer 1 (120 mg, 80%). $^1$H NMR: (400 MHz, CDCl$_3$): δ=0.89 (m, 3H) □1.25 (m, 3H), 1.43 (m, 2H), 1.61-1.82 (m, 9H), 1.94 (m, 4H), 2.18 (m, 1H), 2.36 (m, 2H), 2.48 (m, 2H), 2.68 (m, 1H), 2.85 (m, 1H), 2.92-3.14 (m, 3H), 3.60 (m, 1H), 3.88 (m, 1H), 3.95 (m, 2H), 4.20 (m, 2H), 4.70 (m, 1H), 7.09 (m, 2H), 7.41 (m, 1H).

Step 4

To a solution of ethyl 2-(7-bromo-1'-((1-fluoro-4-adamantyl)carbamoyl)-2,3-dihydrospiro[indene-1,4'-piperidine]-3-yl)acetate isomer 1 (120 mg, 0.22 mmol) in MeOH (6 mL) was added LiOH.H$_2$O (20 mg, 0.44 mmol) at room temperature and the mixture was stirred overnight. The mixture was concentrated to give a residue which was extracted with EtOAc. The organic layer was dried, filtered and concentrated to give crude product, which was purified by TLC to give 2-(7-bromo-1'-(1-fluoro-4-adamantylcarbamoyl)-2,3-dihydrospiro[indene-1,4'-piperidine]-3-yl)acetic acid isomer 1 (100 mg, 88%). LC-MS Method 5 $t_R$=1.227 min, m/z=521.1; $^1$H NMR (CD$_3$OD) δ=1.39 (m, 2H), 1.65-1.80 (m, 7H), 1.83 (m, 2H), 2.05-2.20 (m, 3H), 2.29 (m, 2H), 2.42 (m, 2H), 2.71 (m, 1H), 2.88 (m, 1H), 2.90-3.10 (m, 3H), 3.55 (m, 1H), 3.70 (s, 1H), 4.05 (d, 2H), 7.06 (m, 1H), 7.20 (d, 1H), 7.35 (d, 1H).

Isomer 2: $^1$H NMR: (400 MHz, CDCl$_3$): δ=1.26 (m, 2H), 1.40 (m, 2H), 1.70 (m, 6H), 1.86 (m, 2H), 2.12 (m, 3H), 2.22 (m, 1H), 2.34 (m, 2H), 2.46 (m, 2H), 2.70 (m, 1H), 2.86-3.13 (m, 4H), 3.55 (m, 1H), 3.70 (m, 1H), 4.05 (m, 2H), 7.06 (m, 1H), 7.22 (m, 1H), 7.35 (m, 1H).

Following procedures analogous to those described in Steps 3 and 4, ethyl 2-(7-bromo-1'-((1-hydroxy-4-adamantyl)carbamoyl)-2,3-dihydrospiro[indene-1,4'-piperidine]-3-yl)acetate was converted to 2-(7-bromo-1'-(1-fluoro-4-adamantylcarbamoyl)-2,3-dihydrospiro[indene-1,4'-piperidine]-3-yl)acetic acid isomer 2. LC-MS Method 5 $t_R$=1.235 min, m/z=519.1; $^1$H NMR (CD$_3$OD) δ=1.29 (m, 2H), 1.40 (m, 2H), 1.61 (m, 1H), 1.72-1.92 (m, 5H), 2.10 (m, 3H), 2.34 (m, 2H), 2.62 (m, 1H), 2.79 (m, 1H), 2.85-3.05 (m, 3H), 3:49 (m, 1H), 3.71 (s, 1H), 3.97 (d, 2H), 7.00 (m, 1H), 7.12 (d, 1H), 7.27 (d, 1H).

Following procedures analogous to those described in Steps 1 to 4 but without separation of the isomers in Step 2, tert-butyl 7-bromo-3-(2-ethoxy-2-oxoethyl)-2,3-dihydrospiro[indene-1,4'-piperi-dine]-1'-carboxylate isomer 2 was converted to a mixture of 2-(7-bromo-1'-(1-fluoro-4-adamantylcarbamoyl)-2,3-dihydrospiro[indene-1,4'-piperidine]-3-yl)acetic acid isomers 3 and 4. LC-MS Method 4 $t_R$=2.347 min, m/z=519.2; $^1$H NMR (CDCl$_3$) δ=1.46 (m, 2H), 1.56 (m. 1H), 1.73 (m, 4H), 1.82 (m, 2H), 1.93 (m, 4H), 2.22-2.32 (m, 3H), 2.51 (m, 2H), 2.71 (m, 1H), 2.96 (d, 1H), 3.11 (d, 1H), 3.62 (m, 1H), 3.83 (m, 1H), 3.96 (m, 3H), 7.09 (m, 1H), 7.15 (m, 1H), 7.41 (m, 1H).

Example 75

2-(7-Bromo-1'-(1-hydroxy-4-adamantylcarbamoyl)-2,3-dihydrospiro[indene-1,4'-piperidine]-3-yl)acetic acid A mixture of isomers 1 and 2 of the title compound was prepared from a mixture of isomers 1 and 2 of ethyl 2-(7-bromo-1'-((1-hydroxy-4-adamantyl)carbamoyl)-2,3-dihydrospiro[indene-1,4'-piperidine]-3-yl)acetate following a procedure analogous to that described in Example 66 Step 2. LC-MS Method 4 $t_R$=1.972/1.997 min, m/z=517.1; $^1$H NMR (CDCl$_3$) δ=1.22 (m, 2H), 1.36 (m, 2H), 1.43 (m, 1H), 1.52 (m, 2H), 1.65 (m, 5H), 1.82 (m, 2H), 2.07 (m, 3H), 2.33-2.42 (m, 2H), 2.61 (m, 1H), 2.88 (m, 2H), 2.98 (m, 2H), 3.42 (s, 2H), 3.51 (m, 1H), 3.82-3.89 (m, 2H), 7.01 (m, 1H), 7.06 (m, 1H), 7.29 (m, 1H).

Isomer 3 and 4 of the title compound were prepared from a mixture of isomers 3 and 4 of ethyl 2-(7-bromo-1'-((1-hydroxy-4-adamantyl)carbamoyl)-2,3-dihydrospiro[indene-1, 4'-piperidine]-3-yl)acetate and separated by preparative HPLC.

Isomer 3: LC-MS Method 4 $t_R$=1.972 min, m/z=519; $^1$H NMR (CDCl$_3$) δ=1.37-1.45 (m, 2H), 1.59-1.79 (m, 11H), 1.88 (d, 2H), 2.13 (m, 2H), 2.21 (s, 2H), 2.41-2.52 (m, 2H), 2.63-2.71 (m, 1H), 2.90-3.19 (m, 4H), 3.56 (m, 1H), 3.88-4.00 (m, 3H), 7.03-7.12 (m, 2H), 7.39 (d, 1H).

Isomer 4: LC-MS Method 4 $t_R$=2.007 min, m/z=519; $^1$H NMR (CDCl$_3$) δ=1.42-1.56 (m, 4H), 1.67-1.73 (m. 2H), 1.75 (m, 6H), 1.82-1.91 (m, 2H), 2.16 (m, 3H), 2.44-2.60 (m, 2H), 2.70 (m, 1H), 2.92-3.00 (m, 1H), 3.00-3.22 (m, 3H), 3.58 (m, 1H), 3.82-3.99 (m, 3H), 7.06-7.16 (m, 2H), 7.40 (d, 1H).

Example 76

(±)-2-(7-Bromo-1'-(1,7-dihydroxy-4-adamantylcarbamoyl)-2,3-dihydrospiro[indene-1,4'-piperidine]-3-yl)acetic acid The title compound was prepared from 1,7-dihydroxy-4-aminoadamantane and (±)-ethyl 2-(7-bromo-2,3-dihydrospiro[indene-1,4'-piperidine]-3-yl)acetate following procedures analogous to those described in Example 74 Steps 2 and 4. LC-MS Method 4 $t_R$=1.686 min, m/z=535.1; $^1$H NMR (CD$_3$OD) δ=1.37 (s, 3H), 1.40 (m. 2H), 1.48 (m, 2H), 1.69 (m, 4H), 1.75 (m, 2H), 1.90 (m, 2H), 2.31 (s, 2H), 2.46 (m, 2H), 2.73 (m, 1H), 2.88 (m, 1H), 2.97 (m, 1H), 3.08 (m, 2H), 3.58 (m, 1H), 3.65 (s, 1H), 4.06 (m, 2H), 7.09 (m, 1H), 7.23 (m, 1H), 7.36 (m, 1H).

Example 77

N-(2-Adamantyl)-6-methoxy-3,4-dihydro-2H-spiro[isoquinoline-1,4'-piperidine]-1'-carboxamide

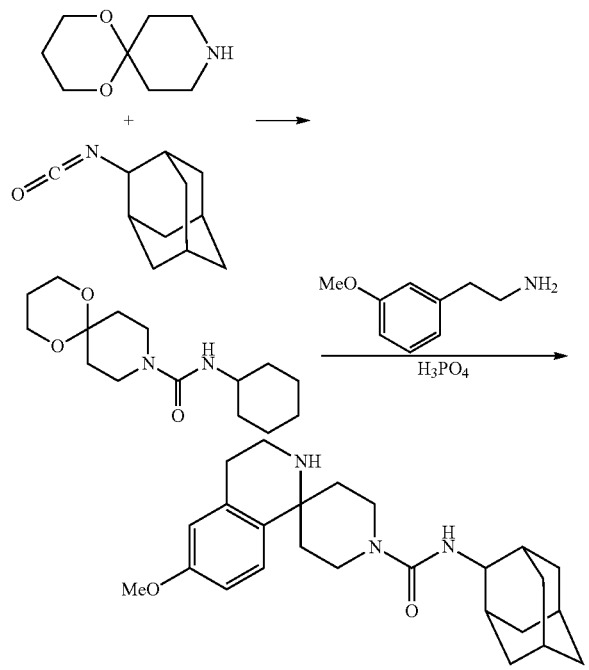

Step 1

A stirred solution of 2-adamantyl isocyanate (0.99 g, 5.6 mmol) in CH₂Cl₂ (40 mL) was cooled in an ice bath and a solution of 1,5-dioxa-9-azaspiro[5,5]undecane (0.97 g, 6.1 mmol) and DIEA (2.2 mL, 12.3 mmol) in CH₂Cl₂ (10 mL) was added over 2 min. The ice bath was allowed to melt and the mixture was stirred overnight at rt. The mixture was diluted with ether (150 mL), washed with 5% aq HCl (2×50 mL) and satd aq NaHCO₃ (50 mL), and dried over MgSO₄. Removal of the solvent left N-(2-adamantyl)-1,5-dioxa-9-azaspiro[5.5]undecane-9-carboxamide (1.55 g, 83%) as a white solid.

Step 2

A stirred mixture of N-(2-adamantyl)-1,5-dioxa-9-azaspiro[5.5]undecane-9-carboxamide (585 mg, 1.75 mmol), 3-methoxyphenethylamine (0.25 mL, 1.75 mmol) and 85% H₃PO₄ (5 mL) was heated at 90° C. for 20 h. The mixture was diluted with water (30 mL) and washed with ether (70 mL). The aqueous layer was basified with NaOH and diluted with water to give a slurry which was extracted with CH₂Cl₂ (2×50 mL). The combined CH₂Cl₂ extracts were washed with brine, dried over Na₂SO₄ and concentrated to afford an amber oil (780 mg). A 50 mg portion was purified by prep HPLC to afford N-(2-adamantyl)-6-methoxy-3,4-dihydro-2H-spiro[isoquinoline-1,4'-piperidine]-1'-carboxamide (13 mg) as an oil. LC-MS Method 1 $t_R$=1.33 min, m/z=. 410; ¹H NMR (CDCl₃) δ=1.60-2.30 (20H), 3.10 (2H), 3.42 (2H), 3.79 (s, 3H), 3.92 (2H), 3.97 (s, 1H), 5.17 (br s, 1H), 6.65 (1H), 6.82 (1H), 7.12 (1H).

Example 78

N-(2-Adamantyl)-3,4-dihydro-2H-spiro[naphthalene-1,4'-piperidine]-1'-carboxamide The title compound was prepared from 3,4-dihydro-2H-spiro[naphthalene-1,4'-piperidine] following a procedure analogous to that described in Example 1. LC-MS Method 5 $t_R$=1.781 min, m/z=379.2; ¹H NMR (CD₃OD) δ=1.65 (m, 4H), 1.82 (m, 5H), 1.86 (m, 5H), 1.95 (m, 6H), 2.03 (m, 2H), 2.76 (m, 2H), 3.12 (m, 2H), 3.87-4.05 (m, 3H), 5.76 (m, 1H), 7.03 (m, 2H), 7.14 (m, 1H), 7.89 (m, 1H).

Example 79

(2-Adamantyl) 9-(2-methoxy-2-oxoethyl)-3-azaspiro[5.5]undecane-3-carboxylate

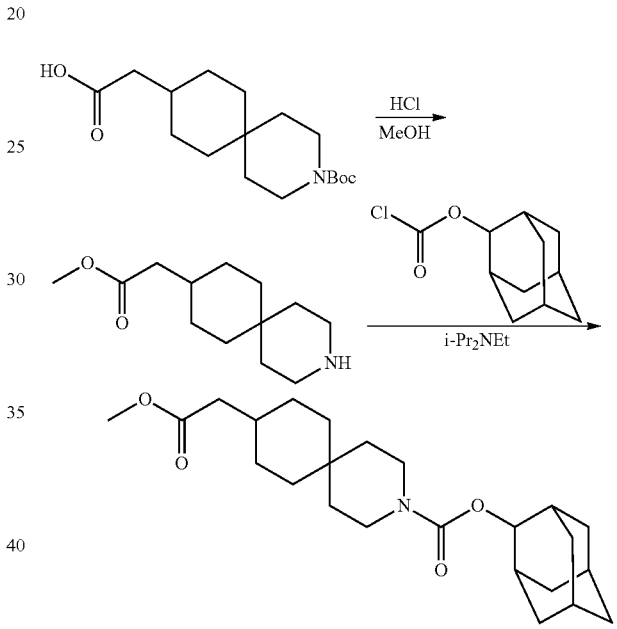

Step 1.

Methanol (50 mL) was cooled in an ice bath and SOCl₂ (2 mL) was added dropwise with stirring. After 15 min, 2-(3-(tert-butoxycarbonyl)-3-azaspiro[5.5]undecan-9-yl)acetic acid (0.34 g, purchased from WuXi Pharmatech) was added. The mixture was stirred at rt for 2 d and concentrated to afford methyl 2-(3-azaspiro[5.5]undecan-9-yl)acetate as its hydrochloride salt.

Step 2.

A vial was charged with methyl 2-(3-azaspiro[5.5]undecan-9-yl)acetate HCl salt (31 mg, 0.12 mmol) and DIEA (45 μL, 0.25 mmol). A solution of 2-adamantyl chloroformate (25 mg, 0.12 mmol) in CH₂Cl₂ (2 mL) was added and the mixture was stirred overnight at rt. A 10-mL Chem-Elut cartridge was wetted with 5% aq HCl (6 mL) and allowed to stand for 5 min. The reaction mixture was applied to the cartridge and eluted with ether (20 mL). The eluate was evaporated to dryness and the residue was purified by preparative HPLC to afford (2-adamantyl) 9-(2-methoxy-2-oxoethyl)-3-azaspiro[5.5]undecane-3-carboxylate (35 mg, 74%). LC-MS Method 1 $t_R$=2.52 min, m/z=404; ¹H NMR (CDCl₃) δ=1.05-2.10 (27H), 2.23 (d, 2H), 3.41 (m, 4H), 3.69 (s, 3H), 4.82 (s, 1H).

Example 80

2-(3-((2-Adamantyl)oxycarbonyl)-3-azaspiro[5.5]undecan-9-yl)acetic acid

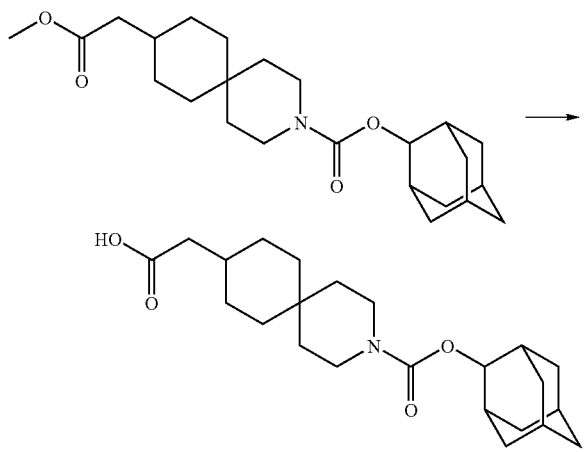

(2-Adamantyl) 9-(2-methoxy-2-oxoethyl)-3-azaspiro[5.5]undecane-3-carboxylate (30 mg, 74 μmol) was dissolved in THF (0.25 mL), water (0.25 mL) and MeOH (0.5 mL) and LiOH.H$_2$O (8 mg, 0.19 mmol) was added. The mixture was stirred at rt for 2 d and TFA (10 mL, 0.14 mmol) was added. The solution was submitted directly to prep HPLC to afford 2-(34(2-adamantyl)oxycarbonyl)-3-azaspiro[5.5]undecan-9-yl)acetic acid (10.5 mg, 36%). LC-MS Method 1 $t_R$=2.17 min, m/z=390; $^1$H NMR (CDCl$_3$) δ=1.0-2.05 (27H), 2.27 (d, 2H), 3.44 (m, 4H), 4.83 (s, 1H).

Example 81

Methyl 2-(3-((2-adamantyl)carbamoyl)-3-azaspiro[5.5]undecan-9-yl)acetate

The title compound was prepared following a procedure analogous to that described in Example 79 using 2-adamantyl isocyanate in place of 2-adamantyl chloroformate. LC-MS Method 1 $t_R$=2.15 min, m/z=403; $^1$H NMR (CDCl$_3$) δ=1.05-2.10 (27H), 2.24 (d, 2H), 3.30 (m, 4H), 3.42 (s, 1H), 3.68 (s, 3H), 4.93 (s, 1H).

Example 82

2-(3-((2-Adamantyl)carbamoyl)-3-azaspiro[5.5]undecan-9-yl)acetic acid

The title compound was prepared following a procedure analogous to that described in Example 80. LC-MS Method 1 $t_R$=1.83 min, m/z=389; $^1$H NMR (CDCl$_3$) δ=1.10-2.00 (29H), 3.33 (m, 4H), 2.27 (d, 2H), (3.93 (s, 1H).

Example 83

N-(2-Adamantyl)-3H-spiro[isobenzofuran-1,4'-piperidine]-1'-carboxamide

The title compound was prepared from 3H-spiro[isobenzofuran-1,4'-piperidine] following a procedure analogous to that described in Example 79 Step 2 using 2-adamantyl isocyanate in place of 2-adamantyl chloroformate. LC-MS Method 1 $t_R$=2.03 min, m/z=367; $^1$H NMR (CDCl$_3$) δ=1.60- 2.00 (18H), 3.29 (m, 2H), 3.94 (m, 2H), 3.99 (s, 1H), 4.95 (1H), 5.08 (s, 2H), 7.05-7.35 (4H).

Example 84

2-Adamantyl 3H-spiro[isobenzofuran-1,4'-piperidine]-1'-carboxylate

The title compound was prepared from 3H-spiro[isobenzofuran-1,4'-piperidine] following a procedure analogous to that described in Example 79. LC-MS Method 1 $t_R$=2.42 min, m/z=368; $^1$HNMR (CDCl$_3$) δ=1.50-2.10 (18H), 3.24 (m, 2H), 4.19 (m, 2H), 4.88 (s, 1H), 5.09 (s, 2H), 7.05-7.35 (4H).

Example 85

1-Tert-butyl 1'-(trans-1-carbamoyl-4-adamantyl)spiro[indoline-3,4'-piperidine]-1,1'-dicarboxylate

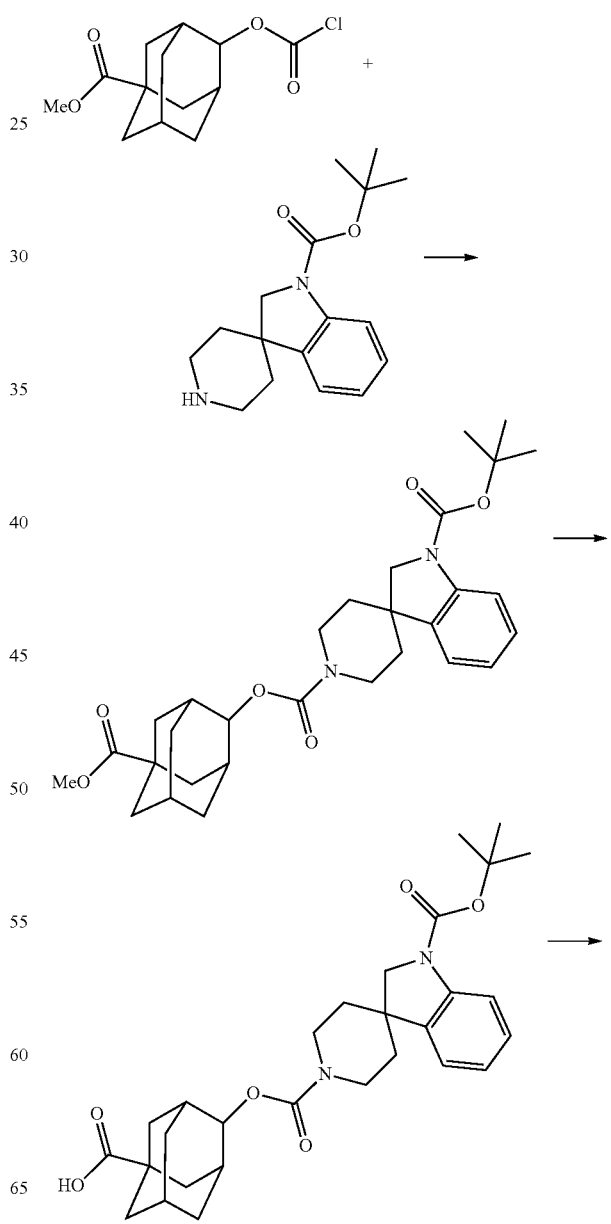

117
-continued

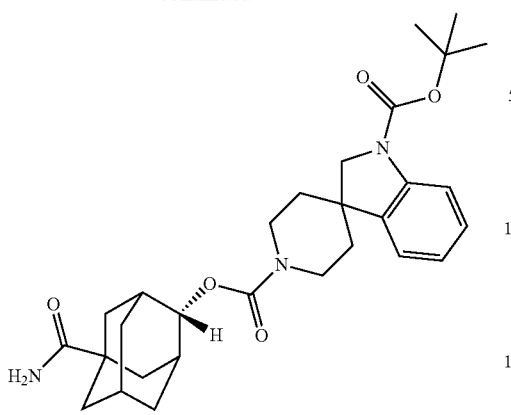

The title compound was prepared from tert-butyl spiro[indoline-3,4'-piperidine]-1-carboxylate and 1-methoxycarbonyl-4-adamantyl chloroformate following procedures analogous to those described in Example 79 Step 2, Example 80 and Example 127. LC-MS Method 5 $t_R$=2.467 min, m/z=410.2; $^1$H NMR (CD$_3$OD) δ=1.53-1.72 (m, 16H), 1.79-2.06 (m, 12H), 2.13 (d, 3H), 3.92 (s, 2H), 4.18 (m, 2H), 6.98 (m, 1H), 7.16 (m, 2H), 7.42-7.98 (br, 1H).

Example 86

N-(2-Adamantyl)-2-methylspiro[isoindoline-1,4'-piperidine]-1'-carboxamide

The title compound was prepared following procedures analogous to those described in Example 87 using 2-methylspiro[isoindoline-1,4'-piperidine]-3-thione in place of spiro[isoindoline-1,4'-piperidine]-3-thione in Step 1. LC-MS Method 1 $t_R$=1.26 min, m/z=380; $^1$H NMR (CD$_3$OD) δ=7.68 (m, 1H), 7.47 (m, 3H), 3.00 (s, 3H), 2.26 (m, 2H), 1.64 (d, 2H).

Example 87

N-(2-Adamantyl)spiro[isoindoline-1,4'-piperidine]-1'-carboxamide

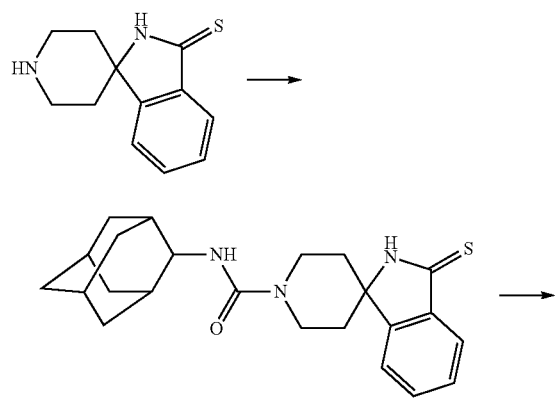

118
-continued

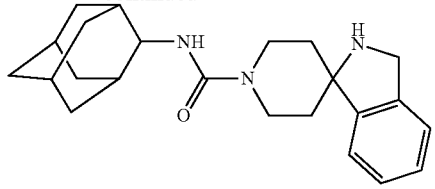

Step 1

Crude spiro[isoindoline-1,4'-piperidine]-3-thione TFA salt was taken up in 1:1 MeCN:10% aq K$_2$CO$_3$ (10 mL) and 2-adamantylisocyanate (52 mg, 0.30 mmol, 2.5 equiv) was added. After 2 h the desired thiolactam, urea was formed. The mixture was concentrated to ~50% of its original volume and diluted with EtOAc. The mixture was washed with 1.0 M aq HCl and brine, dried over Na$_2$SO$_4$, and evaporated. The residue was purified by flash chromatography on silica (4 g), eluting with 20-80% EtOAc in hexanes, affording N-(2-adamantyl)-3-thioxospiro[isoindoline-1,4'-piperidine]-1'-carboxamide (51 mg, 0.093 mmol, 85% yield) as a pale yellow solid.

Step 2

N-(2-adamantyl)-3-thioxospiro[isoindoline-1,4'-piperidine]-1'-carboxamide (6 mg, 0.015 mg, 1.0 equiv) and Raney Nickel (~100 mg) were heated at 60° C. in ethanol (10 mL) for 0.5 h. After this time LC-MS showed complete reduction of the thiolactam. The mixture was cooled to rt, filtered and evaporated. The residue was purified by prep HPLC to afford N-(2-adamantyl)spiro[isoindoline-1,4'-piperidine]-1'-carboxamide as its TFA salt. LC-MS Method 1 $t_R$=1.28 min, m/z=366; $^1$H NMR (CD$_3$OD) δ=7.45 (m, 3H), 4.14 (m, 2H), 2.20 (m, 2H), 1.64 (d, 2H).

Example 88

7-Chloro-N-(2-adamantyl)-2-methylspiro[isoindoline-1,4'-piperidine]-1'-carboxamide

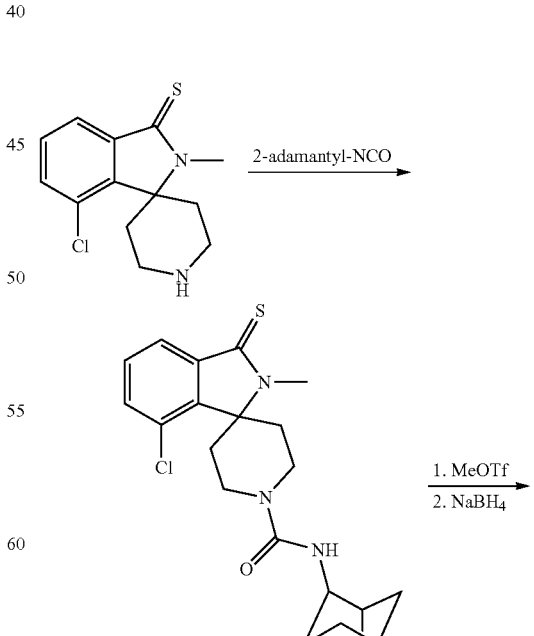

-continued

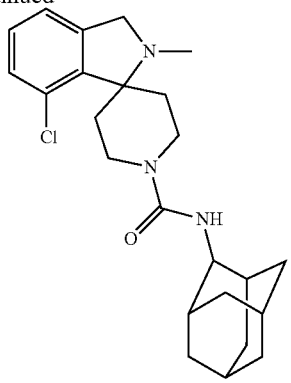

Step 1

7-Chloro-2-methylspiro[isoindoline-1,4'-piperidine]-3-thione TFA salt (0.628 mmol, 1.0 equiv) was dissolved in 1:1 AcCN:10% aq $K_2CO_3$ (10 mL). To this solution 2-adamantyl isocyanate (140 mg, 0.786 mmol, 1.25 equiv) was added and the mixture stirred for 2 h. After this time the desired urea was formed. The mixture was concentrated to ~50% of its original volume and diluted with EtOAC. The mixture was washed with 1.0 M aq HCl and brine, dried over $Na_2SO_4$, and evaporated. The residue was purified by flash chromatography on silica (12 g), eluting with 20-80% EtOAc in hexanes, affording 7-chloro-N-(2-adamantyl)-2-methyl-3-thioxospiro[isoindoline-1,4'-piperidine]-1'-carboxamide (217 mg, 78% yield) as a pale yellow solid.

Step 2

7-Chloro-N-(2-adamantyl)-2-methyl-3-thioxospiro[isoindoline-1,4'-piperidine]-1'-carboxamide (21 mg, 0.038 mmol, 1.0 equiv) was dissolved in $CH_2Cl_2$ (5 mL) and the solution was cooled to 0° C. Methyl triflate (145 mg, 100 μL, 0.84 mmol, 23 equiv) was added and the methylation of the thiolactam, monitored by LC-MS. To this solution was added $NaBH_4$ (100 mg, 2.6 mmol, ~70 equiv) and the mixture allowed to stir for 0.5 h. After this, time LC-MS showed formation of the desired amine. The mixture was diluted with $CH_2Cl_2$ (~10 mL) and quenched by addition of satd aq $NH_4Cl$. The layers were separated and the organic layer was dried over $Na_2SO_4$, and evaporated. The residue was purified by preparative HPLC to afford 7-Chloro-N-(2-adamantyl)-2-methylspiro[isoindoline-1,4'-piperidine]-1'-carboxamide as its TFA salt. LC-MS Method 1 $t_R$=1.35 min, m/z=414; $^1$H NMR ($CD_3OD$) δ=7.4 (m, 3H), 3.87 (m, 1H), 3.11 (s, 3H), Example 89

2-(1'-((1-(Benzylcarbamoyl)-4-adamantyloxy)carbonyl)-2,3-dihydrospiro[indene-1,4'-piperidine]-3-yl)acetic acid The title compound was prepared following procedures analogous to those described in Example 72 using benzylamine in Step 1. LC-MS Method 5 $t_R$=1.317 min, m/Z=557.1; $^1$H NMR ($CDCl_3$) δ=1.23-1.61 (m, 7H), 1.67 (m. 2H), 1.76-2.03 (m, 9H), 2.18 (m, 4H), 2.29-2.61 (m, 9H), 2.61-2.93 (m, 3H), 3.06 (m, 1H), 3.48 (s, 2H), 3.97 (m, 2H), 4.23-4.45 (m, 2H), 4.73 (m, 1H), 6.05-6.26 (d, 2H), 7.02 (m, 3H), 7.06-7.29 (m, 4H), 7.34 (m, 2H).

Example 90

4-(1'-(2-Adamantylcarbamoyl)spiro[indoline-3,4'-piperidine]-1-yl)-4-oxobutanoic acid

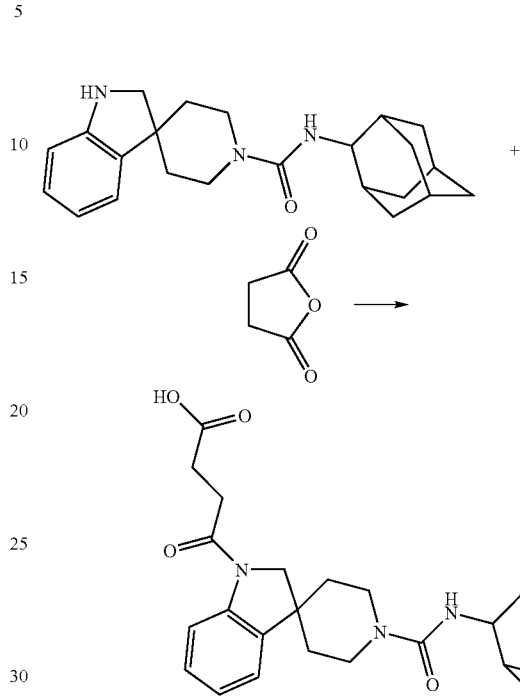

To a solution of N-(2-adamantyl)spiro[indoline-3,4'-piperidine]-1'-carboxamide (20 mg, 0.06 mmol) and succinic anhydride (12 mg, 0.12 mmol) in $CH_2Cl_2$ (5 mL) was added TEA. After stirred for 2 h at rt the solvent was removed to give 4-(1'-(2-adamantylcarbamoyl)spiro[indoline-3,4'-piperidine]-1-yl)-4-oxobutanoic acid (20 mg, 74%). LC-MS Method 5 $t_R$=3.6 min, m/z=953.1; $^1$H NMR ($CD_3OD$) δ=1.69 (d, 2H), 1.75 (d, 2H), 1.80-1.99 (m, 11H), 2.00-2.10 (m, 5H), 2.20 (s, 2H), 2.60-2.70 (m, 2H), 2.80-2.90 (m, 2H), 3.06-3.18 (m, 2H), 3.93 (s, 1H), 4.10-4.19 (m, 2H), 4.20 (s, 2H), 5.90 (d, 1H), 7.10 (m, 1H), 7.19-7.28 (m, 2H), 8.16 (d, 1H).

Example 91

(E)-4-(1'-(2-Adamantyl carbamoyl)-1H-spiro[isoquinoline-4,4'-piperidine]-2(3H)-yl)-4-oxobut-2-enoic acid The title compound was prepared from N-(2-adamantyl)-2,3-dihydro-1H-spiro[isoquinoline-4,4'-piperidine]-1'-carboxamide and maleic anhydride following a procedure analogous to that described in Example 90. LC-MS Method 1 $t_R$=1.7 min, m/z=478; $^1$H NMR ($CDCl_3$) 1.60-2.20 (18H), 3.11 (m, 2H), 3.58 (s, 2H), 3.92 (br s, 4H), 4.39 (s, 2H), 5.00 (br s, 1H), 6.30-7.45 (6H).

Example 92

4-(1'-(2-Adamantylcarbamoyl)-1H-spiro[isoquinoline-4,4'-piperidine]-2(3H)-yl)-4-oxobutanoic acid The title compound was prepared from N-(2-adamantyl)-2,3-dihydro-1H-spiro[isoquinoline-4,4'-piperidine]-1'-carboxamide following a procedure analogous to that described in Example 90. LC-MS Method 5 $t_R$=2.055 min, m/z=480.2;

¹H NMR (CD₃OD) δ=1.56-1.70 (m, 4H), 1.74-1.88 (m, 8H), 1.84-2.08 (m, 6H), 2.65 (m, 2H), 2.76 (m, 2H), 3.15-3.24 (m, 2H), 3.84 (m, 2H), 3.92 (s, 2H), 4.01 (m, 1H), 7.16-7.29 (m, 3H), 7.41 (m, 1H):

Example 93

5-(1'-(2-Adamantylcarbamoyl)spiro[indoline-3,4'-piperidine]-1-yl)-5-oxopentanoic acid The title compound was prepared from glutaric anhydride following a procedure analogous to that described in Example 90. LC-MS Method 4 $t_R$=2.341 min, m/z=480.3; ¹H NMR (CDCl₃) δ=1.62 (m, 4H), 1.69 (m, 6H), 1.79 (m, 6H), 1.88 (m, 3H), 2.05 (m, 4H), 2.51 (m, 4H), 2.95 (m, 2H), 3.87 (m, 1H), 3.91 (m, 2H), 3.94 (m, 1H), 7.02 (m, 1H), 7.09 (m, 1H), 7.19 (m, 1H), 7.24 (m, 1H), 8.16 (m, 1H).

Example 94

4-(1'-(2-Adamantyloxycarbonyl)-1H-spiro[isoquinoline-4,4'-piperidine]-2(3H)-yl)-4-oxobutanoic acid The title compound was prepared from N-(2-adamantyl)-2,3-dihydro-1H-spiro[isoquinoline-4,4'-piperidine]-1'-carboxamide following a procedure analogous to that described in Example 90. LC-MS Method 1 $t_R$=1.95 min, m/z=480; ¹H NMR (CD₃OD) δ=7.38 (m, 1H), 7.26-7.13 (m, 3H), 4.81 (s, 2H), 4.09 (m, 2H), 3.85 (m, 1H), 3.23 (m, 1H), 2.77 (m, 2H), 2.65 (m, 2H).

Example 95

5-(1'(2-Adamantylcarbamoyl)-1H-spiro[isoquinoline-4,4'-piperidine]-2(3H)-yl)-5-oxopentanoic acid The title compound was prepared from N-(2-adamantyl)-2,3-dihydro-1H-spiro[isoquinoline-4,4'-piperidine]-1'-carboxamide and glutaric anhydride following a procedure analogous to that described in Example 90. LC-MS Method 5 tR=2.034 min, m/z=494.3; ¹H NMR (CD₃OD) δ=1.52-1.69 (m, 4H), 1.79-2.04 (m, 16H), 2.41 (m, 2H), 2.62 (m, 2H), 3.16-3.27 (m, 2H), 3.86 (m, 2H), 3.98 (m, 3H), 7.15-7.39 (m, 3H), 7.41 (d, 1H).

Example 96

5-(1'-(2-Adamantylcarbamoyl)spiro[indoline-3,4'-piperidine]-1-yl)-3,3-dim ethyl-5-oxopentanoic acid The title compound was prepared from 3,3-dimethylglutaric anhydride following a procedure analogous to that described in Example 90. LC-MS Method 4 $t_R$=2.815 min, m/z=508.3; ¹H NMR (CDCl₃) δ=1.18 (s, 6H), 1.64 (m, 6H), 1.73 (m, 8H), 1.86 (m, 8H), 1.95 (m, 10H), 2.55 (s, 2H), 2.66 (s, 2H), 3.01 (m, 2H), 4.00 (m, 2H), 4.05 (s, 3H), 4:92 (s, 1H), 7.19 (m, 2H), 7.31 (m, 2H), 8.29 (m, 1H):

Example 97

4-(1'-(2-Adamantylcarbamoyl)-1H-spiro[isoquinoline-4,4'-piperidine]-2(3H)-yl)-2,2-dimethyl-4-oxobutanoic acid

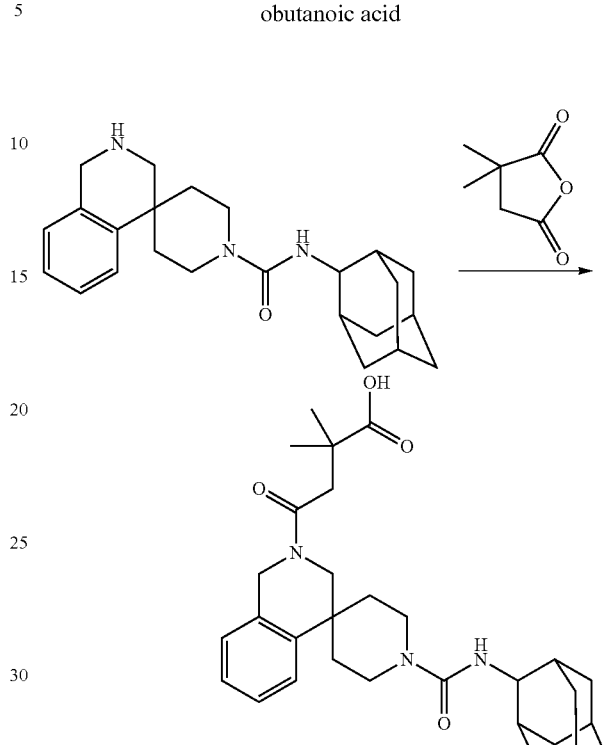

A vial was charged with 3,3-dimethylsuccinic anhydride (7.4 mg, 58 μmol), DIEA (15 mL, 90 μmol) and CH₂Cl₂ (1 mL). A solution of N-(2-adamantyl)-2,3-dihydro-1,4-spiro[isoquinoline-4,4'-piperidine]-1'-carboxamide (25 mg, 53 μmol) in CH₂Cl₂ (1 mL) was added and the mixture was stirred overnight. A 10-mL Chem-Elut cartridge was wetted with 5% aq HCl (6 mL) and allowed to stand for 5 min. The reaction mixture was applied to the cartridge and eluted with ether (20 mL). The eluate was evaporated to dryness and the residue was purified by preparative HPLC to afford 4-(1'-(2-adamantylcarbamoyl)-1H-spiro[isoquinoline-4,4'-piperidine]-2(3H)-yl)-2,2-dimethyl-4-oxobutanoic acid (17 mg, 63%). LC-MS Method 1 $t_R$=1.87 min, m/z=508; ¹H NMR (CDCl₃) 1.32 (s, 6H), 1.50-2.10 (18H), 2.73 (s, 2H), 3.20 (m, 2H), 3.90 (m, 4H), 3.94 (s, 1H), 4.70 (s, 2H), 4.98 (1H), 7.05-7.40 (4H).

Example 98

5-(1'-(2-Adamantylcarbamoyl)-1H-spiro[isoquinoline-4,4'-piperidine]-2(3H)-yl)-3,3-dimethyl-5-oxopentanoic acid The title compound was prepared from N-(2-adamantyl)-2,3-dihydro-1,1-spiro[isoquinoline-4,4'-piperidine]-1'-carboxamide and 3,3-dimethylglutaric anhydride following a procedure analogous to that described in Example 99. LC-MS Method 5 $t_R$=2.508 min, m/z=522.3; ¹H NMR (CD₃OD) δ=1.10-1.20 (m, 6H), 1.53-1.70 (m. 4H), 1.77-1.90 (m, 8H), 1.90-2.06 (m, 6H), 2.40-2.50 (m, 2H), 2.64-2.72 (m, 2H), 3.21 (m, 1H), 3.89 (s, 1H), 3.91-4.04 (m, 3H), 7.13-7.29 (m, 3H), 7.40 (d, 1H).

Example 99

(1S,2R)-2-(1'42-Adamantylcarbamoyl)-2,3-dihydro-1H-spiro[isoquinoline-4,4'-piperidine]-2-ylcarbonyl)cyclopropanecaxboxylic acid The title compound was prepared from N-(2-adamantyl)-2,3-dihydro-1H-spiro[isoquinoline-4,4'-piperidine]-1'-carboxamide and 3-oxabicyclo[3.1.0]hexane-2,4-dione following a procedure analogous to that described in Example 99. LC-MS Method 1 tR=1.7 min, m/z=492; $^1$HNMR (CDCl$_3$) δ=1.45-2.35 (21H), 3.09 (m, 2H), 3.77 (d, 1H), 3.82 (d, 1H), 3.94 (s, 2H), 4.10 (d, 1H), 4.79 (m, 1H), 4.88 (s, 2H), 4.96 (1H), 7.05-7.40 (4H).

Example 100

(1RS,2RS)-2-(1'-(2-Adamantyloxycarbonyl)-2,3-dihydro-1H-spiro[isoquinoline-4,4'-piperidine]-2-ylcarbonyl)cyclopropanecarboxylic acid

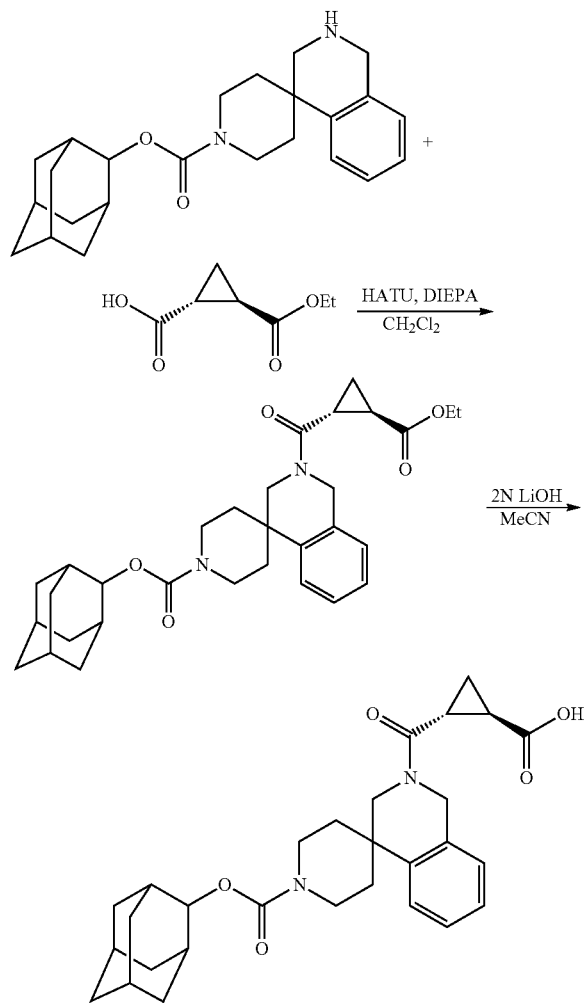

Step 1

2-Adamantyl 2,3-dihydro-1H-spiro[isoquinoline-4,4'-piperidine]-1'-carboxylate (12 mg, 0.025 mmol), trans-2-(ethoxycarbonyl)cyclopropanecarboxylic acid (8 mg, 2.5 equiv), HATU (11 mg, 1.15 equiv), DIEA (13 μL, 3 equiv) were mixed with CH$_2$Cl$_2$ (2 mL) and put on shaker for 1 h at rt. The mixture was diluted with EtOAc (8 mL), washed with 3% aq HCl (2×3 mL), concentrated and purified by preparative HPLC to afford 2-adamantyl 2-((1R,2R)-2-(ethoxycarbonyl)cyclopropanecarbonyl)-2,3-dihydro-1H-spiro[isoquinoline-4,4'-piperidine]-1'-carboxylate (9 mg, 69%).

Step 2

2-Adamantyl 2-((1RS,2RS)-2-(ethoxycarbonyl)cyclopropanecarbonyl)-2,3-dihydro-1H-spiro[isoquinoline-4,4'-piperidine]-1'-carboxylate (9 mg, 0.017 mmol) was mixed with 2N aq LiOH (2004, excess) and acetonitrile (3 mL). The mixture was stirred overnight at rt. LC-MS showed the reaction was complete. The mixture was concentrated, acidified with 5% aq HCl and extracted with EtOAc (3×3 mL). The combined organic layers were concentrated and purified by preparative HPLC to afford (1RS,2RS)-2-(1'-(2-adamantyloxycarbonyl)-2,3-dihydro-1H-spiro[isoquino line-4,4'-piperidine]-2-ylcarbonyl)cyclopropanecarboxylic acid (4.6 mg, 54%). LC-MS Method 1 $t_R$=1.98 min, m/z=493; $^1$H NMR (CDCl$_3$) δ=7.37 (t, 1H), 7.31-7.19 (m, 2H), 7.13 (d, 1H), 4.89 (m, 3H), 4.16 (m, 3H), 3.15 (m, 2H), 2.50 (m, 1H), 2.29 (m, 1H).

Example 101.1

Ethyl 2-(7-bromo-1'-(2-adamantylcarbamoyl)spiro[indene-1,4'-piperidine]-3(2H)-ylidene)acetate

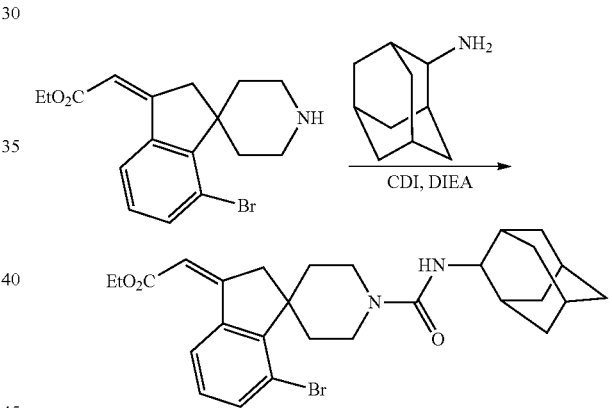

To a solution of 2-aminoadamantane hydrochloride (4.17 g, 22 mmol) and DIEA (28.7 g, 223 mmol) in anhydrous CH$_2$Cl$_2$ (40 mL) was added CDI (4.33 g, 27 mmol) at 0° C. and then stirred for 1 h at 0° C. under N$_2$ atmosphere. Ethyl 2-(7-bromospiro[indene-1,4'-piperidine]-3(2H)-ylidene)acetate (7.77 g, 22 mmol) in CH$_2$Cl$_2$ anhydrous (40 mL) was added dropwise to the above mixture. The mixture was stirred for 8 h at rt under N$_2$. The reaction mixture was washed with 1 N aq HCl. The organic layer was dried over Na$_2$SO$_4$, filtered and concentrated to leave a residue, which was purified by silica gel column chromatography to afford ethyl 2-(7-bromo-1'-(2-adamantylcarbamoyl)spiro[indene-1,4'-piperidine]-3(2H)-ylidene)acetate (4.1 g, 35%). Preparative SFC using a ChiralCel-OJ, 400×25 mm I.D, 20 μm (Daicel Chemical Industries, Ltd) column maintained at 35° C. eluted with 75:25 supercritical CO$_2$/MeOH at a flow rate of 70 mL min$^{-1}$ and a nozzle pressure of 100 bar afforded two isomers.

Isomer 1: LC-MS Method 5 $t_R$=1.799 min, m/z=529; $^1$H NMR (CDCl$_3$) δ=1.22-1.29 (t, 3H), 1.51-1.70 (m, 10H), 1.71-1.81 (m, 4H), 1.82-1.91 (m, 7H), 1.92-2.03 (m, 2H), 2.95-3.21 (m, 4H), 3.53 (m, 2H), 3.98-4.15 (m, 3H), 4.15-

4.24 (m, 2H), 4.98 (br, 1H), 6.91 (s, 1H), 7.02-7.08 (m, 1H), 7.20-7.26 (m, 1H), 7.32-7.36 (m, 1H).

Isomer 2: LC-MS Method 5 $t_R$=1.9 min, m/z=529.1; $^1$H NMR (CDCl$_3$) δ=1.30-1.38 (m, 4H), 1.51-1.70 (m, 8H), 1.70-1.81 (m, 4H), 1.83-1.89 (m, 6H), 1.92-2.01 (m, 2H), 2.78-2.97 (m, 2H), 3.02-3.17 (m, 2H), 3.32 (s, 2H), 3.96-4.08 (m, 3H), 4.20-4.29 (m, 2H), 4.89-5.01 (br, 1H), 6.33 (s, 1H), 7.12-7.20 (t, 1H), 7.52-7.60 (m, 2H).

Example 102

3-Allyl-7-chloro-N-(2-adamantyl)-3H-spiro[isobenzofuran-1,4'-piperidine]-1'-carboxamide

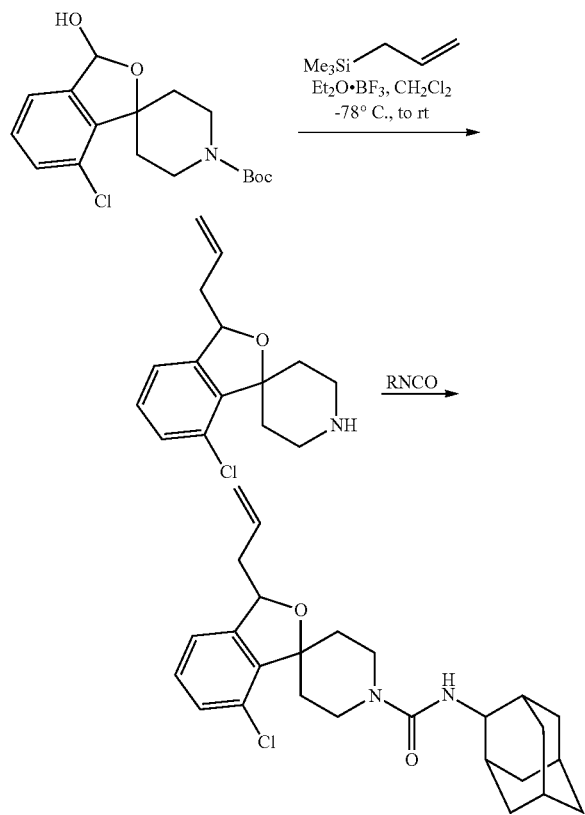

Step 1.

A solution of tert-butyl 7-chloro-3-hydroxy-3H-spiro[isobenzofuran-1,4'-piperidine]-1'-carboxylate (0.0175 g, 0.0514 mmol, 1.0 equiv) and allyltrimethylsilane (0.1660 g, 1.45 mmol, 28 equiv) in CH$_2$Cl$_2$ (2 mL) was cooled to −78° C. Boron trifluoride diethyl etherate was added dropwise (10 drops, 0.0520 g, 7.1 equiv), and the solution was allowed to stir, coming to ambient temperature, for 16 h. The reaction was then quenched with 1 mL of satd aq K$_2$CO$_3$, diluted with CH$_2$Cl$_2$, and dried over K$_2$CO$_3$. After the solvents were evaporated, the crude 3-allyl-7-chloro-3H-spiro[isobenzofuran-1,4'-piperidine] (0.0190 g) was directly used in the next step without further purification. LC-MS Method 1 $t_R$=1.18 min, m/z 266, 264 (MO. Step 2

To a stirred solution of 3-allyl-7-chloro-3H-spiro[isobenzofuran-1,4'-piperidine] (0.0190 g), and DIEA (0.5 mL) in CH$_2$Cl$_2$ (2 mL) was added 2-adamantyl isocyanate (0.0138 g, 0.0778 mmol) at rt. After 19 h, the solvents were removed in vacuo and the residue was purified by reversed-phase HPLC (Phenomenex® Luna 5μ C18(2) 100A, 250×21.20 mm, 5 micron, 70%→90% CH$_3$CN/H$_2$O, 0.1% CF$_3$COOH over 8 min and then 90% CH$_3$CN/H$_2$O, 0.1% CF$_3$COOH over 4 min, flow rate 25 mL/min) to afford N-(2-adamantyl)-3-allyl-7-chloro-3H-spiro[isobenzofuran-1,4'-piperidine]-1'-carboxamide (0.0220 g, 97%). LC-MS Method 1 $t_R$=2.33 min, m/z 443, 441 (MH$^+$); $^1$H NMR (400 MHz, CDCl$_3$) δ=7.24-7.20 (m, 2H), 7.09-7.05 (m, 1H), 5.87-5.77 (m, 1H), 5.25 (t, J=5.7 Hz, 1H), 5.15-5.08 (m, 2H), 3.98 (br s, 1H), 3.94-3.88 (m, 2H), 136-3.28 (m, 2H), 2.66-2.38 (m, 4H), 1.95-1.25 (m, 16H).

Example 103

N-(2-Adamantyl)-2,3,3-trimethylspiro[isoindoline-1,4'-piperidine]-1'-carboxamide

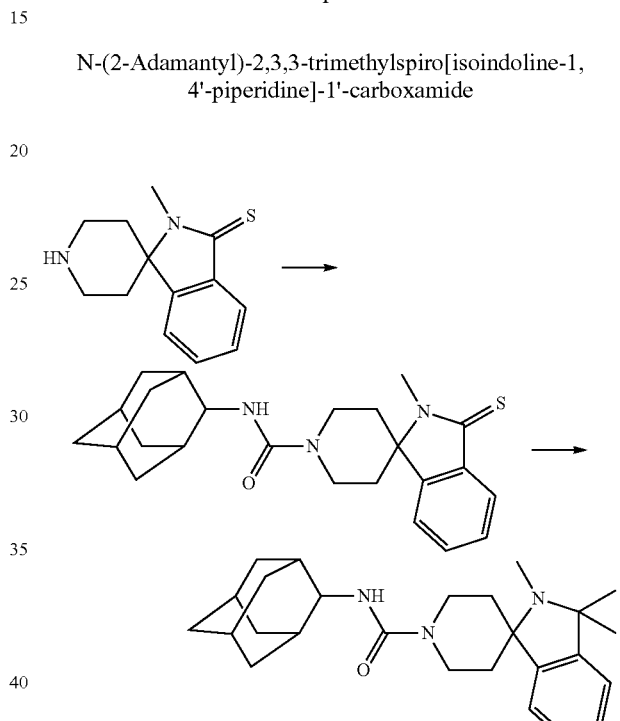

The title compound was prepared from 2-methylspiro[isoindoline-1,4'-piperidine]-3-thione following procedures analogous to those described in Example 104 Steps 1 and 2. LC-MS Method 1 $t_R$=1.33 min, m/z=408; $^1$H NMR (CD$_3$OD) δ=7.81 (d, J=7.4, 1H), 7.50 (m, 3H), 3.00 (s, 3H), 2.37 (m, 2H), 1.64 (d, 2H).

Example 104

7-Chloro-N-(2-adamantyl)-3,3-dimethylspiro[isoindoline-1,4'-piperidine]-1'-carboxamide

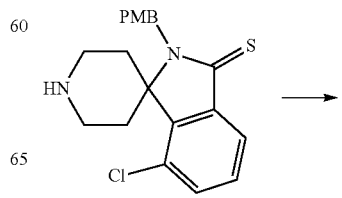

127

-continued

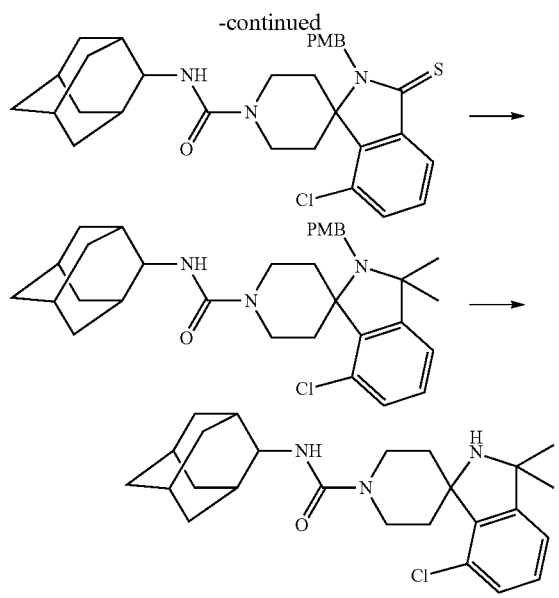

PMB = 4-methoxybenzyl

Step 1

To a solution of crude 7-chloro-2-(4-methoxybenzyl)spiro[isoindoline-1,4'-piperidine]-3-thione TFA salt (prepared from TFA deprotection of tert-butyl 7-chloro-2-(4-methoxybenzyl)-3-thioxospiro[isoindoline-1,4'-piperidine]-1'-carboxylate (52 mg, 0.11 mmol)) in 1:1 MeCN:10% aq $K_2CO_3$ (10 mL), was added 2-adamantylisocyanate (50 mg, 0.30 mmol, 2.6 equiv) and the mixture stirred was for 2 h. After this time LC-MS analysis showed formation of the desired urea. The mixture was concentrated to ~50% of its original volume and diluted with EtOAc. The mixture was washed with 1.0 M aq HCl and brine, dried over $Na_2SO_4$, and evaporated. The residue was purified by flash chromatography on silica gel (4 g), eluting with 20-80% EtOAc in hexanes, affording 7-chloro-N-(2-adamantyl)-2-(4-methoxybenzyl)-3-thioxospiro[isoindoline-1,4'-piperidine]-1'-carboxamide (51 mg, 0.093 mmol, 85% yield) of the desired thiolactam-urea as a pale yellow solid.

Step 2

7-Chloro-N-(2-adamantyl)-2-(4-methoxybenzyl)-3-thioxospiro[isoindoline-1,4'-piperidine]-1'-carboxamide (~10 mg, ~0.018 mmol, 1.0 equiv) was dissolved in $CH_2Cl_2$ (5 mL) and the solution cooled to 0° C. Methyl triflate (9 mg, 6 µL, 0.054 mmol, 3.0 equiv) was added and the methylation of the thiolactam was monitored by LC/MS. To this solution was added MeMgBr (3.0 M in THF, 10 equiv, 6 µL) and the mixture allowed to stir for 0.5 h. After this time LC-MS showed formation of the desired amine. The mixture was diluted with $CH_2Cl_2$ (~10 mL) and quenched by addition of satd aq $NH_4Cl$. The layers were separated and the organic layer was dried over $Na_2SO_4$, and evaporated to afford crude 7-chloro-N-(2-adamantyl)-2-(4-methoxybenzyl)-3,3-dimethylspiro[isoindoline-1,4'-piperidine]-1'-carboxamide which was used without further purification.

Step 3

Crude 7-chloro-N-(2-adamantyl)-2-(4-methoxybenzyl)-3,3-dimethylspiro[isoindoline-1,4'-piperidine]-1'-carboxamide was dissolved in neat TFA (3 mL) and the mixture was heated to 80° C. for 17 h. After this time LC-MS analysis showed complete removal of the p-methoxybenzyl group. The solution was evaporated the amine purified by prep HPLC to afford 7-chloro-N-(2-adamantyl)-3,3-dimethylspiro[isoindoline-1,4'-piperidine]-1'-carboxamide as its TFA salt. LC-MS Method 1 $t_R$=1.43 min, m/z=428; $^1$H NMR ($CD_3OD$) δ=7.47 (m, 2H), 7.37 (m, 1H), 4.22 (m, 2H), 3.89 (s, 1H), 3.21 (t, J=12.9, 2H).

Example 105

7-Chloro-N-(2-adamantyl)-2,3,3-trimethylspiro[isoindoline-1,4'-piperidine]-1'-carboxamide

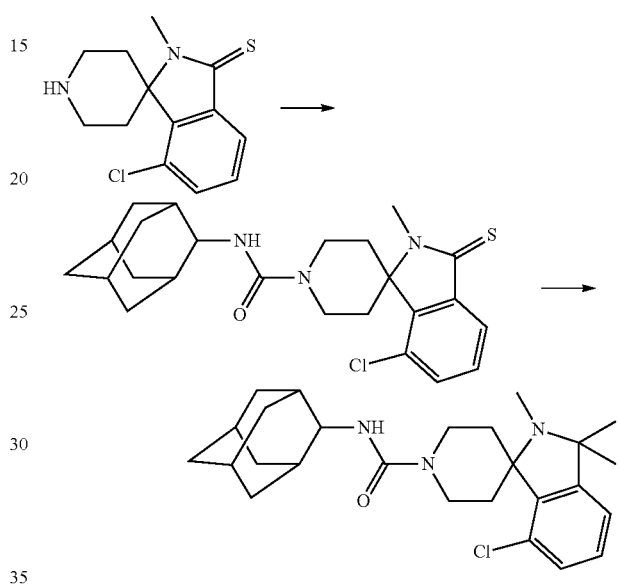

The title compound was prepared from 7-chloro-2-methylspiro[isoindoline-1,4'-piperidine]-3-thione following procedures analogous to those described in Example 104 Steps 1 and 2. LC-MS Method 1 $t_R$=1.42 min, m/z=442; $^1$H NMR ($CD_3OD$) δ=7.51 (m, 2H), 7.42 (m, 1H), 3.88 (m, 1H), 3.53 (m, 2H), 3.26 (s, 3H).

Example 106

Methyl 3-(1'-(2-adamantyl carbamoyl)-1-H-spiro[isoquinoline-4,4'-piperidine]-2(3H)-ylsulfonyl)propanoate The title compound was prepared following a procedure analogous to that described in Example 34 using methyl 3-(chlorosulfonyl)propionate in place of $MeSO_2Cl$. LC-MS Method 1 $t_R$=1.94 min, m/z=530; $^1$H NMR ($CDCl_3$) δ=1.60-2.15 (18H), 2.90 (t, 2H), 3.13 (m, 2H), 3.39 (t, 2H), 3.57 (s, 2H), 3.75 (s, 3H), 3.90 (d, 2H), 3.99 (br s, 1H), 4.49 (s, 2H), 4.86 (br s, 1H), 7.05-7.40 (4H).

Example 107

2-Adamantyl 2-(3-methoxy-3-oxopropylsulfonyl)-2,3-dihydro-1H-spiro[isoquinoline-4,4'-piperidine]-1'-carboxylate The title compound was prepared following a procedure analogous to that described in Example 34 using methyl 3-(chlorosulfonyl)propanoate in place of methanesulfonyl chloride. LC-MS Method 1 $t_R$=2.22 min, m/z=531; $^1$H NMR ($CDCl_3$) δ=7.36 (d, 1H), 7.27 (t, 1H), 7.21 (t, 1H), 7.07 (d, 1H), 4.87 (s, 1H), 4.50 (br s, 2H), 4.30 (br s, 2H), 4.18 (d, 2H), 3.73 (s, 3H), 3.37 (t, 2H), 3.10 (br s, 2H), 2.90 (t, 2H).

Example 108

3-(1'-(2-Adamantylcarbamoyl)-1H-spiro[isoquinoline-4,4'-piperidine]-2(3H)-ylsulfonyl)propanoic acid The title compound was prepared following a procedure analogous to that described in Example 6. LC-MS Method 1 $t_R$=1.83 min, m/z=516; $^1$H NMR (CDCl$_3$) δ=1.60-2.15 (18H), 2.93 (t, 2H), 3.15 (m, 2H), 3.42 (t, 2H), 3.57 (s, 2H), 3.90 (d, 2H), 3.97 (br s, 1H), 4.52 (s, 2H), 7.00-7.40 (4H).

Example 109

3-(1'-(2-Adamantyloxycarbonyl)-1H-spiro[isoquinoline-4,4'-piperidine]-2(3H)-ylsulfonyl)propanoic acid The title compound was prepared following a procedure analogous to that described in Example 6. LC-MS Method 1 tR=2.02 min, m/z=516; $^1$HNMR (CDCl$_3$) δ=7.36 (d, 1H), 7.26 (t, 1H), 7.20 (t, 1H), 7.06 (d, 1H), 4.87 (s, 1H), 4.49 (br d, 2H), 4.17 (d, 2H), 3.74 (br s, 1H), 3.37 (t; 2H), 3.07 (br d, 1H), 2.94 (t, 2H).

Example 110

7-Bromo-N-(2-adamantyl)-3-(2-oxo-2-(piperazin-1-yl)ethyl)-2,3-dihydrospiro[indene-1,4'-piperidine]-1'-carboxamide

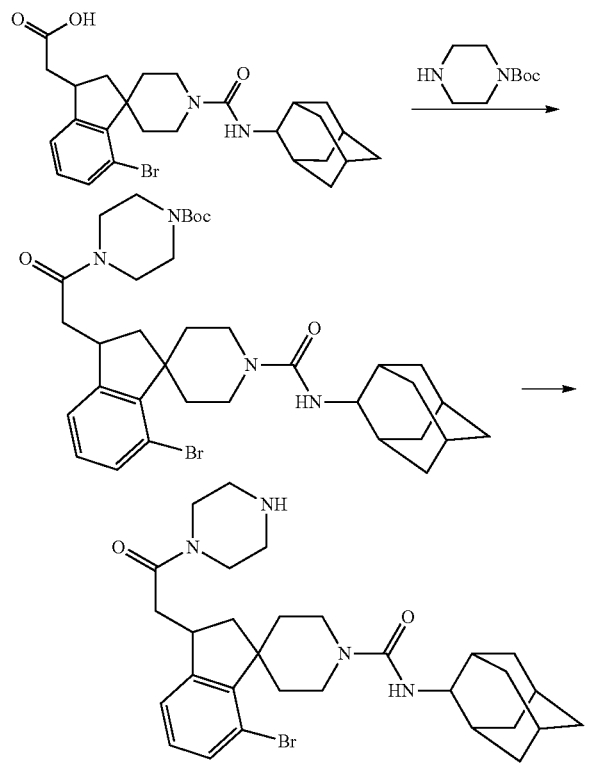

Step 1.

A DMF (0.2 mL) solution of 1-Boc-piperazine (2.5 mg, 0.013 mmol), carboxylic acid (6 mg, 0.012 mmol), HATU (5.7 mg, 0.015 mmol), and i-Pr$_2$NEt (1 drop) was prepared and allowed to stir for several hours. The solution was diluted with CH$_3$CN (0.3 mL) and purified by preparative HPLC to afford tert-butyl 4-(2-(7-bromo-1'-(2-adamantylcarbamoyl)-2,3-dihydrospiro[indene-1,4'-piperidine]-3-yl)acetyl)piperazine-1-carboxylate (6 mg).

Step 2.

tert-Butyl 4-(2-(7-bromo-1'-(2-adamantylcarbamoyl)-2,3-dihydrospiro[indene-1,4'-piperidine]:3-yl)acetyl)piperazine-1-carboxylate (6 mg) was dissolved in CH$_2$Cl$_2$ (1 mL) and treated with 20% TFA for 30 min. The solvent was evaporated and the crude material purified by preparative HPLC to afford (±)-7-bromo-N-(2-adamantyl)-3-(2-oxo-2-(piperazin-1-yl)ethyl)-2,3-dihydrospiro[indene-1,4'-piperidine]-1'-carboxamide (1.83 mg). LC-MS Method 1 $t_R$=1.51 min, m/z=569 (M+1); $^1$H NMR (CD$_3$OD) δ=7.37 (d, 1H), 7.24 (d, 1H), 7.09 m (t, 1H), 4.09-4.04 (m, 2H), 3.66-3.62 (m, 1H), 2.97 (t, 1H), 2.76 (dd, 1H), 2.61 (dd, 1H), 2.45 (dt, 1H), 1.43 (m, 2H).

Example 111

7-Bromo-N-(2-adamantyl)-3-(2-morpholino-2-oxoethyl)-2,3-dihydrospiro[indene-1,4'-piperidine]-1'-carboxamide The title compound was prepared following the procedure of Example 110 Step 1 using morpholine in place of 1-Boc-piperazine. LC-MS Method 1 $t_R$=1.98 min, m/z=570 (M+1); $^1$H NMR (CDCl$_3$) δ=7.38 (d, 1H), 7.12 (d, 1H), 7.06 (t, 1H), 4.95 (br s, 1H), 4.4-3.98 (m, 2H), 3.89 (dd, 1H), 3.72 (3.67 (m, 7H), 3.48 (m, 2H), 3.15-3.06 (m, 2H), 2.99 (dt, 1H), 2.88 (dd, 1H), 2.75 (dd, 1H), 2.51-2.42 (m, 2H), 1.94 (br s, 2H), 1.85 (br s, 6H), 1.79-1.57 (m, 7H), 1.422 (ddd, 2H).

Example 112

7-Bromo-N-(2-adamantyl)-3-(2-(4-methylpiperazin-1-yl)-2-oxoethyl)-2,3-dihydrospiro[indene-1,4'-piperidine]-1'-carboxamide The title compound was prepared following the procedure of Example 110 Step 1 using 1-methylpiperazine in place of 1-Boc-piperazine. LC-MS Method 1 $t_R$=1.52 min, m/z=583 (M+1); $^1$H NMR (CD$_3$OD) δ=7.37 (d, 1H), 7.23 (d, 1H), 7.09 (t, 1H), 4.72 (br s, 1H), 4.24 (br s, 1H), 4.06 (m, 2H), 3.87 (s, 1H), 3.66-3.48 (m, 4H), 3.16-3.04 (m, 5H), 2.94 (s, 3H), 2.77 (dd, 1H), 2.62 (dd, 1H), 2.45 (dt, 1H), 2.03-1.79 (m, 12H), 1.70-1.61 (m, 3H), 1.40 (t, 2H).

Example 113

N-(2-Adamantyl)-2-(4-(dimethylamino)butanoyl)-2,3-dihydro-1H-spiro[isoquinoline-4,4'-piperidine]-1'-carboxamide The title compound was prepared from N-(2-adamantyl)-2,3-dihydro-1H-spiro[isoquinoline-4,4'-piperidine]-1'-carboxamide and 4-(dimethylamino)butanoic acid following the procedure of Example 110 Step 1. LC-MS Method 1 $t_R$=2.4 min, m/z=493.38; $^1$HNMR (CD$_3$OD) δ=1.55-1.73 (m, 4H), 1.80-1.94 (m, 8H), 1.95-2.10 (m, 8H), 2.66-2.72 (m, 2H), 2.82-2.92 (s, 6H), 3.05-3.19 (m, 2H), 3.19-3.28 (m, 2H), 3.80-3.92 (m, 1H), 3.92 (s, 3H), 3.93-4.04 (m, 1H), 4.72-4.80 (m, 2H), 5.78-5.95 (m, 1H), 7.15-7.30 (m, 3H), 7.40-7.47 (m, 1H).

Example 114

7-Bromo-N-(2-adamantyl)-3-(2-(2-(dimethylamino)ethylamino)-2-oxoethyl)-2,3-dihydrospiro[indene-1,4'-piperidine]-1'-carboxamide The title compound was prepared following the procedure of Example 110 Step 1 using N,N-dimethylethylenediamine in place of 1-Boc-piperazine. LC-MS Method 1 $t_R$=1.51 min, m/z=571 (M+); $^1$H NMR (CD$_3$OD) δ 7:38 (d, 114), 7.19 (d, 1H), 7.10 (t, 1H), 4.06 (t, 3H), 2.96 (s, 6H), 283 (dd, 2H), 2.65 (dd, 2H), 2.48 (m, 2H), 2.37 (dd, 2H), 1.62 (d, 3H), 1.39 (d, 3H).

Example 115

7-Bromo-N-(2-adamantyl)-3-(2-(methyl(2-(methylamino)ethyl)amino)-2-oxoethyl)-2,3-dihydrospiro[indene-1,4'-piperidine]-1'-carboxamide The title compound was prepared following the procedure of Example 110 Step 1 using N,N'-dimethylethylenediamine in place of 1-Boc-piperazine. LC-MS Method 1 $t_R$=1.53 min, m/z=571 (M+); $^1$H NMR (CD$_3$OD) δ=7.37 (d, 1H), 7.23 (d, 1H), 7.09 (t, 1H), 4.07 (d, 2H), 3.87 (br s, 1H), 3.22 (t, 2H), 3.10 (s, 3H), 2.75 (s, 3H), 2.59 (dd, 1H), 2.45 (dd, 1H), 1.40 (m, 2H).

Using a procedure analogous to that described in Example 110 Step 1,2-(7-bromo-1'-((2-adamantyl)carbamoyl)-2,3-dihydrospiro[indene-1,4'-piperidine]-3-yl)acetic acid, isomer 1 was converted into 7-bromo-N-(2-adamantyl)-3-(2-(methyl(2-(methylamino)ethyl)amino)-2-oxoethyl)-2,3-dihydrospiro[indene-1,4'-piperidine]-1'-carboxamide, isomer 1. LC-MS Method 5 $t_R$=1.136 min, m/z=571.1; $^1$H NMR (CDCl$_3$) δ=1:34 (m, 2H), 1.52 (m. 1H), 1.60 (m, 2H), 1.65 (m, 3H), 1.78 (m, 6H), 1.86 (m, 2H), 2.26 (m, 7H), 2.42 (m, 2H), 2.62 (m, 1H), 2.70 (m, 2H), 2.89 (m, 2H), 3.02 (m, 4H), 3.23 (m, 1H), 3.46-3.72 (m, 3H), 3.90 (m, 3H), 4.86 (s, 1H), 7.03 (m, 2H), 7.31 (m, 1H).

Using a procedure analogous to that described in Example 110 Step 1, 2-(7-bromo-1'-((2-adamantyl) carbamoyl)-2,3-dihydrospiro[indene-1,4'-piperidine]-3-yl)acetic acid, isomer 2 was converted into 7-bromo-N-(2-adamantyl)-3-(2-(methyl(2-(methylamino)ethyl)amino)-2-oxoethyl)-2,3-dihydrospiro[indene-1,4'-piperidine]-1'-carboxamide, isomer 2. LC-MS Method 5 tR=1.138 min, m/z=571.1; 1H NMR (CDCl$_3$) δ=1.41 (m, 2H), 1.65 (m, 2H), 1.71-1.79 (m, 8H), 1.92 (m, 2H), 2.19 (m, 6H), 2.33-2.68 (m, 2H), 2.79 (m, 4H), 3.01 (m, 5H), 3.32 (m, 1H), 3.41 (m, 1H), 3.71 (m, 2H), 3.99 (m, 2H), 4.11-4.23 (m, 1H), 7.11 (m, 2H), 7.42 (m, 1H), 9.51-9.72 (br, 1H).

Example 116

7-Bromo-N-(2-adamantyl)-3-(24(2-(dimethylamino)ethyl)(methyl)amino)-2-oxoethyl)-2,3-dihydrospiro[indene-1,4'-piperidine]-1'-carboxamide The title compound was prepared following the procedure of Example 110 Step 1 using N,N,N'-trimethylethylenediamine in place of 1-Boc-piperazine. LC-MS Method 1 $t_R$=1.55 min, m/z=585 (M+1); $^1$H NMR (CD$_3$OD) δ=7.37 (d, 1H), 7.23 (d, 1H), 7.09 (t, 1H), 4.07 (d, 2H), 3.87 (s, 1H), 3.85-3.74 (m, 2H), 3.65-3.62 (m, 1H), 3.35 (t, 2H), 3.11 (s, 3H), 2.99 (s, 3H), 2.78 (dd, 1H), 2.59 (dd, 1H), 2.44 (dt, 1H), 1.42-1.38 (m, 2H).

Example 117

7-Bromo-N-(2-adamantyl)-3-(2-(3-(dimethylamino)propylamino)-2-oxoethyl)-2,3-dihydrospiro[indene-1,4'-piperidine]-1'-carboxamide The title compound was prepared following the procedure of Example 110 Step 1 using N,N-dimethylpropylenediamine in place of 1-Boc-piperazine. LC-MS Method 1 $t_R$=1.51 min, m/z=585 (M+); $^1$H NMR (CD$_3$OD) δ=7.37 (d, 1H), 7.19 (d, 1H), 7.09 (t, 1H), 4.07 (t, 2H), 3.87 (s, 1H), 3.60 (m, 1H), 3.16 (dd, 2H), 288 (s, 6H), 2.76 (dd, 1H), 2.61 (dd, 1H), 2.49 (dt, 1H), 2.3 (dd, 1H), 1.39 (d, 2H).

Example 118

7-Bromo-N-(2-adamantyl)-3-(2-(4-(dimethylamino)butylamino)-2-oxoethyl)-2,3-dihydrospiro[indene-1,4-r-piperidine]-1'-carboxamide The title compound was prepared following the procedure of Example 110 Step 1 using N,N-dimethylbutylenediamine in place of 1-Boc-piperazine. LC-MS Method 1 $t_R$=1.52 min, m/z=599 (M+).

Example 119

7-Bromo-N-(2-adamantyl)-3-(2-oxo-2-(2-(piperazin-1-yl)ethylamino)ethyl)-2,3-dihydrospiro[indene-1,4'-piperidine]-1'-carboxamide The title compound was prepared following the procedure of Example 110 using tert-butyl 4-(2-aminoethyl)piperazine-1-carboxylate in place of 1-Boc-piperazine. LC-MS Method 1 $t_R$=1.41 min, m/z=614 (M$^+$); $^1$H NMR (CD$_3$OD) δ=7.38 (d, 1H), 7.22 (d, 114), 7.10 (t, 1H), 4.07 (m, 2H), 3.87 (m, 1H), 2.90 (dd, 1H), 2.66 (dd, 1H), 2.48 (jm, 1H), 2.42 (dd, 1H).

Example 120

7-Bromo-N-(2-adamantyl)-3-(2-(2-morpholinoethylamino)-2-oxoethyl)-2,3-dihydrospiro[indene-1,4'-piperidine]-1'-carboxamide The title compound was prepared following the procedure of Example 110 Step 1 using 2-morpholinoethanamine in place of 1-Boc-piperazine. LC-MS Method 1 $t_R$=1.52 min, m/z=613 (M+); $^1$H NMR (CD$_3$OD) δ=7.38, 7.20, 7.10, 4.07, 2.83, 2.65, 2.48, 2.38, 1.63, 1.39.

Example 121

7-Bromo-N-(2-adamantyl)-3-(2-(2-(4-methylpiperazin-1-yl)ethylamino)-2-oxoethyl)-2,3-dihydrospiro[indene-1,4'-piperidine]-1'-carboxamide The title compound was prepared following the procedure of Example 110 Step 1 using 2-(4-methylpiperazin-1-yl)ethanamine in place of 1-Boc-piperazine. LC-MS Method 1 $t_R$=1.45 min, m/z=626 (M$^+$); $^1$H NMR (CD$_3$OD) δ=7.38 (d, 1H), 7.21 (d, 1H), 7.10 (t, 1H), 4.07 (m, 3H), 3.87 (s, 1H), 3.62

(m, 2H), 2.88 (s, 3H), 2.77 (dd, 2H), 2.70 (t, 2H), 2.62 (dd, 2H), 2.49 (m, 2H), 2.34 (dd, 2H), 1.63 (d, 2H), 1.40 (d, 2H).

Example 122

(±)-7-Bromo-N-(2-adamantyl)-3-(2-hydroxyethyl)-2,3-dihydrospiro[indene-1,4'-piperidine]-1'-carboxamide

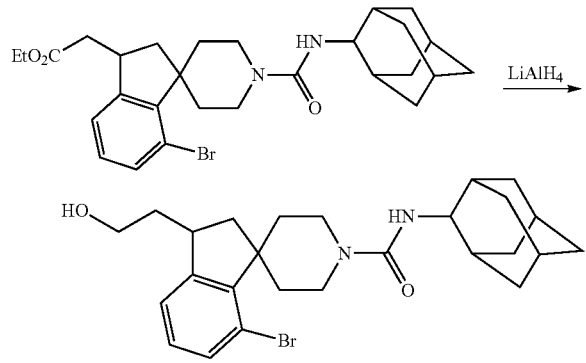

To a solution of (±)-ethyl 2-(7-bromo-1'-((2-adamantyl) carbamoyl)-2,3-dihydrospiro[indene-1,4'-piperidine]-3-yl) acetate (300 mg, 0.566 mmol) in THF (5 mL) was added LiAlH$_4$ (65 mg, 1.132 mmol) at 0° C. under N$_2$. The mixture was stirred overnight at rt. The mixture was separated by preparative TLC to give the crude product, which was purified by preparative HPLC to afford (±)-7-bromo-N-(2-adamantyl)-3-(2-hydroxyethyl)-2,3-dihydrospiro[indene-1,4'-piperidine]-1'-carboxamide (26 mg, 10%). LC-MS Method 5 t$_R$=1.467 min, m/z=489.1; $^1$H NMR: (400 MHz, CDCl$_3$): δ=1.38 (m, 2H), 1.62 (m. 5H), 1.71 (m, 5H), 1.75-1.88 (m, 9H), 2.19 (m, 2H), 2.21-2.49 (m, 5H), 2.52 (m, 1H), 2.95-3.12 (m, 3H), 3.21 (m, 1H), 3.78 (m, 2H), 3.82 (m, 3H), 7.03 (m, 1H), 7.08 (m, 1H), 7.32 (m, 1H).

Example 123

(±)-7-Bromo-N-(2-adamantyl)-3-(1-hydroxy-2-methylpropan-2-yl)-2,3-dihydrospiro[indene-1,4'-piperidine]-1'-carboxamide

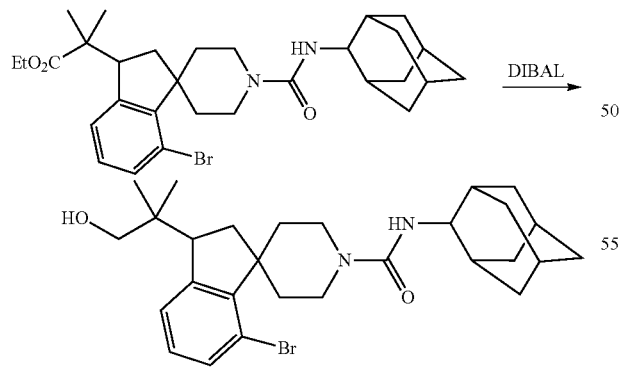

To a solution of (±)-ethyl 2-(7-bromo-1'-((2-adamantyl) carbamoyl)-2,3-dihydrospiro[indene-1,4'-piperidine]-3-yl)-2-methylpropandate (18 mg, 0.0323 mmol) in dry CH$_2$Cl$_2$ was added DIBAL (0.15 mL, 3 eq) at −78° C. The mixture was stirred for 30 min and quenched with methanol. The organic layer was separated, dried and concentrated to give (±)-7-bromo-N-(2-adamantyl)-3-(1-hydroxy-2-methylpropan-2-yl)-2,3-dihydrospiro[indene-1,4'-piperidine]-1'-carboxamide. LC-MS Method 5 t$_R$=1.574 min, m/z=517.1; $^1$H NMR: (400 MHz, CDCl$_3$): δ=0.89 (s, 3H), 0.98 (s, 3H), 1.22 (m, 2H), 1.40 (m, 2H), 1.54 (m, 7H), 1.77 (m, 11H), 1.89 (m, 2H), 2.34 (m, 2H), 3.02 (m, 3H), 3.31 (m, 1H), 3.52 (m, 2H), 3.90 (m, 3H), 6.96 (m, 1H) 7.28 (m, 2H).

Example 124

(±)-2-Adamantyl 3-(aminomethyl)-7-bromo-2,3-dihydrospiro[indene-1,4'-piperidine]-1'-carboxylate

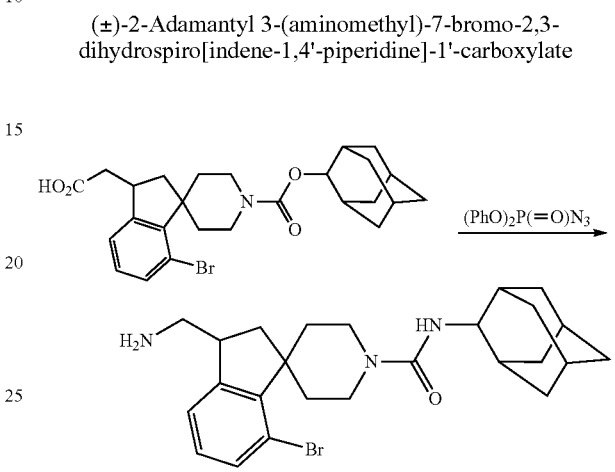

A 100-mL of flask was charged with (±)-2-(7-bromo-1'-((2-adamantyloxy)carbonyl)-2,3-dihydrospiro[indene-1,4'-piperidine]-3-yl)acetic acid (30 mg, 0.06 mmol) dissolved in THF (3 mL) and treated with TEA (2 mL). Then diphenylphosphoryl azide (18 mg, 0.066 mmol) was added dropwise slowly. The mixture was stirred for 3 h at rt. 1 N aq NaOH solution (3 mL) was added and the reaction mixture was reflux overnight. The solvent was removed in vacuo and the aqueous residue was extracted with CH$_2$Cl$_2$ (3×5 mL). The organic layers were combined, washed with brine, dried over Na$_2$SO$_4$, filtered, and concentrated. The residue was purified by preparative HPLC to give (±)-2-adamantyl 3-(aminomethyl)-7-bromo-2,3-dihydrospiro[indene-1,4'-piperidine]-1'-carboxylate (1 mg, 4%). LC-MS Method 5 t$_R$=1.175 min, m/z=475; $^1$H NMR (400 MHz, MeOD): δ=0.71-0.83 (m, 3H), 1.46-1.57 (m. 2H), 1.61-1.81 (m, 6H), 1.81-2.06 (m, 11H), 2.39-2.51 (m, 1H), 2.83-3.00 (m, 2H), 3.41-3.57 (m, 2H), 4.07-4.14 (m, 1H), 4.79 (m, 1H), 6.99-7.10 (m, 2H), 7.37 (m, 1H), 7.95-8.30 (s, 1H).

Example 125

(±)-2-Adamantyl 7-bromo-3-((dimethylamino)methyl)-2,3-dihydro spiro[indene-1,4'-piperidine]-1'-carboxylate

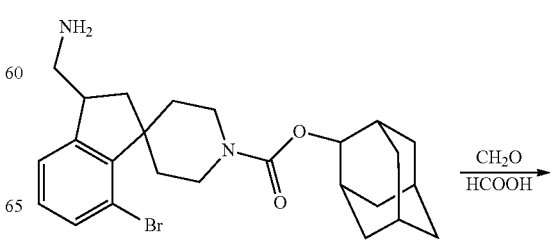

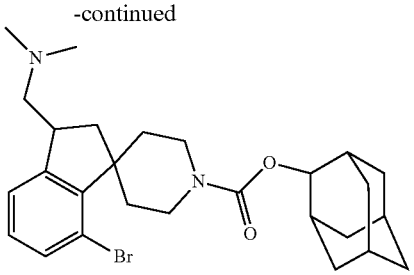

A 50-mL flask was charged with (±)-2-adamantyl 3-(aminomethyl)-7-bromo-2,3-dihydrospiro[indene-1,4'-piperidine]-1'-carboxylate (60 mg, 0.12 mmol), CH$_2$O (16 mg, 0.53 mmol) and HCOOH (33 mg, 0.72 mmol). The mixture was stirred overnight under reflux. 6 N aq HCl (3 mL) was added and the mixture was extracted with CH$_2$Cl$_2$ (3×5 mL). The aqueous layer was basified with 1 N aq NaOH (10 mL) and extracted with CH$_2$Cl$_2$ (3×5 mL). The organic layers were combined, washed with brine, dried over Na$_2$SO$_4$, filtered and concentrated. The crude residue was purified by preparative HPLC to give (±)-2-adamantyl 7-bromo-3-((dimethylamino)methyl)-2,3-dihydrospiro[indene-1,4'-piperidine]-1'-carboxylate (10 mg, 9%). LC-MS Method 5 $t_R$=1.229 min, =503.1; $^1$H NMR (400 MHz, MeOD): δ=1.44 (m, 2H), 1.66 (d, 2H), 1.72-1.90 (m, 8H), 1.94 (m, 2H), 1.98-2.10 (m, 4H), 2.38-2.50 (br, 1H), 2.79 (m, 1H), 3.01 (m, 6H), 3.11 (m, 2H), 3.71 (m, 2H), 4.15-4.30 (m, 2H), 7.07 (m, 1H), 7.29 (d, 1H), 7.45 (d, 1H).

Example 126

(±)-7-Bromo-N-(2-adamantyl)-3-(2-morpholinoethyl)-2,3-dihydrospiro[indene-1,4'-piperidine]-1'-carboxamide

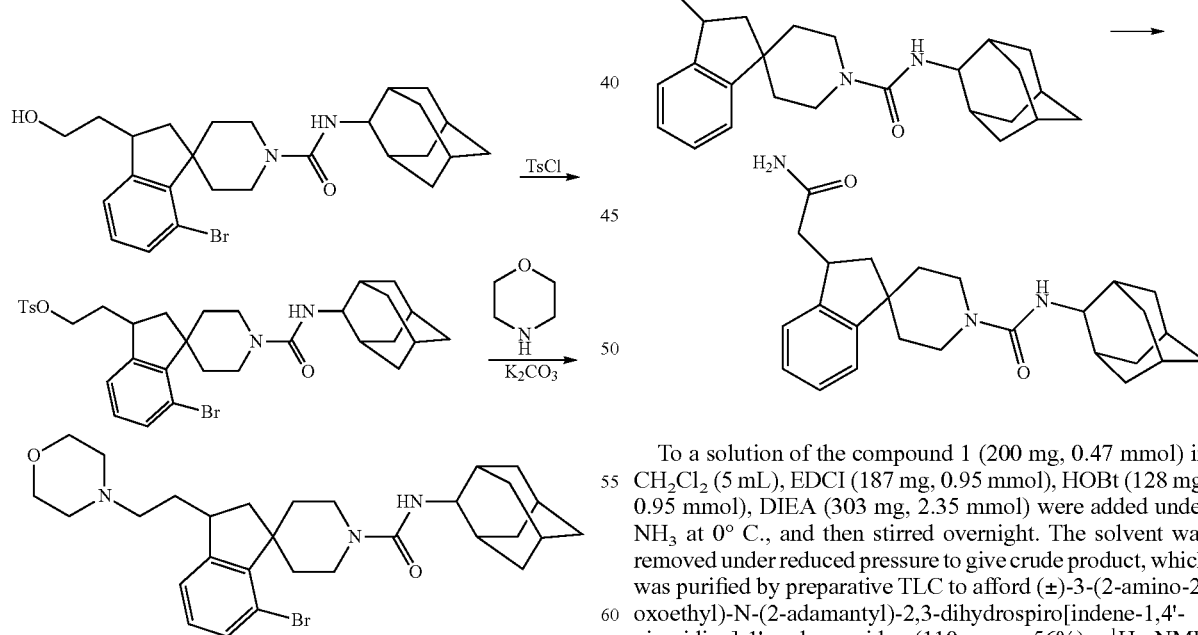

Step 1

To a solution of (±)-7-bromo-N-(2-adamantyl)-3-(2-hydroxyethyl)-2,3-dihydrospiro[indene-1,4'-piperidine]-1'-carboxamide (40 mg, 0.082 mmol) and Et$_3$N (9.9 mg, 0.098 mmol) in dry CH$_2$Cl$_2$ (5 mL) was added TsCl (15.6 mg, 0.082 mmol) at 0° C. The mixture was stirred overnight at rt. The mixture was concentrated to give the crude product, which was purified by preparative TLC to give (±)-7-bromo-N-(2-adamantyl)-3-(2-(p-toluenesulfonyloxy)ethyl)-2,3-dihydrospiro[indene-1,4'-piperidine]-1'-carboxamide (50 mg, crude).

Step 2

To a solution of (±)-7-bromo-N-(2-adamantyl)-3-(2-(p-toluenesulfonyloxy)ethyl)-2,3-dihydrospiro[indene-1,4'-piperidine]-1'-carboxamide (50 mg, 0.078 mmol) and K$_2$CO$_3$ (21.56 mg, 0.156 mmol) in anhydrous CH$_3$CN (3 mL) was added NaI (3 mg, 0.020 mmol) at 0° C. Then the mixture was stirred overnight at 80-90° C. The mixture was concentrated to give the crude product which was purified by preparative HPLC to afford (±)-7-bromo-N-(2-adamantyl)-3-(2-morpholinoethyl)-2,3-dihydrospiro[indene-1,4'-piperidine]-1'-carboxamide (4 mg, 9%). LC-MS Method 5 $t_R$=1.09 min, m/z=558; $^1$H NMR: (400 MHz, CDCl$_3$): δ=1.43 (m, 2H), 1.56-1.69 (m. 3H), 1.75-1.85 (m, 9H), 1.94-2.05 (m, 3H), 2.45-2.59 (m, 4H), 2.91 (m, 2H), 3.12 (m, 5H), 3.25 (m, 2H), 3.56 (m, 3H), 3.91-4.16 (m, 6H), 4.20 (m, 2H), 7.12 (m, 2H), 7.40 (m, 1H).

Example 127

(±)-3-(2-Amino-2-oxoethyl)-N-(2-adamantyl)-2,3-dihydro spiro[indene-1,4'-piperidine]-1'-carboxamide To a solution of the compound 1 (200 mg, 0.47 mmol) in CH$_2$Cl$_2$ (5 mL), EDCI (187 mg, 0.95 mmol), HOBt (128 mg, 0.95 mmol), DIEA (303 mg, 2.35 mmol) were added under NH$_3$ at 0° C., and then stirred overnight. The solvent was removed under reduced pressure to give crude product, which was purified by preparative TLC to afford (±)-3-(2-amino-2-oxoethyl)-N-(2-adamantyl)-2,3-dihydrospiro[indene-1,4'-piperidine]-1'-carboxamide (110 mg, 56%). $^1$H NMR (CDCl$_3$): δ=1.52-1.61 (m, 4H), 1.62-1.66 (m, 2H), 1.68-1.70 (m, 2H), 1.75-1.76 (m, 2H), 1.78-1.80 (m, 1H), 1.82-1.85 (m, 6H), 1.90-1.98 (m, 2H), 2.11-2.21 (m, 1H), 2.30-2.40 (m, 1H), 2.60-2.70 (m, 1H), 2.80-2.88 (m, 1H), 2.95-3.15 (m, 2H), 3.65-3.75 (m, 2H), 3.76-3.88 (m, 1H), 4.00 (s, 2H), 5.40-5.55 (d, 2H), 7.15-7.25 (m, 4H).

Example 128

1-Tert-butyl 1'-(2-adamantyl)spiro[indoline-3,4'-piperidine]-1,1'-dicarboxylate The title compound was prepared from tert-butyl spiro[indoline-3,4'-piperidine]-1-carboxylate following a procedure analogous to that described in Example 24 Step 2.

Example 129

1-Tert-butyl 1'-(2-adamantyl) 5-fluorospiro[indoline-3,4'-piperidine]-1,1'-dicarboxylate The title compound was prepared from tert-butyl 5-fluorospiro[indoline-3,4'-piperidine]-1-carboxylate following a procedure analogous to that described in Example 24 Step 2.

Example 130

1-Tert-butyl 1'-(2-adamantyl) 5-methylspiro[indoline-3,4'-piperidine]-1,1'-dicarboxylate The title compound was prepared from tert-butyl 5-methylspiro[indoline-3,4'-piperidine]-1-carboxylate following a procedure analogous to that described in Example 24 Step 2.

Example 131

(±)-3-(2-amino-2-oxoethyl)-7-bromo-N-(2-adamantyl)-2,3-dihydrospiro[indene-1,4'-piperidine]-1'-carboxamide The title compound was prepared from (±)-2-(7-bromo-1'-((2-adamantyl)carbamoyl)-2,3-dihydrospiro[indene-1,4'-piperidine]-3-yl)acetic acid following a procedure analogous to that described in Example 127 except that 0.5 M $NH_3$ in dioxane was used in place of $NH_3$ gas.

Compounds names were generated with the assistance of ChemDraw® software version 9.0 (Cambridgesoft, Cambridge, Mass., USA).

The following tables (I-VIII) indicate those compounds of the invention that can be prepared by the methods described herein.

TABLE I

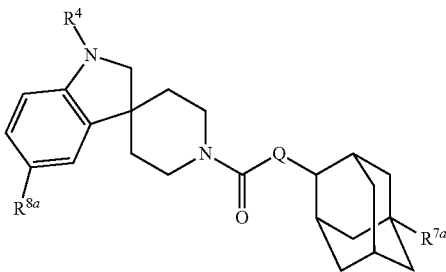

| Prophetic Example | $R^{8a}$ | $R^4$ | Q | $R^{7a}$ |
|---|---|---|---|---|
| 132 | H | H | NH | $CONH_2$ |
| 133 | H | Me | NH | $CONH_2$ |
| 134 | H | Boc | NH | $CONH_2$ |
| 135 | H | MeOCO | NH | $CONH_2$ |
| 136 | H | $CH_3CO$ | NH | $CONH_2$ |
| 137 | H | t-BuCO | NH | $CONH_2$ |
| 138 | H | MeNHCO | NH | $CONH_2$ |
| 139 | H | t-BuNHCO | NH | $CONH_2$ |
| 140 | H | $MeSO_2$ | NH | $CONH_2$ |
| 141 | H | $i-PrSO_2$ | NH | $CONH_2$ |
| 142 | H | $MeNHSO_2$ | NH | $CONH_2$ |
| 143 | H | H | O | $CONH_2$ |
| 144 | H | Me | O | $CONH_2$ |
| 145 | H | MeOCO | O | $CONH_2$ |
| 146 | H | $CH_3CO$ | O | $CONH_2$ |
| 147 | H | t-BuCO | O | $CONH_2$ |
| 148 | H | MeNHCO | O | $CONH_2$ |
| 149 | H | t-BuNHCO | O | $CONH_2$ |
| 150 | H | $MeSO_2$ | O | $CONH_2$ |
| 151 | H | $i-PrSO_2$ | O | $CONH_2$ |
| 152 | H | $MeNHSO_2$ | O | $CONH_2$ |
| 153 | F | Me | NH | H |
| 154 | F | Boc | NH | H |
| 155 | F | t-BuCO | NH | H |
| 156 | F | $MeSO_2$ | NH | H |
| 157 | F | Me | O | H |
| 158 | F | t-BuCO | O | H |
| 159 | F | $MeSO_2$ | O | H |
| 160 | F | H | O | $CONH_2$ |
| 161 | F | Me | O | $CONH_2$ |
| 162 | F | Boc | O | $CONH_2$ |
| 163 | F | $CH_3CO$ | O | $CONH_2$ |
| 164 | F | t-BuCO | O | $CONH_2$ |
| 165 | F | $MeSO_2$ | O | $CONH_2$ |
| 166 | $CF_3$ | H | NH | H |
| 167 | $CF_3$ | Me | NH | H |
| 168 | $CF_3$ | Boc | NH | H |
| 169 | $CF_3$ | $CH_3CO$ | NH | H |
| 170 | $CF_3$ | t-BuCO | NH | H |
| 171 | $CF_3$ | $MeSO_2$ | NH | H |
| 172 | $CF_3$ | H | O | H |
| 173 | $CF_3$ | Me | O | H |
| 174 | $CF_3$ | Boc | O | H |
| 175 | $CF_3$ | $CH_3CO$ | O | H |
| 176 | $CF_3$ | t-BuCO | O | H |
| 177 | $CF_3$ | $MeSO_2$ | O | H |
| 178 | $CF_3$ | H | O | $CONH_2$ |
| 179 | $CF_3$ | Me | O | $CONH_2$ |
| 180 | $CF_3$ | Boc | O | $CONH_2$ |
| 181 | $CF_3$ | $CH_3CO$ | O | $CONH_2$ |
| 182 | $CF_3$ | t-BuCO | O | $CONH_2$ |
| 183 | $CF_3$ | $MeSO_2$ | O | $CONH_2$ |
| 184 | CN | H | NH | H |
| 185 | CN | Me | NH | H |
| 186 | CN | Boc | NH | H |
| 187 | CN | $CH_3CO$ | NH | H |
| 188 | CN | t-BuCO | NH | H |
| 189 | CN | $MeSO_2$ | NH | H |
| 190 | CN | H | O | H |
| 191 | CN | Me | O | H |
| 192 | CN | Boc | O | H |
| 193 | CN | $CH_3CO$ | O | H |
| 194 | CN | t-BuCO | O | H |
| 195 | CN | $MeSO_2$ | O | H |
| 196 | CN | H | O | $CONH_2$ |
| 197 | CN | Me | O | $CONH_2$ |
| 198 | CN | Boc | O | $CONH_2$ |
| 199 | H | H | NH | OH |
| 200 | H | Me | NH | OH |
| 201 | H | Boc | NH | OH |

TABLE I-continued

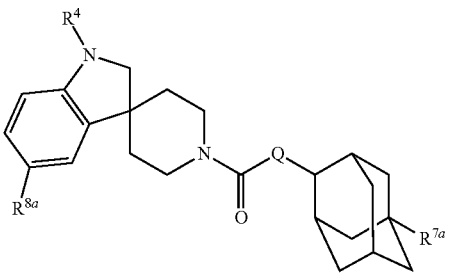

| Prophetic Example | R8a | R4 | Q | R7a |
|---|---|---|---|---|
| 202 | H | MeOCO | NH | OH |
| 203 | H | CH3CO | NH | OH |
| 204 | H | t-BuCO | NH | OH |
| 205 | H | MeNHCO | NH | OH |
| 206 | H | t-BuNHCO | NH | OH |
| 207 | H | MeSO2 | NH | OH |
| 208 | H | i-PrSO2 | NH | OH |
| 209 | H | MeNHSO2 | NH | OH |
| 210 | H | H | O | OH |
| 211 | H | Me | O | OH |
| 212 | H | Boc | O | OH |
| 213 | H | MeOCO | O | OH |
| 214 | H | CH3CO | O | OH |
| 215 | H | t-BuCO | O | OH |
| 216 | H | MeNHCO | O | OH |
| 217 | H | t-BuNHCO | O | OH |
| 218 | H | MeSO2 | O | OH |
| 219 | H | i-PrSO2 | O | OH |
| 220 | H | MeNHSO2 | O | OH |
| 221 | H | H | NH | CH2OH |
| 222 | H | Me | NH | CH2OH |
| 223 | H | Boc | NH | CH2OH |
| 224 | H | MeOCO | NH | CH2OH |
| 225 | H | CH3CO | NH | CH2OH |
| 226 | H | t-BuCO | NH | CH2OH |
| 227 | H | MeNHCO | NH | CH2OH |
| 228 | H | t-BuNHCO | NH | CH2OH |
| 229 | H | MeSO2 | NH | CH2OH |
| 230 | H | i-PrSO2 | NH | CH2OH |
| 231 | H | MeNHSO2 | NH | CH2OH |
| 232 | H | H | O | CH2OH |
| 233 | H | Me | O | CH2OH |
| 234 | H | Boc | O | CH2OH |
| 235 | H | MeOCO | O | CH2OH |
| 236 | H | CH3CO | O | CH2OH |
| 237 | H | t-BuCO | O | CH2OH |
| 238 | H | MeNHCO | O | CH2OH |
| 239 | H | t-BuNHCO | O | CH2OH |
| 240 | H | MeSO2 | O | CH2OH |
| 241 | H | i-PrSO2 | O | CH2OH |
| 242 | H | MeNHSO2 | O | CH2OH |
| 243 | H | H | NH | SO2Me |
| 244 | H | Me | NH | SO2Me |
| 245 | H | Boc | NH | SO2Me |
| 246 | H | MeOCO | NH | SO2Me |
| 247 | H | CH3CO | NH | SO2Me |
| 248 | H | t-BuCO | NH | SO2Me |
| 249 | H | MeNHCO | NH | SO2Me |
| 250 | H | t-BuNHCO | NH | SO2Me |
| 251 | H | MeSO2 | NH | SO2Me |
| 252 | H | i-PrSO2 | NH | SO2Me |
| 253 | H | MeNHSO2 | NH | SO2Me |
| 254 | H | H | O | SO2Me |
| 255 | H | Me | O | SO2Me |
| 256 | H | Boc | O | SO2Me |
| 257 | H | MeOCO | O | SO2Me |
| 258 | H | CH3CO | O | SO2Me |
| 259 | H | t-BuCO | O | SO2Me |
| 260 | H | MeNHCO | O | SO2Me |
| 261 | H | t-BuNHCO | O | SO2Me |
| 262 | H | MeSO2 | O | SO2Me |
| 263 | H | i-PrSO2 | O | SO2Me |
| 264 | H | MeNHSO2 | O | SO2Me |

TABLE I-continued

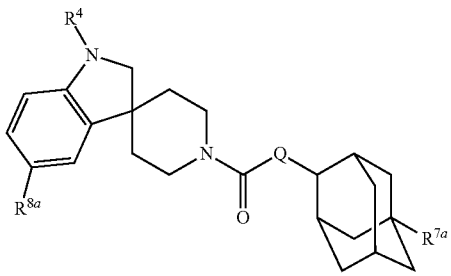

| Prophetic Example | R8a | R4 | Q | R7a |
|---|---|---|---|---|
| 265 | H | H | NH | SO2NH2 |
| 266 | H | Me | NH | SO2NH2 |
| 267 | H | Boc | NH | SO2NH2 |
| 268 | H | MeOCO | NH | SO2NH2 |
| 269 | H | CH3CO | NH | SO2NH2 |
| 270 | H | t-BuCO | NH | SO2NH2 |
| 271 | H | MeNHCO | NH | SO2NH2 |
| 272 | H | t-BuNHCO | NH | SO2NH2 |
| 273 | H | MeSO2 | NH | SO2NH2 |
| 274 | H | i-PrSO2 | NH | SO2NH2 |
| 275 | H | MeNHSO2 | NH | SO2NH2 |
| 276 | H | H | O | SO2NH2 |
| 277 | H | Me | O | SO2NH2 |
| 278 | H | Boc | O | SO2NH2 |
| 279 | H | MeOCO | O | SO2NH2 |
| 280 | H | CH3CO | O | SO2NH2 |
| 281 | H | t-BuCO | O | SO2NH2 |
| 282 | H | MeNHCO | O | SO2NH2 |
| 283 | H | t-BuNHCO | O | SO2NH2 |
| 284 | H | MeSO2 | O | SO2NH2 |
| 285 | H | i-PrSO2 | O | SO2NH2 |
| 286 | H | MeNHSO2 | O | SO2NH2 |

TABLE II

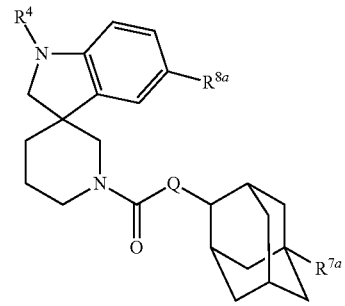

| Prophetic Example | R8a | R4 | Q | R7a |
|---|---|---|---|---|
| 287 | H | H | NH | CONH2 |
| 288 | H | Me | NH | CONH2 |
| 289 | H | Boc | NH | CONH2 |
| 290 | H | MeOCO | NH | CONH2 |
| 291 | H | CH3CO | NH | CONH2 |
| 292 | H | t-BuCO | NH | CONH2 |
| 293 | H | MeNHCO | NH | CONH2 |
| 294 | H | t-BuNHCO | NH | CONH2 |
| 295 | H | MeSO2 | NH | CONH2 |
| 296 | H | i-PrSO2 | NH | CONH2 |
| 297 | H | MeNHSO2 | NH | CONH2 |
| 298 | H | H | O | CONH2 |
| 299 | H | Me | O | CONH2 |
| 300 | H | Boc | O | CONH2 |
| 301 | H | MeOCO | O | CONH2 |
| 302 | H | CH3CO | O | CONH2 |
| 303 | H | t-BuCO | O | CONH2 |
| 304 | H | MeNHCO | O | CONH2 |

TABLE II-continued

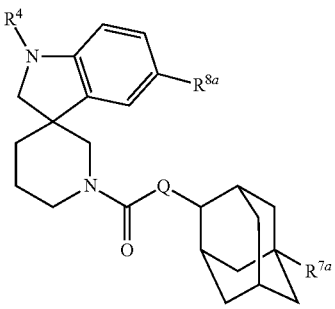

| Prophetic Example | $R^{8a}$ | $R^4$ | Q | $R^{7a}$ |
|---|---|---|---|---|
| 305 | H | t-BuNHCO | O | $CONH_2$ |
| 306 | H | $MeSO_2$ | O | $CONH_2$ |
| 307 | H | $i-PrSO_2$ | O | $CONH_2$ |
| 308 | H | $MeNHSO_2$ | O | $CONH_2$ |
| 309 | F | H | NH | H |
| 310 | F | Me | NH | H |
| 311 | F | Boc | NH | H |
| 312 | F | $CH_3CO$ | NH | H |
| 313 | F | t-BuCO | NH | H |
| 314 | F | $MeSO_2$ | NH | H |
| 315 | F | H | O | H |
| 316 | F | Me | O | H |
| 317 | F | Boc | O | H |
| 318 | F | $CH_3CO$ | O | H |
| 319 | F | t-BuCO | O | H |
| 320 | F | $MeSO_2$ | O | H |
| 321 | F | H | O | $CONH_2$ |
| 322 | F | Me | O | $CONH_2$ |
| 323 | F | Boc | O | $CONH_2$ |
| 324 | F | $CH_3CO$ | O | $CONH_2$ |
| 325 | F | t-BuCO | O | $CONH_2$ |
| 326 | F | $MeSO_2$ | O | $CONH_2$ |
| 327 | $CF_3$ | H | NH | H |
| 328 | $CF_3$ | Me | NH | H |
| 329 | $CF_3$ | Boc | NH | H |
| 330 | $CF_3$ | $CH_3CO$ | NH | H |
| 331 | $CF_3$ | t-BuCO | NH | H |
| 332 | $CF_3$ | $MeSO_2$ | NH | H |
| 333 | $CF_3$ | H | O | H |
| 334 | $CF_3$ | Me | O | H |
| 335 | $CF_3$ | Boc | O | H |
| 336 | $CF_3$ | $CH_3CO$ | O | H |
| 337 | $CF_3$ | t-BuCO | O | H |
| 338 | $CF_3$ | $MeSO_2$ | O | H |
| 339 | $CF_3$ | H | O | $CONH_2$ |
| 340 | $CF_3$ | Me | O | $CONH_2$ |
| 341 | $CF_3$ | Boc | O | $CONH_2$ |
| 342 | $CF_3$ | $CH_3CO$ | O | $CONH_2$ |
| 343 | $CF_3$ | t-BuCO | O | $CONH_2$ |
| 344 | $CF_3$ | $MeSO_2$ | O | $CONH_2$ |
| 345 | CN | H | NH | H |
| 346 | CN | Me | NH | H |
| 347 | CN | Boc | NH | H |
| 348 | CN | $CH_3CO$ | NH | H |
| 349 | CN | t-BuCO | NH | H |
| 350 | CN | $MeSO_2$ | NH | H |
| 351 | CN | H | O | H |
| 352 | CN | Me | O | H |
| 353 | CN | Boc | O | H |
| 354 | CN | $CH_3CO$ | O | H |
| 355 | CN | t-BuCO | O | H |
| 356 | CN | $MeSO_2$ | O | H |
| 357 | CN | H | O | $CONH_2$ |
| 358 | CN | Me | O | $CONH_2$ |
| 359 | CN | Boc | O | $CONH_2$ |
| 360 | H | H | NH | OH |
| 361 | H | Me | NH | OH |
| 362 | H | Boc | NH | OH |
| 363 | H | MeOCO | NH | OH |
| 364 | H | $CH_3CO$ | NH | OH |
| 365 | H | t-BuCO | NH | OH |
| 366 | H | MeNHCO | NH | OH |

TABLE II-continued

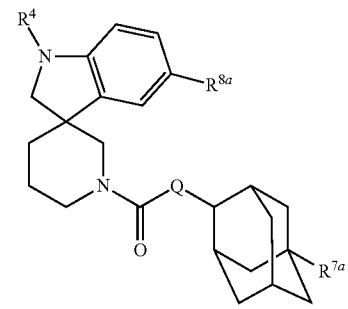

| Prophetic Example | $R^{8a}$ | $R^4$ | Q | $R^{7a}$ |
|---|---|---|---|---|
| 367 | H | t-BuNHCO | NH | OH |
| 368 | H | $MeSO_2$ | NH | OH |
| 369 | H | $i-PrSO_2$ | NH | OH |
| 370 | H | $MeNHSO_2$ | NH | OH |
| 371 | H | H | O | OH |
| 372 | H | Me | O | OH |
| 373 | H | Boc | O | OH |
| 374 | H | MeOCO | O | OH |
| 375 | H | $CH_3CO$ | O | OH |
| 376 | H | t-BuCO | O | OH |
| 377 | H | MeNHCO | O | OH |
| 378 | H | t-BuNHCO | O | OH |
| 379 | H | $MeSO_2$ | O | OH |
| 380 | H | $i-PrSO_2$ | O | OH |
| 381 | H | $MeNHSO_2$ | O | OH |
| 382 | H | H | NH | $CH_2OH$ |
| 383 | H | Me | NH | $CH_2OH$ |
| 384 | H | Boc | NH | $CH_2OH$ |
| 385 | H | MeOCO | NH | $CH_2OH$ |
| 386 | H | $CH_3CO$ | NH | $CH_2OH$ |
| 387 | H | t-BuCO | NH | $CH_2OH$ |
| 388 | H | MeNHCO | NH | $CH_2OH$ |
| 389 | H | t-BuNHCO | NEI | $CH_2OH$ |
| 390 | H | $MeSO_2$ | NH | $CH_2OH$ |
| 391 | H | $i-PrSO_2$ | NH | $CH_2OH$ |
| 392 | H | $MeNHSO_2$ | NH | $CH_2OH$ |
| 393 | H | H | O | $CH_2OH$ |
| 394 | H | Me | O | $CH_2OH$ |
| 395 | H | Boc | O | $CH_2OH$ |
| 396 | H | MeOCO | O | $CH_2OH$ |
| 397 | H | $CH_3CO$ | O | $CH_2OH$ |
| 398 | H | t-BuCO | O | $CH_2OH$ |
| 399 | H | MeNHCO | O | $CH_2OH$ |
| 400 | H | t-BuNHCO | O | $CH_2OH$ |
| 401 | H | $MeSO_2$ | O | $CH_2OH$ |
| 402 | H | $i-PrSO_2$ | O | $CH_2OH$ |
| 403 | H | $MeNHSO_2$ | O | $CH_2OH$ |
| 404 | H | H | NH | $SO_2Me$ |
| 405 | H | Me | NH | $SO_2Me$ |
| 406 | H | Boc | NH | $SO_2Me$ |
| 407 | H | MeOCO | NH | $SO_2Me$ |
| 408 | H | $CH_3CO$ | NH | $SO_2Me$ |
| 409 | H | t-BuCO | NH | $SO_2Me$ |
| 410 | H | MeNHCO | NH | $SO_2Me$ |
| 411 | H | t-BuNHCO | NH | $SO_2Me$ |
| 412 | H | $MeSO_2$ | NH | $SO_2Me$ |
| 413 | H | $i-PrSO_2$ | NH | $SO_2Me$ |
| 414 | H | $MeNHSO_2$ | NH | $SO_2Me$ |
| 415 | H | H | O | $SO_2Me$ |
| 416 | H | Me | O | $SO_2Me$ |
| 417 | H | Boc | O | $SO_2Me$ |
| 418 | H | MeOCO | O | $SO_2Me$ |
| 419 | H | $CH_3CO$ | O | $SO_2Me$ |
| 420 | H | t-BuCO | O | $SO_2Me$ |
| 421 | H | MeNHCO | O | $SO_2Me$ |
| 422 | H | t-BuNHCO | O | $SO_2Me$ |
| 423 | H | $MeSO_2$ | O | $SO_2Me$ |
| 424 | H | $i-PrSO_2$ | O | $SO_2Me$ |
| 425 | H | $MeNHSO_2$ | O | $SO_2Me$ |
| 426 | H | H | NH | $SO_2NH_2$ |
| 427 | H | Me | NH | $SO_2NH_2$ |
| 428 | H | Boc | NH | $SO_2NH_2$ |

TABLE II-continued

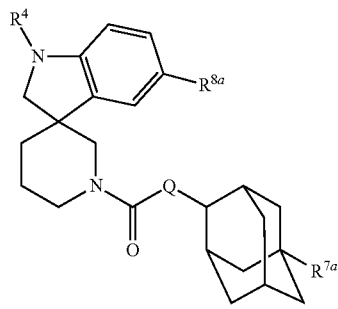

| Prophetic Example | $R^{8a}$ | $R^4$ | Q | $R^{7a}$ |
|---|---|---|---|---|
| 429 | H | MeOCO | NH | $SO_2NH_2$ |
| 430 | H | $CH_3CO$ | NH | $SO_2NH_2$ |
| 431 | H | t-BuCO | NH | $SO_2NH_2$ |
| 432 | H | MeNHCO | NH | $SO_2NH_2$ |
| 433 | H | t-BuNHCO | NH | $SO_2NH_2$ |
| 434 | H | $MeSO_2$ | NH | $SO_2NH_2$ |
| 435 | H | $i-PrSO_2$ | NH | $SO_2NH_2$ |
| 436 | H | $MeNHSO_2$ | NH | $SO_2NH_2$ |
| 437 | H | H | O | $SO_2NH_2$ |
| 438 | H | Me | O | $SO_2NH_2$ |
| 439 | H | Boc | O | $SO_2NH_2$ |
| 440 | H | MeOCO | O | $SO_2NH_2$ |
| 441 | H | $CH_3CO$ | O | $SO_2NH_2$ |
| 442 | H | t-BuCO | O | $SO_2NH_2$ |
| 443 | H | MeNHCO | O | $SO_2NH_2$ |
| 444 | H | t-BuNHCO | O | $SO_2NH_2$ |
| 445 | H | $MeSO_2$ | O | $SO_2NH_2$ |
| 446 | H | $i-PrSO_2$ | O | $SO_2NH_2$ |
| 447 | H | $MeNHSO_2$ | O | $SO_2NH_2$ |

TABLE III

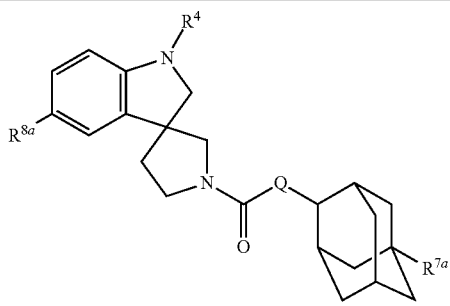

| Prophetic Example | $R^{8a}$ | $R^4$ | Q | $R^{7a}$ |
|---|---|---|---|---|
| 448 | H | H | NH | $CONH_2$ |
| 449 | H | Me | NH | $CONH_2$ |
| 450 | H | Boc | NH | $CONH_2$ |
| 451 | H | MeOCO | NH | $CONH_2$ |
| 452 | H | $CH_3CO$ | NH | $CONH_2$ |
| 453 | H | t-BuCO | NH | $CONH_2$ |
| 454 | H | MeNHCO | NH | $CONH_2$ |
| 455 | H | t-BuNHCO | NH | $CONH_2$ |
| 456 | H | $MeSO_2$ | NH | $CONH_2$ |
| 457 | H | $i-PrSO_2$ | NH | $CONH_2$ |
| 458 | H | $MeNHSO_2$ | NH | $CONH_2$ |
| 459 | H | H | O | $CONH_2$ |
| 460 | H | Me | O | $CONH_2$ |
| 461 | H | Boc | O | $CONH_2$ |
| 462 | H | MeOCO | O | $CONH_2$ |
| 463 | H | $CH_3CO$ | O | $CONH_2$ |
| 464 | H | t-BuCO | O | $CONH_2$ |
| 465 | H | MeNHCO | O | $CONH_2$ |
| 466 | H | t-BuNHCO | O | $CONH_2$ |

TABLE III-continued

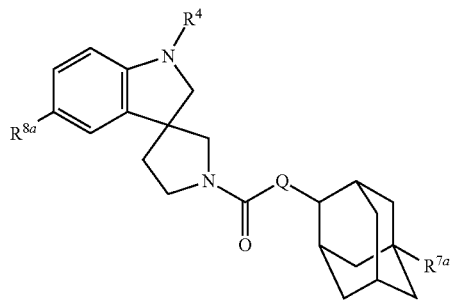

| Prophetic Example | $R^{8a}$ | $R^4$ | Q | $R^{7a}$ |
|---|---|---|---|---|
| 467 | H | $MeSO_2$ | O | $CONH_2$ |
| 468 | H | $i-PrSO_2$ | O | $CONH_2$ |
| 469 | H | $MeNHSO_2$ | O | $CONH_2$ |
| 470 | F | H | NH | H |
| 471 | F | Me | NH | H |
| 472 | F | Boc | NH | H |
| 473 | F | $CH_3CO$ | NH | H |
| 474 | F | t-BuCO | NH | H |
| 475 | F | $MeSO_2$ | NH | H |
| 476 | F | H | O | H |
| 477 | F | Me | O | H |
| 478 | F | Boc | O | H |
| 479 | F | $CH_3CO$ | O | H |
| 480 | F | t-BuCO | O | H |
| 481 | F | $MeSO_2$ | O | H |
| 482 | F | H | O | $CONH_2$ |
| 483 | F | Me | O | $CONH_2$ |
| 484 | F | Boc | O | $CONH_2$ |
| 485 | F | $CH_3CO$ | O | $CONH_2$ |
| 486 | F | t-BuCO | O | $CONH_2$ |
| 487 | F | $MeSO_2$ | O | $CONH_2$ |
| 488 | $CF_3$ | H | NH | H |
| 489 | $CF_3$ | Me | NH | H |
| 490 | $CF_3$ | Boc | NH | H |
| 491 | $CF_3$ | $CH_3CO$ | NH | H |
| 492 | $CF_3$ | t-BuCO | NH | H |
| 493 | $CF_3$ | $MeSO_2$ | NH | H |
| 494 | $CF_3$ | H | O | H |
| 495 | $CF_3$ | Me | O | H |
| 496 | $CF_3$ | Boc | O | H |
| 497 | $CF_3$ | $CH_3CO$ | O | H |
| 498 | $CF_3$ | t-BuCO | O | H |
| 499 | $CF_3$ | $MeSO_2$ | O | H |
| 500 | $CF_3$ | H | O | $CONH_2$ |
| 501 | $CF_3$ | Me | O | $CONH_2$ |
| 502 | $CF_3$ | Boc | O | $CONH_2$ |
| 503 | $CF_3$ | $CH_3CO$ | O | $CONH_2$ |
| 504 | $CF_3$ | t-BuCO | O | $CONH_2$ |
| 505 | $CF_3$ | $MeSO_2$ | O | $CONH_2$ |
| 506 | CN | H | NH | H |
| 507 | CN | Me | NH | H |
| 508 | CN | Boc | NH | H |
| 509 | CN | $CH_3CO$ | NH | H |
| 510 | CN | t-BuCO | NH | H |
| 511 | CN | $MeSO_2$ | NH | H |
| 512 | CN | H | O | H |
| 513 | CN | Me | O | H |
| 514 | CN | Boc | O | H |
| 515 | CN | $CH_3CO$ | O | H |
| 516 | CN | t-BuCO | O | H |
| 517 | CN | $MeSO_2$ | O | H |
| 518 | CN | H | O | $CONH_2$ |
| 519 | CN | Me | O | $CONH_2$ |
| 520 | CN | Boc | O | $CONH_2$ |
| 521 | H | H | NH | OH |
| 522 | H | Me | NH | OH |
| 523 | H | Boc | NH | OH |
| 524 | H | MeOCO | NH | OH |
| 525 | H | $CH_3CO$ | NH | OH |
| 526 | H | t-BuCO | NH | OH |
| 527 | H | MeNHCO | NH | OH |
| 528 | H | t-BuNHCO | NH | OH |

TABLE III-continued

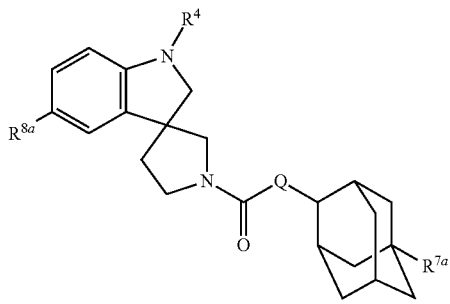

| Prophetic Example | $R^{8a}$ | $R^4$ | Q | $R^{7a}$ |
|---|---|---|---|---|
| 529 | H | MeSO$_2$ | NH | OH |
| 530 | H | i-PrSO$_2$ | NH | OH |
| 531 | H | MeNHSO$_2$ | NH | OH |
| 532 | H | H | O | OH |
| 533 | H | Me | O | OH |
| 534 | H | Boc | O | OH |
| 535 | H | MeOCO | O | OH |
| 536 | H | CH$_3$CO | O | OH |
| 537 | H | t-BuCO | O | OH |
| 538 | H | MeNHCO | O | OH |
| 539 | H | t-BuNHCO | O | OH |
| 540 | H | MeSO$_2$ | O | OH |
| 541 | H | i-PrSO$_2$ | O | OH |
| 542 | H | MeNHSO$_2$ | O | OH |
| 543 | H | H | NH | CH$_2$OH |
| 544 | H | Me | NH | CH$_2$OH |
| 545 | H | Boc | NH | CH$_2$OH |
| 546 | H | MeOCO | NH | CH$_2$OH |
| 547 | H | CH$_3$CO | NH | CH$_2$OH |
| 548 | H | t-BuCO | NH | CH$_2$OH |
| 549 | H | MeNHCO | NH | CH$_2$OH |
| 550 | H | t-BuNHCO | NH | CH$_2$OH |
| 551 | H | MeSO$_2$ | NH | CH$_2$OH |
| 552 | H | i-PrSO$_2$ | NH | CH$_2$OH |
| 553 | H | MeNHSO$_2$ | NH | CH$_2$OH |
| 554 | H | H | O | CH$_2$OH |
| 555 | H | Me | O | CH$_2$OH |
| 556 | H | Boc | O | CH$_2$OH |
| 557 | H | MeOCO | O | CH$_2$OH |
| 558 | H | CH$_3$CO | O | CH$_2$OH |
| 559 | H | t-BuCO | O | CH$_2$OH |
| 560 | H | MeNHCO | O | CH$_2$OH |
| 561 | H | t-BuNHCO | O | CH$_2$OH |
| 562 | H | MeSO$_2$ | O | CH$_2$OH |
| 563 | H | i-PrSO$_2$ | O | CH$_2$OH |
| 564 | H | MeNHSO$_2$ | O | CH$_2$OH |
| 565 | H | H | NH | SO$_2$NH$_2$ |
| 566 | H | Me | NH | SO$_2$NH$_2$ |
| 567 | H | Boc | NH | SO$_2$NH$_2$ |
| 568 | H | MeOCO | NH | SO$_2$NH$_2$ |
| 569 | H | CH$_3$CO | NH | SO$_2$NH$_2$ |
| 570 | H | t-BuCO | NH | SO$_2$NH$_2$ |
| 571 | H | MeNHCO | NH | SO$_2$NH$_2$ |
| 572 | H | t-BuNHCO | NH | SO$_2$NH$_2$ |
| 573 | H | MeSO$_2$ | NH | SO$_2$NH$_2$ |
| 574 | H | i-PrSO$_2$ | NH | SO$_2$NH$_2$ |
| 575 | H | MeNHSO$_2$ | NH | SO$_2$NH$_2$ |
| 576 | H | H | O | SO$_2$NH$_2$ |
| 577 | H | Me | O | SO$_2$NH$_2$ |
| 578 | H | Boc | O | SO$_2$NH$_2$ |
| 579 | H | MeOCO | O | SO$_2$NH$_2$ |
| 580 | H | CH$_3$CO | O | SO$_2$NH$_2$ |
| 581 | H | t-BuCO | O | SO$_2$NH$_2$ |
| 582 | H | MeNHCO | O | SO$_2$NH$_2$ |
| 583 | H | t-BuNHCO | O | SO$_2$NH$_2$ |
| 584 | H | MeSO$_2$ | O | SO$_2$NH$_2$ |
| 585 | H | i-PrSO$_2$ | O | SO$_2$NH$_2$ |
| 586 | H | MeNHSO$_2$ | O | SO$_2$NH$_2$ |

TABLE IV

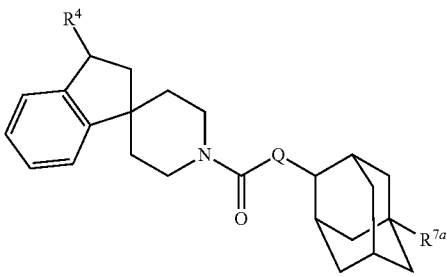

| Prophetic Example | $R^4$ | Q | $R^{7a}$ |
|---|---|---|---|
| 587 | CO$_2$H | NH | CONH$_2$ |
| 588 | CH$_2$CO$_2$H | NH | CONH$_2$ |
| 589 | CH$_2$CH$_2$CO$_2$H | NH | CONH$_2$ |
| 590 | CH$_2$CH$_2$CH$_2$CO$_2$H | NH | CONH$_2$ |
| 591 | CO$_2$Me | NH | CONH$_2$ |
| 592 | CH$_2$CO$_2$Me | NH | CONH$_2$ |
| 593 | CH$_2$CH$_2$CO$_2$Me | NH | CONH$_2$ |
| 594 | CH$_2$CH$_2$CH$_2$CO$_2$Me | NH | CONH$_2$ |
| 595 | C(CH$_3$)$_2$CO$_2$H | NH | CONH$_2$ |
| 596 | C(CH$_3$)$_2$CO$_2$Me | NH | CONH$_2$ |
| 597 | CH$_2$(5-tetrazolyl) | NH | CONH$_2$ |
| 598 | CH$_2$CONHSO$_2$Me | NH | CONH$_2$ |
| 599 | CO$_2$H | O | CONH$_2$ |
| 600 | CH$_2$CH$_2$CO$_2$H | O | CONH$_2$ |
| 601 | CH$_2$CH$_2$CH$_2$CO$_2$H | O | CONH$_2$ |
| 602 | CO$_2$Me | O | CONH$_2$ |
| 603 | CH$_2$CO$_2$Me | O | CONH$_2$ |
| 604 | CH$_2$CH$_2$CO$_2$Me | O | CONH$_2$ |
| 605 | CH$_2$CH$_2$CH$_2$CO$_2$Me | O | CONH$_2$ |
| 606 | C(CH$_3$)$_2$CO$_2$H | O | CONH$_2$ |
| 607 | C(CH$_3$)$_2$CO$_2$Me | O | CONH$_2$ |
| 608 | CH$_2$(5-tetrazolyl) | O | CONH$_2$ |
| 609 | CH$_2$CONHSO$_2$Me | O | CONH$_2$ |
| 610 | CO$_2$H | NH | OH |
| 611 | CH$_2$CO$_2$H | NH | OH |
| 612 | CH$_2$CH$_2$CO$_2$H | NH | OH |
| 613 | CH$_2$CH$_2$CH$_2$CO$_2$H | NH | OH |
| 614 | CO$_2$Me | NH | OH |
| 615 | CH$_2$CO$_2$Me | NH | OH |
| 616 | CH$_2$CH$_2$CO$_2$Me | NH | OH |
| 617 | CH$_2$CH$_2$CH$_2$CO$_2$Me | NH | OH |
| 618 | C(CH$_3$)$_2$CO$_2$H | NH | OH |
| 619 | C(CH$_3$)$_2$CO$_2$Me | NH | OH |
| 620 | CH$_2$(5-tetrazolyl) | NH | OH |
| 621 | CH$_2$CONHSO$_2$Me | NH | OH |
| 622 | CO$_2$H | NH | CH$_2$OH |
| 623 | CH$_2$CO$_2$H | NH | CH$_2$OH |
| 624 | CH$_2$CH$_2$CO$_2$H | NH | CH$_2$OH |
| 625 | CH$_2$CH$_2$CH$_2$CO$_2$H | NH | CH$_2$OH |
| 626 | CO$_2$Me | NH | CH$_2$OH |
| 627 | CH$_2$CO$_2$Me | NH | CH$_2$OH |
| 628 | CH$_2$CH$_2$CO$_2$Me | NH | CH$_2$OH |
| 629 | CH$_2$CH$_2$CH$_2$CO$_2$Me | NH | CH$_2$OH |
| 630 | C(CH$_3$)$_2$CO$_2$H | NH | CH$_2$OH |
| 631 | C(CH$_3$)$_2$CO$_2$Me | NH | CH$_2$OH |
| 632 | CH$_2$(5-tetrazolyl) | NH | CH$_2$OH |
| 633 | CH$_2$CONHSO$_2$Me | NH | CH$_2$OH |
| 634 | CO$_2$H | O | SO$_2$NH$_2$ |
| 635 | CH$_2$CO$_2$H | O | SO$_2$NH$_2$ |
| 636 | CH$_2$CH$_2$CH$_2$CO$_2$H | O | SO$_2$NH$_2$ |
| 637 | CO$_2$NH$_2$ | O | SO$_2$NH$_2$ |
| 638 | CH$_2$CONH$_2$ | O | SO$_2$NH$_2$ |
| 639 | CH$_2$CH$_2$CO$_2$NH$_2$ | O | SO$_2$NH$_2$ |
| 640 | CH$_2$CH$_2$CH$_2$CONH$_2$ | O | SO$_2$NH$_2$ |
| 641 | C(CH$_3$)$_2$CO$_2$H | O | SO$_2$NH$_2$ |
| 642 | C(CH$_3$)$_2$CONH$_2$ | O | SO$_2$NH$_2$ |
| 643 | CH$_2$(5-tetrazolyl) | O | SO$_2$NH$_2$ |
| 644 | CH$_2$CONHSO$_2$Me | O | SO$_2$NH$_2$ |
| 645 | CO$_2$H | NH | SO$_2$NH$_2$ |
| 646 | CH$_2$CO$_2$H | NH | SO$_2$NH$_2$ |
| 647 | CH$_2$CH$_2$CH$_2$CO$_2$H | NH | SO$_2$NH$_2$ |
| 648 | CO$_2$NH$_2$ | NH | SO$_2$NH$_2$ |
| 649 | CH$_2$CONH$_2$ | NH | SO$_2$NH$_2$ |

TABLE IV-continued

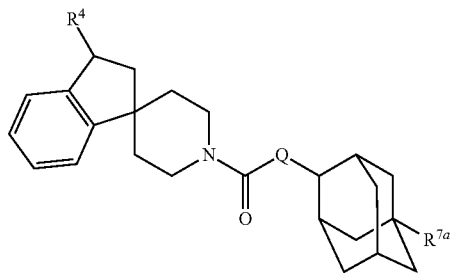

| Prophetic Example | $R^4$ | Q | $R^{7a}$ |
|---|---|---|---|
| 650 | $CH_2CH_2CO_2NH_2$ | NH | $SO_2NH_2$ |
| 651 | $CH_2CH_2CH_2CONH_2$ | NH | $SO_2NH_2$ |
| 652 | $C(CH_3)_2CO_2H$ | NH | $SO_2NH_2$ |
| 653 | $C(CH_3)_2CONH_2$ | NH | $SO_2NH_2$ |
| 654 | $CH_2(5\text{-tetrazolyl})$ | NH | $SO_2NH_2$ |
| 655 | $CH_2CONHSO_2Me$ | NH | $SO_2NH_2$ |
| 656 | $CO_2H$ | O | $SO_2Me$ |
| 657 | $CH_2CH_2CO_2H$ | O | $SO_2Me$ |
| 658 | $CH_2CH_2CH_2CO_2H$ | O | $SO_2Me$ |
| 659 | $CO_2NH_2$ | O | $SO_2Me$ |
| 660 | $CH_2CONH_2$ | O | $SO_2Me$ |
| 661 | $CH_2CH_2CO_2NH_2$ | O | $SO_2Me$ |
| 662 | $CH_2CH_2CH_2CONH_2$ | O | $SO_2Me$ |
| 663 | $C(CH_3)_2CO_2H$ | O | $SO_2Me$ |
| 664 | $C(CH_3)_2CONH_2$ | O | $SO_2Me$ |
| 665 | $CH_2(5\text{-tetrazolyl})$ | O | $SO_2Me$ |
| 666 | $CH_2CONHSO_2Me$ | O | $SO_2Me$ |
| 667 | $CO_2H$ | NH | $SO_2Me$ |
| 668 | $CH_2CH_2CO_2H$ | NH | $SO_2Me$ |
| 669 | $CH_2CH_2CH_2CO_2H$ | NH | $SO_2Me$ |
| 670 | $CO_2NH_2$ | NH | $SO_2Me$ |
| 671 | $CH_2CONH_2$ | NH | $SO_2Me$ |
| 672 | $CH_2CH_2CO_2NH_2$ | NH | $SO_2Me$ |
| 673 | $CH_2CH_2CH_2CONH_2$ | NH | $SO_2Me$ |
| 674 | $C(CH_3)_2CO_2H$ | NH | $SO_2Me$ |
| 675 | $C(CH_3)_2CONH_2$ | NH | $SO_2Me$ |
| 676 | $CH_2(5\text{-tetrazolyl})$ | NH | $SO_2Me$ |
| 677 | $CH_2CONHSO_2Me$ | NH | $SO_2Me$ |

TABLE V

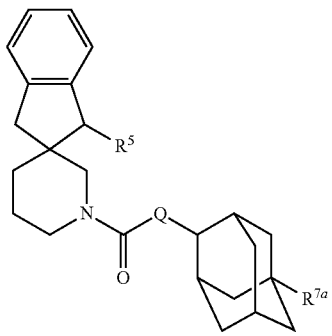

| Prophetic Example | $R^5$ | Q | $R^{7a}$ |
|---|---|---|---|
| 678 | H | NH | H |
| 679 | $CO_2H$ | NH | H |
| 680 | $CO_2Me$ | NH | H |
| 681 | $CH_2CO_2H$ | NH | H |
| 682 | $CH_2CO_2Me$ | NH | H |
| 683 | H | O | H |
| 684 | $CO_2H$ | O | H |
| 685 | $CO_2Me$ | O | H |
| 686 | $CH_2CO_2H$ | O | H |
| 687 | $CH_2CO_2Me$ | O | H |

TABLE V-continued

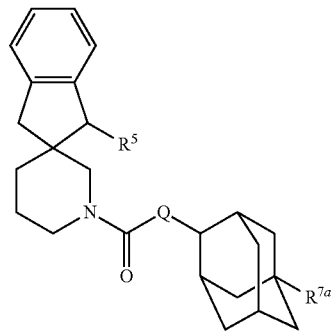

| Prophetic Example | $R^5$ | Q | $R^{7a}$ |
|---|---|---|---|
| 688 | H | NH | $CONH_2$ |
| 689 | $CO_2H$ | NH | $CONH_2$ |
| 690 | $CO_2Me$ | NH | $CONH_2$ |
| 691 | $CH_2CO_2H$ | NH | $CONH_2$ |
| 692 | $CH_2CO_2Me$ | NH | $CONH_2$ |
| 693 | H | O | $CONH_2$ |
| 694 | $CO_2H$ | O | $CONH_2$ |
| 695 | $CO_2Me$ | O | $CONH_2$ |
| 696 | $CH_2CO_2H$ | O | $CONH_2$ |
| 697 | $CH_2CO_2Me$ | O | $CONH_2$ |
| 698 | H | NH | OH |
| 699 | $CO_2H$ | NH | OH |
| 700 | $CO_2Me$ | NH | OH |
| 701 | $CH_2CO_2H$ | NH | OH |
| 702 | $CH_2CO_2Me$ | NH | OH |
| 703 | H | O | OH |
| 704 | $CO_2H$ | O | OH |
| 705 | $CO_2Me$ | O | OH |
| 706 | $CH_2CO_2H$ | O | OH |
| 707 | $CH_2CO_2Me$ | O | OH |
| 708 | H | NH | $CH_2OH$ |
| 709 | $CO_2H$ | NH | $CH_2OH$ |
| 710 | $CO_2Me$ | NH | $CH_2OH$ |
| 711 | $CH_2CO_2H$ | NH | $CH_2OH$ |
| 712 | $CH_2CO_2Me$ | NH | $CH_2OH$ |
| 713 | H | O | $CH_2OH$ |
| 714 | $CO_2H$ | O | $CH_2OH$ |
| 715 | $CO_2Me$ | O | $CH_2OH$ |
| 716 | $CH_2CO_2H$ | O | $CH_2OH$ |
| 717 | $CH_2CO_2Me$ | O | $CH_2OH$ |
| 718 | H | NH | $SO_2Me$ |
| 719 | $CO_2H$ | NH | $SO_2Me$ |
| 720 | $CONH_2$ | NH | $SO_2Me$ |
| 721 | $CH_2CO_2H$ | NH | $SO_2Me$ |
| 722 | $CH_2CONH_2$ | NH | $SO_2Me$ |
| 723 | H | O | $SO_2Me$ |
| 724 | $CO_2H$ | O | $SO_2Me$ |
| 725 | $CONH_2$ | O | $SO_2Me$ |
| 726 | $CH_2CO_2H$ | O | $SO_2Me$ |
| 727 | $CH_2CONH_2$ | O | $SO_2Me$ |
| 728 | H | NH | $SO_2NH_2$ |
| 729 | $CO_2H$ | NH | $SO_2NH_2$ |
| 730 | $CONH_2$ | NH | $SO_2NH_2$ |
| 731 | $CH_2CO_2H$ | NH | $SO_2NH_2$ |
| 732 | $CH_2CONH_2$ | NH | $SO_2NH_2$ |
| 733 | H | O | $SO_2NH_2$ |
| 734 | $CO_2H$ | O | $SO_2NH_2$ |
| 735 | $CONH_2$ | O | $SO_2NH_2$ |
| 736 | $CH_2CO_2H$ | O | $SO_2NH_2$ |
| 737 | $CH_2CONH_2$ | O | $SO_2NH_2$ |

TABLE VI

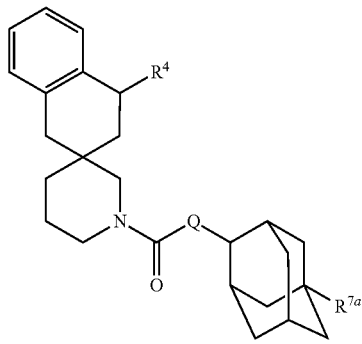

| Prophetic Example | R5 | Q | R7a |
|---|---|---|---|
| 738 | H | NH | H |
| 739 | CO2H | NH | H |
| 740 | CO2Me | NH | H |
| 741 | CH2CO2H | NH | H |
| 742 | CH2CO2Me | NH | H |
| 743 | H | O | H |
| 744 | CO2H | O | H |
| 745 | CO2Me | O | H |
| 746 | CH2CO2H | O | H |
| 747 | CH2CO2Me | O | H |
| 748 | H | NH | CONH2 |
| 749 | CO2H | NH | CONH2 |
| 750 | CO2Me | NH | CONH2 |
| 751 | CH2CO2H | NH | CONH2 |
| 752 | CH2CO2Me | NH | CONH2 |
| 753 | H | O | CONH2 |
| 754 | CO2H | O | CONH2 |
| 755 | CO2Me | O | CONH2 |
| 756 | CH2CO2H | O | CONH2 |
| 757 | CH2CO2Me | O | CONH2 |
| 758 | H | NH | OH |
| 759 | CO2H | NH | OH |
| 760 | CO2Me | NH | OH |
| 761 | CH2CO2H | NH | OH |
| 762 | CH2CO2Me | NH | OH |
| 763 | H | O | OH |
| 764 | CO2H | O | OH |
| 765 | CO2Me | O | OH |
| 766 | CH2CO2H | O | OH |
| 767 | CH2CO2Me | O | OH |
| 768 | H | NH | CH2OH |
| 769 | CO2H | NH | CH2OH |
| 770 | CO2Me | NH | CH2OH |
| 771 | CH2CO2H | NH | CH2OH |
| 772 | CH2CO2Me | NH | CH2OH |
| 773 | H | O | CH2OH |
| 774 | CO2H | O | CH2OH |
| 775 | CO2Me | O | CH2OH |
| 776 | CH2CO2H | O | CH2OH |
| 777 | CH2CO2Me | O | CH2OH |
| 778 | H | NH | SO2Me |
| 779 | CO2H | NH | SO2Me |
| 780 | CONH2 | NH | SO2Me |
| 781 | CH2CO2H | NH | SO2Me |
| 782 | CH2CONH2 | NH | SO2Me |
| 783 | H | O | SO2Me |
| 784 | CO2H | O | SO2Me |
| 785 | CONH2 | O | SO2Me |
| 786 | CH2CO2H | O | SO2Me |
| 787 | CH2CONH2 | O | SO2Me |
| 788 | H | NH | SO2NH2 |
| 789 | CO2H | NH | SO2NH2 |
| 790 | CONH2 | NH | SO2NH2 |
| 791 | CH2CO2H | NH | SO2NH2 |
| 792 | CH2CONH2 | NH | SO2NH2 |
| 793 | H | O | SO2NH2 |
| 794 | CO2H | O | SO2NH2 |
| 795 | CONH2 | O | SO2NH2 |

TABLE VI-continued

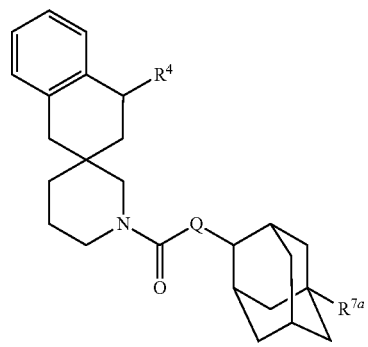

| Prophetic Example | R5 | Q | R7a |
|---|---|---|---|
| 796 | CH2CO2H | O | SO2NH2 |
| 797 | CH2CONH2 | O | SO2NH2 |

TABLE VII

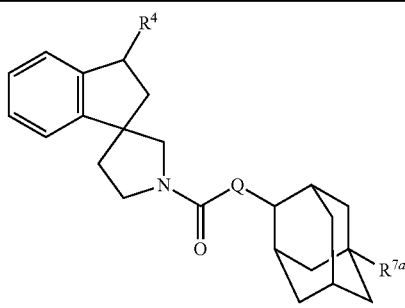

| Prophetic Example | R5 | Q | R7a |
|---|---|---|---|
| 798 | H | NH | H |
| 799 | CO2H | NH | H |
| 800 | CO2Me | NH | H |
| 801 | CH2CO2H | NH | H |
| 802 | CH2CO2Me | NH | H |
| 803 | H | O | H |
| 804 | CO2H | O | H |
| 805 | CO2Me | O | H |
| 806 | CH2CO2H | O | H |
| 807 | CH2CO2Me | O | H |
| 808 | H | NH | CONH2 |
| 809 | CO2H | NH | CONH2 |
| 810 | CO2Me | NH | CONH2 |
| 811 | CH2CO2H | NH | CONH2 |
| 812 | CH2CO2Me | NH | CONH2 |
| 813 | H | O | CONH2 |
| 814 | CO2H | O | CONH2 |
| 815 | CO2Me | O | CONH2 |
| 816 | CH2CO2H | O | CONH2 |
| 817 | CH2CO2Me | O | CONH2 |
| 818 | H | NH | OH |
| 819 | CO2H | NH | OH |
| 820 | CO2Me | NH | OH |
| 821 | CH2CO2H | NH | OH |
| 822 | CH2CO2Me | NH | OH |
| 823 | H | O | OH |
| 824 | CO2H | O | OH |
| 825 | CO2Me | O | OH |
| 826 | CH2CO2H | O | OH |
| 827 | CH2CO2Me | O | OH |
| 828 | H | NH | CH2OH |
| 829 | CO2H | NH | CH2OH |
| 830 | CO2Me | NH | CH2OH |
| 831 | CH2CO2H | NH | CH2OH |

TABLE VII-continued

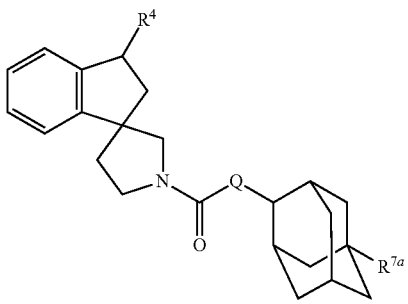

| Prophetic Example | R$^5$ | Q | R$^{7a}$ |
|---|---|---|---|
| 832 | CH$_2$CO$_2$Me | NH | CH$_2$OH |
| 833 | H | O | CH$_2$OH |
| 834 | CO$_2$H | O | CH$_2$OH |
| 835 | CO$_2$Me | O | CH$_2$OH |
| 836 | CH$_2$CO$_2$H | O | CH$_2$OH |
| 837 | CH$_2$CO$_2$Me | O | CH$_2$OH |
| 838 | H | NH | SO$_2$Me |
| 839 | CO$_2$H | NH | SO$_2$Me |
| 840 | CONH$_2$ | NH | SO$_2$Me |
| 841 | CH$_2$CO$_2$H | NH | SO$_2$Me |
| 842 | CH$_2$CONH$_2$ | NH | SO$_2$Me |
| 843 | H | O | SO$_2$Me |
| 844 | CO$_2$H | O | SO$_2$Me |
| 845 | CONH$_2$ | O | SO$_2$Me |
| 846 | CH$_2$CO$_2$H | O | SO$_2$Me |
| 847 | CH$_2$CONH$_2$ | O | SO$_2$Me |
| 848 | H | NH | SO$_2$NH$_2$ |
| 849 | CO$_2$H | NH | SO$_2$NH$_2$ |
| 850 | CONH$_2$ | NH | SO$_2$NH$_2$ |
| 851 | CH$_2$CO$_2$H | NH | SO$_2$NH$_2$ |
| 852 | CH$_2$CONH$_2$ | NH | SO$_2$NH$_2$ |
| 853 | H | O | SO$_2$NH$_2$ |
| 854 | CO$_2$H | O | SO$_2$NH$_2$ |
| 855 | CONH$_2$ | O | SO$_2$NH$_2$ |
| 856 | CH$_2$CO$_2$H | O | SO$_2$NH$_2$ |
| 857 | CH$_2$CONH$_2$ | O | SO$_2$NH$_2$ |

TABLE VIII

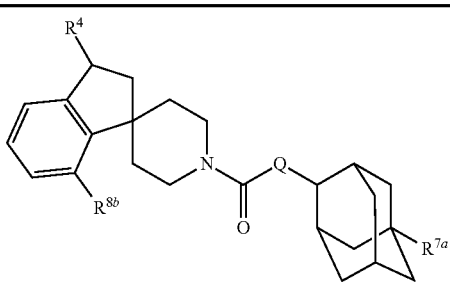

| Prophetic Example | R$^4$ | Q | R$^{7a}$ | R$^{8b}$ |
|---|---|---|---|---|
| 858 | CO$_2$H | NH | H | Me |
| 859 | CO$_2$H | O | H | Me |
| 860 | CH$_2$CO$_2$H | O | H | Me |
| 861 | CO$_2$H | NH | CONH$_2$ | Me |
| 862 | CH$_2$CO$_2$H | NH | CONH$_2$ | Me |
| 863 | CO$_2$H | O | CONH$_2$ | Me |
| 864 | CH$_2$CO$_2$H | O | CONH$_2$ | Me |
| 865 | CO$_2$H | NH | H | cyclopropyl |
| 866 | CH$_2$CO$_2$H | NH | H | cyclopropyl |
| 867 | CO$_2$H | O | H | cyclopropyl |
| 868 | CH$_2$CO$_2$H | O | H | cyclopropyl |
| 869 | CO$_2$H | NH | CONH$_2$ | cyclopropyl |
| 870 | CH$_2$CO$_2$H | NH | CONH$_2$ | cyclopropyl |
| 871 | CO$_2$H | O | CONH$_2$ | cyclopropyl |

TABLE VIII-continued

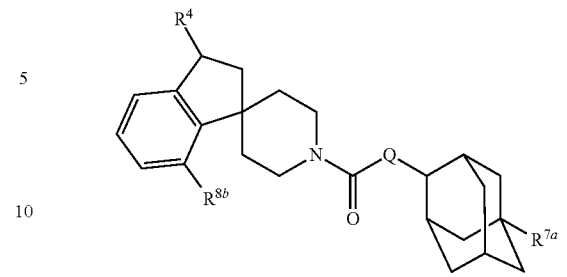

| Prophetic Example | R$^4$ | Q | R$^{7a}$ | R$^{8b}$ |
|---|---|---|---|---|
| 872 | CH$_2$CO$_2$H | O | CONH$_2$ | cyclopropyl |
| 873 | CO$_2$H | NH | H | Et |
| 874 | CH$_2$CO$_2$H | NH | H | Et |
| 875 | CO$_2$H | O | H | Et |
| 876 | CH$_2$CO$_2$H | O | H | Et |
| 877 | CO$_2$H | NH | CONH$_2$ | Et |
| 878 | CH$_2$CO$_2$H | NH | CONH$_2$ | Et |
| 879 | CO$_2$H | O | CONH$_2$ | Et |
| 880 | CH$_2$CO$_2$H | O | CONH$_2$ | Et |
| 881 | CO$_2$H | NH | H | CF$_3$ |
| 882 | CH$_2$CO$_2$H | NH | H | CF$_3$ |
| 883 | CO$_2$H | O | H | CF$_3$ |
| 884 | CH$_2$CO$_2$H | O | H | CF$_3$ |
| 885 | CO$_2$H | NH | CONH$_2$ | CF$_3$ |
| 886 | CH$_2$CO$_2$H | NH | CONH$_2$ | CF$_3$ |
| 887 | CO$_2$H | O | CONH$_2$ | CF$_3$ |
| 888 | CH$_2$CO$_2$H | O | CONH$_2$ | CF$_3$ |
| 889 | CO$_2$H | NH | H | Cl |
| 890 | CH$_2$CO$_2$H | NH | H | Cl |
| 891 | CO$_2$H | O | H | Cl |
| 892 | CH$_2$CO$_2$H | O | H | Cl |
| 893 | CO$_2$H | NH | CONH$_2$ | Cl |
| 894 | CH$_2$CO$_2$H | NH | CONH$_2$ | Cl |
| 895 | CO$_2$H | O | CONH$_2$ | Cl |
| 896 | CH$_2$CO$_2$H | O | CONH$_2$ | Cl |
| 897 | CO$_2$H | NH | SO$_2$NH$_2$ | Cl |
| 898 | CH$_2$CO$_2$H | NH | SO$_2$NH$_2$ | Cl |
| 899 | CO$_2$H | O | SO$_2$NH$_2$ | Cl |
| 900 | CH$_2$CO$_2$H | O | SO$_2$NH$_2$ | Cl |
| 901 | CO$_2$H | NH | SO$_2$Me | Cl |
| 902 | CH$_2$CO$_2$H | NH | SO$_2$Me | Cl |
| 903 | CO$_2$H | O | SO$_2$Me | Cl |
| 904 | CH$_2$CO$_2$H | O | SO$_2$Me | Cl |
| 905 | CONH$_2$ | NH | H | Cl |
| 906 | CH$_2$CONH$_2$ | NH | H | Cl |
| 907 | CONH$_2$ | O | H | Cl |
| 908 | CH$_2$CONH$_2$ | O | H | Cl |
| 909 | CONH$_2$ | NH | CONH$_2$ | Cl |
| 910 | CH$_2$CONH$_2$ | NH | CONH$_2$ | Cl |
| 911 | CONH$_2$ | O | CONH$_2$ | Cl |
| 912 | CH$_2$CONH$_2$ | O | CONH$_2$ | Cl |
| 913 | CONH$_2$ | NH | SO$_2$NH$_2$ | Cl |
| 914 | CH$_2$CONH$_2$ | NH | SO$_2$NH$_2$ | Cl |
| 915 | CONH$_2$ | O | SO$_2$NH$_2$ | Cl |
| 916 | CH$_2$CONH$_2$ | O | SO$_2$NH$_2$ | Cl |
| 917 | CONH$_2$ | NH | SO$_2$Me | Cl |
| 918 | CH$_2$CONH$_2$ | NH | SO$_2$Me | Cl |
| 919 | CONH$_2$ | O | SO$_2$Me | Cl |
| 920 | CH$_2$CONH$_2$ | O | SO$_2$Me | Cl |

Biological Test Example 1

The inhibition of purified 11β-HSD1 by compounds of Formula I or I* is measured using a Scintillation Proximity Assay. All reactions are carried out at room temperature in 96 well flexible Microbeta reaction plates. First, 1 μL of a 0.1 mM solution of a compound of Formula I or I* is mixed in DMSO diluted in half-log increments (8 points) starting at 1 μM final concentration. To this dot is added 50 μL of substrate solution (50 mM HEPES, pH 7.4, 100 mM KCl, 5 mM NaCl, 2 mM MgCl$_2$ containing 20 μM $^3$H cortisone, 1 mM NADPH). After a 10 minute incubation, 50 μL of enzyme solution containing 20 nM recombinant 11β-HSD1 (expressed in *E. coli*, and affinity purified) is added. The reaction is then incubated for 90 minutes, and stopped by adding 50 μl of SPA bead mix (18-β-glycyrrhetinic acid, 10 μM final, 5 mg/ml protein A coated YSi SPA beads, and 1 μg/ml α-cortisol antibody (East Coast Biologics)). The plate is shaken for 120 minutes, and the radioactivity corresponding to $^3$H cortisol is measured on a Wallac Microbeta.

Biological Test Example 2

The inhibition of a microsomal preparation of 11β-HSD1 by compounds of the invention is measured essentially as previously described (K. Solly, et al., High-Throughput Screening of 11-Beta-Hydroxysteroid Dehydrogenase Type 1 in Scintillation Proximity Assay Format, Assay Drug Dev Technol 3 (2005) 377-384). All reactions are carried out at room temperature in 96 well clear flexible PET Microbeta plates (PerkinElmer). First, 49 μl of substrate solution (50 mM HEPES, pH 7.4, 100 mM KCl, 5 mM NaCl, 2 mM MgCl$_2$, 2 mM NADPH and 160 nM [$^3$H]cortisone (1 Ci/mmol)) is mixed in 1 μl, of a test compound in DMSO diluted in half-log increments (8 points) starting at 0.1 mM. After a 10 minute pre-incubation, 50 μL of enzyme solution containing microsomes isolated from CHO cells overexpressing human 11β-HSD1 (10-20 μg/ml of total protein) is added, and the plates are then incubated for 90 minutes at room temperature. The reaction is stopped by adding 50 μl of the SPA beads suspension containing 10 nM 18β-glycyrrhetinic acid, 5 mg/ml protein A coated YSi SPA beads (GE Healthcare) and 3.3 μg/ml of anti-cortisol antibody (East Coast Biologics) in Superblock buffer (Bio-Rad). The plates are then shaken for 120 minutes at room temperature, and the SPA signal corresponding to [$^3$H]cortisol is measured on a Microbeta plate reader.

Biological Test Example 3

The inhibition of 11β-HSD1 by compounds of this invention is measured in whole cells as follows. Cells for the assay can be obtained from two sources: fully differentiated human omental adipocytes from Zen-Bio, Inc.; and human omental pre-adipocytes from Lonza Group Ltd. Pre-differentiated omental adipocytes from Zen-Bio Inc. are purchased in 96-well plates and used in the assay at least two weeks after differentiation from precursor preadipocytes. Zen-Bio induced differentiation of pre-adipocytes by supplementing medium with adipogenic and lipogenic hormones (human insulin, dexamethasone, isobutylmethylxanthine and PPAR-γ agonist). The cells are maintained in full adipocyte medium (DMEM/Ham's F-12 (1:1, v/v), HEPES pH 7.4, fetal bovine serum, penicillin, streptomycin and Amphotericin B, supplied by Zen-Bio, Inc.) at 37° C., 5% CO$_2$.

Pre-adipocytes (purchased from Lonza Group Ltd.) are placed in culture in Preadipocyte Growth Medium-2 supplemented with fetal bovine serum, penicillin, and streptomycin (supplied by Lonza) at 37° C., CO$_2$. Pre-adipocytes are differentiated by the addition of insulin, dexamethasone, indomethacin and isobutyl-methylxanthine (supplied by Lonza) to the Preadipocyte Growth Medium-2. Cells are then exposed to the differentiating factors for 7 days, at which point the cells are differentiated and ready for the assay. One day before running the assay, the differentiated omental adipocytes are transferred into serum- and phenol-red-free medium for overnight incubation. The assay is performed in a total volume of 200 μL. The cells are pre-incubated with serum-free, phenol-red-free medium containing 0.1% (v/v) of DMSO and various concentrations of the test compounds at least 1 h before [$^3$H]cortisone in ethanol (50 Ci/mmol, ARC, Inc.) is added to achieve a final concentration of cortisone of 100 nM. The cells are then incubated for 3-4 hrs at 37° C., 5% CO$_2$. Negative controls are incubated without radioactive substrate and receive the same amount of [$^3$H]cortisone at the end of the incubation. Formation of [$^3$H]cortisol is monitored by analyzing 25 μL of each supernatant in a scintillation proximity assay (SPA). (Solly, K., et al., Assay Drug Dev. Technol. 2005, 3, 377-384).

The inhibition of 11β-HSD1 by compounds of Formulae I, Ia, Ib, Ic, Id, Ie, If, Ig, Ih, or Ii, in whole cells is measured as follows. Omental adipocytes cultured in 96-well plates (purchased from Zen-Bio, Inc.) are used at least two weeks after differentiation from precursor preadipocytes started in medium supplemented with adipogenic and lipogenic hormones (human insulin, dexamethasone, isobutylmethylxanthine and PPARγ agonist). The cells are maintained in full adipocyte medium (DMEM/Ham's F-12 (1:1, v/v), HEPES pH 7.4, fetal bovine serum, penicillin, streptomycin and Amphotericin B, supplied by Zen-Bio, Inc.) at 37° C., 5% CO$_2$ and then transferred into serum-free, phenol red free medium for overnight incubation. The assay is performed in a total volume of 200 μL. The cells are pre-incubated with serum-free, phenol red free medium containing 0.1% (v/v) of DMSO and various concentrations of compounds of Formulae I, Ia, Ib, Ic, Id, Ie, If, Ig, Ih, or Ii, for at least 1 h before [$^3$H]cortisone in ethanol (50 Ci/mmol, ARC, Inc.) is added to achieve final concentration of cortisone of 100 nM. The cells are then incubated for 3-4 h at 37° C., 5% CO$_2$. Negative controls are incubated without radioactive substrate and receive the same amount of [$^3$H]cortisone at the end of the incubation. Formation of [$^3$H]cortisol is monitored by analyzing 25 μL of each supernatant in scintillation proximity assay (SPA). (Solly, K.; et al., *Assay Drug Dev. Technol.* 2005, 3, 377-384).

| Example | Biological Test Example 1[a] | Biological Test Example 2[a] |
|---|---|---|
| 1 | ++ | nt |
| 2 | ++ | nt |
| 3 | ++ | ++ |
| 4 | ++ | nt |
| 5 Isomer 1 | ++ | nt |
| 5 Isomer 2 | ++ | nt |
| 6 Isomer 1 | + | nt |
| 6 Isomer 2 | ++ | nt |
| 7 | ++ | nt |
| 8 | + | nt |
| 9 | + | nt |
| 10 | + | nt |
| 11 | ++ | nt |
| 12 | ++ | nt |
| 13 | + | nt |
| 14 | + | nt |
| 15 | ++ | nt |
| 16 | ++ | nt |
| 17 | + | nt |
| 18 | + | nt |
| 19 | ++ | nt |
| 20 | ++ | nt |
| 21 | ++ | nt |
| 22 | ++ | nt |
| 23 | ++ | ++ |
| 24 | ++ | nt |
| 25 | ++ | nt |
| 26 | ++ | nt |
| 27 | nt | ++ |

| Example | Biological Test Example 1[a] | Biological Test Example 2[a] |
|---|---|---|
| 27, Step 1 Product | nt | ++ |
| 27, Step 2 Product | nt | ++ |
| 28 | nt | ++ |
| 29 | ++ | nt |
| 30 | ++ | ++ |
| 31 | ++ | ++ |
| 32 | nt | ++ |
| 33 | nt | ++ |
| 34 | nt | ++ |
| 35 | nt | ++ |
| 36 | nt | ++ |
| 37 | nt | ++ |
| 38 | nt | ++ |
| 39 | nt | ++ |
| 40 | nt | ++ |
| 41 | nt | ++ |
| 42 | nt | ++ |
| 43 | nt | ++ |
| 43 Isomer 1 | nt | ++ |
| 43 Isomer 2 | nt | ++ |
| 44 | nt | ++ |
| 45 | nt | ++ |
| 46 | nt | ++ |
| 47 | nt | ++ |
| 48 | nt | ++ |
| 49 | nt | ++ |
| 50 | nt | ++ |
| 51 | nt | ++ |
| 52 | nt | ++ |
| 53 | nt | ++ |
| 54 | nt | ++ |
| 55 | nt | ++ |
| 56 | nt | ++ |
| 57 | nt | ++ |
| 58 | nt | ++ |
| 59 | nt | ++ |
| 60 | nt | ++ |
| 61 | nt | ++ |
| 62 | nt | ++ |
| 63 | nt | ++ |
| 63 Isomer 1 | nt | ++ |
| 63 Isomer 2 | nt | ++ |
| 64 | nt | ++ |
| 65 | nt | ++ |
| 66 | nt | ++ |
| 67 | nt | ++ |
| 68 | nt | ++ |
| 69 | nt | ++ |
| 70 | nt | ++ |
| 71 | nt | ++ |
| 72 | nt | + |
| 73 | nt | ++ |
| 74 | nt | ++ |
| 74 Isomer 1 | nt | ++ |
| 74 Isomer 2 | nt | ++ |
| 74 Isomer 3 | nt | ++ |
| 75 Isomer 1 | nt | ++ |
| 75 Isomer 2 | nt | ++ |
| 75 Isomer 3 | nt | + |
| 76 | nt | + |
| 77 | nt | ++ |
| 78 | nt | ++ |
| 79 | nt | ++ |
| 80 | nt | + |
| 81 | nt | ++ |
| 82 | nt | + |
| 83 | nt | ++ |
| 84 | ++ | ++ |
| 85 | nt | ++ |
| 86 | nt | ++ |
| 86, Step 1 Product | nt | ++ |
| 87 | nt | ++ |
| 87, Step 1 Product | nt | ++ |
| 88 | nt | ++ |
| 88, Step 1 Product | nt | nt |
| 89 | nt | + |
| 90 | nt | ++ |
| 91 | nt | ++ |
| 92 | nt | ++ |
| 93 | nt | ++ |
| 94 | nt | ++ |
| 95 | + | ++ |
| 96 | nt | ++ |
| 97 | nt | ++ |
| 98 | nt | + |
| 99 | nt | + |
| 100 | nt | ++ |
| 101 Isomer 1 | nt | ++ |
| 101 Isomer 2 | nt | ++ |
| 102 | nt | ++ |
| 103 | nt | ++ |
| 103, Step 1 Product | nt | ++ |
| 104 | nt | ++ |
| 104, Step 1 Product | nt | nt |
| 105 | nt | ++ |
| 105, Step 1 Product | nt | nt |
| 106 | nt | ++ |
| 107 | nt | ++ |
| 108 | nt | ++ |
| 109 | nt | ++ |
| 110 | nt | ++ |
| 111 | nt | ++ |
| 112 | nt | ++ |
| 113 | nt | ++ |
| 114 | nt | ++ |
| 115 | nt | ++ |
| 115 Isomer 1 | nt | ++ |
| 115 Isomer 2 | nt | ++ |
| 116 | nt | ++ |
| 117 | nt | ++ |
| 118 | nt | ++ |
| 119 | nt | ++ |
| 120 | nt | ++ |
| 121 | nt | ++ |
| 122 | nt | ++ |
| 123 | nt | ++ |
| 124 | nt | ++ |
| 125 | nt | ++ |
| 126 | nt | ++ |
| 127 | nt | ++ |
| 128 | + | nt |
| 129 | + | nt |
| 130 | + | nt |
| 131 | nt | ++ |

[a]++ means $IC_{50} < 50$ nM, + means $IC_{50} = 50$ nM to 1000 nM; nt = not tested.

All publications, patents and patent applications mentioned in this specification are herein incorporated by reference to the same extent as if each individual publication or patent application were specifically and individually designated as having been incorporated by reference. It is understood that the examples and embodiments described herein are for illustrative purposes only, and it will be appreciated that the invention is susceptible to modification, variation and change without departing from the proper scope or fair meaning of the appended claims.

What is claimed is:

1. A compound represented by the following structural formula:

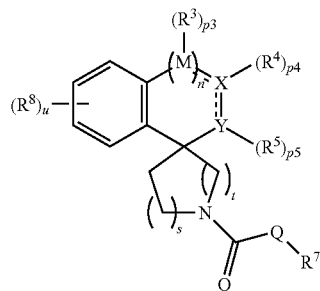

Ic' wherein:
M, X and Y are independently C;
n=0, 1, or 2;
s=1;
t=1 or 2;
u=0, 1, 2 or 3;
$R^4$ is A-(5-tetrazolyl), A-(cycloalkyl), A-(heteroaryl), A-(heterocyclyl), A-(aryl), A-COOR$^6$, A-CON(R$^6$)$_2$, A-COR$^6$, A-CONHSO$_2$R$^6$, A-CONHSO$_2$OR$^6$, A-CONHSO$_2$N(R$^6$)$_2$, A-C≡N, alkyl, alkenyl, cycloalkyl, heteroaryl, heterocyclyl, aryl, or arylalkyl;
$R^3$ and $R^5$ are independently hydrogen, A-(5-tetrazolyl), A-(cycloalkyl), A-(heteroaryl), A-(heterocyclyl), A-(aryl), A-COOR$^6$, A-CON(R$^6$)$_2$, A-COR$^6$, A-SO$_2$R$^6$, A-CONHSO$_2$R$^6$, A-CONHSO$_2$OR$^6$, A-CONHSO$_2$N(R$^6$)$_2$, A-C≡N, alkyl, alkenyl, cycloalkyl, heteroaryl, heterocyclyl, aryl, or arylalkyl, wherein the alkyl, alkenyl, cycloalkyl, heteroaryl, heterocyclyl, aryl, A-(cycloalkyl), A-(heteroaryl), A-(heterocyclyl), A-(aryl) or arylalkyl groups represented by $R^3$-$R^5$ are optionally and independently substituted with 1-3 groups independently selected from the group consisting of halogen, hydroxy, cyano, —N(R$^6$)$_2$, —NR$^6$C(O)N(R$^6$)$_2$, —NR$^6$C(O)R$^6$, (C$_1$-C$_6$)alkyl, halo(C$_1$-C$_6$)alkyl, (C$_1$-C$_6$)alkoxy, halo(C$_1$-C$_6$)alkoxy, CONH$_2$, —SO$_2$R$^6$, —NR$^6$SO$_2$R$^6$, —NR$^6$SO$_2$N(R$^6$)$_2$ and —NR$^6$SO$_2$OR$^6$;
p3, p4 or p5, respectively, is 1;
A is a single bond, (C$_1$-C$_6$)alkylene, (C$_2$-C$_6$)alkenylene, (C$_1$-C$_5$)alkyleneCH═, C(O)(C$_0$-C$_3$)alkylene(C$_3$-C$_6$)cycloalkyl(C$_0$-C$_3$)alkylene, C(O)(C$_1$-C$_6$)alkylene, C(O)(C$_2$-C$_6$)alkenylene, S(O)$_2$(C$_1$-C$_6$)alkylene, S(O)$_2$(C$_2$-C$_6$)alkenylene, or S(O)$_2$(C$_0$-C$_3$)alkylene(C$_3$-C$_6$)cycloalkyl(C$_0$-C$_3$)alkylene, each optionally substituted with up to 4 groups, R$^6$;
$R^6$ is hydrogen, (C$_1$-C$_{10}$)alkyl, halo(C$_1$-C$_{10}$)alkyl, hydroxy(C$_1$-C$_{10}$)alkyl, (R$^6$)$_2$N(C$_1$-C$_{10}$)alkyl, aryl or arylalkyl, wherein the aryl and arylalkyl groups are optionally substituted with up to three groups independently selected from halogen, hydroxy, cyano, —N(R$^6$)$_2$, —NR$^6$C(O)N(R$^6$)$_2$, —NR$^6$C(O)R$^6$, (C$_1$-C$_6$)alkyl, halo(C$_1$-C$_6$)alkyl, (C$_1$-C$_6$)alkoxy, halo(C$_1$-C$_6$)alkoxy, CON(R$^6$)$_2$, SO$_2$N(R$^6$)$_2$, —SO$_2$R$^6$, —NR$^6$SO$_2$R$^6$, —NR$^6$SO$_2$N(R$^6$)$_2$ and —NR$^6$SO$_2$OR$^6$; or
N(R$^6$)$_2$ is a heterocyclyl group containing at least one nitrogen atom selected from W$^1$-W$^7$:

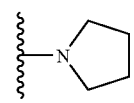

W$^1$

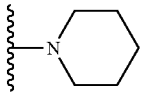

W$^2$

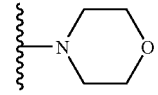

W$^3$

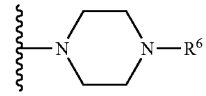

W$^4$

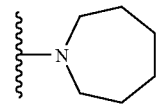

W$^5$

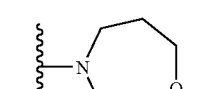

W$^6$

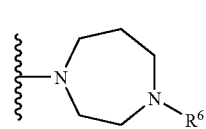

W$^7$

Q is O or NR$^6$; and
$R^7$ is a saturated C$_9$-C$_{12}$ tricycloalkyl—which is optionally substituted with 1-3 substituents independently selected from the group consisting of R$^6$, heteroaryl, oxo-substituted heteroaryl, amino-substituted heteroaryl, heterocyclyl, oxo-substituted heterocyclyl, halogen, hydroxy, hydroxy(C$_1$-C$_6$)alkyl, C(NOH)NH$_2$, CONHR$^6$, CH$_2$CONHR$^6$, CON(R$^6$)$_2$, CH$_2$CON(R$^6$)$_2$, SO$_2$NHR$^6$, SO$_2$N(R$^6$)$_2$, CO$_2$R$^6$, CH$_2$CO$_2$R$^6$, SO$_2$R$^6$, NHCOR$^6$, NR$^6$COR$^6$, NHCO$_2$R$^6$, NR$^6$CO$_2$R$^6$, NHSO$_2$R$^6$, and NR$^6$SO$_2$R$^6$;
$R^8$ is independently selected from halogen, hydroxy, cyano, —N(R$^6$)$_2$, —NR$^6$C(O)N(R$^6$)$_2$, —NR$^6$C(O)R$^6$, (C$_1$-C$_6$)alkyl, halo(C$_1$-C$_6$)alkyl, (C$_1$-C$_6$)alkoxy, halo(C$_1$-C$_6$)alkoxy, CON(R$^6$)$_2$, SO$_2$N(R$^6$)$_2$, —SO$_2$R$^6$, —NR$^6$SO$_2$R$^6$, —NR$^6$SO$_2$N(R$^6$)$_2$ and —NR$^6$SO$_2$OR$^6$;
or an enantiomer, diastereomer, geometrical isomer or pharmaceutically acceptable salt thereof.

2. The compound of claim 1, represented by the formula:

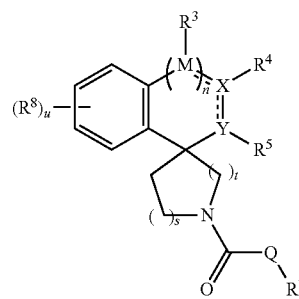

Ic wherein:
n=0, 1 or 2;
s=1;
t=1 or 2;
u=0, 1, 2 or 3;
$R^8$ is independently selected from halogen, cyano, (C$_1$-C$_6$)alkyl, halo(C$_1$-C$_6$)alkyl, (C$_1$-C$_6$)alkoxy, halo(C$_1$-C$_6$)alkoxy, CONH$_2$ and NR$^6$SO$_2$R$^6$;

R$^4$ is COOR$^6$, CH$_2$COOR$^6$, CON(R$^6$)$_2$, CH$_2$CON(R$^6$)$_2$, COR$^6$, SO$_2$R$^6$, CONHSO$_2$R$^6$, CH$_2$CONHSO$_2$R$^6$, alkyl, cycloalkyl, heteroaryl, aryl or arylalkyl;

R$^3$ and R$^5$ are independently H, COOR$^6$, CH$_2$COOR$^6$, CON(R$^6$)$_2$, CH$_2$CON(R$^6$)$_2$, COR$^6$, SO$_2$R$^6$, CONHSO$_2$R$^6$, CH$_2$CONHSO$_2$R$^6$, alkyl, cycloalkyl, heteroaryl, aryl or arylalkyl, wherein the cyclohexyl, heteroaryl, aryl or arylalkyl groups represented by R$^3$-R$^5$ are optionally and independently substituted with 1-3 groups independently selected from the group consisting of halogen, cyano, (C$_1$-C$_6$)alkyl, halo(C$_1$-C$_6$)alkyl, CONH$_2$ and NR$^6$SO$_2$R$^6$;

R$^6$ is hydrogen, (C$_1$-C$_4$)alkyl, aryl or arylalkyl;

Q is O or NR$^6$; and

R$^7$ is a saturated C$_9$-C$_{12}$ tricycloalkyl which is optionally substituted with 1-3 substituents independently selected from the group consisting of R$^6$, heteroaryl, oxo-substituted heteroaryl, amino-substituted heteroaryl, heterocyclyl, oxo-substituted heterocyclyl, halogen, hydroxy, hydroxymethyl, C(NOH)NH$_2$, CONHR$^6$, CH$_2$CONHR$^6$, CON(R$^6$)$_2$, CH$_2$CON(R$^6$)$_2$, SO$_2$NHR$^6$, SO$_2$N(R$^6$)$_2$, CO$_2$R$^6$, CH$_2$CO$_2$R$^6$, SO$_2$R$^6$, NHCOR$^6$, NR$^6$COR$^6$, NHCO$_2$R$^6$, NR$^6$CO$_2$R$^6$, NHSO$_2$R$^6$, and NR$^6$SO$_2$R$^6$;

or an enantiomer, diastereomer, geometrical isomer or pharmaceutically acceptable salt thereof.

3. The compound of claim 2, where n is 0.

4. The compound of claim 3, where s is 1 and t is 2.

5. The compound of claim 4, where R$^4$ is COOR$^6$ or CH$_2$COOR$^6$.

6. The compound of claim 3, where R$^5$ is H, R$^6$ is hydrogen or (C$_1$-C$_4$)alkyl Q is O, NH or NR$^6$; and R$^7$ is 2-adamantyl, 1-hydroxy-4-adamantyl, 1-hydroxymethyl-4-adamantyl, 1-carbamoyl-4-adamantyl, 1-(methylsulfonyl)-4-adamantyl, 1-(aminosulfonyl)-4-adamantyl, 1-bicyclo[2.2.2]octyl, 1-carbamoyl-4-bicyclo[2.2.2]octyl, 9-bicyclo[3.3.1]nonyl or 3-carbamoyl-9-bicyclo[3.3.1]nonyl.

7. The compound according to claim 2, wherein Q is O or NH.

8. The compound according to claim 2, wherein Q is O and R$^7$ is selected from the group consisting of 2-adamantyl, 1-hydroxy-4-adamantyl, 1-hydroxymethyl-4-adamantyl, and 1-carbamoyl-4-adamantyl.

9. The compound according to claim 2, wherein Q is NH and R$^7$ is selected from the group consisting of 2-adamantyl, 1-hydroxy-4-adamantyl, 1-hydroxymethyl-4-adamantyl, and 1-carbamoyl-4-adamantyl.

10. The compound of claim 1, represented by the formula:

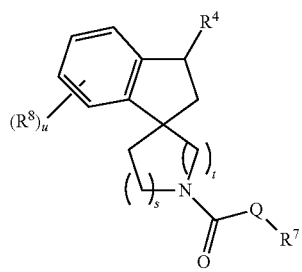

Ie or an enantiomer, diastereomer, geometrical isomer or pharmaceutically acceptable salt thereof.

11. A compound according to claim 10, wherein:

R$^4$ is A-(5 tetrazolyl), A-COOR$^6$, ACON(R$^6$)$_2$, A-CONHSO$_2$R$^6$ or alkyl, wherein the alkyl is optionally and independently substituted with 1-3 groups independently selected from the group consisting of hydroxy, cyano, —N(R$^6$)$_2$, —NR$^6$C(O)N(R$^6$)$_2$, —NR$^6$C(O)R$^6$, (C$_1$-C$_6$)alkyl, halo(C$_1$-C$_6$)alkyl, —CONH$_2$, —SO$_2$R$^6$, —NR$^6$SO$_2$R$^6$, —NR$^6$SO$_2$N(R$^6$)$_2$ and —NR$^6$SO$_2$OR$^6$;

A is a bond or (C$_1$-C$_3$)alkylene;

s=1;

t=2;

u=1;

Q is NH or O;

R$^7$ is 2-adamantyl, 1-hydroxy-4-adamantyl, 1-hydroxymethyl-4-adamantyl, 1-carbamoyl-4-adamantyl, 1-(methylsulfonyl)-4-adamantyl, 1-(aminosulfonyl)-4-adamantyl, 1-bicyclo[2.2.2]octyl, 1-carbamoyl-4-bicyclo[2.2.2]octyl, 9-bicyclo[3.3.1]nonyl or 3-carbamoyl-9-bicyclo[3.3.1]nonyl; and R$^8$ is halogen or methyl.

12. A pharmaceutical composition comprising an effective amount of a compound according of claim 1, and a pharmaceutically acceptable carrier.

13. The compound of claim 1, wherein the compound is of a formula selected from:

(±)-2-(1'-((2-Adamantyl)carbamoyl)-2,3-dihydrospiro[indene-1,4'-piperidine]-3-yl)acetic acid;

(±)-Methyl 2-(1'-((2-adamantyl)carbamoyl)-2,3-dihydrospiro[indene-1,4'-piperidine]-3-yl)acetate;

2-(1'-((2-Adamantyl)carbamoyl)-2,3-dihydrospiro[indene-1,4'-piperidine]-3-yl)acetic acid;

(±)-1'((2-Adamantyl)carbamoyl)-2,3-dihydrospiro[indene-1,4'-piperidine]-3-carboxylic acid;

(±)-Ethyl 1'-(cyclohexylcarbamoyl)-2,3-dihydrospiro[indene-1,4'-piperidine]-3-carboxylate;

(±)-2-Adamantyl 3-(2-methoxy-2-oxoethyl)-2,3-dihydrospiro[indene-1,4'-piperidine]-1'-carboxylate;

2-(1'((2-Adamantyloxy)carbonyl)-2,3-dihydrospiro[indene-1,4'-piperidine]-3-yl)acetic acid;

(±)-2-Adamantyl 3-(2-(methylamino)-2-oxoethyl)-2,3-dihydrospiro[indene-1,4'-piperidine]-1'-carboxylate;

(±)-Ethyl 2-(7-bromo-1'-((2-adamantyl)carbamoyl)-2,3-dihydrospiro[indene-1,4'-piperidine]-3-yl)acetate;

(±)-2-(7-Bromo-1'((2-adamantyl)carbamoyl)-2,3-dihydrospiro[indene-1,4'-piperidine]-3-yl)acetic acid;

(±)-N-(2-Adamantyl)-3-(2-(methylsulfonamido)-2-oxoethyl)-2,3-dihydrospiro[indene-1,4'-piperidine]-1'-carboxamide;

(±)-3-(Cyanomethyl)-N-cyclohexyl-2,3-dihydrospiro[indene-1,4'-piperidine]-1'-carboxamide;

(±)-3-((1H-Tetrazol-5-yl)methyl)-N-(2-adamantyl)-2,3-dihydrospiro[indene-1,4'-piperidine]-1'-carboxamide;

(±)-Ethyl 2-(1'-((2-adamantyl)carbamoyl)-7-methyl-2,3-dihydrospiro[indene-1,4'-piperidine]-3-yl)acetate;

(±)-2-(1'-((2-Adamantyl)carbamoyl)-7-methyl-2,3-dihydrospiro[indene-1,4'-piperidine]-3-yl)acetic acid;

(±)-Ethyl 2-(1'-((2-adamantyl)carbamoyl)-4-methyl-2,3-dihydrospiro[indene-1,4'-piperidine]-3-yl)acetate;

(±)-2-(1'-((2-Adamantyl)carbamoyl)-4-methyl-2,3-dihydrospiro[indene-1,4'-piperidine]-3-yl)acetic acid;

(±)-Ethyl 2-(1'-((2-adamantyl)carbamoyl)-7-chloro-2,3-dihydrospiro[indene-1,4'-piperidine]-3-yl)acetate;

(±)-2-(1'-((2-Adamantyl)carbamoyl)-7-chloro-2,3-dihydrospiro[indene-1,4'-piperidine]-3-yl)acetic acid;

(±)-Ethyl 2-(1'-((2-adamantyl)carbamoyl)-6-chloro-2,3-dihydrospiro[indene-1,4'-piperidine]-3-yl)acetate;

(±)-2-(1'-((2-Adamantyl)carbamoyl)-6-chloro-2,3-dihydrospiro[indene-1,4'-piperidine]-3-yl)acetic acid;
(±)-Ethyl 2-(1'-((2-adamantyl)carbamoyl)-5-chloro-2,3-dihydrospiro[indene-1,4'-piperidine]-3-yl)acetate;
(±)-2-(1'-((2-Adamantyl)carbamoyl)-5-chloro-2,3-dihydrospiro[indene-1,4'-piperidine]-3-yl)acetic acid;
(±)-2-(1'-((2-Adamantyl)carbamoyl)-6-methyl-2,3-dihydrospiro[indene-1,4'-piperidine]-3-yl)acetic acid;
(±)-2-(1'-((2-Adamantyl)carbamoyl)-5-methyl-2,3-dihydrospiro[indene-1,4'-piperidine]-3-yl)acetic acid;
(±)-2-(1'-((2-Adamantyl)carbamoyl)-6-methoxy-2,3-dihydrospiro[indene-1,4'-piperidine]-3-yl)acetic acid;
(±)-2-(1'-((2-Adamantyl)carbamoyl)-6-fluoro-2,3-dihydrospiro[indene-1,4'-piperidine]-3-yl)acetic acid;
(±)-Ethyl 2-(7-bromo-1'-((1-adamantyl)carbamoyl)-2,3-dihydrospiro[indene-1,4'-piperidine]-3-yl)acetate;
(±)-2-(7-Bromo-1'-((1-adamantyl)carbamoyl)-2,3-dihydrospiro[indene-1,4'-piperidine]-3-yl)acetic acid;
(±)-2-(7-Bromo-1'((2-adamantyloxy)carbonyl)-2,3-dihydrospiro[indene-1,4'-piperidine]-3-yl)acetic acid;
(±)-2-(6-Methyl-1'-((2-adamantyloxy)carbonyl)-2,3-dihydrospiro[indene-1,4'-piperidine]-3-yl)acetic acid;
(±)-2-(5-Methyl-1'-((2-adamantyloxy)carbonyl)-2,3-dihydrospiro[indene-1,4'-piperidine]-3-yl)acetic acid;
2-(7-Bromo-1'-((2-adamantyl)carbamoyl)-2,3-dihydrospiro[indene-1,4'-piperidine]-3-yl)propanoic acid;
(±)-Ethyl 2-(7-bromo-1'-((2-adamantyl)carbamoyl)-2,3-dihydrospiro[indene-1,4'-piperidine]-3-yl)-2-methylpropanoate;
(±)-2-(7-Bromo-1'((2-adamantyl)carbamoyl)-2,3-dihydrospiro[indene-1,4'-piperidine]-3-yl)-2-methylpropanoic acid;
(±)-2-Adamantyl 7-bromo-3-(2-(methylsulfonamido)-2-oxoethyl)-2,3-dihydrospiro[indene-1,4'-piperidine]-1'-carboxylate;
(±)-7-Bromo-N-(2-adamantyl)-3-(2-(methylsulfonamido)-2-oxoethyl)-2,3-dihydrospiro[indene-1,4'-piperidine]-1'-carboxamide;
(±)-2-Adamantyl 3-(2-(dimethylamino)-2-oxoethyl)-2,3-dihydrospiro[indene-1,4'-piperidine]-1'-carboxylate;
2-(1'-((1-(3,5-Dimethoxybenzylcarbamoyl)4-adamantyloxy)carbonyl)-2,3-dihydrospiro[indene-1,4'-piperidine]-3-yl)acetic acid;
2-(1'-((1-Carbamoyl-4adamantyloxy)carbonyl)-2,3-dihydrospiro[indene-1,4'-piperidine]-3-yl)acetic acid;
2-(7-Bromo-1'-(1-fluoro-4-adamantylcarbamoyl)-2,3-dihydrospiro[indene-1,4'-piperidine]-3-yl)acetic acid;
2-(7-Bromo-1'-(1-hydroxy-4-adamantylcarbamoyl)-2,3-dihydrospiro[indene-1,4'-piperidine]-3-yl)acetic acid;
(±)-2-(7-Bromo-1'-(1,7-dihydroxy-4-adamantylcarbamoyl)-2,3-dihydrospiro[indene-1,4'-piperidine]-3-yl)acetic acid;
2-(1'-((1-(Benzylcarbamoyl)-4-adamantyloxy)carbonyl)-2,3-dihydrospiro[indene-1,4'-piperidine]-3-yl)acetic acid;
7-Bromo-N-(2-adamantyl)-3-(2-oxo-2-(piperazin-1-yl)ethyl)-2,3-dihydrospiro[indene-1,4'-piperidine]-1'-carboxamide;
7-Bromo-N-(2-adamantyl)-3-(2-(4-methylpiperazin-1-yl)-2-oxoethyl)-2,3-dihydrospiro[indene-1,4'-piperidine]-1'-carboxamide;
7-Bromo-N-(2-adamantyl)-3-(2-(2-(dimethylamino)ethylamino)-2-oxoethyl)-2,3-dihydrospiro[indene-1,4'-piperidine]-1'-carboxamide;
7-Bromo-N-(2-adamantyl)-3-(2-(methyl(2-(methylamino)ethyl)amino)-2-oxoethyl)-2,3-dihydrospiro[indene-1,4'-piperidine]-1'-carboxamide;
7-Bromo-N-(2-adamantyl)-3-(2-(2-(dimethylamino)ethyl)(methyl)amino)-2-oxoethyl)-2,3-dihydrospiro[indene-1,4'-piperidine]-1'-carboxamide;
7-Bromo-N-(2-adamantyl)-3-(2-(3-(dimethylamino)propylamino)-2-oxoethyl)-2,3-dihydrospiro[indene-1,4'-piperidine]-1'-carboxamide;
7-Bromo-N-(2-adamantyl)-3-(2-(4-(dimethylamino)butylamino)-2-oxoethyl)-2,3-dihydrospiro[indene-1,4'-piperidine]-1'-carboxamide;
7-Bromo-N-(2-adamantyl)-3-(2-oxo-2-(2-(piperazin-1-yl)ethylamino)ethyl)-2,3-dihydrospiro[indene-1,4'-piperidine]-1'-carboxamide;
7-Bromo-N-(2-adamantyl)-3-(2-(2-(4-methylpiperazin-1-yl)ethylamino)-2-oxoethyl)-2,3-dihydrospiro[indene-1,4'-piperidine]-1'-carboxamide;
(±)-7-Bromo-N-(2-adamantyl)-3-(2-hydroxyethyl)-2,3-dihydrospiro[indene-1,4'-piperidine]-1'-carboxamide;
(±)-7-Bromo-N-(2-adamantyl)-3-(1-hydroxy-2-methylpropan-2-yl)-2,3-dihydrospiro[indene-1,4'-piperidine]-1'-carboxamide;
(±)-2-Adamantyl 3-(aminomethyl)-7-bromo-2,3-dihydrospiro[indene-1,4'-piperidine]-1'-carboxylate;
(±)-2-Adamantyl 7-bromo-3-((dimethylamino)methyl)-2,3-dihydrospiro[indene-1,4'-piperidine]-1'-carboxylate;
(±)-7-Bromo-N-(2-adamantyl)-3-(2-morpholinoethyl)-2,3-dihydrospiro[indene-1,4'-piperidine]-1'-carboxamide;
(±)-3-(2-Amino-2-oxoethyl)-N-(2-adamantyl)-2,3-dihydrospiro[indene-1,4'-piperidine]-1'-carboxamide; and
(±)-3-(2-amino-2-oxoethyl)-7-bromo-N-(2-adamantyl)-2,3-dihydrospiro[indene-1,4'-piperidine]-1'-carboxamide;

or a pharmaceutically acceptable salt thereof.

14. The compound of claim 1, represented by the formula:

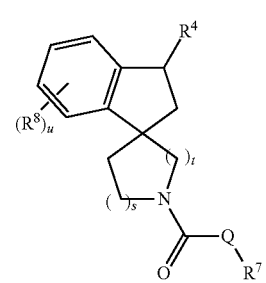

Ie wherein:
s=1;
t=1 or 2;
u=0, 1, 2 or 3;
$R^4$ is A-(5-tetrazolyl), A-(cycloalkyl), A-(heteroaryl), A-(heterocyclyl), A-(aryl), A-COOR$^6$, A-CON(R$^6$)$_2$, A-COR$^6$, A-SO$_2$R$^6$, A-CONHSO$_2$R$^6$, A-CONHSO$_2$OR$^6$, A-CONHSO$_2$N(R$^6$)$_2$, A-C≡N, alkyl, alkenyl, cycloalkyl, heteroaryl, heterocyclyl, aryl, or arylalkyl, wherein the alkyl, alkenyl, cycloalkyl, heteroaryl, heterocyclyl, aryl, A-(cycloalkyl), A-(heteroaryl), A-(heterocyclyl), A-(aryl) or arylalkyl groups represented by R$^4$ are optionally and independently substituted with 1-3 groups independently selected from the group consisting of halogen, hydroxy, cyano, —N(R$^6$)$_2$, —NR$^6$C(O)N(R$^6$)$_2$, —NR$^6$C(O)R$^6$, (C$_1$-C$_6$)alkyl, halo (C$_1$-C$_6$)alkyl, (C$_1$-C$_6$)alkoxy, halo(C$_1$-C$_6$)alkoxy, CONH$_2$, —SO$_2$R$^6$, —NR$^6$SO$_2$R$^6$, —NR$^6$SO$_2$N(R$^6$)$_2$ and —NR$^6$SO$_2$OR$^6$;

A is a single bond, $(C_1-C_6)$alkylene, $(C_2-C_6)$alkenylene, $(C_1-C_5)$alkyleneCH=, $C(O)(C_0-C_3)$alkylene$(C_3-C_6)$cycloalkyl$(C_0-C_3)$alkylene, $C(O)(C_1-C_6)$alkylene, $C(O)(C_2-C_6)$alkenylene, $S(O)_2(C_1-C_6)$alkylene, $S(O)_2(C_2-C_6)$alkenylene, or $S(O)_2(C_0-C_3)$alkylene$(C_3-C_6)$cycloalkyl$(C_0-C_3)$alkylene, each optionally substituted with up to 4 groups, $R^6$;

$R^6$ is hydrogen, $(C_1-C_{10})$alkyl, halo$(C_1-C_{10})$alkyl, hydroxy$(C_1-C_{10})$alkyl, $(R^6)_2N(C_1-C_{10})$alkyl, aryl or arylalkyl, wherein the aryl and arylalkyl groups are optionally substituted with up to three groups independently selected from halogen, hydroxy, cyano, —$N(R^6)_2$, —$NR^6C(O)N(R^6)_2$, —$NR^6C(O)R^6$, $(C_1-C_6)$alkyl, halo$(C_1-C_6)$alkyl, $(C_1-C_6)$alkoxy, halo$(C_1-C_6)$alkoxy, CON$(R^6)_2$, $SO_2N(R^6)_2$, —$SO_2R^6$, —$NR^6SO_2R^6$, —$NR^6SO_2N(R^6)_2$ and —$NR^6SO_2OR^6$; or $N(R^6)_2$ is a heterocyclyl group containing at least one nitrogen atom selected from $W^1$-$W^7$:

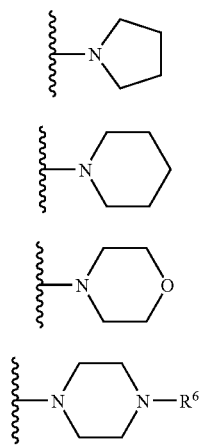

$W^1$ $W^2$ $W^3$ $W^4$

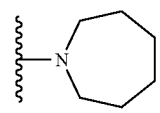

$W^5$

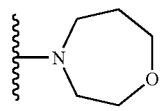

$W^6$

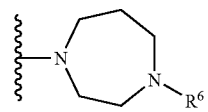

$W^7$

Q is O or $NR^6$; and $R^7$ is a saturated $C_9-C_{12}$ tricycloalkyl which is optionally substituted with 1-3 substituents independently selected from the group consisting of $R^6$, heteroaryl, oxo-substituted heteroaryl, amino-substituted heteroaryl, heterocyclyl, oxo-substituted heterocyclyl, halogen, hydroxy, hydroxy$(C_1-C_6)$alkyl, $C(NOH)NH_2$, $CONHR^6$, $CH_2CONHR^6$, $CON(R^6)_2$, $CH_2CON(R^6)_2$, $SO_2NHR^6$, $SO_2N(R^6)_2$, $CO_2R^6$, $CH_2CO_2R^6$, $SO_2R^6$, $NHCOR^6$, $NR^6COR^6$, $NHCO_2R^6$, $NR^6CO_2R^6$, $NHSO_2R^6$, and $NR^6SO_2R^6$;

$R^8$ is independently selected from halogen, hydroxy, cyano, —$N(R^6)_2$, —$NR^6C(O)N(R^6)_2$, —$NR^6C(O)R^6$, $(C_1-C_6)$alkyl, halo$(C_1-C_6)$alkyl, $(C_1-C_6)$alkoxy, halo$(C_1-C_6)$alkoxy, $CON(R^6)_2$, $SO_2N(R^6)_2$, —$SO_2R^6$, —$NR^6SO_2R^6$, —$NR^6SO_2N(R^6)_2$ and —$NR^6SO_2OR^6$;

or an enantiomer, diastereomer, geometrical isomer or pharmaceutically acceptable salt thereof.

* * * * *